US012767722B2

(12) United States Patent
Olsen et al.

(10) Patent No.: US 12,767,722 B2
(45) **Date of Patent: *Oct. 20, 2026**

(54) ANTI-4-1BB ANTIBODIES AND METHODS OF MAKING AND USING THEREOF

(71) Applicants: SYSTIMMUNE, INC., Redmond, WA (US); BAILI-BIO (CHENGDU) PHARMACEUTICAL CO., LTD., Chengdu (CN)

(72) Inventors: Ole Olsen, Everett, WA (US); Dong Xia, Redmond, WA (US); David Jellyman, Duvall, WA (US); Brian Kovacevich, Snohomish, WA (US); Bill Brady, Bothell, MA (US); Blair Renshaw, Renton, WA (US); Zeren Gao, Redmond, WA (US); Yi Zhu, Chengdu (CN)

(73) Assignee: SYSTIMMUNE, INC., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/358,849

(22) Filed: Jul. 25, 2023

(65) Prior Publication Data

US 2024/0084026 A1 Mar. 14, 2024
US 2025/0376531 A9 Dec. 11, 2025

Related U.S. Application Data

(62) Division of application No. 16/615,119, filed as application No. PCT/US2018/039155 on Jun. 22, 2018, now Pat. No. 11,987,635.

(60) Provisional application No. 62/551,032, filed on Aug. 28, 2017, provisional application No. 62/551,065, filed on Aug. 28, 2017, provisional application No. 62/551,035, filed on Aug. 28, 2017, provisional application No. 62/545,603, filed on Aug. 15, 2017, provisional application No. 62/524,554, filed on Jun. 25, 2017, provisional application No. 62/524,557, filed on Jun. 25, 2017, provisional application No. 62/524,558, filed on Jun. 25, 2017.

(51) Int. Cl.

| | |
|---|---|
| ***C07K 16/28*** | (2006.01) |
| ***A61K 39/00*** | (2006.01) |
| ***A61K 39/395*** | (2006.01) |
| ***A61K 45/06*** | (2006.01) |

(52) U.S. Cl.

CPC ...... *C07K 16/2878* (2013.01); *A61K 39/3955* (2013.01); *A61K 45/06* (2013.01); *C07K 16/2803* (2013.01); *A61K 2039/505* (2013.01); *C07K 2317/24* (2013.01); *C07K 2317/31* (2013.01); *C07K 2317/92* (2013.01)

(58) Field of Classification Search

None
See application file for complete search history.

(56) References Cited

U.S. PATENT DOCUMENTS

| | | | | |
|---|---|---|---|---|
| 11,787,863 | B2 * | 10/2023 | Zhu | C07K 16/2827 424/135.1 |
| 12,029,761 | B2 * | 7/2024 | Zhu | C07K 14/7051 |
| 2020/0157224 | A1 * | 5/2020 | Zhu | A61K 35/16 |
| 2021/0008113 | A1 * | 1/2021 | Zhu | C12N 5/0636 |
| 2021/0024630 | A1 * | 1/2021 | Zhu | A61K 39/464402 |
| 2022/0002406 | A1 * | 1/2022 | Zhu | C07K 16/2863 |
| 2022/0002425 | A1 * | 1/2022 | Zhu | A61P 35/02 |

FOREIGN PATENT DOCUMENTS

| | | | | |
|---|---|---|---|---|
| WO | WO-2019005639 | A2 * | 1/2019 | A61P 35/00 |
| WO | WO-2019005640 | A2 * | 1/2019 | A61K 35/16 |
| WO | WO-2019005641 | A1 * | 1/2019 | A61K 35/17 |
| WO | WO-2019005642 | A1 * | 1/2019 | A61K 35/17 |
| WO | WO-2019191120 | A1 * | 10/2019 | A61K 35/13 |
| WO | WO-2019191125 | A1 * | 10/2019 | A61K 35/13 |

* cited by examiner

*Primary Examiner* — Marianne P Allen
(74) *Attorney, Agent, or Firm* — EpiMED LLC

(57) ABSTRACT

The application provides anti-4-1BB monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

8 Claims, 10 Drawing Sheets

Specification includes a Sequence Listing.

FIG. 1 (Cohort 1)

| Day | Cohort | Antigen | Adjuvant |
|---|---|---|---|
| 0 | 1 | Human 41BB transfected 293 cells | Titermax |
| 7 | 1 | Cynomolgus 41BB transfected 293 cells | Alyhrodgel 2% + CpG 2007 |
| 14 | 1 | Human 41BB transfected 293 cells | Titermax |
| 21 | 1 | Cynomolgus 41BB transfected 293 cells | Alyhrodgel 2% + CpG 2007 |
| 27 | 1 | Serum collection | |
| 28 | 1 | Human 41BB transfected 293 cells | Titermax |
| 37 | 1 | Cynomolgus 41BB transfected 293 cells | Alyhrodgel 2% + CpG 2007 |
| 44 | 1 | Serum collection | |
| | 1 | Human 41BB transfected 293 cells | Titermax |
| 51 | 1 | Cynomolgus 41BB transfected 293 cells | Alyhrodgel 2% + CpG 2007 |
| 58 | 1 | Human 41BB transfected 293 cells | Titermax |
| 62 | 1 | Serum collection | |

FIG. 1 (Continued, Cohort 2)

| Day | Cohort | Antigen | Adjuvant |
|---|---|---|---|
| 0 | 2 | Human 41BB transfected 293 cells | Complete Freund's |
| 7 | 2 | Cynomolgus 41BB transfected 293 cells | Alyhrodgel 2% + CpG 2007 |
| 14 | 2 | Human 41BB transfected 293 cells | Incomplete Freund's |
| 21 | 2 | Cynomolgus 41BB transfected 293 cells | Alyhrodgel 2% + CpG 2007 |
| 27 | 2 | Serum collection | |
| 28 | 2 | Human 41BB transfected 293 cells | Incomplete Freund's |
| 37 | 2 | Cynomolgus 41BB transfected 293 cells | Alyhrodgel 2% + CpG 2007 |
| 44 | 2 | Serum collection | |
| | 2 | Human 41BB transfected 293 cells | Incomplete Freund's |
| 51 | 2 | Cynomolgus 41BB transfected 293 cells | Alyhrodgel 2% + CpG 2007 |
| 58 | 2 | Human 41BB transfected 293 cells | Titermax |
| 62 | 2 | Serum collection | |

FIG. 2

| | | B cell culture supernatant | | Transfection Supernatant | |
|---|---|---|---|---|---|
| | | Proliferation | Gamma Interferon | Octet Binding to recombinant 41BB kdis(1/s) | |
| | Original BCC well ID | RLU | $OD_{450}$ | Human | Cynomolgus |
| 1 | 419D9 | 8.0E+07 | 2.2 | 6.3E-04 | 1.4E-03 |
| 2 | 418H5 | 8.9E+07 | 1.8 | 1.4E-03 | 1.6E-03 |
| 3 | 411H11 | 3.3E+07 | 2.2 | 1.0E-03 | 1.5E-03 |
| 4 | 413F3 | 1.8E+07 | 0.3 | 5.4E-04 | 7.9E-04 |
| 5 | 416G1 | 9.0E+07 | 2.0 | 1.4E-03 | 1.9E-03 |
| 6 | 416H5 | 7.8E+07 | 2.1 | 1.1E-02 | 3.2E-03 |
| 7 | 418E10 | 7.6E+07 | 1.5 | 1.1E-03 | 1.5E-03 |
| 8 | 418E4 | 9.4E+07 | 2.5 | 3.6E-03 | 5.0E-03 |
| 9 | 420H6 | 7.0E+07 | 2.5 | 9.4E-04 | 2.0E-03 |
| 10 | 459F1 | 3.2E+07 | 0.3 | 7.5E-04 | 7.5E-03 |
| 11 | 464C11 | 5.5E+07 | 1.0 | 4.5E-03 | 8.3E-03 |
| 12 | 470B6 | 1.4E+08 | 2.4 | 1.3E-03 | 1.2E-03 |
| 13 | 472E4 | 8.8E+07 | 1.9 | 1.1E-03 | 1.8E-03 |
| 14 | 418E8 | 9.8E+07 | 3.0 | 3.0E-03 | 3.6E-03 |
| 15 | 468C11 | 6.6E+07 | 2.2 | 2.7E-03 | 1.2E-03 |
| 16 | 470H2 | 5.5E+07 | 2.2 | 4.3E-03 | 6.9E-03 |
| 17 | 460C3 | 3.6E+07 | 0.3 | 6.7E-04 | 4.1E-03 |
| 18 | 413G3 | 2.4E+07 | 0.5 | 4.2E-04 | 7.9E-04 |
| 19 | 414A8 | 2.2E+07 | 0.4 | 2.9E-04 | 3.9E-04 |
| 20 | 415E8 | 5.4E+07 | 2.2 | 2.2E-03 | 5.8E-04 |
| 21 | 416G6 | 8.0E+07 | 2.5 | 7.0E-04 | 5.6E-03 |
| 22 | 416H7 | 8.1E+07 | 2.4 | 3.1E-03 | 2.5E-03 |
| 23 | 418H1 | 1.5E+08 | 2.4 | 1.4E-02 | 1.0E-02 |
| 24 | 420A11 | 7.6E+07 | 1.1 | 3.1E-03 | 1.1E-01 |
| 25 | 420G12 | 0.0E+00 | 2.2 | 1.4E-02 | 1.1E-03 |
| 26 | 459E8 | 4.4E+07 | 0.9 | 3.1E-04 | 6.4E-04 |
| 27 | 459H12 | 5.5E+07 | 2.2 | 1.4E-03 | 1.4E-03 |
| 28 | 464B12 | 7.5E+07 | 2.4 | 1.3E-03 | 6.4E-04 |
| 29 | 466G10 | 4.4E+07 | 0.3 | 2.8E-03 | 2.3E-03 |
| 30 | 468E5 | 0.0E+00 | 0.4 | 4.2E-04 | 1.1E-03 |
| 31 | 416F8 | 7.7E+07 | 1.8 | 4.3E-03 | 3.0E-03 |
| 32 | 420H5 | 8.1E+07 | 1.7 | 1.3E-03 | 2.3E-03 |
| 33 | 466F6 | 8.6E+07 | 1.7 | 2.1E-03 | 2.6E-03 |
| 34 | 470C6 | 8.1E+07 | 2.3 | 1.0E-03 | 1.4E-03 |

FIG. 3

| Original BCC well ID | Gamma-interferon $EC_{50}$ [ng/ml] | 3000 | 1000 | 333.3 | 111.1 | 37.0 | 12.3 | 4.1 | 1.4 | 0.5 | 0.2 | 0 |
|---|---|---|---|---|---|---|---|---|---|---|---|---|
| 411H11 | 18.9 | 2.9 | 2.4 | 2.2 | 2.7 | 2.5 | 1.8 | 1.4 | 1.5 | 1.4 | 1.3 | 1.0 |
| 413F3 | 11.3 | 1.4 | 1.4 | 1.3 | 1.2 | 1.5 | 1.3 | 1.1 | 1.1 | 1.0 | 1.1 | 1.0 |
| 413G3 | 23.7 | 1.3 | 1.4 | 1.3 | 1.4 | 1.3 | 1.2 | 1.0 | 1.0 | 1.1 | 0.9 | 1.0 |
| 414A8 | 90.3 | 1.1 | 1.5 | 1.2 | 1.4 | 1.4 | 1.2 | 1.2 | 1.1 | 1.2 | 1.1 | 1.0 |
| 415E8 | 10.3 | 1.7 | 1.6 | 1.8 | 1.8 | 1.5 | 1.4 | 1.2 | 1.0 | 1.0 | 1.0 | 1.0 |
| 416F8 | 7.3 | 1.3 | 1.6 | 1.6 | 1.8 | 1.6 | 2.2 | 1.3 | 1.1 | 1.2 | 1.2 | 1.0 |
| 416G1 | 11.9 | 1.3 | 1.6 | 1.1 | 1.5 | 1.6 | 1.0 | 1.0 | 1.1 | 1.1 | 1.0 | 1.0 |
| 416G6 | 7.3 | 1.5 | 1.8 | 1.8 | 1.8 | 1.9 | 1.8 | 1.7 | 1.1 | 1.1 | 1.1 | 1.0 |
| 416H5 | 39.1 | 1.5 | 1.6 | 1.5 | 1.6 | 1.5 | 1.2 | 1.0 | 1.0 | 1.0 | 1.1 | 1.0 |
| 416H7 | 17.1 | 1.9 | 1.9 | 2.3 | 2.6 | 1.9 | 1.7 | 1.2 | 1.3 | 1.2 | 1.2 | 1.0 |
| 418E10 | 20.9 | 1.6 | 1.6 | 1.7 | 1.7 | 1.8 | 1.3 | 1.0 | 0.8 | 1.0 | 1.0 | 1.0 |
| 418E4 | 24.4 | 2.3 | 1.6 | 1.5 | 1.5 | 1.5 | 1.8 | 1.0 | 1.1 | 0.8 | 0.9 | 1.0 |
| 418E8 | 5.6 | 1.7 | 1.5 | 1.5 | 1.5 | 1.6 | 1.6 | 1.5 | 1.3 | 1.2 | 1.0 | 1.0 |
| 418H1 | 28.9 | 1.7 | 1.6 | 1.9 | 1.8 | 1.7 | 1.4 | 1.0 | 1.3 | 1.1 | 1.1 | 1.0 |
| 418H5 | 25.5 | 1.6 | 1.4 | 1.8 | 2.0 | 1.9 | 1.1 | 1.1 | 1.1 | 1.1 | 1.1 | 1.0 |
| 419D9 | 17.6 | 1.1 | 1.6 | 1.7 | 1.8 | 1.8 | 1.3 | 1.0 | 1.1 | 1.1 | 1.1 | 1.0 |
| 420A11 | 23.8 | 1.4 | 1.4 | 1.6 | 1.6 | 1.6 | 1.2 | 0.9 | 0.7 | 0.9 | 0.9 | 1.0 |
| 420G12 | 5.7 | 1.6 | 1.9 | 1.6 | 1.6 | 1.7 | 1.6 | 1.4 | 1.3 | 1.2 | 1.1 | 1.0 |
| 420H5 | 5.2 | 1.6 | 1.9 | 2.1 | 2.2 | 2.2 | 2.2 | 1.7 | 1.4 | 1.5 | 1.3 | 1.0 |
| 420H6 | 17.1 | 1.2 | 1.8 | 2.0 | 2.0 | 2.0 | 1.4 | 1.3 | 1.1 | 1.3 | 1.2 | 1.0 |
| 459E8 | 71.9 | 1.1 | 1.3 | 1.2 | 1.5 | 1.3 | 1.1 | 1.1 | 1.1 | 1.1 | 1.1 | 1.0 |
| 459F1 | 23.7 | 1.6 | 1.9 | 2.2 | 2.3 | 2.3 | 1.5 | 1.5 | 1.4 | 1.3 | 1.3 | 1.0 |
| 459H12 | 8.4 | 1.1 | 1.3 | 1.3 | 1.4 | 1.3 | 1.4 | 0.9 | 0.8 | 1.0 | 1.0 | 1.0 |
| 460C3 | 8.8 | 1.4 | 1.7 | 1.9 | 2.6 | 1.7 | 1.6 | 1.4 | 1.1 | 1.0 | 1.2 | 1.0 |
| 464B12 | 18.1 | 1.9 | 1.8 | 2.0 | 1.9 | 1.7 | 1.3 | 1.0 | 1.0 | 1.0 | 1.1 | 1.0 |
| 464C11 | 25.3 | 1.2 | 1.4 | 1.5 | 1.5 | 1.6 | 1.3 | 1.6 | 1.1 | 1.1 | 1.1 | 1.0 |
| 466F6 | 8.8 | 1.7 | 1.7 | 1.8 | 1.9 | 2.1 | 1.5 | 1.3 | 1.1 | 1.2 | 1.0 | 1.0 |
| 466G10 | 11.1 | 2.5 | 2.1 | 2.5 | 2.3 | 1.9 | 2.1 | 1.4 | 1.3 | 1.3 | 1.3 | 1.0 |
| 468C11 | 12.4 | 1.8 | 1.9 | 1.9 | 1.9 | 1.8 | 1.5 | 1.2 | 1.1 | 1.0 | 1.1 | 1.0 |
| 468E5 | 22.7 | 0.9 | 1.3 | 1.2 | 1.4 | 1.5 | 1.2 | 1.4 | 1.1 | 1.1 | 1.2 | 1.0 |
| 470B6 | | | | | | | | | | | | |
| 470C6 | 6.9 | 2.3 | 2.5 | 2.4 | 2.8 | 2.8 | 2.4 | 1.7 | 1.6 | 1.4 | 1.4 | 1.0 |
| 470H2 | 10.5 | 1.4 | 1.6 | 1.7 | 1.7 | 1.9 | 1.6 | 1.5 | 1.1 | 0.9 | 1.1 | 1.0 |
| 472E4 | 14.1 | 1.9 | 1.4 | 1.5 | 1.5 | 1.5 | 1.3 | 0.9 | 1.0 | 0.9 | 1.0 | 1.0 |
| Positive control.1 | 14.1 | 1.9 | 1.9 | 2.1 | 2.7 | 2.7 | 1.7 | 1.3 | 1.1 | 1.0 | 1.1 | 1.0 |

FIG. 3 (Continued)

| Original BCC well ID | Gamma-interferon $EC_{50}$ [ng/ml] | 3000 | 1000 | 333.3 | 111.1 | 37.0 | 12.3 | 4.1 | 1.4 | 0.5 | 0.2 | 0 |
|---|---|---|---|---|---|---|---|---|---|---|---|---|
| 411H11 | 14.6 | 1.1 | 2.0 | 1.7 | 2.1 | 2.1 | 1.5 | 1.2 | 1.0 | 0.9 | 1.0 | 1.0 |
| 413F3 | 44.7 | 0.7 | 0.8 | 0.9 | 1.0 | 0.9 | 0.9 | 0.9 | 0.9 | 0.9 | 1.0 | 1.0 |
| 413G3 | 21.3 | 0.9 | 1.0 | 1.4 | 2.0 | 1.7 | 1.2 | 0.9 | 1.0 | 0.9 | 1.0 | 1.0 |
| 414A8 | 71.3 | 1.1 | 1.3 | 1.4 | 1.3 | 1.1 | 1.1 | 0.8 | 0.8 | 0.8 | 1.0 | 1.0 |
| 415E8 | 17.5 | 0.8 | 1.1 | 1.4 | 1.6 | 1.5 | 1.0 | 0.8 | 0.7 | 0.6 | 0.8 | 1.0 |
| 416F8 | 11.2 | 1.0 | 1.0 | 1.3 | 1.2 | 1.4 | 1.2 | 0.9 | 0.7 | 0.6 | 0.7 | 1.0 |
| 416G1 | 12.8 | 0.9 | 1.3 | 1.4 | 2.3 | 2.3 | 1.6 | 1.1 | 1.0 | 0.8 | 1.0 | 1.0 |
| 416G6 | 13.1 | 0.6 | 1.4 | 1.3 | 2.0 | 1.7 | 1.1 | 0.6 | 0.7 | 0.7 | 0.9 | 1.0 |
| 416H5 | 44.5 | 1.6 | 1.6 | 1.8 | 1.8 | 1.4 | 1.1 | 0.9 | 0.7 | 0.8 | 0.9 | 1.0 |
| 416H7 | 28.0 | 0.9 | 1.5 | 1.6 | 1.5 | 1.6 | 1.0 | 0.7 | 0.8 | 0.7 | 0.9 | 1.0 |
| 418E10 | 20.4 | 2.0 | 2.2 | 2.2 | 2.1 | 2.0 | 1.2 | 1.0 | 0.9 | 0.9 | 0.7 | 1.0 |
| 418E4 | 31.0 | 1.2 | 1.6 | 1.8 | 1.7 | 1.7 | 1.0 | 0.9 | 0.9 | 0.8 | 1.0 | 1.0 |
| 418E8 | 12.8 | 1.2 | 1.8 | 1.6 | 2.2 | 1.9 | 1.4 | 1.0 | 0.9 | 0.8 | 0.9 | 1.0 |
| 418H1 | 25.0 | 0.8 | 1.2 | 1.3 | 1.4 | 1.4 | 1.0 | 0.9 | 0.7 | 0.8 | 0.8 | 1.0 |
| 418H5 | 37.5 | 2.2 | 1.8 | 1.6 | 2.0 | 1.1 | 1.0 | 0.7 | 0.9 | 0.9 | 1.1 | 1.0 |
| 419D9 | 13.0 | 1.5 | 1.4 | 1.5 | 2.0 | 1.8 | 1.2 | 0.7 | 0.9 | 0.7 | 0.8 | 1.0 |
| 420A11 | 25.3 | 2.3 | 1.7 | 1.9 | 1.7 | 1.4 | 1.0 | 0.8 | 0.8 | 0.9 | 0.8 | 1.0 |
| 420G12 | 20.8 | 1.0 | 1.2 | 1.4 | 1.7 | 1.6 | 1.1 | 0.8 | 0.8 | 0.8 | 0.9 | 1.0 |
| 420H5 | 8.9 | 3.2 | 2.6 | 2.3 | 2.4 | 3.0 | 1.9 | 1.2 | 1.0 | 0.9 | 1.0 | 1.0 |
| 420H6 | 14.9 | 1.5 | 1.9 | 1.7 | 2.8 | 1.9 | 1.2 | 1.0 | 0.9 | 0.9 | 1.0 | 1.0 |
| 459E8 | 42.3 | 1.1 | 1.2 | 1.6 | 1.4 | 1.2 | 1.0 | 0.8 | 0.8 | 1.0 | 1.1 | 1.0 |
| 459F1 | 17.4 | 1.1 | 1.7 | 1.9 | 2.4 | 2.1 | 1.6 | 1.0 | 1.1 | 1.2 | 0.8 | 1.0 |
| 459H12 | 19.2 | 1.8 | 1.1 | 1.2 | 1.5 | 1.3 | 1.2 | 0.9 | 0.8 | 1.0 | 0.8 | 1.0 |
| 460C3 | 10.4 | 1.1 | 1.4 | 1.7 | 2.0 | 2.3 | 1.5 | 1.1 | 0.9 | 1.1 | 0.8 | 1.0 |
| 464B12 | 13.1 | 0.8 | 1.3 | 1.2 | 1.9 | 1.7 | 1.3 | 0.9 | 0.8 | 0.9 | 0.6 | 1.0 |
| 464C11 | 40.3 | 1.5 | 1.4 | 1.1 | 1.6 | 1.3 | 1.1 | 1.0 | 0.9 | 0.9 | 0.9 | 1.0 |
| 466F6 | 8.2 | 1.1 | 1.7 | 2.0 | 3.1 | 2.8 | 2.3 | 1.6 | 1.0 | 1.2 | 1.1 | 1.0 |
| 466G10 | 15.8 | 0.8 | 1.1 | 1.1 | 1.4 | 1.5 | 1.2 | 1.0 | 1.0 | 0.9 | 0.9 | 1.0 |
| 468C11 | 15.2 | 0.7 | 1.5 | 1.3 | 2.2 | 2.0 | 1.4 | 0.9 | 0.8 | 0.8 | 0.8 | 1.0 |
| 468E5 | 22.1 | 1.2 | 1.0 | 1.2 | 0.8 | 1.2 | 0.9 | 0.8 | 0.8 | 0.7 | 0.8 | 1.0 |
| 470B6 | 24.1 | 0.7 | 1.5 | 1.6 | 2.1 | 1.5 | 1.3 | 1.0 | 1.0 | 0.9 | 0.8 | 1.0 |
| 470C6 | 7.2 | 1.0 | 1.5 | 1.4 | 2.1 | 3.2 | 2.6 | 1.4 | 1.2 | 1.0 | 1.1 | 1.0 |
| 470H2 | 22.0 | 2.4 | 2.0 | 1.9 | 2.6 | 2.0 | 1.2 | 1.2 | 1.2 | 1.2 | 1.1 | 1.0 |
| 472E4 | 16.4 | 0.7 | 1.1 | 1.2 | 1.4 | 1.4 | 1.1 | 1.0 | 0.8 | 1.0 | 0.8 | 1.0 |
| Positive control.1 | 12.5 | 0.7 | 1.5 | 2.1 | 2.1 | 2.7 | 1.7 | 1.2 | 1.0 | 0.9 | 0.9 | 1.0 |

FIG. 4

| Antibody ID | Humanized Variant | Binding off-rate kdis(1/s) |
|---|---|---|
| 411H11 | VHv1VLv1 | 1.79E-03 |
| 413F3 | VHv1VLv1 | 2.24E-03 |
| 416F8 | VHv3VLv1 | 6.45E-03 |
| 416G1 | VHv1VLv1 | 1.66E-03 |
| 418E10 | VHv1VLv1 | 9.58E-04 |
| 418E4 | VHv1VLv1 | 2.77E-03 |
| 418H5 | VHv2VLv1 | 2.45E-03 |
| 419D9 | VHv3VLv3 | 2.84E-03 |
| 420H5 | VHv3VLv3 | 1.78E-03 |
| 420H6 | VHv1VLv1 | 1.28E-03 |
| 459F1 | VHv1VLv1 | 1.31E-03 |
| 460C3 | VHv1VLv1 | 7.28E-04 |
| 464C11 | VHv1VLv1 | 7.84E-04 |
| 466F6 | VHv2VLv5 | 2.54E-03 |
| 470B6 | VHv1VLv1 | 9.10E-04 |
| 470C6 | VHv3VLv3 | 1.83E-03 |
| 472E4 | VHv1VLv1 | 2.65E-03 |

FIG. 5

| Original BCC well ID | Gamma-interferon $EC_{50}$ [ng/ml] | 3000 | 1000 | 333.3 | 111.1 | 37.0 | 12.3 | 4.1 | 1.4 | 0.5 | 0.2 | 0 |
|---|---|---|---|---|---|---|---|---|---|---|---|---|
| 411H11 | 5.8 | 0.9 | 1.3 | 1.2 | 1.3 | 1.3 | 1.3 | 1.3 | 0.9 | 1.0 | 0.8 | 1.0 |
| 413F3 | 139.4 | 0.8 | 1.5 | 1.3 | 0.9 | 1.0 | 1.1 | 1.3 | 1.1 | 1.3 | 1.0 | 1.0 |
| 416F8 | 37.5 | 1.1 | 1.4 | 1.7 | 2.1 | 1.4 | 1.6 | 1.2 | 1.6 | 0.8 | 1.2 | 1.0 |
| 416G1 | 36.7 | 1.5 | 1.7 | 2.4 | 2.3 | 1.7 | 1.8 | 1.4 | 1.6 | 1.5 | 1.2 | 1.0 |
| 416H5 | - | 0.5 | 0.7 | 0.6 | 0.7 | 0.7 | 1.1 | 0.9 | 1.3 | 1.1 | 0.9 | 1.0 |
| 418E4 | 12.3 | 1.1 | 1.7 | 1.7 | 1.6 | 2.3 | 1.4 | 1.1 | 1.3 | 1.2 | 1.2 | 1.0 |
| 418E10 | 7.1 | 0.9 | 1.3 | 1.8 | 1.5 | 2.2 | 2.2 | 1.4 | 1.4 | 1.0 | 1.1 | 1.0 |
| 418H5 | 14.5 | 1.2 | 2.0 | 1.5 | 2.1 | 2.2 | 1.4 | 1.3 | 0.9 | 1.2 | 0.7 | 1.0 |
| 419D9 | 13 | 1.0 | 1.1 | 1.4 | 1.5 | 1.9 | 1.3 | 1.0 | 0.9 | 1.1 | 0.8 | 1.0 |
| 420H5 | 50.7 | 1.8 | 1.8 | 1.3 | 1.3 | 1.7 | 1.3 | 1.0 | 1.4 | 1.1 | 1.1 | 1.0 |
| 420H6 | 26 | 0.9 | 1.4 | 1.7 | 1.8 | 1.5 | 1.5 | 1.3 | 0.9 | 1.0 | 1.0 | 1.0 |
| 459F1 | 21.2 | 0.5 | 0.7 | 0.8 | 1.1 | 1.3 | 1.4 | 0.9 | 1.2 | 0.9 | 0.8 | 1.0 |
| 460C3 | 11.5 | 0.7 | 0.9 | 1.2 | 1.4 | 1.8 | 1.6 | 1.2 | 1.6 | 1.4 | 1.1 | 1.0 |
| 464C11 | 8.4 | 1.1 | 1.4 | 1.8 | 2.0 | 2.1 | 1.8 | 1.0 | 1.0 | 1.1 | 0.9 | 1.0 |
| 466F6 | 9.8 | 1.1 | 0.9 | 1.8 | 1.4 | 1.4 | 2.0 | 1.4 | 1.2 | 0.8 | 1.1 | 1.0 |
| 470B6 | 17.8 | 1.1 | 2.2 | 1.4 | 1.3 | 1.8 | 1.8 | 1.2 | 1.1 | 1.0 | 1.0 | 1.0 |
| 470C6 | 5.7 | 1.6 | 2.1 | 2.0 | 2.3 | 2.6 | 2.2 | 2.1 | 1.7 | 1.4 | 1.4 | 1.0 |
| 472E4 | 11.6 | 1.2 | 2.0 | 1.9 | 2.4 | 2.0 | 1.6 | 1.2 | 1.2 | 1.4 | 0.9 | 1.0 |
| Positive control.1 | 4.3 | 1.5 | 1.8 | 1.5 | 1.5 | 1.7 | 1.7 | 1.4 | 1.4 | 1.2 | 1.3 | 1.0 |

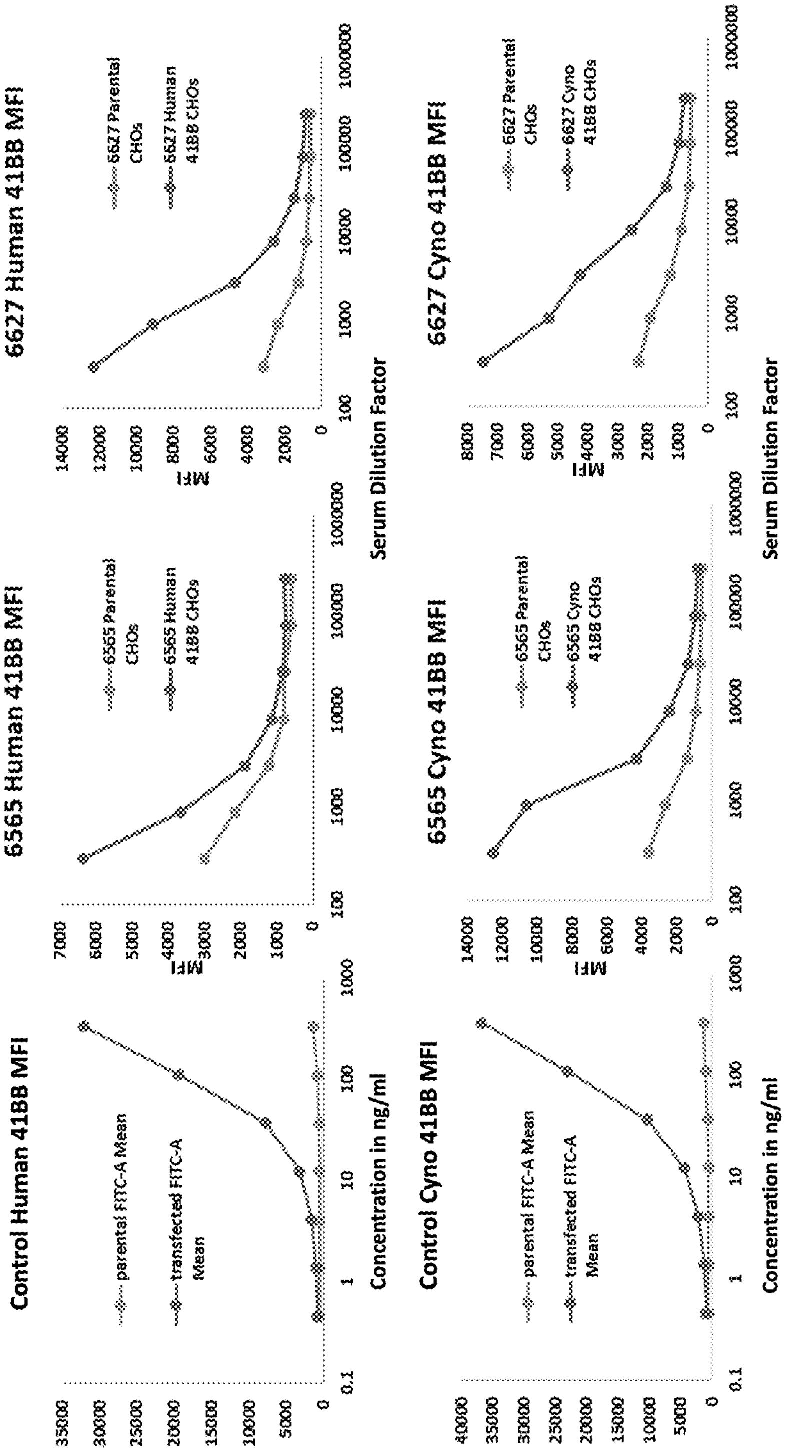
FIG. 6 (left panel)

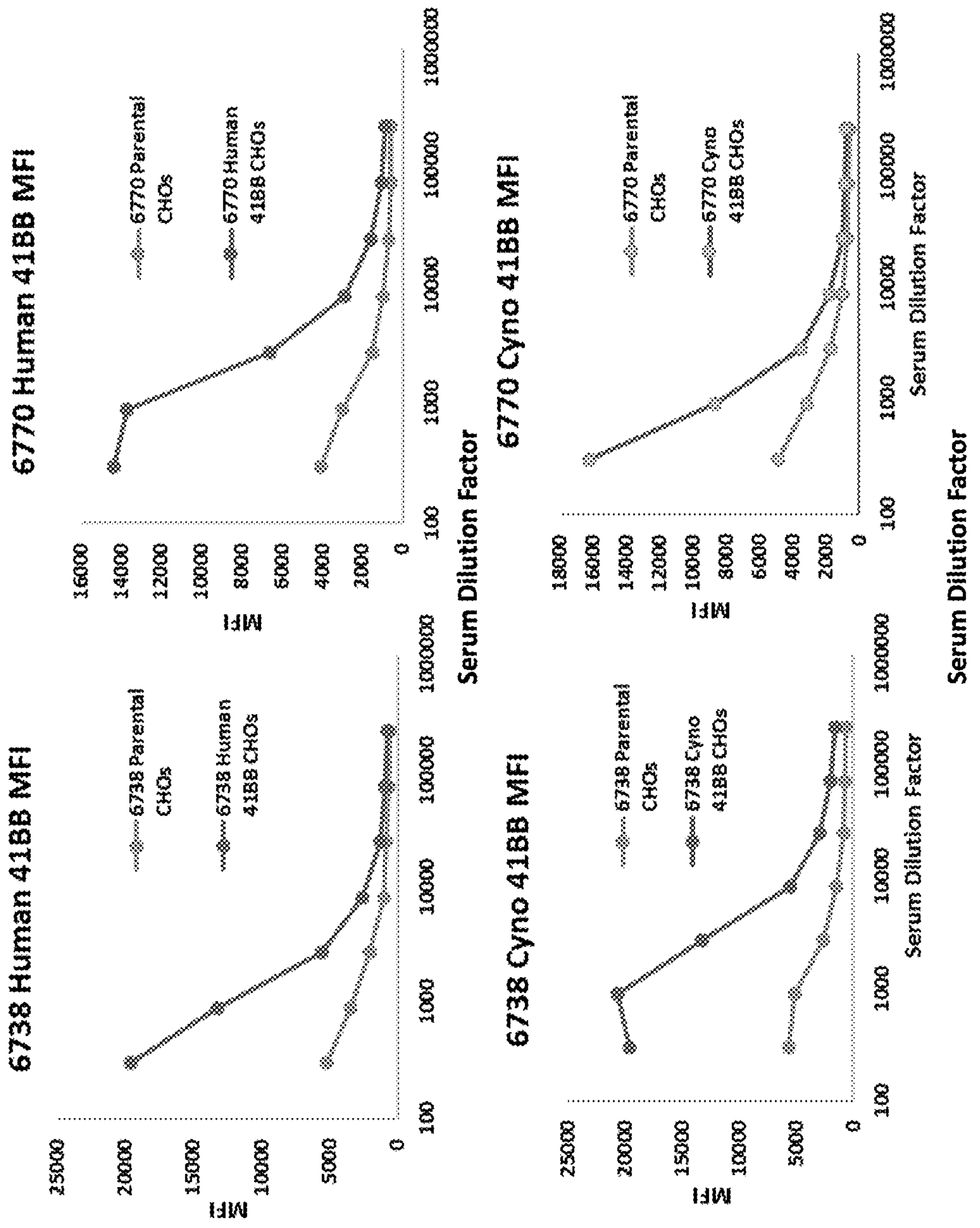
FIG. 6 (Continued, right panel)

ANTI-4-1BB ANTIBODIES AND METHODS OF MAKING AND USING THEREOF

CROSS REFERENCE TO RELATED APPLICATIONS

This application is a divisional application of U.S. application Ser. No. 16/615,119, filed Nov. 19, 2019, which is a U.S. national stage of PCT/US2018/039155, filed Jun. 22, 2018, which claims the benefit of U.S. Provisional Patent Application No. 62/551,065, filed Aug. 28, 2017, U.S. Provisional Patent Application No. 62/551,032 filed Aug. 28, 2017, U.S. Provisional Patent Application No. 62/524,554 filed Jun. 25, 2017, U.S. Provisional Patent Application No. 62/524,557 filed Jun. 25, 2017, U.S. Provisional Patent Application No. 62/524,558 filed Jun. 25, 2017, U.S. Provisional Patent Application No. 62/545,603 filed Aug. 15, 2017, and U.S. Provisional Patent Application No. 62/551,035 filed Aug. 28, 2017, the entire disclosures of which are expressly incorporated by reference herein.

SEQUENCE LISTING

This application contains a computer readable Sequence Listing which has been submitted in XML file format via Patent Center, the entire content of which is incorporated by reference herein in its entirety. The Sequence Listing XML file submitted via Patent Center is entitled "SIBA028US_DIV2.xml", was created on Aug. 26, 2025, and is 361,000 bytes in size.

TECHNICAL FIELD

The present disclosure generally relates to the technical field of antibodies, and more particularly relates to making and using anti-4-1BB antibodies, and applications of the antibodies in cancer treatment and therapy.

BACKGROUND

Cancer is a major health problem across the world. In the United States alone it is estimated that in 2016 there were 1,685,210 new cases of cancer diagnosed and 595,690 deaths from the disease (http://www.cancer.gov). As such, any pharmaceutical agent that can reduce the severity or mortality rate from cancer is desirable.

In the immune system, resting T-cells can be activated to respond to antigen through a primary signal delivered through the T-cell receptor (TCR) by foreign antigen peptides presented by antigen-presenting cells (APCs). In addition to this primary signal, there are secondary positive and negative co-stimulatory signals that further influence the response of the T-cells. A secondary positive signal is required for full T-cell activation ((Lafferty et al., Ausl. J. Exp. Biol. Med. Sci. 53: 27-42 (1975)). Negative secondary signals can result in T-cell suppression and tolerance.

4-1BB is a co-stimulatory immune checkpoint molecule with the ability to active T cells. 4-1BB, also named as CD137, tumour necrosis factor receptor superfamily member 9 (TNFRSF9), and induced by lymphocyte activation (ILA), is a member of the tumour necrosis factor (TNF) receptor family. It has been reported that Crosslinking of CD137 enhances T cell proliferation, IL-2 secretion, survival and cytolytic activity. Further, it can enhance immune activity to eliminate tumours in mice.

Pfizer's Utomilumab (PF-05082566) targets 4-1BB, when in combination with Merck's Keytruda, stimulates a more intense immune system attack on cancers in a small clinical trial (https://www.reuters.com/article/us-health-cancer-pfizer-immunotherapy-idUSKCNOY92W2). And seven clinical trials of PF-05082566 are ongoing. (www.clinicaltrials.gov).

SUMMARY

The present disclosure provides, among others, anti-4-1BB monoclonal antibodies, antigen binding portions thereof, therapeutic compositions thereof and/or nucleic acid encoding the same, and their use to upregulate the function of T-cells to enhance cell-mediated immune responses in the treatment of cancer and other T-cell dysfunctional disorders.

In one embodiment, an isolated monoclonal antibody (mAb) or antigen-binding fragment that binds specifically to human or cynomolgus 4-1BB is provided. In one embodiment, the isolated mAb or antigen-binding fragment include an amino acid sequence having a percentage homology with SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, or SEQ ID NO:272. The percentage homology is not less than 70%, 80%, 90%, 95%, 98%, or 99%.

In one embodiment, the isolated mAb or antigen-binding fragment, has a binding affinity to human or cynomolgus 4-1BB with a Kd not greater than 30 nM, 40 nM, 50 nM, 60 nM, 70 nM, 80 nM, 90 nM, or 100 nM.

In one embodiment, the isolated mAb or antigen-binding fragment exhibits one or more functional properties such as, without limitation, high affinity binding to human or cynomolgus 4-1BB, inhibiting human or cynomolgus 4-1BB activity, induction of apoptosis, regulation of EGFR signalling pathway, upregulation of EMT genes, enhancing T cell activation, stimulating antibody response, reversing the suppressive function of an immunosuppressive cell, or a combination thereof. In one embodiment, the immunosuppressive cell comprises a regulatory cell. In one embodiment, the isolated mAb or antigen-binding fragment enhances T-cell activation via mechanisms or pathways including T-cell proliferation, IFN-γ and/or IL-2 secretion, or a combination thereof.

In one embodiment, the isolated mAb or antigen-binding fragment comprises a human framework region. In one embodiment, the isolated mAb or antigen-binding fragment is a humanized antibody, a chimeric antibody, or a recombinant antibody.

In one embodiment, the isolated mAb or antigen-binding fragment is an IgG. In one embodiment, the antigen-binding fragment is a Fv, a Fab, a F(ab')2, a scFV or a scFV2 fragment. In one embodiment, the isolated mAb is a bispecific antibody, tri-specific antibody, or multi-specific antibody.

In one embodiment, the isolated mAb or antigen-binding fragment may include an IgG1 heavy chain. In one embodiment, the IgG1 heavy chain comprises an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, SEQ ID NO:79, SEQ ID NO:87, SEQ ID NO:95, SEQ ID NO:103, SEQ ID NO:111, SEQ ID NO:119, SEQ ID NO:127, SEQ ID NO:135, SEQ ID NO:143, SEQ ID NO:151, SEQ ID NO:159, SEQ ID NO:167, SEQ ID NO:175, SEQ ID NO:183, SEQ ID NO:191, SEQ ID NO:199, SEQ ID NO:207, SEQ ID NO:215, SEQ ID NO:223, SEQ ID NO:231, SEQ ID NO:239, SEQ ID NO:247, SEQ ID NO:255, SEQ ID NO:263, or SEQ ID NO:271. The percentage homology is not less than 70%, 80%, 90%, 95%, 98%, or 99%.

In one embodiment, the isolated mAb or antigen-binding fragment may include a kappa light chain. In one embodiment, the kappa light chain comprises an amino acid sequence having a percentage homology with SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, SEQ ID NO:75, SEQ ID NO:83, SEQ ID NO:91, SEQ ID NO:99, SEQ ID NO:107, SEQ ID NO:115, SEQ ID NO:123, SEQ ID NO:131, SEQ ID NO:139, SEQ ID NO:147, SEQ ID NO:155, SEQ ID NO:163, SEQ ID NO:171, SEQ ID NO:179, SEQ ID NO:187, SEQ ID NO:195, SEQ ID NO:203, SEQ ID NO:211, SEQ ID NO:219, SEQ ID NO:1 SEQ ID NO:227, SEQ ID NO:235, SEQ ID NO:243, SEQ ID NO:257, or SEQ ID NO:263. The percentage homology is not less than 70%, 80%, 90%, 95%, 98%, or 99%.

In one embodiment, the isolated mAb or antigen-binding fragment may include a variable light chain. In one embodiment, the variable light chain comprises an amino acid sequence having a percentage homology with SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, SEQ ID NO:76, SEQ ID NO:84, SEQ ID NO:92, SEQ ID NO:100, SEQ ID NO:108, SEQ ID NO:116, SEQ ID NO:124, SEQ ID NO:132, SEQ ID NO:140, SEQ ID NO:148, SEQ ID NO:156, SEQ ID NO:164, SEQ ID NO:172, SEQ ID NO:180, SEQ ID NO:188, SEQ ID NO:196, SEQ ID NO:204, SEQ ID NO:212, SEQ ID NO:220, SEQ ID NO:228, SEQ ID NO:236, SEQ ID NO:244, SEQ ID NO:252, SEQ ID NO:260, or SEQ ID NO:268. The percentage homology is not less than 70%, 80%, 90%, 95%, 98%, or 99%.

In one embodiment, the isolated mAb or antigen-binding fragment may include a variable heavy chain. In one embodiment, the variable heavy chain comprises an amino acid sequence having a percentage homology with SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, SEQ ID NO:80, SEQ ID NO:88, SEQ ID NO:96, SEQ ID NO:104, SEQ ID NO:112, SEQ ID NO:120, SEQ ID NO:128, SEQ ID NO:136, SEQ ID NO:144, SEQ ID NO:152, SEQ ID NO:160, SEQ ID NO:168, SEQ ID NO:176, SEQ ID NO:184, SEQ ID NO:192, SEQ ID NO:200, SEQ ID NO:208, SEQ ID NO:216, SEQ ID NO:224, SEQ ID NO:232, SEQ ID NO:240, SEQ ID NO:248, SEQ ID NO:256, SEQ ID NO:264, or SEQ ID NO:272. The percentage homology is not less than 70%, 80%, 90%, 95%, 98%, or 99%.

The application further provides isolated nucleic acids encoding at least a portion of the isolated mAb or antigen-binding fragment disclosed herein. In one embodiments, the nucleic acid encodes an IgG1 heavy chain that includes an amino acid sequence having a percentage homology with SEQ ID NO:7, SEQ ID NO:15, SEQ ID NO:23, SEQ ID NO:31, SEQ ID NO:39, SEQ ID NO:47, SEQ ID NO:55, SEQ ID NO:63, SEQ ID NO:71, SEQ ID NO:79, SEQ ID NO:87, SEQ ID NO:95, SEQ ID NO:103, SEQ ID NO:111, SEQ ID NO:119, SEQ ID NO:127, SEQ ID NO:135, SEQ ID NO:143, SEQ ID NO:151, SEQ ID NO:159, SEQ ID NO:167, SEQ ID NO:175, SEQ ID NO:183, SEQ ID NO:191, SEQ ID NO:199, SEQ ID NO:207, SEQ ID NO:215, SEQ ID NO:223, SEQ ID NO:231, SEQ ID NO:239, SEQ ID NO:247, SEQ ID NO:255, SEQ ID NO:263, or SEQ ID NO:271. In one embodiment, the nucleic acid encodes a kappa light chain that comprises an amino acid sequence having a percentage homology with SEQ ID NO:3, SEQ ID NO:11, SEQ ID NO:19, SEQ ID NO:27, SEQ ID NO:35, SEQ ID NO:43, SEQ ID NO:51, SEQ ID NO:59, SEQ ID NO:67, SEQ ID NO:75, SEQ ID NO:83, SEQ ID NO:91, SEQ ID NO:99, SEQ ID NO:107, SEQ ID NO:115, SEQ ID NO:123, SEQ ID NO:131, SEQ ID NO:139, SEQ ID NO:147, SEQ ID NO:155, SEQ ID NO:163, SEQ ID NO:171, SEQ ID NO:179, SEQ ID NO:187, SEQ ID NO:195, SEQ ID NO:203, SEQ ID NO:211, SEQ ID NO:219, SEQ ID NO:1 SEQ ID NO:227, SEQ ID NO:235, SEQ ID NO:243, SEQ ID NO:257, or SEQ ID NO:263. In one embodiment, the nucleic acid encodes a variable light chain that comprises an amino acid sequence having a percentage homology with SEQ ID NO:4, SEQ ID NO:12, SEQ ID NO:20, SEQ ID NO:28, SEQ ID NO:36, SEQ ID NO:44, SEQ ID NO:52, SEQ ID NO:60, SEQ ID NO: 68, SEQ ID NO:76, SEQ ID NO:84, SEQ ID NO:92, SEQ ID NO:100, SEQ ID NO:108, SEQ ID NO:116, SEQ ID NO:124, SEQ ID NO:132, SEQ ID NO:140, SEQ ID NO:148, SEQ ID NO:156, SEQ ID NO:164, SEQ ID NO:172, SEQ ID NO:180, SEQ ID NO:188, SEQ ID NO:196, SEQ ID NO:204, SEQ ID NO:212, SEQ ID NO:220, SEQ ID NO:228, SEQ ID NO:236, SEQ ID NO:244, SEQ ID NO:252, SEQ ID NO:260, or SEQ ID NO:268. In one embodiment, the nucleic acid encodes a variable heavy chain that comprises an amino acid sequence having a percentage homology with SEQ ID NO:8, SEQ ID NO:16, SEQ ID NO:24, SEQ ID NO:32, SEQ ID NO:40, SEQ ID NO:48, SEQ ID NO:56, SEQ ID NO:64, SEQ ID NO:72, SEQ ID NO:80, SEQ ID NO:88, SEQ ID NO:96, SEQ ID NO:104, SEQ ID NO:112, SEQ ID NO:120, SEQ ID NO:128, SEQ ID NO:136, SEQ ID NO:144, SEQ ID NO:152, SEQ ID NO:160, SEQ ID NO:168, SEQ ID NO:176, SEQ ID NO:184, SEQ ID NO:192, SEQ ID NO:200, SEQ ID NO:208, SEQ ID NO:216, SEQ ID NO:224, SEQ ID NO:232, SEQ ID NO:240, SEQ ID NO:248, SEQ ID NO:256, SEQ ID NO:264, or SEQ ID NO:272. The percentage homology is not less than 70%, 80%, 90%, 95%, 98%, or 99%.

In one embodiment, an expression vector is provided comprising at least one of the isolated nucleic acids described infra. In one embodiment, the expression vector is expressible in a cell.

In one embodiment, a host cell is provided, comprising at least one of the nucleic acids that is described infra. In one embodiment, a host cell is provided, comprising the expression vector described infra. In one embodiment, the host cell can be a prokaryotic cell or a eukaryotic cell.

The application further provides methods for producing the isolated mAb or antigen-binding fragment disclosed herein. In one embodiment, the method uses the host cell described above. In one embodiment, the method includes the steps of providing a host cell that contains an expression vector expressible in the host cell, wherein the expression vector comprises at least one of the nucleic acids that is described infra, and culturing the host cells to produce an antibody by the expression of the nucleic acids.

The application further provides an immuno-conjugate that comprises a drug unit or an imaging agent linked to an isolated mAb or antigen-binding fragment with the sequences disclosed herein through a linker. The linker may be cleavable or noncleavable. In one embodiment, the linker is a chemical linker. In one embodiment, the linker comprises a covalent bond such as an ester bond, an ether bond, an amine bond, an amide bond, a disulphide bond, an imide bond, a sulfone bond, a phosphate bond, a phosphorus ester bond, a peptide bond, a hydrazone bond or a combination thereof. In one embodiment, the linker comprises a hydrophobic poly(ethylene glycol) linker. In one embodiment, the linker comprises a peptide bond.

In one embodiment, the drug unit in the immuno-conjugate comprises a chemotherapeutic agent, a growth inhibitory agent, a cytotoxic agent from class of calicheamicin, an antimitotic agent, a toxin, a radioactive isotope, a therapeutic agent, or a combination thereof. In one embodiment, the therapeutic agent comprises an antibody, an enzyme, or a combination thereof. In one embodiment, the drug unit comprises a calicheamicin, ozogamicin, monomethyl auristatin E, emtansine, a derivative or a combination thereof.

In one embodiment, the drug unit is selected from a cytotoxic agent, an immune regulatory reagent, an imaging agent or a combination thereof. In one embodiment, the cytotoxic agent is selected from a growth inhibitory agent or a chemotherapeutic agent from a class of tubulin binders, DNA intercalators, DNA alkylators, enzyme inhibitors, immune modulators, antimetabolite agents, radioactive isotopes, or a combination thereof. In one embodiment, the cytotoxic agent is selected from a calicheamicin, ozogamicin, monomethyl auristatin E, emtansine, a derivative or a combination thereof. In one embodiment, the immune regulatory reagents activate or suppress immune cells, T cell, NK cell, B cell, macrophage, or dendritic cell.

In one embodiment, the imaging agent may be a radionuclide, a florescent agent, a quantum dots, or a combination thereof.

The application further provides pharmaceutical compositions. In one embodiment, a pharmaceutical composition comprises the isolated mAb or antigen-binding disclosed herein and a pharmaceutically acceptable carrier. In one embodiment, a pharmaceutical composition comprises the immuno-conjugate and pharmaceutically acceptable carrier.

In a further aspect, the application provides methods for treating cancer. In one embodiment, the method comprising administering to the subject an effective amount of the isolated mAb or antigen-binding fragment with the sequences disclosed herein. In one embodiment, the method includes directly injecting into the tumour site an effective amount of the monoclonal antibodies, the antigen-binding fragment thereof, and the immuno-conjugates and disclosed herein.

In some embodiments of the disclosure, the cancer has cells that express 4-1BB. Example cancer can be treated using the disclosed mAbs or their antigen-binding fragments include without limitation breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer.

In one embodiment, the method further includes co-administering an effective amount of a therapeutic agent. In one embodiment, the therapeutic agent can include an antibody, a chemotherapy agent, an enzyme, or a combination thereof. In one embodiment, the therapeutic agent may be capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, calicheamicin, antimitotic agent, monomethyl auristatin E, emtansine, ozogamicin, or a derivative or a combination thereof.

The subject receiving the treatment may be a human. In one embodiment, a solution is provided that comprises an effective concentration of the isolated mAb or an antigen-binding disclosed herein, wherein the solution is blood plasma in a subject.

Still other embodiments will become readily apparent to those skilled in the art from the following detailed description, wherein are described embodiments by way of illustrating the best mode contemplated. As will be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments arranged in accordance with the disclosure and are, therefore, not to be considered limiting of its scope, the disclosure will be described with additional specificity and detail through use of the accompanying drawings, in which:

FIG. 1 Immunization schedule for rabbit cohorts no.1 and 2 with human 41BB or cynomolgus 41BB transiently transfected HEK293 cells.

FIG. 2 41BB-specific rabbit IgG antibodies in B cell culture supernatant enhance activation of anti-CD3 activated human T cells and corresponding binding of chimeric rabbit/human IgG 41BB-specific antibodies rescued from the parental B cell culture wells to recombinant human and cynomolgus 41BB protein.

FIG. 3 Chimeric rabbit/human IgG antibodies specific for 41BB enhance T cell activation, proliferation, and gamma interferon secretion.

FIG. 4. Octet analysis of dissociation rate for humanized 41BB-specific IgG antibodies.

FIG. 5. Humanized 41BB-specific IgG antibodies enhance T cell activation, proliferation, and gamma interferon secretion.

FIG. 6. Serum from rabbits immunized with human or cynomolgus 41BB expressing HEK293's analyzed for 41BB-specific IgG antibody binding to parental CHO or human or cynomolgus 41BB-transfected CHO cells.[

DETAILED DESCRIPTION

Figure 7:
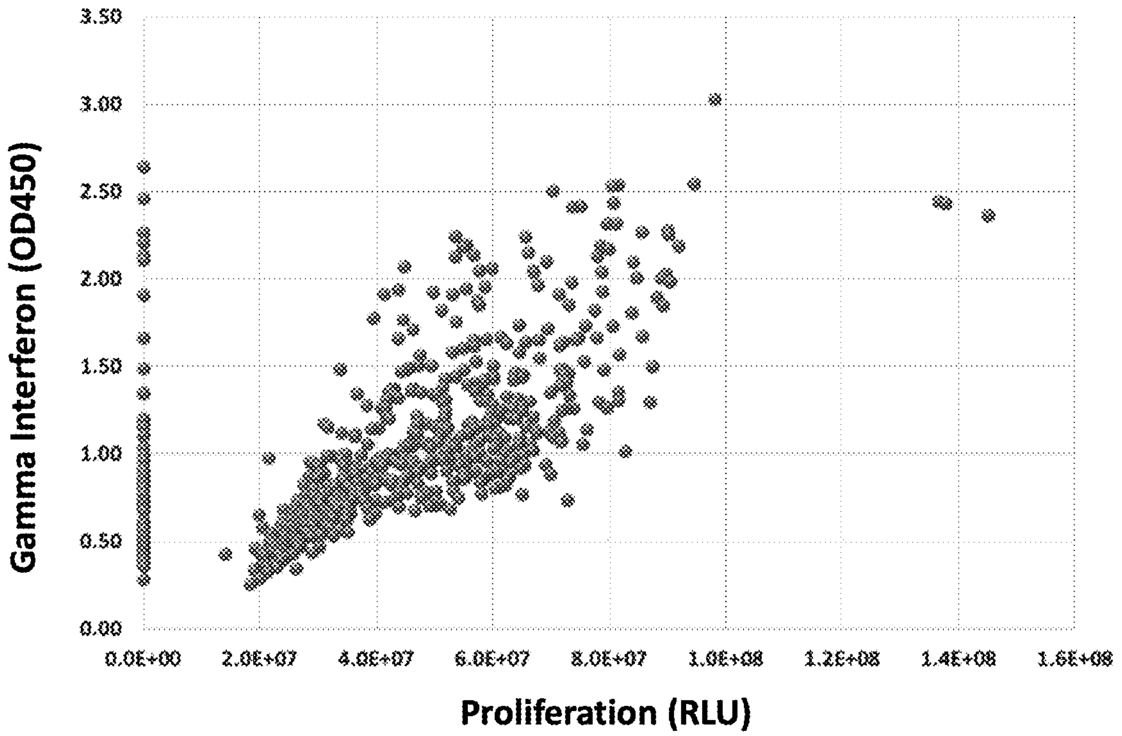
FIG. 7. Correlation of 41BB-specific IgG antibody in B cell culture supernatant enhancement of Gamma interferon secretion versus proliferation of human T cells.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The disclosure provides, among others, isolated antibodies, methods of making such antibodies, bispecific or multi-specific molecules, antibody-drug conjugates and/or immuno-conjugates composed from such antibodies or antigen binding fragments and pharmaceutical compositions containing the antibodies, bispecific or multi-specific molecules, antibody-drug conjugates and/or immuno-conjugates.

In one aspect, the disclosure provides isolated monoclonal antibodies that bind to human or cynomolgus 4-1BB. The antibodies may exhibit one or more desirable functional properties, such as high affinity binding to 4-1BB, the ability to enhance T cell activation including proliferation, IFN-γ and/or CD3+T cell proliferation, IL-2 secretion, survival and cytolytic activity, the ability to stimulate antibody responses and/or the ability to reverse the suppressive function of immunosuppressive cells, such as T regulatory cells. In addition, the antibodies of the disclosure are derived from specific heavy and light chain amino acid sequences and/or structural features such as complementarity determining regions (CDRs) composed of specific amino acid sequences.

The term "antibody" is used in the broadest sense and specifically covers single monoclonal antibodies (including agonist and antagonist antibodies), antibody compositions with polyepitopic specificity, as well as antibody fragments (e.g., Fab, $F(ab')_2$, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, $F(ab')_2$, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, Nature, 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA, 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with cells transiently expressing human or cynomolgus 4-1BB on the cell surface. Rabbits are known to create antibodies of high affinity, diversity and specificity (Weber et al. Exp. Mol. Med. 49: e305). B cells from immunized animals were cultured in vitro and screened for the production of anti-4-1BB antibodies. The antibody variable genes were isolated using recombinant DNA techniques and the resulting antibodies were expressed recombinantly and further screened for desired features such as the ability to enhance human T-cell activation. This general method of antibody discovery is similar to that described in Seeber et al. PLOS One. 9: e86184 (2014).

The term "antigen- or epitope-binding portion or fragment" refers to fragments of an antibody that are capable of binding to an antigen (4-1BB in this case). These fragments may be capable of the antigen-binding function and additional functions of the intact antibody. Examples of binding fragments include, but are not limited to, a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller subfragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen- or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called α, delta, epsilon, γ, and μ, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide will be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$ M, alternatively at least about $10^{-10}$ M, at least about $10^{-11}$ M, at least about $10^{-12}$ M, or greater, where KD refers to a dissociation rate of a particular antibody-antigen interaction. Typically, an antibody that specifically binds an antigen will have a KD that is 20-, 50-, 100-, 500-, 1000-, 5,000-, 10,000- or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

In another aspect, the application provides pharmaceutical composition including the mAbs and their antigen-binding fragments disclosed herein. In one embodiment, the pharmaceutical composition includes the mAbs or their antigen-binding fragments and a pharmaceutically acceptable carrier. In one embodiment, the pharmaceutical composition includes the immuno-conjugate and a pharmaceutically acceptable carrier. Formulation of the pharmaceutical composition according to the disclosure can be accomplished according to standard methodology know to those of ordinary skill in the art.

The antibodies or immuno-conjugates according to the disclosure can be prepared in a physiologically acceptable formulation and may comprise a pharmaceutically acceptable carrier, diluent and/or excipient using known techniques. For example, the antibody according to the disclosure may include any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Suitable pharmaceutical carriers, diluents and/or excipients are well known in the art and include, for example, phosphate buffered saline solutions, water, emulsions such as oil/water emulsions.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio.

In one embodiment, the pharmaceutical composition may comprise proteinaceous carriers such as, for example, serum albumin or immunoglobulin, particularly of human origin. Further biologically active agents may be present in the pharmaceutical composition of the disclosure dependent on the intended use. Proteinaceous pharmaceutically active matter may be present in amounts between 1 ng and 10 mg per dose. Generally, the regime of administration should be in the range of between 0.1 μg and 10 mg of the antibody according to the disclosure, particularly in a range 1.0 μg to 1.0 mg, and more particularly in a range of between 1.0 μg and 100 μg, with all individual numbers falling within these ranges also being part of the disclosure. If the administration occurs through continuous infusion a more proper dosage may be in the range of between 0.01 μg and 10 mg units per kilogram of body weight per hour with all individual numbers falling within these ranges also being part of the disclosure.

In a further aspect, the disclosure provide method for treating cancer using anti-4-1BB antibodies or other molecules containing the antigen-binding portion of an anti-4-1BB antibody. In one embodiment, the method is used to inhibit growth of tumour cells. In one embodiment, the method is used to stimulate a protective autoimmune response, to modify an immune response or to stimulate antigen-specific immune responses.

In one embodiment, the method for treating cancer includes administering to a subject in need of such treatment an effective amount of the mAbs, their antigen-binding fragments as disclosed herein. In one embodiment, the composition may be administered in combination with other compositions comprising a biologically active substance or compound. In one embodiment, the biologically active substance may include capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, a derivative or a combination thereof.

The compositions of the present disclosure may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumour site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

The compositions may be administered by standard routes of administration. For example, the composition may be administered by topical, oral, rectal, nasal, interdermal, intraperitoneal, or parenteral (for example, intravenous, subcutaneous, or intramuscular) routes. In one embodiment, administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegetable oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

In one embodiment, the composition may be incorporated into sustained release matrices such as biodegradable polymers, the polymers being implanted in the vicinity of where delivery is desired, for example, at the site of a tumour. The method includes administration of a single dose, administration of repeated doses at predetermined time intervals, and sustained administration for a predetermined period of time.

It is known to those of ordinary skill in the art that the dosage of the composition will depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

In one embodiment, the term "therapeutically effective amount" refers to the amount of antibody which, when administered to a human or animal, elicits a response which is sufficient to result in a therapeutic effect in said human or animal. The effective amount is readily determined by one of ordinary skill in the art following routine procedures.

Varieties of cancer may be treated using the mAbs, their antigen-binding fragments, and compositions disclosed herein. Example cancer including without limitation breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer. In one embodiment, the cancer may express 4-1BB genes. Inhibition of 4-1BB activity with anti-4-1BB monoclonal antibodies or antigen-binding fragment provides therapeutic effect. In one embodiment, administering a therapeutically effective amount of composition comprising anti-4-1BB monoclonal antibodies or antigen-binding fragment may cure, prevent, ameliorate, and delay the development or metastasis of cancers, through the effect of the drug unit.

The present disclosure may be understood more readily by reference to the following detailed description of specific embodiments included herein. Although the present disclosure has been described with reference to specific details of certain embodiments thereof, it is not intended that such details should be regarded as limitations upon the scope of the disclosure.

EXAMPLES

Example 1: Generation of Anti-4-1BB Antibodies

Monoclonal antibodies against human or cynomolgus 4-1BB were developed by immunizing New Zealand white rabbits. As shown in FIG. 1, animals were immunized with recombinant human embryonic kidney 293 (HEK) cells transiently transfected with human or cynomolgus 4-1BB mixed 1:1 v/v with Titermax Gold (Cohort 1) or Complete or incomplete Freund's adjuvant (Cohort 2) alternating with Alhydrogel 2% (Alum) plus CpG 2007 and were performed by subcutaneous injection. Blood samples were drawn at different timepoints during the immunization schedule as shown in FIG. 1. Serum which was drawn from all 4 animals on day 62 was analyzed for human or cynomolgus 4-166-specific IgG by FACS analysis as shown in FIG. 6. All 4 animals developed human or cynomolgus-specific IgG after immunization.

Antigen-specific B cells were labeled with biotinylated human and cynomolgus 4-1BB recombinant protein followed by streptavidin-alexafluor647 and then sorted into multiple 96 well tissue culture plates at 1 antigen-specific IgG+ B cell per well and cultured for 9 days to allow their differentiation into plasma cells and for secretion of antibodies. The supernatants from these B cell culture (BCC) plates were screened by ELISA and functional assay for the presence of 4-16B-specific antibodies in the assays as listed below:

- Binding to recombinant human and cynomolgus 4-1BB—IgG ELISA
- Enhancement of CD3-induced T cell activation of purified human CD3+ T cells—detection of gamma interferon secretion by ELISA and quantitation of CD3+ T cell proliferation by alamar blue cell viability assay A total of 693 wells from the BCC plates had human and cynomolgus 4-16B-specific IgG. The 4-1BB-specific antibody from these 693 BCC wells were then analyzed for agonist activity to enhance anti-CD3-induced activation of CD3+ human T cells. A fixed concentration of a control anti-human CD3-specific antibody was combined with a fixed concentration of 4-1BB-specific antibody from the BCC supernatants and then captured on and ELISA plate that was previously coated with a goat anti-rabbit IgG Fc polyclonal antibody. Purified human CD3+ T cells were added at 100,000 per each assay well and the plate was incubated for 5 days. On day 5 of the assay the contents of each assay well were collected and analyzed for the amount of gamma interferon secreted into the culture supernatant and for the number of CD3+ T cells in each assay well which is shown in FIG. 7. From these data the best 92 BCC wells were advanced to molecular rescue of the rabbit antibody heavy and light chain variable regions by RT-PCR.

On day 9 of B cell culture the supernatants were separated from the B cells and stored in a separate plate for later analysis. RNAlater tissue storage reagent was added to each well in the B cell culture plate to preserve the RNA in the B cells for RT-PCR amplification of antibody variable regions. The set of 92 BCC wells were advanced to molecular "rescue" of the antibody variable regions. The light and heavy chain variable sequences were amplified by multiplex RT-PCR using degenerate primers designed to anneal to leader sequences and the constant regions of rabbit IgG and rabbit kappa sequences. Secondary PCR was performed separately for the light and heavy chains using nested primers containing restriction sites. Amplicons from the variable heavy chain PCR were cloned into an expression vector containing human IgG1. Light chain amplicons were cloned into an expression vector containing human IgK. Resulting clones were sequenced and analyzed.

The heavy and light chain expression plasm ids generated from each well were transiently co-transfected to produce rabbit/human chimeric antibodies. Recombinant antibody supernatants were confirmed to contain antibodies specific for human and cynomolgus 4-1BB using bio-layer interferometry analysis on a ForteBio Octet Red 96 instrument. Anti-human Fc biosensors (Pall ForteBio) were used to capture antibodies in the supernatants. Association to human or cynomolgus 4-1BB was observed by real-time interferometry by placing the biosensors in wells containing recombinant human or cynomolgus 4-1BB extracellular domain protein. Dissociation was measured after transfer of the biosensors into wells containing 10×kinetics buffer (Pall ForteBio). The software provided by the manufacturer was used to analyze the interferometry data. A summary of the primary BCC screening data and the corresponding screening data for 34 recombinant chimeric rabbit/human IgG antibodies is shown in FIG. 2. From the original 92 BCC wells 34 chimeric antibodies were rescued and were shown to bind human and cynomolgus recombinant 4-1BB protein (FIG. 2)

The panel of 34 chimeric rabbit/human IgG antibodies specific for human and cynomolgus 4-1BB were then assayed for agonist activity which enhanced the anti-CD3-induced activation of human CD3+ T cells. As shown in FIG. 3, $EC_{50}$ for secretion of gamma interferon were calculated for each chimeric antibody as well as the fold-over-background of the enhancement of proliferation of human CD3+ T cells. Proliferation of human CD3+ T cells with anti-CD3 antibody alone, without additional 4-1BB antibody, is set to the background value of 1.0 and then the fold-over-background is calculated at different concentrations of the chimeric 4-1BB antibodies are tested. From these data 18 chimeric 4-1BB-specific antibodies were advanced to humanization.

From the panel of 34 chimeric rabbit/human IgG antibodies specific for human and cynomolgus 4-1BB that were advanced to humanization 18 were successfully humanized as shown in FIG. 4 where binding to human and recombinant 4-1BB by octet assay was performed. These 18 humanized antibodies specific for human or cynomolgus 4-1BB were then assayed for agonist activity which enhanced the anti-CD3-induced activation of human CD3+ T cells. As shown in FIG. 5, $EC_{50}$ for secretion of gamma interferon were calculated for each humanized antibody as well as the fold-over-background of the enhancement of proliferation of human CD3+ T cells. Proliferation of human CD3+ T cells with anti-CD3 antibody alone, without additional 4-1BB antibody, is set to the background value of 1.0 and then the fold-over-background is calculated at different concentrations of the humanized 4-1BB antibodies are tested. From these data 17 of the 18 humanized 4-1BB-specific antibodies showed enhancement of anti-CD3-induced activation of human CD3+ T cells.

While the disclosure has been particularly shown and described as referenced to the embodiments thereof, those skilled in the art will understand that the foregoing and other changes in form and detail may be made therein without departing from the spirit and scope. All references cited or referred to in this disclosure are hereby incorporated by reference in their entireties.

SEQUENCE LISTING

411H11CHIMERICLIGHTCHAINFULL-LENGTHNUCLEOTIDESEQUENCE

SEQ ID NO: 1

GATGTTGTGATGACCCAGACTCCAGCCTCCGTGTCTGAACCTGTGAGAGCCACAGTCACCATCAAGTGCCAGGCCA

GTCAGAGCATTGGTGCTGATTTAGCCTGGTATCAGCAGAAACCAGGGCAGCCTCCCAAGCTCCTGATCTACAGGG

CATCCACTCTGGCCTCTGGGGTCCCATCGCGGTTCAGCGGCAGTGGATCTGGGACAGAGTTCACTCTCACCATCAG

CGACCTGGAGTGTGCCGATGCTGCCACTTACTACTGTCAATGTATTTATTATGGTACTGATGATGTCATATACCATA

CTTTCGGCGGAGGGACCGAGGTGGTGTTCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

411H11CHIMERICLIGHTCHAINVARIABLELIGHTCHAINNUCLEOTIDESEQUENCE

SEQ ID NO: 2

GATGTTGTGATGACCCAGACTCCAGCCTCCGTGTCTGAACCTGTGAGAGCCACAGTCACCATCAAGTGCCAGGCCA

GTCAGAGCATTGGTGCTGATTTAGCCTGGTATCAGCAGAAACCAGGGCAGCCTCCCAAGCTCCTGATCTACAGGG

CATCCACTCTGGCCTCTGGGGTCCCATCGCGGTTCAGCGGCAGTGGATCTGGGACAGAGTTCACTCTCACCATCAG

CGACCTGGAGTGTGCCGATGCTGCCACTTACTACTGTCAATGTATTTATTATGGTACTGATGATGTCATATACCATA

CTTTCGGCGGAGGGACCGAGGTGGTGTTCAAA

411H11CHIMERICLIGHTCHAINFULL-LENGTHAMINOACIDSEQUENCE. HUMANKAPPACONSTANT DOMAINISUNDERLINED

SEQ ID NO: 3

DVVMTQTPASVSEPVRATVTIKCQASQSIGADLAWYQQKPGQPPKLLIYRASTLASGVPSRFSGSGSGTEFTLTISDLEC

ADAATYYCQCIYYGTDDVIYHTFGGGTEVVFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

411H11CHIMERICLIGHTCHAINVARIABLELIGHTCHAINAMINOACIDSEQUENCE. COMPIMENTARITY DETERMININGREGIONSAREUNDERLINED

SEQ ID NO: 4

DVVMTQTPASVSEPVRATVTIKCQASQSIGADLAWYQQKPGQPPKLLIYRASTLASGVPSRFSGSGSGTEFTLTISDLEC

ADAATYYCQCIYYGTDDVIYHTFGGGTEVVFK

411H11CHIMERICHEAVYCHAINFULL-LENGTHNUCLEOTIDESEQUENCE

-continued

SEQ ID NO: 5

CAGTCGGTGGAGGAGTCCGGGGGTCGCCTGGTCACGCCTGGGACACCCCTAACACTCACCTGCACAGTATCTGGA

TTCACCATCAGTAGCCACCACATGATCTGGGTCCGCCAGGCTCCAGGAGAGGGGCTGCAATACATCGGATTCATTA

ATGATGGTGACTATACATACTACACGAACTGGGCAAAAGGCCGATTCACCATCTCCAGAACCTCGACTACGGTGG

ACCTGAAAATGACCAGTCTGACAGCCGCGGACACGGCCACCTATTTCTGTGCCAGAGGGGTTGATGGTACTAGTT

ATCCTGGCTTGTGGGGCCCAGGCACCCTGGTCACCGTCTCGAGCGCTAGCACCAAGGGCCCATCGGTCTTCCCCCT

GGCACCCTCCTCCAAGAGCACCTCTGGGGGCACAGCGGCCCTGGGCTGCCTGGTCAAGGACTACTTCCCCGAACC

GGTGACGGTGTCGTGGAACTCAGGCGCCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGCACCCAGACCTACATCTGCAACGTGAAT

CACAAGCCCAGCAACACCAAGGTGGACAAGAGAGTTGAGCCCAAATCTTGTGACAAAACTCACACATGCCCACCG

TGCCCAGCACCTGAAGCCGCGGGGGCACCGTCAGTCTTCCTCTTCCCCCCAAAACCCAAGGACACCCTCATGATCT

CCCGGACCCCTGAGGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAGTGCGCGGTCTCCAACAAAGCCC

TCCCAGCCCCCATCGAGAAAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGT

411H11CHIMERICHEAVYCHAINVARIABLEHEAVYCHAINNUCLEOTIDESEQUENCE

SEQ ID NO: 6

CAGTCGGTGGAGGAGTCCGGGGGTCGCCTGGTCACGCCTGGGACACCCCTAACACTCACCTGCACAGTATCTGGA

TTCACCATCAGTAGCCACCACATGATCTGGGTCCGCCAGGCTCCAGGAGAGGGGCTGCAATACATCGGATTCATTA

ATGATGGTGACTATACATACTACACGAACTGGGCAAAAGGCCGATTCACCATCTCCAGAACCTCGACTACGGTGG

ACCTGAAAATGACCAGTCTGACAGCCGCGGACACGGCCACCTATTTCTGTGCCAGAGGGGTTGATGGTACTAGTT

ATCCTGGCTTGTGGGGCCCAGGCACCCTGGTCACCGTCTCGAGC

411H11CHIMERICHEAVYCHAINFULL-LENGTHAMINOACIDSEQUENCE. HUMANGAMMA-1 CONSTANTDOMAINISUNDERLINED

SEQ ID NO: 7

QSVEESGGRLVTPGTPLTLTCTVSGFTISSHHMIWVRQAPGEGLQYIGFINDGDYTYYTNWAKGRFTISRTSTTVDLKM

TSLTAADTATYFCARGVDGTSYPGLWGPGTLVTVSS<u>ASTKGPSVFPLAPSSKSTSGGTAALGCLVKDYFPEPVTVSWNS</u>

<u>GALTSGVHTFPAVLQSSGLYSLSSVVTVPSSSLGTQTYICNVNHKPSNTKVDKRVEPKSCDKTHTCPPCPAPEAAGAPSV</u>

<u>FLFPPKPKDTLMISRTPEVTCVVVDVSHEDPEVKFNWYVDGVEVHNAKTKPREEQYNSTYRVVSVLTVLHQDWLNGKE</u>

<u>YKCAVSNKALPAPIEKTISKAKGQPREPQVYTLPPSRDELTKNQVSLTCLVKGFYPSDIAVEWESNGQPENNYKTTPPVL</u>

<u>DSDGSFFLYSKLTVDKSRWQQGNVFSCSVMHEALHNHYTQKSLSLSPG</u>

411H11CHIMERICHEAVYCHAINVARIABLEHEAVYCHAINAMINOACIDSEQUENCE. COMPLIMENTARITYDETERMININGREGIONSAREUNDERLINED

SEQ ID NO: 8

QSVEESGGRLVTPGTPLTLTCTVSGFTIS<u>SHHMI</u>WVRQAPGEGLQYIG<u>FINDGDYTYYTNWAKG</u>RFTISRTSTTVDLKM

TSLTAADTATYFCAR<u>GVDGTSYPGL</u>WGPGTLVTVSS

413F3CHIMERICLIGHTCHAINFULL-LENGTHNUCLEOTIDESEQUENCE

SEQ ID NO: 9

GACGTCGTGATGACCCAGACTCCAGCCTCCGTGGAGGCAGCTGTGGGAGGCACAGTCACCATCAAGTGCCAGGC

CAGTCAGAGCATTTACAGCAATTTAGCCTGGTATCAGCAGAAACCAGGGCAGCCTCCCAAACTCCTAATCTATTCT

ACATCCACTCTGGCATCTGGGGTCCCATCGCGGTTCAGCGGCAGTGGATCCGGGACAGAGTTCACTCTCACCATCA

GCGACCTGGAGTGTGCCGATGCTGCCACTTACTACTGTCAAAACTATTATGGTAGTAGTACTGATAGTTATGGGAA

-continued

TCCTTTCGGCGGAGGCACCGAGGTGGTGTTCAAACGTACGGTGGCTGCACCATCTGTCTTCATCTTCCCGCCATCT

GATGAGCAGTTGAAATCTGGAACTGCCTCTGTTGTGTGCCTGCTGAATAACTTCTATCCCAGAGAGGCCAAAGTAC

AGTGGAAGGTGGATAACGCCCTCCAATCGGGTAACTCCCAGGAGAGTGTCACAGAGCAGGACAGCAAGGACAGC

ACCTACAGCCTCAGCAGCACCCTGACGCTGAGCAAAGCAGACTACGAGAAACACAAAGTCTACGCCTGCGAAGTC

ACCCATCAGGGCCTGAGCTCGCCCGTCACAAAGAGCTTCAACAGGGGAGAGTGT

413F3CHIMERICLIGHTCHAINVARIABLELIGHTCHAINNUCLEOTIDESEQUENCE

SEQ ID NO: 10

GACGTCGTGATGACCCAGACTCCAGCCTCCGTGGAGGCAGCTGTGGGAGGCACAGTCACCATCAAGTGCCAGGC

CAGTCAGAGCATTTACAGCAATTTAGCCTGGTATCAGCAGAAACCAGGGCAGCCTCCCAAACTCCTAATCTATTCT

ACATCCACTCTGGCATCTGGGGTCCCATCGCGGTTCAGCGGCAGTGGATCCGGGACAGAGTTCACTCTCACCATCA

GCGACCTGGAGTGTGCCGATGCTGCCACTTACTACTGTCAAAACTATTATGGTAGTAGTACTGATAGTTATGGGAA

TCCTTTCGGCGGAGGCACCGAGGTGGTGTTCAAA

413F3CHIMERICLIGHTCHAINFULL-LENGTHAMINOACIDSEQUENCE. HUMANKAPPACONSTANT DOMAINISUNDERLINED

SEQ ID NO: 11

DVVMTQTPASVEAAVGGTVTIKCQASQSIYSNLAWYQQKPGQPPKLLIYSTSTLASGVPSRFSGSGSGTEFTLTISDLEC

ADAATYYCQNYYGSSTDSYGNPFGGGTEVVFKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFNRGEC

413F3CHIMERICLIGHTCHAINVARIABLELIGHTCHAINAMINOACIDSEQUENCE. COMPIMENTARITY DETERMININGREGIONSAREUNDERLINED

SEQ ID NO: 12

DVVMTQTPASVEAAVGGTVTIKCQASQSIYSNLAWYQQKPGQPPKLLIYSTSTLASGVPSRFSGSGSGTEFTLTISDLEC

ADAATYYCQNYYGSSTDSYGNPFGGGTEVVFK

413F3CHIMERICHEAVYCHAINFULL-LENGTHNUCLEOTIDESEQUENCE

SEQ ID NO: 13

CAGTCGCTGGAGGAGTCCGGGGGAGACCTGGTCAAGCCTGAGGGATCCCTGACACTCACCTGCACAGGCTCTGG

AATCGACTTCAGTAGCAACTACATGTGCTGGGTCCGCCAGGCTCCAGGGAAGGGGCTGGAGTGGATCGCATGCAT

TTATGGTGATAGTAGTGATAATAGTTACTCCGCGAGCTGGGCGAAAGGGCGATTCACCATCTCCAAAACCTCGTCG

ACCACGGTGACTCTGCAAATGACCAGTCTGACAGCCGCGGACACGGCCACCTATTTCTGTGCGAGATCTGGTTATA

GCTATTTAGGCTACTTTAACTTGTGGGGCCCAGGGACCCTGGTCACCGTCTCGAGCGCTAGCACCAAGGGCCCATC

GGTCTTCCCCCTGGCACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTACATCT

GCAACGTGAATCACAAGCCCAGCAACACCAAGGTGGACAAGAGAGTTGAGCCCAAATCTTGTGACAAAACTCACA

CATGCCCACCGTGCCCAGCACCTGAAGCCGCGGGGGCACCGTCAGTCTTCCTCTTCCCCCCAAAACCCAAGGACAC

CCTCATGATCTCCCGGACCCCTGAGGTCACATGCGTGGTGGTGGACGTGAGCCACGAAGACCCTGAGGTCAAGTT

CAACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCGCGGTCTCC

AACAAAGCCCTCCCAGCCCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGACCACGCCTCCCGTGCTGGAC

TCCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

413F3CHIMERICHEAVYCHAINVARIABLEHEAVYCHAINNUCLEOTIDESEQUENCE

SEQ ID NO: 14

CAGTCGCTGGAGGAGTCCGGGGGAGACCTGGTCAAGCCTGAGGGATCCCTGACACTCACCTGCACAGGCTCTGG

AATCGACTTCAGTAGCAACTACATGTGCTGGGTCCGCCAGGCTCCAGGGAAGGGGCTGGAGTGGATCGCATGCAT

-continued

TTATGGTGATAGTAGTGATAATAGTTACTCCGCGAGCTGGGCGAAAGGGCGATTCACCATCTCCAAAACCTCGTCG

ACCACGGTGACTCTGCAAATGACCAGTCTGACAGCCGCGGACACGGCCACCTATTTCTGTGCGAGATCTGGTTATA

GCTATTTAGGCTACTTTAACTTGTGGGGCCCAGGGACCCTGGTCACCGTCTCGAGC

413F3CHIMERICHEAVYCHAINFULL-LENGTHAMINOACIDSEQUENCE. HUMANGAMMA-1CONSTANT DOMAINISUNDERLINED

SEQ ID NO: 15

QSLEESGGDLVKPEGSLTLTCTGSGIDFSSNYMCWVRQAPGKGLEWIACIYGDSSDNSYSASWAKGRFTISKTSSTTVTL

QMTSLTAADTATYFCARSGYSYLGYFNLWGPGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPG

413F3CHIMERICHEAVYCHAINVARIABLEHEAVYCHAINAMINOACIDSEQUENCE. COMPLIMENTARITY DETERMININGREGIONSAREUNDERLINED

SEQ ID NO: 16

QSLEESGGDLVKPEGSLTLTCTGSGIDFSSNYMCWVRQAPGKGLEWIACIYGDSSDNSYSASWAKGRFTISKTSSTTVTL

QMTSLTAADTATYFCARSGYSYLGYFNLWGPGTLVTVSS

416F8CHIMERICLIGHTCHAINFULL-LENGTHNUCLEOTIDESEQUENCE

SEQ ID NO: 17

GCGCAAGTGCTGACCCAGACTGCATCGTCCGTGTCTGCACCTGTGGGCGGCACAGTCACCATCAGTTGCCAGTCCA

GTCAGACTGTTTATAATAACAACTTGTTATCCTGGTATCAGCAGAAACCAGGGCAGCGTCCCAAGCTCCTGATCTA

TTATGCATCCACTCTGGCATTTGGGGTCCCATCGCGGTTCAAAGGCAGTGGATCTGGGACAGAGTTCACTCTCACC

ATCAGCGACCTGGAGTGTGACGATGCTGCCACTTACTTCTGTCAAGGCGGTTATAGTGGTTGGATTTATGTTTTCG

GCGGAGGCACCGAGGTGGAGGTCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

416F8CHIMERICLIGHTCHAINVARIABLELIGHTCHAINNUCLEOTIDESEQUENCE

SEQ ID NO: 18

GCGCAAGTGCTGACCCAGACTGCATCGTCCGTGTCTGCACCTGTGGGCGGCACAGTCACCATCAGTTGCCAGTCCA

GTCAGACTGTTTATAATAACAACTTGTTATCCTGGTATCAGCAGAAACCAGGGCAGCGTCCCAAGCTCCTGATCTA

TTATGCATCCACTCTGGCATTTGGGGTCCCATCGCGGTTCAAAGGCAGTGGATCTGGGACAGAGTTCACTCTCACC

ATCAGCGACCTGGAGTGTGACGATGCTGCCACTTACTTCTGTCAAGGCGGTTATAGTGGTTGGATTTATGTTTTCG

GCGGAGGCACCGAGGTGGAGGTCAAA

416F8CHIMERICLIGHTCHAINFULL-LENGTHAMINOACIDSEQUENCE. HUMANKAPPACONSTANT DOMAINISUNDERLINED

SEQ ID NO: 19

AQVLTQTASSVSAPVGGTVTISCQSSQTVYNNNLLSWYQQKPGQRPKLLIYYASTLAFGVPSRFKGSGSGTEFTLTISDLE

CDDAATYFCQGGYSGWIYVFGGGTEVEVKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

416F8CHIMERICLIGHTCHAINVARIABLELIGHTCHAINAMINOACIDSEQUENCE. COMPIMENTARITY DETERMININGREGIONSAREUNDERLINED

SEQ ID NO: 20

AQVLTQTASSVSAPVGGTVTISCQSSQTVYNNNLLSWYQQKPGQRPKLLIYYASTLAFGVPSRFKGSGSGTEFTLTISDLE

CDDAATYFCQGGYSGWIYVFGGGTEVEVK

416F8CHIMERICHEAVYCHAINFULL-LENGTHNUCLEOTIDESEQUENCE

SEQ ID NO: 21

CAGTCGCTGGAGGAGTCCGGGGGTCGCCTGGTCACGCCTGGGACACCCCTGACACTCACCTGCACAGCCTCTGGA

-continued

TTCTCCCTCAGTAACTACTACATGAACTGGGTCCGCCAGGCTCCAGGGAAGGGGCTGGAATACATCGGAATCATTA

GTAGTAGTGGTAGCGCATACTACGCGAGCTGGGCTAAAGGCCGATTCACCATCTCCAGAACCTCGACCACGGTGG

ACCTGAGAATCACCAGTCCGACAACCGAGGACACGGCCACCTATTTCTGTGCCAGAGGGGACTACGGCATGGACC

TCTGGGGCCAAGGGACCCTGGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT

416F8CHIMERICHEAVYCHAINVARIABLEHEAVYCHAINNUCLEOTIDESEQUENCE

SEQ ID NO: 22

CAGTCGCTGGAGGAGTCCGGGGGTCGCCTGGTCACGCCTGGGACACCCCTGACACTCACCTGCACAGCCTCTGGA

TTCTCCCTCAGTAACTACTACATGAACTGGGTCCGCCAGGCTCCAGGGAAGGGGCTGGAATACATCGGAATCATTA

GTAGTAGTGGTAGCGCATACTACGCGAGCTGGGCTAAAGGCCGATTCACCATCTCCAGAACCTCGACCACGGTGG

ACCTGAGAATCACCAGTCCGACAACCGAGGACACGGCCACCTATTTCTGTGCCAGAGGGGACTACGGCATGGACC

TCTGGGGCCAAGGGACCCTGGTCACCGTCTCGAGC

416F8 CHIMERIC HEAVY CHAIN FULL-LENGTH AMINO ACID SEQUENCE. HUMAN GAMMA-1 CONSTANT DOMAINISUNDERLINED

SEQ ID NO: 23

QSLEESGGRLVTPGTPLTLTCTASGFSLSNYYMNWVRQAPGKGLEYIGIISSSGSAYYASWAKGRFTISRTSTTVDLRITSP

TTEDTATYFCARGDYGMDLWGQGTLVTVSS<u>ASTKGPSVFPLAPSSKSTSGGTAALGCLVKDYFPEPVTVSWNSGALTS</u>

<u>GVHTFPAVLQSSGLYSLSSVVTVPSSSLGTQTYICNVNHKPSNTKVDKRVEPKSCDKTHTCPPCPAPEAAGAPSVFLFPPK</u>

<u>PKDTLMISRTPEVTCVVVDVSHEDPEVKFNWYVDGVEVHNAKTKPREEQYNSTYRVVSVLTVLHQDWLNGKEYKCAV</u>

<u>SNKALPAPIEKTISKAKGQPREPQVYTLPPSRDELTKNQVSLTCLVKGFYPSDIAVEWESNGQPENNYKTTPPVLDSDGS</u>

<u>FFLYSKLTVDKSRWQQGNVFSCSVMHEALHNHYTQKSLSLSPG</u>

416F8CHIMERICHEAVYCHAINVARIABLEHEAVYCHAINAMINOACIDSEQUENCE. COMPLIMENTARITY DETERMININGREGIONSAREUNDERLINED

SEQ ID NO: 24

QSLEESGGRLVTPGTPLTLTCTASGFSLS<u>NYYMN</u>WVRQAPGKGLEYIG<u>IISSSGSAYYASWAKG</u>RFTISRTSTTVDLRITSP

TTEDTATYFCAR<u>GDYGMDL</u>WGQGTLVTVSS

416G1CHIMERICLIGHTCHAINFULL-LENGTHNUCLEOTIDESEQUENCE

SEQ ID NO: 25

GACGTCGTGATGACCCAGACTCCAGCCTCCGTGTCTGAACCTGTGGGAGGCGCAGTCACCATCAAGTGCCAGGCC

AGTCAGAGCATTGGTAGTGATTTAGCCTGGTATCAGCAGAAACCAGGGCAGCCTCCCAAGCTCCTGATCTACAGG

GCATCCACTCTGGCATCTGGGGTCTCATCGCGGTTCAAAGGCAGTGGATCTGGGACAGAGTTCACTCTCACCATCA

GCGACCTGGAGTGTGCCGATGCTGCCACTTACTACTGTCAATGTATTTATTATGGTAGTGATGATGTCATATACCAT

ACTTTCGGCGGAGGGACCGAGGTGGTGGTCAAACGTACGGTGGCTGCACCATCTGTCTTCATCTTCCCGCCATCTG

-continued

ATGAGCAGTTGAAATCTGGAACTGCCTCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCACAGAGCAGGACAGCAAGGACAGCA

CCTACAGCCTCAGCAGCACCCTGACGCTGAGCAAAGCAGACTACGAGAAACACAAAGTCTACGCCTGCGAAGTCA

CCCATCAGGGCCTGAGCTCGCCCGTCACAAAGAGCTTCAACAGGGGAGAGTGT

416G1CHIMERICLIGHTCHAINVARIABLELIGHTCHAINNUCLEOTIDESEQUENCE

SEQ ID NO: 26

GACGTCGTGATGACCCAGACTCCAGCCTCCGTGTCTGAACCTGTGGGAGGCGCAGTCACCATCAAGTGCCAGGCC

AGTCAGAGCATTGGTAGTGATTTAGCCTGGTATCAGCAGAAACCAGGGCAGCCTCCCAAGCTCCTGATCTACAGG

GCATCCACTCTGGCATCTGGGGTCTCATCGCGGTTCAAAGGCAGTGGATCTGGGACAGAGTTCACTCTCACCATCA

GCGACCTGGAGTGTGCCGATGCTGCCACTTACTACTGTCAATGTATTTATTATGGTAGTGATGATGTCATATACCAT

ACTTTCGGCGGAGGGACCGAGGTGGTGGTCAAA

416G1CHIMERICLIGHTCHAINFULL-LENGTHAMINOACIDSEQUENCE. HUMANKAPPACONSTANT DOMAINISUNDERLINED

SEQ ID NO: 27

DVVMTQTPASVSEPVGGAVTIKCQASQSIGSDLAWYQQKPGQPPKLLIYRASTLASGVSSRFKGSGSGTEFTLTISDLEC

ADAATYYCQCIYYGSDDVIYHTFGGGTEVVVKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

416G1CHIMERICLIGHTCHAINVARIABLELIGHTCHAINAMINOACIDSEQUENCE. COMPIMENTARITY DETERMININGREGIONSAREUNDERLINED

SEQ ID NO: 28

DVVMTQTPASVSEPVGGAVTIKCQASQSIGSDLAWYQQKPGQPPKLLIYRASTLASGVSSRFKGSGSGTEFTLTISDLEC

ADAATYYCQCIYYGSDDVIYHTFGGGTEVVVK

416G1CHIMERICHEAVYCHAINFULL-LENGTHNUCLEOTIDESEQUENCE

SEQ ID NO: 29

CAGTCGGTGGAGGAGTCCGGGGGTCGCCTGGTCACGCCTGGGACACCCCTGACACTCACCTGCACAGTCTCTGGA

TTCACTATCAATAGCTACCACATGATCTGGGTCCGCCAGGCTCCAGGGGAGGGGCTGGAATACATCGGATTCATTA

ATGATGGTGGTTTCACATACTACGCGAGCTGGGCAAAAGGCCGATTTATCATCTCCAGAACCTCGACCACGGTGG

ATCTGAAAATGACCAGTCTGACAGTCGCGGACACGGCCACCTATTTCTGTGCCAGAGGGGTTGATGGTACTAGTT

ATCCTGACTTATGGGGCCCGGGCACCCTGGTCACCGTCTCGAGCGCTAGCACCAAGGGCCCATCGGTCTTCCCCCT

GGCACCCTCCTCCAAGAGCACCTCTGGGGGCACAGCGGCCCTGGGCTGCCTGGTCAAGGACTACTTCCCCGAACC

GGTGACGGTGTCGTGGAACTCAGGCGCCCTGACCAGCGGCGTGCACACCTTCCCGGCTGTCCTACAGTCCTCAGG

ACTCTACTCCCTCAGCAGCGTGGTGACCGTGCCCTCCAGCAGCTTGGGCACCCAGACCTACATCTGCAACGTGAAT

CACAAGCCCAGCAACACCAAGGTGGACAAGAGAGTTGAGCCCAAATCTTGTGACAAAACTCACACATGCCCACCG

TGCCCAGCACCTGAAGCCGCGGGGGCACCGTCAGTCTTCCTCTTCCCCCCAAAACCCAAGGACACCCTCATGATCT

CCCGGACCCCTGAGGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAGTGCGCGGTCTCCAACAAAGCCC

TCCCAGCCCCCATCGAGAAAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGT

416G1CHIMERICHEAVYCHAINVARIABLEHEAVYCHAINNUCLEOTIDESEQUENCE

SEQ ID NO: 30

CAGTCGGTGGAGGAGTCCGGGGGTCGCCTGGTCACGCCTGGGACACCCCTGACACTCACCTGCACAGTCTCTGGA

TTCACTATCAATAGCTACCACATGATCTGGGTCCGCCAGGCTCCAGGGGAGGGGCTGGAATACATCGGATTCATTA

ATGATGGTGGTTTCACATACTACGCGAGCTGGGCAAAAGGCCGATTTATCATCTCCAGAACCTCGACCACGGTGG

-continued

ATCTGAAAATGACCAGTCTGACAGTCGCGGACACGGCCACCTATTTCTGTGCCAGAGGGGTTGATGGTACTAGTT

ATCCTGACTTATGGGGCCCGGGCACCCTGGTCACCGTCTCGAGC

416G1CHIMERICHEAVYCHAINFULL-LENGTHAMINOACIDSEQUENCE. HUMANGAMMA-1CONSTANT DOMAINISUNDERLINED

SEQ ID NO: 31

QSVEESGGRLVTPGTPLTLTCTVSGFTINSYHMIWVRQAPGEGLEYIGFINDGGFTYYASWAKGRFIISRTSTTVDLKMTS

LTVADTATYFCARGVDGTSYPDLWGPGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLF

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

416G1CHIMERICHEAVYCHAINVARIABLEHEAVYCHAINAMINOACIDSEQUENCE. COMPLIMENTARITY DETERMININGREGIONSAREUNDERLINED

SEQ ID NO: 32

QSVEESGGRLVTPGTPLTLTCTVSGFTINSYHMIWVRQAPGEGLEYIGFINDGGFTYYASWAKGRFIISRTSTTVDLKMTS

LTVADTATYFCARGVDGTSYPDLWGPGTLVTVSS

418E10CHIMERICLIGHTCHAINFULL-LENGTHNUCLEOTIDESEQUENCE

SEQ ID NO: 33

GCCCTGGTGATGACCCAGACTCCATCCCCTGTGTCTGCGGCTGTGGGAGGCACAGTCACCATCAACTGCCAGGCC

AGTCAGAGCATTGGTAGTAACTTGAACTGGTATCAGCAGAAACCAGGGCAGCCTCCCAAGCTCCTGATTTATTATG

TATCCACTCTGGCATCTGGGGTCCCATCGCGGTTCAAAGGCAGTGGATCTGGGACAGAGTACACTCTCACCATCAG

CGGCGTGCAGTGTGACGATGCTGCCACTTACTACTGCCTAGGTGTTTGGAATTATTGGGGTGATGACGGTACTGCT

TTCGGCGGAGGCACCGAGGTGGAGGTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

418E10CHIMERICLIGHTCHAINVARIABLELIGHTCHAINNUCLEOTIDESEQUENCE

SEQ ID NO: 34

GCCCTGGTGATGACCCAGACTCCATCCCCTGTGTCTGCGGCTGTGGGAGGCACAGTCACCATCAACTGCCAGGCC

AGTCAGAGCATTGGTAGTAACTTGAACTGGTATCAGCAGAAACCAGGGCAGCCTCCCAAGCTCCTGATTTATTATG

TATCCACTCTGGCATCTGGGGTCCCATCGCGGTTCAAAGGCAGTGGATCTGGGACAGAGTACACTCTCACCATCAG

CGGCGTGCAGTGTGACGATGCTGCCACTTACTACTGCCTAGGTGTTTGGAATTATTGGGGTGATGACGGTACTGCT

TTCGGCGGAGGCACCGAGGTGGAGGTCAAA

418E10CHIMERICLIGHTCHAINFULL-LENGTHAMINOACIDSEQUENCE. HUMANKAPPACONSTANT DOMAINISUNDERLINED

SEQ ID NO: 35

ALVMTQTPSPVSAAVGGTVTINCQASQSIGSNLNWYQQKPGQPPKLLIYYVSTLASGVPSRFKGSGSGTEYTLTISGVQ

CDDAATYYCLGVWNYWGDDGTAFGGGTEVEVKRTVAAPSVFIFPPSDEQLKSGTASVVCLLNNFYPREAKVQWKVD

NALQSGNSQESVTEQDSKDSTYSLSSTLTLSKADYEKHKVYACEVTHQGLSSPVTKSFNRGEC

418E10CHIMERICLIGHTCHAINVARIABLELIGHTCHAINAMINOACIDSEQUENCE. COMPIMENTARITY DETERMININGREGIONSAREUNDERLINED

SEQ ID NO: 36

ALVMTQTPSPVSAAVGGTVTINCQASQSIGSNLNWYQQKPGQPPKLLIYYVSTLASGVPSRFKGSGSGTEYTLTISGVQ

CDDAATYYCLGVWNYWGDDGTAFGGGTEVEVK

418E10CHIMERICHEAVYCHAINFULL-LENGTHNUCLEOTIDESEQUENCE

SEQ ID NO: 37

CAGTCGCTGGAGGAGTCCGGGGGTCGCCTGGTCACGCCTGGGACACCCCTGACACTCACCTGCACAGCCTCTGAT

TTCTCCCTCAGTACCTATTATATGAGCTGGGTCCGCCAGGCTCCAGGGAAGGGGCTGGAGTGGATCGGAAGTATT

-continued

TATGATAGTGGTGCCGCATACTACGCGACCTGGGCGAAGGGCCGATTCACCATCTCCAGAACGTCGACCACGGTG

GATCTGAGAATGACCAGTCTGACAGCCGCGGACACGGCCACCTATTTCTGTGCCAGAGATCCTATTAATAATGCCA

TCTGGGGCCAAGGGACCCTCGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT

418E10CHIMERICHEAVYCHAINVARIABLEHEAVYCHAINNUCLEOTIDESEQUENCE

SEQ ID NO: 38

CAGTCGCTGGAGGAGTCCGGGGGTCGCCTGGTCACGCCTGGGACACCCCTGACACTCACCTGCACAGCCTCTGAT

TTCTCCCTCAGTACCTATTATATGAGCTGGGTCCGCCAGGCTCCAGGGAAGGGGCTGGAGTGGATCGGAAGTATT

TATGATAGTGGTGCCGCATACTACGCGACCTGGGCGAAGGGCCGATTCACCATCTCCAGAACGTCGACCACGGTG

GATCTGAGAATGACCAGTCTGACAGCCGCGGACACGGCCACCTATTTCTGTGCCAGAGATCCTATTAATAATGCCA

TCTGGGGCCAAGGGACCCTCGTCACCGTCTCGAGC

418E10CHIMERICHEAVYCHAINFULL-LENGTHAMINOACIDSEQUENCE. HUMANGAMMA-1 CONSTANTDOMAINISUNDERLINED

SEQ ID NO: 39

QSLEESGGRLVTPGTPLTLTCTASDFSLSTYYMSWVRQAPGKGLEWIGSIYDSGAAYYATWAKGRFTISRTSTTVDLRM

TSLTAADTATYFCARDPINNAIWGQGTLVTVSSASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVDKRVEPKSCDKTHTCPPCPAPEAAGAPSVFLFPP

KPKDTLMISRTPEVTCVVVDVSHEDPEVKFNWYVDGVEVHNAKTKPREEQYNSTYRVVSVLTVLHQDWLNGKEYKCA

VSNKALPAPIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

418E10CHIMERICHEAVYCHAINVARIABLEHEAVYCHAINAMINOACIDSEQUENCE. COMPLIMENTARITYDETERMININGREGIONSAREUNDERLINED

SEQ ID NO: 40

QSLEESGGRLVTPGTPLTLTCTASDFSLSTYYMSWVRQAPGKGLEWIGSIYDSGAAYYATWAKGRFTISRTSTTVDLRM

TSLTAADTATYFCARDPINNAIWGQGTLVTVSS

418E4CHIMERICLIGHTCHAINFULL-LENGTHNUCLEOTIDESEQUENCE

SEQ ID NO: 41

GCCCTGGTGATGACCCAGACTCCATCCCCTGTGTCTGCGGCTGTGGGAGGCACAGTCACCATCAACTGCCAGGCC

AGTCAGAGTATTGCTACTAACTTGAACTGGTATCAGCAGAAACCAGGGCAGCCTCCCAAGCTCCTGATCTATTATA

CATCCAGTCTGGCATCTGGGGTCCCATCGCGGTTCAGCGGCAGTGGATCTGGCACAGAGTTCACTCTCACCATCAG

CGGTGTGCAGTGTGACGATGCTGCCACTTACTACTGCCTAGGTGTTTGGAATTATTGGGGTGATGATGGTACTGCT

TTCGGCGGAGGGACCGAGGTGGAGTTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

-continued

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

418E4CHIMERICLIGHTCHAINVARIABLELIGHTCHAINNUCLEOTIDESEQUENCE

SEQ ID NO: 42

GCCCTGGTGATGACCCAGACTCCATCCCCTGTGTCTGCGGCTGTGGGAGGCACAGTCACCATCAACTGCCAGGCC

AGTCAGAGTATTGCTACTAACTTGAACTGGTATCAGCAGAAACCAGGGCAGCCTCCCAAGCTCCTGATCTATTATA

CATCCAGTCTGGCATCTGGGGTCCCATCGCGGTTCAGCGGCAGTGGATCTGGCACAGAGTTCACTCTCACCATCAG

CGGTGTGCAGTGTGACGATGCTGCCACTTACTACTGCCTAGGTGTTTGGAATTATTGGGGTGATGATGGTACTGCT

TTCGGCGGAGGGACCGAGGTGGAGTTCAAA

418E4CHIMERICLIGHTCHAINFULL-LENGTHAMINOACIDSEQUENCE. HUMANKAPPACONSTANT DOMAINISUNDERLINED

SEQ ID NO: 43

ALVMTQTPSPVSAAVGGTVTINCQASQSIATNLNWYQQKPGQPPKLLIYYTSSLASGVPSRFSGSGSGTEFTLTISGVQC

DDAATYYCLGVWNYWGDDGTAFGGGTEVEFKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSFNRGEC

418E4CHIMERICLIGHTCHAINVARIABLELIGHTCHAINAMINOACIDSEQUENCE. COMPIMENTARITY DETERMININGREGIONSAREUNDERLINED

SEQ ID NO: 44

ALVMTQTPSPVSAAVGGTVTINCQASQSIATNLNWYQQKPGQPPKLLIYYTSSLASGVPSRFSGSGSGTEFTLTISGVQC

DDAATYYCLGVWNYWGDDGTAFGGGTEVEFK

418E4CHIMERICHEAVYCHAINFULL-LENGTHNUCLEOTIDESEQUENCE

SEQ ID NO: 45

CAGTCGCTGGAGGAGTCCGGGGGTCGCCTGGTCACGCCTGGGACACCCCTGACACTCACCTGCACAGCCTCTGAA

TTCTCCCTCAGTAGCTACTACATGAGCTGGGTCCGCCAGGCTCCAGGGAAGGGGCTGGAATGGATCGGAAGTATT

TATGCTAGTGGTAGCGCATACTACGCGAGTTGGGCGAAGGGCCGATTCACCATCTCCAGAACGTCGACCACGGTG

GATCTGAAAATGACCAGTCTGACAGCCGCGGACACGGCCACCTATTTCTGTGTCAGAGATCCTATTAACAATGACA

TCTGGGGCCCAGGCACCCTGGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT

418E4CHIMERICHEAVYCHAINVARIABLEHEAVYCHAINNUCLEOTIDESEQUENCE

SEQ ID NO: 46

CAGTCGCTGGAGGAGTCCGGGGGTCGCCTGGTCACGCCTGGGACACCCCTGACACTCACCTGCACAGCCTCTGAA

TTCTCCCTCAGTAGCTACTACATGAGCTGGGTCCGCCAGGCTCCAGGGAAGGGGCTGGAATGGATCGGAAGTATT

TATGCTAGTGGTAGCGCATACTACGCGAGTTGGGCGAAGGGCCGATTCACCATCTCCAGAACGTCGACCACGGTG

GATCTGAAAATGACCAGTCTGACAGCCGCGGACACGGCCACCTATTTCTGTGTCAGAGATCCTATTAACAATGACA

-continued

TCTGGGGCCCAGGCACCCTGGTCACCGTCTCGAGC

418E4 CHIMERIC HEAVY CHAIN FULL-LENGTH AMINO ACID SEQUENCE. HUMAN GAMMA-1 CONSTANT DOMAINISUNDERLINED

SEQ ID NO: 47

QSLEESGGRLVTPGTPLTLTCTASEFSLSSYYMSWVRQAPGKGLEWIGSIYASGSAYYASWAKGRFTISRTSTTVDLKMT

SLTAADTATYFCVRDPINNDIWGPGTLVTVSSASTKGPSVFPLAPSSKSTSGGTAALGCLVKDYFPEPVTVSWNSGALTS

GVHTFPAVLQSSGLYSLSSVVTVPSSSLGTQTYICNVNHKPSNTKVDKRVEPKSCDKTHTCPPCPAPEAAGAPSVFLFPPK

PKDTLMISRTPEVTCVVVDVSHEDPEVKFNWYVDGVEVHNAKTKPREEQYNSTYRVVSVLTVLHQDWLNGKEYKCAV

SNKALPAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPG

418E4CHIMERICHEAVYCHAINVARIABLEHEAVYCHAINAMINOACIDSEQUENCE. COMPLIMENTARITY DETERMININGREGIONSAREUNDERLINED

SEQ ID NO: 48

QSLEESGGRLVTPGTPLTLTCTASEFSLSSYYMSWVRQAPGKGLEWIGSIYASGSAYYASWAKGRFTISRTSTTVDLKMT

SLTAADTATYFCVRDPINNDIWGPGTLVTVSS

418H5CHIMERICLIGHTCHAINFULL-LENGTHNUCLEOTIDESEQUENCE

SEQ ID NO: 49

GCCCAAGTGCTGACCCAGACTCCAGCCTCCGTGTCTGCAACTGTGGGAAGCACAGTCACCATCAGTTGCCAGTCCA

GTCCGAGTGTTTATAAGAACAACCAATTAGCCTGGTATCAGCAGAAACCAGGGCAGCCTCCCAAACTCCTGATCTA

TCTGGCATCTACTCTGGCATCTGGGGTCCCATCGCGGTTCAAAGGCAGTGGATCTGGGACAGAGTTCACTCTCACC

ATCAGCGACCTGGAGTGTGCCGATGCTGCCACTTACTACTGTGCAGGCGGTTATAGTAGTAGTAGTGATACTGCTT

TCGGCGGAGGGACCGAGGTGGAGGTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

418H5CHIMERICLIGHTCHAINVARIABLELIGHTCHAINNUCLEOTIDESEQUENCE

SEQ ID NO: 50

GCCCAAGTGCTGACCCAGACTCCAGCCTCCGTGTCTGCAACTGTGGGAAGCACAGTCACCATCAGTTGCCAGTCCA

GTCCGAGTGTTTATAAGAACAACCAATTAGCCTGGTATCAGCAGAAACCAGGGCAGCCTCCCAAACTCCTGATCTA

TCTGGCATCTACTCTGGCATCTGGGGTCCCATCGCGGTTCAAAGGCAGTGGATCTGGGACAGAGTTCACTCTCACC

ATCAGCGACCTGGAGTGTGCCGATGCTGCCACTTACTACTGTGCAGGCGGTTATAGTAGTAGTAGTGATACTGCTT

TCGGCGGAGGGACCGAGGTGGAGGTCAAA

418H5CHIMERICLIGHTCHAINFULL-LENGTHAMINOACIDSEQUENCE. HUMANKAPPACONSTANT DOMAINISUNDERLINED

SEQ ID NO: 51

AQVLTQTPASVSATVGSTVTISCQSSPSVYKNNQLAWYQQKPGQPPKLLIYLASTLASGVPSRFKGSGSGTEFTLTISDLE

CADAATYYCAGGYSSSSDTAFGGGTEVEVKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

418H5CHIMERICLIGHTCHAINVARIABLELIGHTCHAINAMINOACIDSEQUENCE. COMPIMENTARITY DETERMININGREGIONSAREUNDERLINED

SEQ ID NO: 52

AQVLTQTPASVSATVGSTVTISCQSSPSVYKNNQLAWYQQKPGQPPKLLIYLASTLASGVPSRFKGSGSGTEFTLTISDLE

CADAATYYCAGGYSSSSDTAFGGGTEVEVK

418H5CHIMERICHEAVYCHAINFULL-LENGTHNUCLEOTIDESEQUENCE

SEQ ID NO: 53

CAGTCGCTGGAGGAGTCCGGGGGTCGCCTGGTCACGCCTGGGACACCCCTGACACTCACCTGCACAGTCTCTGGA

ATCGACCTCAGTGCCTACCACATGAGCTGGGTCCGCCAGGCTCCAGGGAAGGGGCTGGAATACATCGGAATGATT

GGTAGTAGTGGTACCATACACTACGCGAACTGGGCGAAAGGCCGATTCACCATCTCCAAAACCTCGACCACGGTG

-continued

GATCTGAAAATCACCAGTCCGACAACCGAGGACACGGCCACCTATTTCTGTGCCAGGGACAGTTATAATAGTGATT

ATGCCTTTAACTTATGGGGCCCAGGGACCCTGGTCACCGTCTCGAGCGCTAGCACCAAGGGCCCATCGGTCTTCCC

CCTGGCACCCTCCTCCAAGAGCACCTCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGTGCGCGGTCTCCAACAAAGC

CCTCCCAGCCCCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

418H5CHIMERICHEAVYCHAINVARIABLEHEAVYCHAINNUCLEOTIDESEQUENCE

SEQ ID NO: 54

CAGTCGCTGGAGGAGTCCGGGGGTCGCCTGGTCACGCCTGGGACACCCCTGACACTCACCTGCACAGTCTCTGGA

ATCGACCTCAGTGCCTACCACATGAGCTGGGTCCGCCAGGCTCCAGGGAAGGGGCTGGAATACATCGGAATGATT

GGTAGTAGTGGTACCATACACTACGCGAACTGGGCGAAAGGCCGATTCACCATCTCCAAAACCTCGACCACGGTG

GATCTGAAAATCACCAGTCCGACAACCGAGGACACGGCCACCTATTTCTGTGCCAGGGACAGTTATAATAGTGATT

ATGCCTTTAACTTATGGGGCCCAGGGACCCTGGTCACCGTCTCGAGC

418H5 CHIMERIC HEAVY CHAIN FULL-LENGTH AMINO ACID SEQUENCE. HUMAN GAMMA-1 CONSTANT DOMAINISUNDERLINED

SEQ ID NO: 55

QSLEESGGRLVTPGTPLTLTCTVSGIDLSAYHMSWVRQAPGKGLEYIGMIGSSGTIHYANWAKGRFTISKTSTTVDLKITS

PTTEDTATYFCARDSYNSDYAFNLWGPGTLVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKSCDKTHTCPPCPAPEAAGAPSVFL

FPPKPKDTLMISRTPEVTCVVVDVSHEDPEVKFNWYVDGVEVHNAKTKPREEQYNSTYRVVSVLTVLHQDWLNGKEY

KCAVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

418H5CHIMERICHEAVYCHAINVARIABLEHEAVYCHAINAMINOACIDSEQUENCE. COMPLIMENTARITY DETERMININGREGIONSAREUNDERLINED

SEQ ID NO: 56

QSLEESGGRLVTPGTPLTLTCTVSGIDLSAYHMSWVRQAPGKGLEYIGMIGSSGTIHYANWAKGRFTISKTSTTVDLKITS

PTTEDTATYFCARDSYNSDYAFNLWGPGTLVTVSS

419D9CHIMERICLIGHTCHAINFULL-LENGTHNUCLEOTIDESEQUENCE

SEQ ID NO: 57

GCTCAAGTGCTGACCCAGACTGCATCGCCCGTGTCTGCCGCTGTGGGAGGCACAGTCACCATCAACTGCCAGTCCA

GTCAGAGTGTTTATAGTAACTGGTTATCCTGGTATCAGCAGAAACCAGGGCAGCCTCCCAAGCGCCTGATCTATTC

TGCATCCACTCTGGCATCTGGGGTCCCATCGCGGTTCAAAGGCAGTGGATCTGGGACACAGTTCACTCTCACCATC

AGCGACCTGGAGTGTGACGATGCTGCCACTTACTACTGTGCAGGCGGTTATAATACTGTTACTGATACTTTTGCTTT

CGGCAGAGGCACCGAGGTGGAGGTCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

-continued

TCAGGGCCTGAGCTCGCCCGTCACAAAGAGCTTCAACAGGGGAGAGTGT

419D9CHIMERICLIGHTCHAINVARIABLELIGHTCHAINNUCLEOTIDESEQUENCE

SEQ ID NO: 58

GCTCAAGTGCTGACCCAGACTGCATCGCCCGTGTCTGCCGCTGTGGGAGGCACAGTCACCATCAACTGCCAGTCCA

GTCAGAGTGTTTATAGTAACTGGTTATCCTGGTATCAGCAGAAACCAGGGCAGCCTCCCAAGCGCCTGATCTATTC

TGCATCCACTCTGGCATCTGGGGTCCCATCGCGGTTCAAAGGCAGTGGATCTGGGACACAGTTCACTCTCACCATC

AGCGACCTGGAGTGTGACGATGCTGCCACTTACTACTGTGCAGGCGGTTATAATACTGTTACTGATACTTTTGCTTT

CGGCAGAGGCACCGAGGTGGAGGTCAAA

419D9CHIMERICLIGHTCHAINFULL-LENGTHAMINOACIDSEQUENCE. HUMANKAPPACONSTANT DOMAINISUNDERLINED

SEQ ID NO: 59

AQVLTQTASPVSAAVGGTVTINCQSSQSVYSNWLSWYQQKPGQPPKRLIYSASTLASGVPSRFKGSGSGTQFTLTISDL

ECDDAATYYCAGGYNTVTDTFAFGRGTEVEVKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFNRGEC

419D9CHIMERICLIGHTCHAINVARIABLELIGHTCHAINAMINOACIDSEQUENCE. COMPIMENTARITY DETERMININGREGIONSAREUNDERLINED

SEQ ID NO: 60

AQVLTQTASPVSAAVGGTVTINCQSSQSVYSNWLSWYQQKPGQPPKRLIYSASTLASGVPSRFKGSGSGTQFTLTISDL

ECDDAATYYCAGGYNTVTDTFAFGRGTEVEVK

419D9CHIMERICHEAVYCHAINFULL-LENGTHNUCLEOTIDESEQUENCE

SEQ ID NO: 61

CAGTCGTTGGAGGAGTCCGGGGGAGACCTGGTCAAGCCTGGGGCATCCCTGACACTCACCTGCACAGCCTCTGGA

TTCTCCTTCAGTAGCAGGCACTACATGTGTTGGGTCCGCCAGGCTCCAGGGGAGGGGCTGGAGTGGATCGCATGC

ATTTATACTGGTAGTAGTGGTACTCCTCACTACGCGAGCTGGGCGAAAGGCCGATTCACCATCTCCCAAACCTCGT

CGACCACGGTGACTCTGCAAATGACCAGTCTGACAGCCGCGGACACGGCCACCTATTTCTGTTCGAGCGAAGGTA

ACCTGTGGGGCCCAGGCACCCTGGTCACCGTCTCGAGCGCTAGCACCAAGGGCCCATCGGTCTTCCCCCTGGCACC

CTCCTCCAAGAGCACCTCTGGGGGCACAGCGGCCCTGGGCTGCCTGGTCAAGGACTACTTCCCCGAACCGGTGAC

GGTGTCGTGGAACTCAGGCGCCCTGACCAGCGGCGTGCACACCTTCCCGGCTGTCCTACAGTCCTCAGGACTCTAC

TCCCTCAGCAGCGTGGTGACCGTGCCCTCCAGCAGCTTGGGCACCCAGACCTACATCTGCAACGTGAATCACAAGC

CCAGCAACACCAAGGTGGACAAGAGAGTTGAGCCCAAATCTTGTGACAAAACTCACACATGCCCACCGTGCCCAG

CACCTGAAGCCGCGGGGGCACCGTCAGTCTTCCTCTTCCCCCCAAAACCCAAGGACACCCTCATGATCTCCCGGAC

CCCTGAGGTCACATGCGTGGTGGTGGACGTGAGCCACGAAGACCCTGAGGTCAAGTTCAACTGGTACGTGGACG

GCGTGGAGGTGCATAATGCCAAGACAAAGCCGCGGGAGGAGCAGTACAACAGCACGTACCGTGTGGTCAGCGTC

CTCACCGTCCTGCACCAGGACTGGCTGAATGGCAAGGAGTACAAGTGCGCGGTCTCCAACAAAGCCCTCCCAGCC

CCCATCGAGAAAACCATCTCCAAAGCCAAAGGGCAGCCCCGAGAACCACAGGTGTACACCCTGCCCCCATCCCGG

GATGAGCTGACCAAGAACCAGGTCAGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTGCTGGACTCCGACGGCTCCTTCTTC

CTCTATAGCAAGCTCACCGTGGACAAGAGCAGGTGGCAGCAGGGGAACGTCTTCTCATGCTCCGTGATGCATGAG

GCTCTGCACAACCACTACACGCAGAAGAGCCTCTCCCTGTCTCCGGGT

419D9CHIMERICHEAVYCHAINVARIABLEHEAVYCHAINNUCLEOTIDESEQUENCE

SEQ ID NO: 62

CAGTCGTTGGAGGAGTCCGGGGGAGACCTGGTCAAGCCTGGGGCATCCCTGACACTCACCTGCACAGCCTCTGGA

TTCTCCTTCAGTAGCAGGCACTACATGTGTTGGGTCCGCCAGGCTCCAGGGGAGGGGCTGGAGTGGATCGCATGC

ATTTATACTGGTAGTAGTGGTACTCCTCACTACGCGAGCTGGGCGAAAGGCCGATTCACCATCTCCCAAACCTCGT

CGACCACGGTGACTCTGCAAATGACCAGTCTGACAGCCGCGGACACGGCCACCTATTTCTGTTCGAGCGAAGGTA

ACCTGTGGGGCCCAGGCACCCTGGTCACCGTCTCGAGC

-continued

419D9CHIMERICHEAVYCHAINFULL-LENGTHAMINOACIDSEQUENCE. HUMANGAMMA-1CONSTANT DOMAINISUNDERLINED

SEQ ID NO: 63

QSLEESGGDLVKPGASLTLTCTASGFSFSSRHYMCWVRQAPGEGLEWIACIYTGSSGTPHYASWAKGRFTISQTSSTTV

TLQMTSLTAADTATYFCSSEGNLWGPGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLE

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

419D9CHIMERICHEAVYCHAINVARIABLEHEAVYCHAINAMINOACIDSEQUENCE. COMPLIMENTARITY DETERMININGREGIONSAREUNDERLINED

SEQ ID NO: 64

QSLEESGGDLVKPGASLTLTCTASGFSFSSRHYMCWVRQAPGEGLEWIACIYTGSSGTPHYASWAKGRFTISQTSSTTV

TLQMTSLTAADTATYFCSSEGNLWGPGTLVTVSS

420H5CHIMERICLIGHTCHAINFULL-LENGTHNUCLEOTIDESEQUENCE

SEQ ID NO: 65

GCCCTTGTGATGACCCAGACTCCAGCCTCCGTGTCTGCAGCTGTGGGAGGCACAGTCACCATCAATTGCCAGGCCA

GTGAGGACATTGATACCTATTTAGCCTGGTATCAGCAGAAACCAGGGCAGCCTCCCAAGCTCCTGATCTTTTATGC

ATCCGATCTGGCATCTGGGGTCCCATCGCGGTTCAAAGGCAGTGGATCTGGGACAGAGTTCACTCTCACCATCAGC

GGTGTGCAGTGTGACGATGCTGCCACTTACTACTGTCAAGGCGGTTACTATACTAGTAGTGCTGATACGAGGGGT

GCTTTCGGCGGAGGCACCGAGGTGGTGGTCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCACAGAGCAGGACAGCAAGGACAGCA

CCTACAGCCTCAGCAGCACCCTGACGCTGAGCAAAGCAGACTACGAGAAACACAAAGTCTACGCCTGCGAAGTCA

CCCATCAGGGCCTGAGCTCGCCCGTCACAAAGAGCTTCAACAGGGGAGAGTGT

420H5CHIMERICLIGHTCHAINVARIABLELIGHTCHAINNUCLEOTIDESEQUENCE

SEQ ID NO: 66

GCCCTTGTGATGACCCAGACTCCAGCCTCCGTGTCTGCAGCTGTGGGAGGCACAGTCACCATCAATTGCCAGGCCA

GTGAGGACATTGATACCTATTTAGCCTGGTATCAGCAGAAACCAGGGCAGCCTCCCAAGCTCCTGATCTTTTATGC

ATCCGATCTGGCATCTGGGGTCCCATCGCGGTTCAAAGGCAGTGGATCTGGGACAGAGTTCACTCTCACCATCAGC

GGTGTGCAGTGTGACGATGCTGCCACTTACTACTGTCAAGGCGGTTACTATACTAGTAGTGCTGATACGAGGGGT

GCTTTCGGCGGAGGCACCGAGGTGGTGGTCAAA

420H5CHIMERICLIGHTCHAINFULL-LENGTHAMINOACIDSEQUENCE. HUMANKAPPACONSTANT DOMAINISUNDERLINED

SEQ ID NO: 67

ALVMTQTPASVSAAVGGTVTINCQASEDIDTYLAWYQQKPGQPPKLLIFYASDLASGVPSRFKGSGSGTEFTLTISGVQC

DDAATYYCQGGYYTSSADTRGAFGGGTEVVVKRTVAAPSVFIFPPSDEQLKSGTASVVCLLNNFYPREAKVQWKVDNA

LQSGNSQESVTEQDSKDSTYSLSSTLTLSKADYEKHKVYACEVTHQGLSSPVTKSFNRGEC

420H5CHIMERICLIGHTCHAINVARIABLELIGHTCHAINAMINOACIDSEQUENCE. COMPIMENTARITY DETERMININGREGIONSAREUNDERLINED

SEQ ID NO: 68

ALVMTQTPASVSAAVGGTVTINCQASEDIDTYLAWYQQKPGQPPKLLIFYASDLASGVPSRFKGSGSGTEFTLTISGVQC

DDAATYYCQGGYYTSSADTRGAFGGGTEVVVK

420H5CHIMERICHEAVYCHAINFULL-LENGTHNUCLEOTIDESEQUENCE

SEQ ID NO: 69

CAGTCGTTGGAGGAGTCCGGGGGAGACCTGGTCAAGCCTGGGGCATCCCTGACACTCACCTGCACAGCCTCTGGA

TTCTCCTTCAGTAGCAACTACTGGATATGCTGGGTCCGCCAGGCTCCAGGGAAGGGGCTGGAGTGGATCGCATGC

ATTTATGTTGGTAGTAGTGGTGACACTTACTACGCGAGCTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

GTAGTTATTATATGTTTAACTTGTGGGGCCAGGGGACCCTGGTCACCGTCTCGAGCGCTAGCACCAAGGGCCCATC

-continued

GGTCTTCCCCCTGGCACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTACATCT

GCAACGTGAATCACAAGCCCAGCAACACCAAGGTGGACAAGAGAGTTGAGCCCAAATCTTGTGACAAAACTCACA

CATGCCCACCGTGCCCAGCACCTGAAGCCGCGGGGGCACCGTCAGTCTTCCTCTTCCCCCCAAAACCCAAGGACAC

CCTCATGATCTCCCGGACCCCTGAGGTCACATGCGTGGTGGTGGACGTGAGCCACGAAGACCCTGAGGTCAAGTT

CAACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCGCGGTCTCC

AACAAAGCCCTCCCAGCCCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGACCACGCCTCCCGTGCTGGAC

TCCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

420H5CHIMERICHEAVYCHAINVARIABLEHEAVYCHAINNUCLEOTIDESEQUENCE

SEQ ID NO: 70

CAGTCGTTGGAGGAGTCCGGGGGAGACCTGGTCAAGCCTGGGGCATCCCTGACACTCACCTGCACAGCCTCTGGA

TTCTCCTTCAGTAGCAACTACTGGATATGCTGGGTCCGCCAGGCTCCAGGGAAGGGGCTGGAGTGGATCGCATGC

ATTTATGTTGGTAGTAGTGGTGACACTTACTACGCGAGCTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

GTAGTTATTATATGTTTAACTTGTGGGGCCAGGGGACCCTGGTCACCGTCTCGAGC

420H5CHIMERICHEAVYCHAINFULL-LENGTHAMINOACIDSEQUENCE. HUMANGAMMA-1CONSTANT DOMAINISUNDERLINED

SEQ ID NO: 71

QSLEESGGDLVKPGASLTLTCTASGFSFSSNYWICWVRQAPGKGLEWIACIYVGSSGDTYYASWAKGRFTISKTSSTTVT

LQMTSLTAADTATYFCARDSSSYYMFNLWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPG

420H5CHIMERICHEAVYCHAINVARIABLEHEAVYCHAINAMINOACIDSEQUENCE. COMPLIMENTARITY DETERMININGREGIONSAREUNDERLINED

SEQ ID NO: 72

QSLEESGGDLVKPGASLTLTCTASGFSFSSNYWICWVRQAPGKGLEWIACIYVGSSGDTYYASWAKGRFTISKTSSTTVT

LQMTSLTAADTATYFCARDSSSYYMFNLWGQGTLVTVSS

420H6CHIMERICLIGHTCHAINFULL-LENGTHNUCLEOTIDESEQUENCE

SEQ ID NO: 73

GCTCAAGTGCTGACCCAGACTGCATCGCCCGTGTCTGCCGCTGTGGGAGGCACAGTCACCATCAACTGCCAGGCC

AGTCAGAGTGTTTATAGTAACTGGTTATCCTGGTATCAGCAGAAACCAGGGCAGCCTCCCAAGCGCCTGATCTATT

CTGCATCCACTCTGGCATCTGGGGTCCCATCGCGGTTCAAAGGCAGTGGATCTGGGACACAGTTCACTCTCACCAT

TAGCGACCTGGAGTGTGACGATGCTGCCACTTACTACTGTGCAGGCGGTTACAATACTGTTATTGATACTTTTGCTT

TCGGCGGAGGCACCGAGGTGGAGTTCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

-continued

420H6CHIMERICLIGHTCHAINVARIABLELIGHTCHAINNUCLEOTIDESEQUENCE

SEQ ID NO: 74

GCTCAAGTGCTGACCCAGACTGCATCGCCCGTGTCTGCCGCTGTGGGAGGCACAGTCACCATCAACTGCCAGGCC

AGTCAGAGTGTTTATAGTAACTGGTTATCCTGGTATCAGCAGAAACCAGGGCAGCCTCCCAAGCGCCTGATCTATT

CTGCATCCACTCTGGCATCTGGGGTCCCATCGCGGTTCAAAGGCAGTGGATCTGGGACACAGTTCACTCTCACCAT

TAGCGACCTGGAGTGTGACGATGCTGCCACTTACTACTGTGCAGGCGGTTACAATACTGTTATTGATACTTTTGCTT

TCGGCGGAGGCACCGAGGTGGAGTTCAAA

420H6CHIMERICLIGHTCHAINFULL-LENGTHAMINOACIDSEQUENCE. HUMANKAPPACONSTANT DOMAINISUNDERLINED

SEQ ID NO: 75

AQVLTQTASPVSAAVGGTVTINCQASQSVYSNWLSWYQQKPGQPPKRLIYSASTLASGVPSRFKGSGSGTQFTLTISDL

ECDDAATYYCAGGYNTVIDTFAFGGGTEVEFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

420H6CHIMERICLIGHTCHAINVARIABLELIGHTCHAINAMINOACIDSEQUENCE. COMPIMENTARITY DETERMININGREGIONSAREUNDERLINED

SEQ ID NO: 76

AQVLTQTASPVSAAVGGTVTINCQASQSVYSNWLSWYQQKPGQPPKRLIYSASTLASGVPSRFKGSGSGTQFTLTISDL

ECDDAATYYCAGGYNTVIDTFAFGGGTEVEFK

420H6CHIMERICHEAVYCHAINFULL-LENGTHNUCLEOTIDESEQUENCE

SEQ ID NO: 77

CAGCAGCAGCTGGAGGAGTCCGGGGGAGGCCTGGTCAAGCCTGGAGGAACCCTGACACTCACCTGCAAAGCCTC

TGGAATTGACTTCAGTAGTAGTTACTACATGTGCTGGGTCCGCCAGGCTCCAGGGGAGGGGCTGGAGTGGATCGC

ATGCATTTATACTGGTGGTAGTGGTACTCCTCACTACGCGAGCTGGGCGAAAGGCCGATTCACCATCTCCCAAACC

TCGTCGACCACGGTGACTCTGCAAATGACCAGTCTGACAGCCGCGGACACGGCCACCTATTTCTGTGCGAGAGAA

GGTAGCCTGTGGGGCCAGGGCACCCTGGTCACCGTCTCGAGCGCTAGCACCAAGGGCCCATCGGTCTTCCCCCTG

GCACCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAGACCTACATCTGCAACGTGAATC

ACAAGCCCAGCAACACCAAGGTGGACAAGAGAGTTGAGCCCAAATCTTGTGACAAAACTCACACATGCCCACCGT

GCCCAGCACCTGAAGCCGCGGGGGCACCGTCAGTCTTCCTCTTCCCCCCAAAACCCAAGGACACCCTCATGATCTC

CCGGACCCCTGAGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGTACCGTGTGGTC

AGCGTCCTCACCGTCCTGCACCAGGACTGGCTGAATGGCAAGGAGTACAAGTGCGCGGTCTCCAACAAAGCCCTC

CCAGCCCCCATCGAGAAAACCATCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGTGCTGGACTCCGACGGCTC

CTTCTTCCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGT

420H6CHIMERICHEAVYCHAINVARIABLEHEAVYCHAINNUCLEOTIDESEQUENCE

SEQ ID NO: 78

CAGCAGCAGCTGGAGGAGTCCGGGGGAGGCCTGGTCAAGCCTGGAGGAACCCTGACACTCACCTGCAAAGCCTC

TGGAATTGACTTCAGTAGTAGTTACTACATGTGCTGGGTCCGCCAGGCTCCAGGGGAGGGGCTGGAGTGGATCGC

ATGCATTTATACTGGTGGTAGTGGTACTCCTCACTACGCGAGCTGGGCGAAAGGCCGATTCACCATCTCCCAAACC

TCGTCGACCACGGTGACTCTGCAAATGACCAGTCTGACAGCCGCGGACACGGCCACCTATTTCTGTGCGAGAGAA

GGTAGCCTGTGGGGCCAGGGCACCCTGGTCACCGTCTCGAGC

420H6CHIMERICHEAVYCHAINFULL-LENGTHAMINOACIDSEQUENCE. HUMANGAMMA-1CONSTANT DOMAINISUNDERLINED

-continued

SEQ ID NO: 79
QQQLEESGGGLVKPGGTLTLTCKASGIDFSSSYYMCWVRQAPGEGLEWIACIYTGGSGTPHYASWAKGRFTISQTSSTT
VTLQMTSLTAADTATYFCAREGSLWGQGTLVTVSSASTKGPSVFPLAPSSKSTSGGTAALGCLVKDYFPEPVTVSWNSG
ALTSGVHTFPAVLQSSGLYSLSSVVTVPSSSLGTQTYICNVNHKPSNTKVDKRVEPKSCDKTHTCPPCPAPEAAGAPSVFL
FPPKPKDTLMISRTPEVTCVVVDVSHEDPEVKFNWYVDGVEVHNAKTKPREEQYNSTYRVVSVLTVLHQDWLNGKEY
KCAVSNKALPAPIEKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG

420H6CHIMERICHEAVYCHAINVARIABLEHEAVYCHAINAMINOACIDSEQUENCE. COMPLIMENTARITY DETERMININGREGIONSAREUNDERLINED

SEQ ID NO: 80
QQQLEESGGGLVKPGGTLTLTCKASGIDFSSSYYMCWVRQAPGEGLEWIACIYTGGSGTPHYASWAKGRFTISQTSSTT
VTLQMTSLTAADTATYFCAREGSLWGQGTLVTVSS

459F1CHIMERICLIGHTCHAINFULL-LENGTHNUCLEOTIDESEQUENCE

SEQ ID NO: 81
GCTCAAGTGCTGACCCAGACTGCATCGCCCGTGTCTGCCGCTGTGGGAGGCACAGTCACCATCAACTGCCAGTCCA
GTCAGAGTGTTTATAGTAACTGGTTCTCCTGGTATCAGCAGAAACCAGGGCAGCCTCCCAAGCTCCTGATCTATTCT
GCATCCACTCTGGCATCTGGGGTCCCCTCGCGGTTTAAAGGCAGTGGATCTGGGACACAGTTCACTCTCACCATCA
GCGACCTGGAGTGTGACGATGCTGCCACTTACTACTGTGCAGGCGGTTACAATACTGTAACTGATACTTTTGCTTTC
GGCGGAGGCACCGAGGTGGAGTTCAAACGTACGGTGGCTGCACCATCTGTCTTCATCTTCCCGCCATCTGATGAG
CAGTTGAAATCTGGAACTGCCTCTGTTGTGTGCCTGCTGAATAACTTCTATCCCAGAGAGGCCAAAGTACAGTGGA
AGGTGGATAACGCCCTCCAATCGGGTAACTCCCAGGAGAGTGTCACAGAGCAGGACAGCAAGGACAGCACCTAC
AGCCTCAGCAGCACCCTGACGCTGAGCAAAGCAGACTACGAGAAACACAAAGTCTACGCCTGCGAAGTCACCCAT
CAGGGCCTGAGCTCGCCCGTCACAAAGAGCTTCAACAGGGGAGAGTGT

459F1CHIMERICLIGHTCHAINVARIABLELIGHTCHAINNUCLEOTIDESEQUENCE

SEQ ID NO: 82
GCTCAAGTGCTGACCCAGACTGCATCGCCCGTGTCTGCCGCTGTGGGAGGCACAGTCACCATCAACTGCCAGTCCA
GTCAGAGTGTTTATAGTAACTGGTTCTCCTGGTATCAGCAGAAACCAGGGCAGCCTCCCAAGCTCCTGATCTATTCT
GCATCCACTCTGGCATCTGGGGTCCCCTCGCGGTTTAAAGGCAGTGGATCTGGGACACAGTTCACTCTCACCATCA
GCGACCTGGAGTGTGACGATGCTGCCACTTACTACTGTGCAGGCGGTTACAATACTGTAACTGATACTTTTGCTTTC
GGCGGAGGCACCGAGGTGGAGTTCAAA

459F1CHIMERICLIGHTCHAINFULL-LENGTHAMINOACIDSEQUENCE. HUMANKAPPACONSTANT DOMAINISUNDERLINED

SEQ ID NO: 83
AQVLTQTASPVSAAVGGTVTINCQSSQSVYSNWFSWYQQKPGQPPKLLIYSASTLASGVPSRFKGSGSGTQFTLTISDLE
CDDAATYYCAGGYNTVTDTFAFGGGTEVEFKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGEC

459F1CHIMERICLIGHTCHAINVARIABLELIGHTCHAINAMINOACIDSEQUENCE. COMPIMENTARITY DETERMININGREGIONSAREUNDERLINED

SEQ ID NO: 84
AQVLTQTASPVSAAVGGTVTINCQSSQSVYSNWFSWYQQKPGQPPKLLIYSASTLASGVPSRFKGSGSGTQFTLTISDLE
CDDAATYYCAGGYNTVTDTFAFGGGTEVEFK

459F1CHIMERICHEAVYCHAINFULL-LENGTHNUCLEOTIDESEQUENCE

SEQ ID NO: 85
GAGTCGTTGGAGGAGTCCGGGGGAGACCTGGTCAAGCCTGGGGCATCCCTGACACTCACCTGCACAGCCTCTGG
AATCGACTTCAGTAGGAGATACTACATGTGCTGGGTCCGCCAGGCTCCAGGGAAGGGGCTGGAGTGGATCGCAT
GCATGTATACTGGTAGCCGCGATACTCCTCACTACGCGAGCTGGGCGAAAGGCCGGTTCACCATCTCCCAAACCTC
GTCGACCACGGTGACTCTGCAAATGACCAGTCTGACAGCCGCGGACACGGCCACCTATTTCTGTGCGAGAGAAGG
TAACCTGTGGGGCCCGGGGACCCTGGTCACCGTCTCGAGCGCTAGCACCAAGGGCCCATCGGTCTTCCCCCTGGC
ACCCTCCTCCAAGAGCACCTCTGGGGGCACAGCGGCCCTGGGCTGCCTGGTCAAGGACTACTTCCCCGAACCGGT

-continued

GACGGTGTCGTGGAACTCAGGCGCCCTGACCAGCGGCGTGCACACCTTCCCGGCTGTCCTACAGTCCTCAGGACT

CTACTCCCTCAGCAGCGTGGTGACCGTGCCCTCCAGCAGCTTGGGCACCCAGACCTACATCTGCAACGTGAATCAC

AAGCCCAGCAACACCAAGGTGGACAAGAGAGTTGAGCCCAAATCTTGTGACAAAACTCACACATGCCCACCGTGC

CCAGCACCTGAAGCCGCGGGGGCACCGTCAGTCTTCCTCTTCCCCCCAAAACCCAAGGACACCCTCATGATCTCCC

GGACCCCTGAGGTCACATGCGTGGTGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCGCGGTCTCCAACAAAGCCCTCC

CAGCCCCCATCGAGAAAACCATCTCCAAAGCCAAAGGGCAGCCCCGAGAACCACAGGTGTACACCCTGCCCCCAT

CCCGGGATGAGCTGACCAAGAACCAGGTCAGCCTGACCTGCCTGGTCAAAGGCTTCTATCCCAGCGACATCGCCG

TGGAGTGGGAGAGCAATGGGCAGCCGGAGAACAACTACAAGACCACGCCTCCCGTGCTGGACTCCGACGGCTCC

TTCTTCCTCTATAGCAAGCTCACCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGT

459F1CHIMERICHEAVYCHAINVARIABLEHEAVYCHAINNUCLEOTIDESEQUENCE

SEQ ID NO: 86

GAGTCGTTGGAGGAGTCCGGGGGAGACCTGGTCAAGCCTGGGGCATCCCTGACACTCACCTGCACAGCCTCTGG

AATCGACTTCAGTAGGAGATACTACATGTGCTGGGTCCGCCAGGCTCCAGGGAAGGGGCTGGAGTGGATCGCAT

GCATGTATACTGGTAGCCGCGATACTCCTCACTACGCGAGCTGGGCGAAAGGCCGGTTCACCATCTCCCAAACCTC

GTCGACCACGGTGACTCTGCAAATGACCAGTCTGACAGCCGCGGACACGGCCACCTATTTCTGTGCGAGAGAAGG

TAACCTGTGGGGCCCGGGGACCCTGGTCACCGTCTCGAGC

459F1 CHIMERIC HEAVY CHAIN FULL-LENGTH AMINO ACID SEQUENCE. HUMAN GAMMA-1 CONSTANT DOMAINISUNDERLINED

SEQ ID NO: 87

ESLEESGGDLVKPGASLTLTCTASGIDFSRRYYMCWVRQAPGKGLEWIACMYTGSRDTPHYASWAKGRFTISQTSSTTV

TLQMTSLTAADTATYFCAREGNLWGPGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLF

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

459F1CHIMERICHEAVYCHAINVARIABLEHEAVYCHAINAMINOACIDSEQUENCE. COMPLIMENTARITY DETERMININGREGIONSAREUNDERLINED

SEQ ID NO: 88

ESLEESGGDLVKPGASLTLTCTASGIDFSRRYYMCWVRQAPGKGLEWIACMYTGSRDTPHYASWAKGRFTISQTSSTTV

TLQMTSLTAADTATYFCAREGNLWGPGTLVTVSS

460C3CHIMERICLIGHTCHAINFULL-LENGTHNUCLEOTIDESEQUENCE

SEQ ID NO: 89

GCCCAAGTGCTGACCCAGACTCCATCGTCCGTGTCTGCAGCTGTGGGAGGCACAGTCAGCATCAGTTGCCAGTCC

AGTCAGAGTGTTTATAGTAACTGGTTCTCCTGGTATCAGCAGAAACCAGGGCAGCCTCCCAAGCTCCTGATCTATT

CTGCATCCACTCTGGCATCTGGGGTCCCCTCGCGGTTTAAAGGCAGTGGATCTGGGACACAGTTCACTCTCACCAT

CAGCGACCTGGAGTGTGACGATGCTGCCACTTACTACTGTGCAGGCGGTTACAATACTGTTATTGATACTTTTGCTT

TCGGCGGAGGCACCGAGGTGGAGTTCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

460C3CHIMERICLIGHTCHAINVARIABLELIGHTCHAINNUCLEOTIDESEQUENCE

-continued

SEQ ID NO: 90

GCCCAAGTGCTGACCCAGACTCCATCGTCCGTGTCTGCAGCTGTGGGAGGCACAGTCAGCATCAGTTGCCAGTCC

AGTCAGAGTGTTTATAGTAACTGGTTCTCCTGGTATCAGCAGAAACCAGGGCAGCCTCCCAAGCTCCTGATCTATT

CTGCATCCACTCTGGCATCTGGGGTCCCCTCGCGGTTTAAAGGCAGTGGATCTGGGACACAGTTCACTCTCACCAT

CAGCGACCTGGAGTGTGACGATGCTGCCACTTACTACTGTGCAGGCGGTTACAATACTGTTATTGATACTTTTGCTT

TCGGCGGAGGCACCGAGGTGGAGTTCAAA

460C3CHIMERICLIGHTCHAINFULL-LENGTHAMINOACIDSEQUENCE. HUMANKAPPACONSTANT DOMAINISUNDERLINED

SEQ ID NO: 91

AQVLTQTPSSVSAAVGGTVSISCQSSQSVYSNWFSWYQQKPGQPPKLLIYSASTLASGVPSRFKGSGSGTQFTLTISDLE

CDDAATYYCAGGYNTVIDTFAFGGGTEVEFKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

460C3CHIMERICLIGHTCHAINVARIABLELIGHTCHAINAMINOACIDSEQUENCE. COMPIMENTARITY DETERMININGREGIONSAREUNDERLINED

SEQ ID NO: 92

AQVLTQTPSSVSAAVGGTVSISCQSSQSVYSNWFSWYQQKPGQPPKLLIYSASTLASGVPSRFKGSGSGTQFTLTISDLE

CDDAATYYCAGGYNTVIDTFAFGGGTEVEFK

460C3CHIMERICHEAVYCHAINFULL-LENGTHNUCLEOTIDESEQUENCE

SEQ ID NO: 93

CAGTCGTTGGAGGAGTCCGGGGGAGACCTGGTCAAGCCTGGGGCATCCCTGACACTCACCTGCACAGCCTCTGGA

ATCGACTTCAGTAGGAGATACTACATGTGCTGGGTCCGCCAGGCTCCAGGGAAGGGGCTGGAGTGGATCGCATG

CATATATACTGGTAGCCGCGATACTCCTCACTACGCGAGCTGGGCGAAAGGCCGATTCACCATCTCCCAAACCTCG

TCGACCACGGTGACTCTGCAAATGACCAGTCTGACAGCCGCGGACACGGCCACCTATTTCTGTGCGAGAGAAGGT

AGCCTGTGGGGCCAGGGCACCCTGGTCACCGTCTCGAGCGCTAGCACCAAGGGCCCATCGGTCTTCCCCCTGGCA

CCCTCCTCCAAGAGCACCTCTGGGGGCACAGCGGCCCTGGGCTGCCTGGTCAAGGACTACTTCCCCGAACCGGTG

ACGGTGTCGTGGAACTCAGGCGCCCTGACCAGCGGCGTGCACACCTTCCCGGCTGTCCTACAGTCCTCAGGACTCT

ACTCCCTCAGCAGCGTGGTGACCGTGCCCTCCAGCAGCTTGGGCACCCAGACCTACATCTGCAACGTGAATCACAA

GCCCAGCAACACCAAGGTGGACAAGAGAGTTGAGCCCAAATCTTGTGACAAAACTCACACATGCCCACCGTGCCC

AGCACCTGAAGCCGCGGGGGCACCGTCAGTCTTCCTCTTCCCCCCAAAACCCAAGGACACCCTCATGATCTCCCGG

ACCCCTGAGGTCACATGCGTGGTGGTGGACGTGAGCCACGAAGACCCTGAGGTCAAGTTCAACTGGTACGTGGA

CGGCGTGGAGGTGCATAATGCCAAGACAAAGCCGCGGGAGGAGCAGTACAACAGCACGTACCGTGTGGTCAGC

GTCCTCACCGTCCTGCACCAGGACTGGCTGAATGGCAAGGAGTACAAGTGCGCGGTCTCCAACAAAGCCCTCCCA

GCCCCCATCGAGAAAACCATCTCCAAAGCCAAAGGGCAGCCCCGAGAACCACAGGTGTACACCCTGCCCCCATCC

CGGGATGAGCTGACCAAGAACCAGGTCAGCCTGACCTGCCTGGTCAAAGGCTTCTATCCCAGCGACATCGCCGTG

GAGTGGGAGAGCAATGGGCAGCCGGAGAACAACTACAAGACCACGCCTCCCGTGCTGGACTCCGACGGCTCCTT

CTTCCTCTATAGCAAGCTCACCGTGGACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGGGT

460C3CHIMERICHEAVYCHAINVARIABLEHEAVYCHAINNUCLEOTIDESEQUENCE

SEQ ID NO: 94

CAGTCGTTGGAGGAGTCCGGGGGAGACCTGGTCAAGCCTGGGGCATCCCTGACACTCACCTGCACAGCCTCTGGA

ATCGACTTCAGTAGGAGATACTACATGTGCTGGGTCCGCCAGGCTCCAGGGAAGGGGCTGGAGTGGATCGCATG

CATATATACTGGTAGCCGCGATACTCCTCACTACGCGAGCTGGGCGAAAGGCCGATTCACCATCTCCCAAACCTCG

TCGACCACGGTGACTCTGCAAATGACCAGTCTGACAGCCGCGGACACGGCCACCTATTTCTGTGCGAGAGAAGGT

AGCCTGTGGGGCCAGGGCACCCTGGTCACCGTCTCGAGC

460C3CHIMERICHEAVYCHAINFULL-LENGTHAMINOACIDSEQUENCE. HUMANGAMMA-1CONSTANT DOMAINISUNDERLINED

SEQ ID NO: 95

QSLEESGGDLVKPGASLTLTCTASGIDFSRRYYMCWVRQAPGKGLEWIACIYTGSRDTPHYASWAKGRFTISQTSSTTV

-continued

TLQMTSLTAADTATYFCAREGSLWGQGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLF

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

460C3CHIMERICHEAVYCHAINVARIABLEHEAVYCHAINAMINOACIDSEQUENCE. COMPLIMENTARITY DETERMININGREGIONSAREUNDERLINED

SEQ ID NO: 96

QSLEESGGDLVKPGASLTLTCTASGIDFSRRYYMCWVRQAPGKGLEWIACIYTGSRDTPHYASWAKGRFTISQTSSTTV

TLQMTSLTAADTATYFCAREGSLWGQGTLVTVSS

464D11CHIMERICLIGHTCHAINFULL-LENGTHNUCLEOTIDESEQUENCE

SEQ ID NO: 97

GCGCAAGTGCTGACCCAGACTCCATCGCCTGTGTCTGCAGCTGTGGGAGGCACAGTCACCATCAATTGCCAGTCCA

GTCAGAGTGTTTATAGTAACAGCTTCTTATCCTGGTATCAGCAGAAACCAGGGCAGCCTCCCAAGCGCCTGATCTA

TTCTGCATCCGATCTGGCATCTGGGGTCCCATCGCGGTTCAAAGGCAGTGGATCTGGGACACAGTTCACTCTCACC

ATCAGCGACCTGGAGTGTGACGATGCTGCCACTTACTACTGTGCAGGCGTTTATAGTGATAATACTTATGTTTTCG

GCGGAGGCACCGAGGTGGAGTTCAAACGTACGGTGGCTGCACCATCTGTCTTCATCTTCCCGCCATCTGATGAGC

AGTTGAAATCTGGAACTGCCTCTGTTGTGTGCCTGCTGAATAACTTCTATCCCAGAGAGGCCAAAGTACAGTGGAA

GGTGGATAACGCCCTCCAATCGGGTAACTCCCAGGAGAGTGTCACAGAGCAGGACAGCAAGGACAGCACCTACA

GCCTCAGCAGCACCCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGT

464D11CHIMERICLIGHTCHAINVARIABLELIGHTCHAINNUCLEOTIDESEQUENCE

SEQ ID NO: 98

GCGCAAGTGCTGACCCAGACTCCATCGCCTGTGTCTGCAGCTGTGGGAGGCACAGTCACCATCAATTGCCAGTCCA

GTCAGAGTGTTTATAGTAACAGCTTCTTATCCTGGTATCAGCAGAAACCAGGGCAGCCTCCCAAGCGCCTGATCTA

TTCTGCATCCGATCTGGCATCTGGGGTCCCATCGCGGTTCAAAGGCAGTGGATCTGGGACACAGTTCACTCTCACC

ATCAGCGACCTGGAGTGTGACGATGCTGCCACTTACTACTGTGCAGGCGTTTATAGTGATAATACTTATGTTTTCG

GCGGAGGCACCGAGGTGGAGTTCAAA

464D11CHIMERICLIGHTCHAINFULL-LENGTHAMINOACIDSEQUENCE. HUMANKAPPACONSTANT DOMAINISUNDERLINED

SEQ ID NO: 99

AQVLTQTPSPVSAAVGGTVTINCQSSQSVYSNSFLSWYQQKPGQPPKRLIYSASDLASGVPSRFKGSGSGTQFTLTISDL

ECDDAATYYCAGVYSDNTYVFGGGTEVEFKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

464D11CHIMERICLIGHTCHAINVARIABLELIGHTCHAINAMINOACIDSEQUENCE. COMPIMENTARITY DETERMININGREGIONSAREUNDERLINED

SEQ ID NO: 100

AQVLTQTPSPVSAAVGGTVTINCQSSQSVYSNSFLSWYQQKPGQPPKRLIYSASDLASGVPSRFKGSGSGTQFTLTISDL

ECDDAATYYCAGVYSDNTYVFGGGTEVEFK

464D11CHIMERICHEAVYCHAINFULL-LENGTHNUCLEOTIDESEQUENCE

SEQ ID NO: 101

CAGTCGGTGGAGGAGTCCGGCGGTCGCCTGGTAAAGCCTGACGAATCCCTGACACTCACCTGCACAGCCTCTGGA

TTCTCCCTCAGTCACTACTGGATGACTTGGGTCCGACAGGCTCCAGGGAAGGGACTGGAATACATCGGATTCATTA

ATGTTGGTGGTGACACATCTTACGCGAGCTGGTCGAAAGGCCGATTCACCATCTCCAAGGCCTCGACCACGGTGG

ATCTGAAGATCAGTAGTCTGACAACCGAGGACACGGCCACCTATTTCTGTGGCAGAGGTGGTCTGACTTTTGGTTG

GGACTTGTGGGGCCCAGGGACCCTCGTCACCGTCTCGAGCGCTAGCACCAAGGGCCCATCGGTCTTCCCCCTGGC

ACCCTCCTCCAAGAGCACCTCTGGGGGCACAGCGGCCCTGGGCTGCCTGGTCAAGGACTACTTCCCCGAACCGGT

-continued

GACGGTGTCGTGGAACTCAGGCGCCCTGACCAGCGGCGTGCACACCTTCCCGGCTGTCCTACAGTCCTCAGGACT

CTACTCCCTCAGCAGCGTGGTGACCGTGCCCTCCAGCAGCTTGGGCACCCAGACCTACATCTGCAACGTGAATCAC

AAGCCCAGCAACACCAAGGTGGACAAGAGAGTTGAGCCCAAATCTTGTGACAAAACTCACACATGCCCACCGTGC

CCAGCACCTGAAGCCGCGGGGGCACCGTCAGTCTTCCTCTTCCCCCCAAAACCCAAGGACACCCTCATGATCTCCC

GGACCCCTGAGGTCACATGCGTGGTGGTGGACGTGAGCCACGAAGACCCTGAGGTCAAGTTCAACTGGTACGTG

GACGGCGTGGAGGTGCATAATGCCAAGACAAAGCCGCGGGAGGAGCAGTACAACAGCACGTACCGTGTGGTCA

GCGTCCTCACCGTCCTGCACCAGGACTGGCTGAATGGCAAGGAGTACAAGTGCGCGGTCTCCAACAAAGCCCTCC

CAGCCCCCATCGAGAAAACCATCTCCAAAGCCAAAGGGCAGCCCCGAGAACCACAGGTGTACACCCTGCCCCCAT

CCCGGGATGAGCTGACCAAGAACCAGGTCAGCCTGACCTGCCTGGTCAAAGGCTTCTATCCCAGCGACATCGCCG

TGGAGTGGGAGAGCAATGGGCAGCCGGAGAACAACTACAAGACCACGCCTCCCGTGCTGGACTCCGACGGCTCC

TTCTTCCTCTATAGCAAGCTCACCGTGGACAAGAGCAGGTGGCAGCAGGGGAACGTCTTCTCATGCTCCGTGATGC

ATGAGGCTCTGCACAACCACTACACGCAGAAGAGCCTCTCCCTGTCTCCGGGT

464D11CHIMERICHEAVYCHAINVARIABLEHEAVYCHAINNUCLEOTIDESEQUENCE

SEQ ID NO: 102

CAGTCGGTGGAGGAGTCCGGCGGTCGCCTGGTAAAGCCTGACGAATCCCTGACACTCACCTGCACAGCCTCTGGA

TTCTCCCTCAGTCACTACTGGATGACTTGGGTCCGACAGGCTCCAGGGAAGGGACTGGAATACATCGGATTCATTA

ATGTTGGTGGTGACACATCTTACGCGAGCTGGTCGAAAGGCCGATTCACCATCTCCAAGGCCTCGACCACGGTGG

ATCTGAAGATCAGTAGTCTGACAACCGAGGACACGGCCACCTATTTCTGTGGCAGAGGTGGTCTGACTTTTGGTTG

GGACTTGTGGGGCCCAGGGACCCTCGTCACCGTCTCGAGC

464D11CHIMERICHEAVYCHAINFULL-LENGTHAMINOACIDSEQUENCE. HUMANGAMMA-1 CONSTANTDOMAINISUNDERLINED

SEQ ID NO: 103

QSVEESGGRLVKPDESLTLTCTASGFSLSHYWMTWVRQAPGKGLEYIGFINVGGDTSYASWSKGRFTISKASTTVDLKIS

SLTTEDTATYFCGRGGLTFGWDLWGPGTLVTVSSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKRVEPKSCDKTHTCPPCPAPEAAGAPSVFL

FPPKPKDTLMISRTPEVTCVVVDVSHEDPEVKFNWYVDGVEVHNAKTKPREEQYNSTYRVVSVLTVLHQDWLNGKEY

KCAVSNKALPAPIEKTISKAKGQPREPQVYTLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPG

464D11CHIMERICHEAVYCHAINVARIABLEHEAVYCHAINAMINOACIDSEQUENCE. COMPLIMENTARITYDETERMININGREGIONSAREUNDERLINED

SEQ ID NO: 104

QSVEESGGRLVKPDESLTLTCTASGFSLSHYWMTWVRQAPGKGLEYIGFINVGGDTSYASWSKGRFTISKASTTVDLKIS

SLTTEDTATYFCGRGGLTFGWDLWGPGTLVTVSS

466F6CHIMERICLIGHTCHAINFULL-LENGTHNUCLEOTIDESEQUENCE

SEQ ID NO: 105

GATGTTGTGATGACCCAGACTCCAGCCTCCGTGTCTGAACCTGTGGGAGGCACAGTCACCATCAAGTGCCAGGCC

AGTCAGAACATTAGGACTTACTTATCCTGGTATCAGCAGAAACCAGGGCAGCGTCCCAAGCTCCTGATCTATGCTG

CAGCCAATCTGGCATCTGGGGTCCCATCGCGGTTCAGTGGCAGTAGATCTGGGACAGAGTTCACTCTCACCATCAG

CGACCTGGAGTGTGCCGATGCTGCCACTTACTATTGTCAGTGTACCTATCTTGGTACTGATTATGTTGGCGGTGCTT

TCGGCGGAGGCACCGAGGTGGAGTTCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

466F6CHIMERICLIGHTCHAINVARIABLELIGHTCHAINNUCLEOTIDESEQUENCE

SEQ ID NO: 106

GATGTTGTGATGACCCAGACTCCAGCCTCCGTGTCTGAACCTGTGGGAGGCACAGTCACCATCAAGTGCCAGGCC

-continued

AGTCAGAACATTAGGACTTACTTATCCTGGTATCAGCAGAAACCAGGGCAGCGTCCCAAGCTCCTGATCTATGCTG

CAGCCAATCTGGCATCTGGGGTCCCATCGCGGTTCAGTGGCAGTAGATCTGGGACAGAGTTCACTCTCACCATCAG

CGACCTGGAGTGTGCCGATGCTGCCACTTACTATTGTCAGTGTACCTATCTTGGTACTGATTATGTTGGCGGTGCTT

TCGGCGGAGGCACCGAGGTGGAGTTCAAA

466F6CHIMERICLIGHTCHAINFULL-LENGTHAMINOACIDSEQUENCE. HUMANKAPPACONSTANT DOMAINISUNDERLINED

SEQ ID NO: 107

DVVMTQTPASVSEPVGGTVTIKCQASQNIRTYLSWYQQKPGQRPKLLIYAAANLASGVPSRFSGSRSGTEFTLTISDLEC

ADAATYYCQCTYLGTDYVGGAFGGGTEVEFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

466F6CHIMERICLIGHTCHAINVARIABLELIGHTCHAINAMINOACIDSEQUENCE. COMPIMENTARITY DETERMININGREGIONSAREUNDERLINED

SEQ ID NO: 108

DVVMTQTPASVSEPVGGTVTIKCQASQNIRTYLSWYQQKPGQRPKLLIYAAANLASGVPSRFSGSRSGTEFTLTISDLEC

ADAATYYCQCTYLGTDYVGGAFGGGTEVEFK

466F6CHIMERICHEAVYCHAINFULL-LENGTHNUCLEOTIDESEQUENCE

SEQ ID NO: 109

CGGTCGCTGGAGGAGTCCGGGGGTCGCCTGGTCACGCCTGGGACACCCCTGACACTCACCTGCACAGCCTCTGGA

TTCACCATCAGTAGCTACCACATGCAGTGGGTCCGCCAGGCTCCAGGGAAGGGGCTGGAATACATCGGAACCATT

AGTAGTGGTGGTAATGTATACTACGCGAGCTGGGCGAGAGGCCGATTCACCATCTCCAGACCCTCGTCGACCACG

GTGGATCTGAAGATGACCAGTCTGACAACCGAGGACACGGCCACCTATTTCTGTGCCAGAGACTCTGGTTATAGT

GATCCTATGTGGGGCCCGGGCACCCTGGTCACCGTCTCGAGCGCTAGCACCAAGGGCCCATCGGTCTTCCCCCTG

GCACCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAGACCTACATCTGCAACGTGAATC

ACAAGCCCAGCAACACCAAGGTGGACAAGAGAGTTGAGCCCAAATCTTGTGACAAAACTCACACATGCCCACCGT

GCCCAGCACCTGAAGCCGCGGGGGCACCGTCAGTCTTCCTCTTCCCCCCAAAACCCAAGGACACCCTCATGATCTC

CCGGACCCCTGAGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGTACCGTGTGGTC

AGCGTCCTCACCGTCCTGCACCAGGACTGGCTGAATGGCAAGGAGTACAAGTGCGCGGTCTCCAACAAAGCCCTC

CCAGCCCCCATCGAGAAAACCATCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGTGCTGGACTCCGACGGCTC

CTTCTTCCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGT

466F6CHIMERICHEAVYCHAINVARIABLEHEAVYCHAINNUCLEOTIDESEQUENCE

SEQ ID NO: 110

CGGTCGCTGGAGGAGTCCGGGGGTCGCCTGGTCACGCCTGGGACACCCCTGACACTCACCTGCACAGCCTCTGGA

TTCACCATCAGTAGCTACCACATGCAGTGGGTCCGCCAGGCTCCAGGGAAGGGGCTGGAATACATCGGAACCATT

AGTAGTGGTGGTAATGTATACTACGCGAGCTGGGCGAGAGGCCGATTCACCATCTCCAGACCCTCGTCGACCACG

GTGGATCTGAAGATGACCAGTCTGACAACCGAGGACACGGCCACCTATTTCTGTGCCAGAGACTCTGGTTATAGT

GATCCTATGTGGGGCCCGGGCACCCTGGTCACCGTCTCGAGC

466F6CHIMERICHEAVYCHAINFULL-LENGTHAMINOACIDSEQUENCE. HUMANGAMMA-1CONSTANT DOMAINISUNDERLINED

SEQ ID NO: 111

RSLEESGGRLVTPGTPLTLTCTASGFTISSYHMQWVRQAPGKGLEYIGTISSGGNVYYASWARGRFTISRPSSTTVDLKM

TSLTTEDTATYFCARDSGYSDPMWGPGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLF

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

466F6CHIMERICHEAVYCHAINVARIABLEHEAVYCHAINAMINOACIDSEQUENCE. COMPLIMENTARITY DETERMININGREGIONSAREUNDERLINED

SEQ ID NO: 112

RSLEESGGRLVTPGTPLTLTCTASGFTISSYHMQWVRQAPGKGLEYIGTISSGGNVYYASWARGRFTISRPSSTTVDLKM

TSLTTEDTATYFCARDSGYSDPMWGPGTLVTVSS

470B6CHIMERICLIGHTCHAINFULL-LENGTHNUCLEOTIDESEQUENCE

SEQ ID NO: 113

GCAGCCGTGCTGACCCAGACACCATCGCCCGTGTCTGCAGCTGTGGGAGGCACAGTCACCATCAGTTGCCAGTCC

AGTCAGAGTGTTTATAGTAACAACCAATTATCCTGGTTTCAGCAGAAATCAGGGCAGCCTCCCAAGCTCCTGATCT

ATGATGCATCCAATCTGGCATCTGGGGTCCCATCACGGTTCAGCGGCAGTGGATCTGGGACACAGTTCACTCTCAC

CATCAGCAGCGTGCAGTGTGACGATGCTGCCACTTACCACTGTCTAGGCGGTAGTGATGATGATGGTGATATTGCT

TTCGGCGGAGGCACCGAGGTGGTGTTCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

470B6CHIMERICLIGHTCHAINVARIABLELIGHTCHAINNUCLEOTIDESEQUENCE

SEQ ID NO: 114

GCAGCCGTGCTGACCCAGACACCATCGCCCGTGTCTGCAGCTGTGGGAGGCACAGTCACCATCAGTTGCCAGTCC

AGTCAGAGTGTTTATAGTAACAACCAATTATCCTGGTTTCAGCAGAAATCAGGGCAGCCTCCCAAGCTCCTGATCT

ATGATGCATCCAATCTGGCATCTGGGGTCCCATCACGGTTCAGCGGCAGTGGATCTGGGACACAGTTCACTCTCAC

CATCAGCAGCGTGCAGTGTGACGATGCTGCCACTTACCACTGTCTAGGCGGTAGTGATGATGATGGTGATATTGCT

TTCGGCGGAGGCACCGAGGTGGTGTTCAAA

470B6CHIMERICLIGHTCHAINFULL-LENGTHAMINOACIDSEQUENCE. HUMANKAPPACONSTANT DOMAINISUNDERLINED

SEQ ID NO: 115

AAVLTQTPSPVSAAVGGTVTISCQSSQSVYSNNQLSWFQQKSGQPPKLLIYDASNLASGVPSRFSGSGSGTQFTLTISSV

QCDDAATYHCLGGSDDDGDIAFGGGTEVVFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

470B6CHIMERICLIGHTCHAINVARIABLELIGHTCHAINAMINOACIDSEQUENCE. COMPIMENTARITY DETERMININGREGIONSAREUNDERLINED

SEQ ID NO: 116

AAVLTQTPSPVSAAVGGTVTISCQSSQSVYSNNQLSWFQQKSGQPPKLLIYDASNLASGVPSRFSGSGSGTQFTLTISSV

QCDDAATYHCLGGSDDDGDIAFGGGTEVVFK

470B6CHIMERICHEAVYCHAINFULL-LENGTHNUCLEOTIDESEQUENCE

SEQ ID NO: 117

CAGTCACTGGAGGAGTCCGGGGGTCGCCTGGTCACGCCTGGGACACCCCTGACACTCACCTGCACAGCCTCTGGA

TTCTCCCTCAGTAGCTACTACATGAGCTGGGTCCGCCAGGCTCCAGGGAAGGGACTGGAATGGATCGGAAGTATT

TATGGTAGTGGTGCCGCATACTACGCGAGCTGGGCGAAAGGCCGATTCACCATCTCCAGAACGTCGACCACGGTG

GATCTGAAAATGACCAGTCTGACAGCCGCGGACACGGCCACCTATTTCTGTGCCAGAGATCCTATTAACAATGCCA

TGTGGGGCCCAGGCACCCTGGTCACCGTCTCGAGCGCTAGCACCAAGGGCCCATCGGTCTTCCCCCTGGCACCCTC

CTCCAAGAGCACCTCTGGGGGCACAGCGGCCCTGGGCTGCCTGGTCAAGGACTACTTCCCCGAACCGGTGACGGT

GTCGTGGAACTCAGGCGCCCTGACCAGCGGCGTGCACACCTTCCCGGCTGTCCTACAGTCCTCAGGACTCTACTCC

CTCAGCAGCGTGGTGACCGTGCCCTCCAGCAGCTTGGGCACCCAGACCTACATCTGCAACGTGAATCACAAGCCC

-continued

AGCAACACCAAGGTGGACAAGAGAGTTGAGCCCAAATCTTGTGACAAAACTCACACATGCCCACCGTGCCCAGCA

CCTGAAGCCGCGGGGGCACCGTCAGTCTTCCTCTTCCCCCCAAAACCCAAGGACACCCTCATGATCTCCCGGACCC

CTGAGGTCACATGCGTGGTGGTGGACGTGAGCCACGAAGACCCTGAGGTCAAGTTCAACTGGTACGTGGACGGC

GTGGAGGTGCATAATGCCAAGACAAAGCCGCGGGAGGAGCAGTACAACAGCACGTACCGTGTGGTCAGCGTCCT

CACCGTCCTGCACCAGGACTGGCTGAATGGCAAGGAGTACAAGTGCGCGGTCTCCAACAAAGCCCTCCCAGCCCC

CATCGAGAAAACCATCTCCAAAGCCAAAGGGCAGCCCCGAGAACCACAGGTGTACACCCTGCCCCCATCCCGGGA

TGAGCTGACCAAGAACCAGGTCAGCCTGACCTGCCTGGTCAAAGGCTTCTATCCCAGCGACATCGCCGTGGAGTG

GGAGAGCAATGGGCAGCCGGAGAACAACTACAAGACCACGCCTCCCGTGCTGGACTCCGACGGCTCCTTCTTCCT

CTATAGCAAGCTCACCGTGGACAAGAGCAGGTGGCAGCAGGGGAACGTCTTCTCATGCTCCGTGATGCATGAGGC

TCTGCACAACCACTACACGCAGAAGAGCCTCTCCCTGTCTCCGGGT

470B6CHIMERICHEAVYCHAININVARIABLEHEAVYCHAINNUCLEOTIDESEQUENCE

SEQ ID NO: 118

CAGTCACTGGAGGAGTCCGGGGGTCGCCTGGTCACGCCTGGGACACCCCTGACACTCACCTGCACAGCCTCTGGA

TTCTCCCTCAGTAGCTACTACATGAGCTGGGTCCGCCAGGCTCCAGGGAAGGGACTGGAATGGATCGGAAGTATT

TATGGTAGTGGTGCCGCATACTACGCGAGCTGGGCGAAAGGCCGATTCACCATCTCCAGAACGTCGACCACGGTG

GATCTGAAAATGACCAGTCTGACAGCCGCGGACACGGCCACCTATTTCTGTGCCAGAGATCCTATTAACAATGCCA

TGTGGGGCCCAGGCACCCTGGTCACCGTCTCGAGC

470B6 CHIMERIC HEAVY CHAIN FULL-LENGTH AMINO ACID SEQUENCE. HUMAN GAMMA-1 CONSTANT DOMAINISUNDERLINED

SEQ ID NO: 119

QSLEESGGRLVTPGTPLTLTCTASGFSLSSYYMSWVRQAPGKGLEWIGSIYGSGAAYYASWAKGRFTISRTSTTVDLKMT

SLTAADTATYFCARDPINNAMWGPGTLVTVSSASTKGPSVFPLAPSSKSTSGGTAALGCLVKDYFPEPVTVSWNSGALT

SGVHTFPAVLQSSGLYSLSSVVTVPSSSLGTQTYICNVNHKPSNTKVDKRVEPKSCDKTHTCPPCPAPEAAGAPSVFLFPP

KPKDTLMISRTPEVTCVVVDVSHEDPEVKFNWYVDGVEVHNAKTKPREEQYNSTYRVVSVLTVLHQDWLNGKEYKCA

VSNKALPAPIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPG

470B6CHIMERICHEAVYCHAINVARIABLEHEAVYCHAINAMINOACIDSEQUENCE. COMPLIMENTARITY DETERMININGREGIONSAREUNDERLINED

SEQ ID NO: 120

QSLEESGGRLVTPGTPLTLTCTASGFSLSSYYMSWVRQAPGKGLEWIGSIYGSGAAYYASWAKGRFTISRTSTTVDLKMT

SLTAADTATYFCARDPINNAMWGPGTLVTVSS

470C6CHIMERICLIGHTCHAINFULL-LENGTHNUCLEOTIDESEQUENCE

SEQ ID NO: 121

GCCCTTGTGATGACCCAGACTCCAGCCTCCGTGTCTGCAGCTGTGGGAGGCACAGTCACCATCAATTGCCAGGCCA

GTGAGGACATTGATAACTATTTAGCCTGGTATCAGCAGAAACCAGGGCAGCCTCCCAAGCTCCTGATCTTTTATGC

ATCCGATCTGGCATCTGGGGTCCCATCGCGGTTCTCAGGCAGTGGATCTGGGACACAGTTCACTCTCACCATCAGC

GGTGTGCAGTGTGACGATGCTGCCACTTACTACTGTCAAGGCGGTTACTATACTAGTAGTACTGATACGAGGGGT

GCTTTCGGCGGAGGCACCGAGGTGGTGGTCAAACGTACGGTGGCTGCACCATCTGTCTTCATCTTCCCGCCATCTG

ATGAGCAGTTGAAATCTGGAACTGCCTCTGTTGTGTGCCTGCTGAATAACTTCTATCCCAGAGAGGCCAAAGTACA

GTGGAAGGTGGATAACGCCCTCCAATCGGGTAACTCCCAGGAGAGTGTCACAGAGCAGGACAGCAAGGACAGCA

CCTACAGCCTCAGCAGCACCCTGACGCTGAGCAAAGCAGACTACGAGAAACACAAAGTCTACGCCTGCGAAGTCA

CCCATCAGGGCCTGAGCTCGCCCGTCACAAAGAGCTTCAACAGGGGAGAGTGT

470C6CHIMERICLIGHTCHAINVARIABLELIGHTCHAINNUCLEOTIDESEQUENCE

SEQ ID NO: 122

GCCCTTGTGATGACCCAGACTCCAGCCTCCGTGTCTGCAGCTGTGGGAGGCACAGTCACCATCAATTGCCAGGCCA

GTGAGGACATTGATAACTATTTAGCCTGGTATCAGCAGAAACCAGGGCAGCCTCCCAAGCTCCTGATCTTTTATGC

-continued

ATCCGATCTGGCATCTGGGGTCCCATCGCGGTTCTCAGGCAGTGGATCTGGGACACAGTTCACTCTCACCATCAGC

GGTGTGCAGTGTGACGATGCTGCCACTTACTACTGTCAAGGCGGTTACTATACTAGTAGTACTGATACGAGGGGT

GCTTTCGGCGGAGGCACCGAGGTGGTGGTCAAA

470C6CHIMERICLIGHTCHAINFULL-LENGTHAMINOACIDSEQUENCE. HUMANKAPPACONSTANT DOMAINISUNDERLINED

SEQ ID NO: 123

ALVMTQTPASVSAAVGGTVTINCQASEDIDNYLAWYQQKPGQPPKLLIFYASDLASGVPSRFSGSGSGTQFTLTISGVQ

CDDAATYYCQGGYYTSSTDTRGAFGGGTEVVVKRTVAAPSVFIFPPSDEQLKSGTASVVCLLNNFYPREAKVQWKVDN

ALQSGNSQESVTEQDSKDSTYSLSSTLTLSKADYEKHKVYACEVTHQGLSSPVTKSFNRGEC

470C6CHIMERICLIGHTCHAINVARIABLELIGHTCHAINAMINOACIDSEQUENCE. COMPIMENTARITY DETERMININGREGIONSAREUNDERLINED

SEQ ID NO: 124

ALVMTQTPASVSAAVGGTVTINCQASEDIDNYLAWYQQKPGQPPKLLIFYASDLASGVPSRFSGSGSGTQFTLTISGVQ

CDDAATYYCQGGYYTSSTDTRGAFGGGTEVVVK

470C6CHIMERICHEAVYCHAINFULL-LENGTHNUCLEOTIDESEQUENCE

SEQ ID NO: 125

CAGTCATTGGAGGAGGCCGGGGGAGACCTGGTCAAGCCTGGGGCATCCCTGACACTCACCTGCACAGCCTCTGGC

TTCTCCTTCACTAGCAGCTACTACATGTGCTGGGTCCGCCAGGCTCCAGGGAAGGGGCTGGAGTGGATCGCATGC

ATTTATACTGGTAGTAGTGGTAGCACTTACTACGCGAACTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

GTAGTTATTATATGTTTAACTTGTGGGGCCAGGGCACCCTCGTCACCGTCTCGAGCGCTAGCACCAAGGGCCCATC

GGTCTTCCCCCTGGCACCCTCCTCCAAGAGCACCTCTGGGGGCACAGCGGCCCTGGGCTGCCTGGTCAAGGACTA

CTTCCCCGAACCGGTGACGGTGTCGTGGAACTCAGGCGCCCTGACCAGCGGCGTGCACACCTTCCCGGCTGTCCTA

CAGTCCTCAGGACTCTACTCCCTCAGCAGCGTGGTGACCGTGCCCTCCAGCAGCTTGGGCACCCAGACCTACATCT

GCAACGTGAATCACAAGCCCAGCAACACCAAGGTGGACAAGAGAGTTGAGCCCAAATCTTGTGACAAAACTCACA

CATGCCCACCGTGCCCAGCACCTGAAGCCGCGGGGGCACCGTCAGTCTTCCTCTTCCCCCCAAAACCCAAGGACAC

CCTCATGATCTCCCGGACCCCTGAGGTCACATGCGTGGTGGTGGACGTGAGCCACGAAGACCCTGAGGTCAAGTT

CAACTGGTACGTGGACGGCGTGGAGGTGCATAATGCCAAGACAAAGCCGCGGGAGGAGCAGTACAACAGCACG

TACCGTGTGGTCAGCGTCCTCACCGTCCTGCACCAGGACTGGCTGAATGGCAAGGAGTACAAGTGCGCGGTCTCC

AACAAAGCCCTCCCAGCCCCCATCGAGAAAACCATCTCCAAAGCCAAAGGGCAGCCCCGAGAACCACAGGTGTAC

ACCCTGCCCCCATCCCGGGATGAGCTGACCAAGAACCAGGTCAGCCTGACCTGCCTGGTCAAAGGCTTCTATCCCA

GCGACATCGCCGTGGAGTGGGAGAGCAATGGGCAGCCGGAGAACAACTACAAGACCACGCCTCCCGTGCTGGAC

TCCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

470C6CHIMERICHEAVYCHAINVARIABLEHEAVYCHAINNUCLEOTIDESEQUENCE

SEQ ID NO: 126

CAGTCATTGGAGGAGGCCGGGGGAGACCTGGTCAAGCCTGGGGCATCCCTGACACTCACCTGCACAGCCTCTGGC

TTCTCCTTCACTAGCAGCTACTACATGTGCTGGGTCCGCCAGGCTCCAGGGAAGGGGCTGGAGTGGATCGCATGC

ATTTATACTGGTAGTAGTGGTAGCACTTACTACGCGAACTGGGCGAAAGGCCGATTCACCATCTCCAAAACCTCGT

CGACCACGGTGACTCTGCAAATGACCAGTCTGACAGCCGCGGACACGGCCACCTATTTCTGTGCGAGAGATAGTA

GTAGTTATTATATGTTTAACTTGTGGGGCCAGGGCACCCTCGTCACCGTCTCGAGC

470C6CHIMERICHEAVYCHAINFULL-LENGTHAMINOACIDSEQUENCE. HUMANGAMMA-1CONSTANT DOMAINISUNDERLINED

SEQ ID NO: 127

QSLEEAGGDLVKPGASLTLTCTASGFSFTSSYYMCWVRQAPGKGLEWIACIYTGSSGSTYYANWAKGRFTISKTSSTTVT

LQMTSLTAADTATYFCARDSSSYYMFNLWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

-continued

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPG

470C6CHIMERICHEAVYCHAINVARIABLEHEAVYCHAINAMINOACIDSEQUENCE. COMPLIMENTARITY DETERMININGREGIONSAREUNDERLINED

SEQ ID NO: 128

QSLEEAGGDLVKPGASLTLTCTASGFSFTSSYYMCWVRQAPGKGLEWIACIYTGSSGSTYYANWAKGRFTISKTSSTTVT

LQMTSLTAADTATYFCARDSSSYYMFNLWGQGTLVTVSS

472E4CHIMERICLIGHTCHAINFULL-LENGTHNUCLEOTIDESEQUENCE

SEQ ID NO: 129

GCAGCCGTGCTGACCCAGACTCCATCTTCCACGTCTGCAGCTGTGGGAGGCACAGTCACCATCAGTTGCCAGTCCA

GTCAGAGTGTTTATAATAACAATGCTTTAGCCTGGTATCAGAAAAAACCAGGACAGCCTCCCAAGCTCCTGATCTA

TTTGGCTTCCACTCTGGCATCTGGGGTCCCATCGCGGTTCAGCGGCAGTGGATCTGGGACACAGTTCACTCTCACC

ATCAGCGACCTGGAGTGTGACGATGCTGCCACTTATTATTGTCTAGGTGTTTATAATGATGATGTTGATAATGGTTT

CGGCGGAGGCACCGAGGTGGTGTTCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

472E4CHIMERICLIGHTCHAINVARIABLELIGHTCHAINNUCLEOTIDESEQUENCE

SEQ ID NO: 130

GCAGCCGTGCTGACCCAGACTCCATCTTCCACGTCTGCAGCTGTGGGAGGCACAGTCACCATCAGTTGCCAGTCCA

GTCAGAGTGTTTATAATAACAATGCTTTAGCCTGGTATCAGAAAAAACCAGGACAGCCTCCCAAGCTCCTGATCTA

TTTGGCTTCCACTCTGGCATCTGGGGTCCCATCGCGGTTCAGCGGCAGTGGATCTGGGACACAGTTCACTCTCACC

ATCAGCGACCTGGAGTGTGACGATGCTGCCACTTATTATTGTCTAGGTGTTTATAATGATGATGTTGATAATGGTTT

CGGCGGAGGCACCGAGGTGGTGTTCAAA

472E4CHIMERICLIGHTCHAINFULL-LENGTHAMINOACIDSEQUENCE. HUMANKAPPACONSTANT DOMAINISUNDERLINED

SEQ ID NO: 131

AAVLTQTPSSTSAAVGGTVTISCQSSQSVYNNNALAWYQKKPGQPPKLLIYLASTLASGVPSRFSGSGSGTQFTLTISDLE

CDDAATYYCLGVYNDDVDNGFGGGTEVVFKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

472E4CHIMERICLIGHTCHAINVARIABLELIGHTCHAINAMINOACIDSEQUENCE. COMPIMENTARITY DETERMININGREGIONSAREUNDERLINED

SEQ ID NO: 132

AAVLTQTPSSTSAAVGGTVTISCQSSQSVYNNNALAWYQKKPGQPPKLLIYLASTLASGVPSRFSGSGSGTQFTLTISDLE

CDDAATYYCLGVYNDDVDNGFGGGTEVVFK

472E4CHIMERICHEAVYCHAINFULL-LENGTHNUCLEOTIDESEQUENCE

SEQ ID NO: 133

CAGTCGCTGGAGGAGTCCGGGGGTCGCCTGGTCACGCCTGGAGGATCCCTGACACTCACCTGCACCGTCTCTGGA

TTCTCCCTCAATAACAATGCAATAAGCTGGGTCCGCCAGGCTCCAGGGAAGGGGCTGGAATGGGTTGCAATCATA

CAAAATACTGGTACCACAGACTACGCGAGGTGGGCGAAAGGCCGATTCACCATCTCCAAAACCTCGACCACGGTG

GATTTGAAAATCAACAGTCCGACAACCGAGGACACGGCCACCTATTTCTGTGGCAGAGGGTATGGTTTTGAGTCG

GAGCTTGTCATCTGGGGCCCGGGCACCCTGGTCACCGTCTCGAGCGCTAGCACCAAGGGCCCATCGGTCTTCCCCC

TGGCACCCTCCTCCAAGAGCACCTCTGGGGGCACAGCGGCCCTGGGCTGCCTGGTCAAGGACTACTTCCCCGAAC

CGGTGACGGTGTCGTGGAACTCAGGCGCCCTGACCAGCGGCGTGCACACCTTCCCGGCTGTCCTACAGTCCTCAG

GACTCTACTCCCTCAGCAGCGTGGTGACCGTGCCCTCCAGCAGCTTGGGCACCCAGACCTACATCTGCAACGTGAA

TCACAAGCCCAGCAACACCAAGGTGGACAAGAGAGTTGAGCCCAAATCTTGTGACAAAACTCACACATGCCCACC

-continued

GTGCCCAGCACCTGAAGCCGCGGGGGCACCGTCAGTCTTCCTCTTCCCCCCAAAACCCAAGGACACCCTCATGATC

TCCCGGACCCCTGAGGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAGTGCGCGGTCTCCAACAAAGCCC

TCCCAGCCCCCATCGAGAAAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCTTCTATCCCAGCGACATCG

CCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGT

472E4CHIMERICHEAVYCHAINVARIABLEHEAVYCHAINNUCLEOTIDESEQUENCE

SEQ ID NO: 134

CAGTCGCTGGAGGAGTCCGGGGGTCGCCTGGTCACGCCTGGAGGATCCCTGACACTCACCTGCACCGTCTCTGGA

TTCTCCCTCAATAACAATGCAATAAGCTGGGTCCGCCAGGCTCCAGGGAAGGGGCTGGAATGGGTTGCAATCATA

CAAAATACTGGTACCACAGACTACGCGAGGTGGGCGAAAGGCCGATTCACCATCTCCAAAACCTCGACCACGGTG

GATTTGAAAATCAACAGTCCGACAACCGAGGACACGGCCACCTATTTCTGTGGCAGAGGGTATGGTTTTGAGTCG

GAGCTTGTCATCTGGGGCCCGGGCACCCTGGTCACCGTCTCGAGC

472E4 CHIMERIC HEAVY CHAIN FULL-LENGTH AMINO ACID SEQUENCE. HUMAN GAMMA-1 CONSTANT DOMAINISUNDERLINED

SEQ ID NO: 135

QSLEESGGRLVTPGGSLTLTCTVSGFSLNNNAISWVRQAPGKGLEWVAIIQNTGTTDYARWAKGRFTISKTSTTVDLKIN

SPTTEDTATYFCGRGYGFESELVIWGPGTLVTVSSASTKGPSVFPLAPSSKSTSGGTAALGCLVKDYFPEPVTVSWNSGA

LTSGVHTFPAVLQSSGLYSLSSVVTVPSSSLGTQTYICNVNHKPSNTKVDKRVEPKSCDKTHTCPPCPAPEAAGAPSVFLF

PPKPKDTLMISRTPEVTCVVVDVSHEDPEVKFNWYVDGVEVHNAKTKPREEQYNSTYRVVSVLTVLHQDWLNGKEYK

CAVSNKALPAPIEKTISKAKGQPREPQVYTLPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

472E4CHIMERICHEAVYCHAINVARIABLEHEAVYCHAINAMINOACIDSEQUENCE. COMPLIMENTARITY DETERMININGREGIONSAREUNDERLINED

SEQ ID NO: 136

QSLEESGGRLVTPGGSLTLTCTVSGFSLNNNAISWVRQAPGKGLEWVAIIQNTGTTDYARWAKGRFTISKTSTTVDLKIN

SPTTEDTATYFCGRGYGFESELVIWGPGTLVTVSS

411H11HUMANIZEDLIGHTCHAINFULL-LENGTHNUCLEOTIDESEQUENCE

SEQ ID NO: 137

GACGTTGTGATGACCCAGTCTCCATCTTCCGTGTCTGCATCTGTAGGAGACAGAGTCACCATCACCTGTCAGGCCA

GTCAGAGCATTGGTGCTGATTTAGCCTGGTATCAGCAGAAACCAGGGAAAGCCCCTAAGCTCCTGATCTATAGGG

CATCCACTCTGGCCTCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAAGCTATTTATTATGGTACTGATGATGTCATATACCATA

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

411H11HUMANIZEDLIGHTCHAINVARIABLELIGHTCHAINNUCLEOTIDESEQUENCE

SEQ ID NO: 138

GACGTTGTGATGACCCAGTCTCCATCTTCCGTGTCTGCATCTGTAGGAGACAGAGTCACCATCACCTGTCAGGCCA

GTCAGAGCATTGGTGCTGATTTAGCCTGGTATCAGCAGAAACCAGGGAAAGCCCCTAAGCTCCTGATCTATAGGG

CATCCACTCTGGCCTCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAAGCTATTTATTATGGTACTGATGATGTCATATACCATA

-continued

CTTTCGGCGGAGGGACCAAGGTGGAGATCAAA

411H11 HUMANIZED LIGHT CHAIN FULL-LENGTH AMINO ACID SEQUENCE. HUMAN KAPPA CONSTANT DOMAINISUNDERLINED

SEQ ID NO: 139

DVVMTQSPSSVSASVGDRVTITCQASQSIGADLAWYQQKPGKAPKLLIYRASTLASGVPSRFSGSGSGTDFTLTISSLQP

EDFATYYCQAIYYGTDDVIYHTFGGGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

411H11HUMANIZEDLIGHTCHAINVARIABLELIGHTCHAINAMINOACIDSEQUENCE. COMPIMENTARITYDETERMININGREGIONSAREUNDERLINED

SEQ ID NO: 140

DVVMTQSPSSVSASVGDRVTITCQASQSIGADLAWYQQKPGKAPKLLIYRASTLASGVPSRFSGSGSGTDFTLTISSLQP

EDFATYYCQAIYYGTDDVIYHTFGGGTKVEIK

411H11HUMANIZEDHEAVYCHAINFULL-LENGTHNUCLEOTIDESEQUENCE

SEQ ID NO: 141

GAGGTGCAGCTGGTGGAGTCTGGGGGAGGCTTGGTCCAGCCTGGGGGGTCCCTGAGACTCTCCTGTGCAGCCTC

TGGATTCACCATCAGTAGCCACCACATGATCTGGGTCCGCCAGGCTCCAGGGAAGGGGCTGCAATACATCGGATT

CATTAATGATGGTGACTATACATACTACACGAACTCCGCAAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

GGTACTAGTTATCCTGGCTTGTGGGGCCAGGGAACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAGGAGTACAAGTGCGCGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGATGAGCTGACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACAAGACCACGCCTCCCGTGCTGGACT

CCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

411H11HUMANIZEDHEAVYCHAINVARIABLEHEAVYCHAINNUCLEOTIDESEQUENCE

SEQ ID NO: 142

GAGGTGCAGCTGGTGGAGTCTGGGGGAGGCTTGGTCCAGCCTGGGGGGTCCCTGAGACTCTCCTGTGCAGCCTC

TGGATTCACCATCAGTAGCCACCACATGATCTGGGTCCGCCAGGCTCCAGGGAAGGGGCTGCAATACATCGGATT

CATTAATGATGGTGACTATACATACTACACGAACTCCGCAAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

GGTACTAGTTATCCTGGCTTGTGGGGCCAGGGAACCCTGGTCACCGTCTCGAGC

411H11HUMANIZEDHEAVYCHAINFULL-LENGTHAMINOACIDSEQUENCE. HUMANGAMMA-1 CONSTANTDOMAINISUNDERLINED

SEQ ID NO: 143

EVQLVESGGGLVQPGGSLRLSCAASGFTISSHHMIWVRQAPGKGLQYIGFINDGDYTYYTNSAKGRFTISRDNSKNTLYL

QMNSLRAEDTAVYYCARGVDGTSYPGLWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

-continued

PPVLDSDGSFFLYSKLTVDKSRWQQGNVFSCSVMHEALHNHYTQKSLSLSPG

411H11HUMANIZEDHEAVYCHAINVARIABLEHEAVYCHAINAMINOACIDSEQUENCE. COMPLIMENTARITYDETERMININGREGIONSAREUNDERLINED

SEQ ID NO: 144

EVQLVESGGGLVQPGGSLRLSCAASGFTISSHHMIWVRQAPGKGLQYIGFINDGDYTYYTNSAKGRFTISRDNSKNTLYL

QMNSLRAEDTAVYYCARGVDGTSYPGLWGQGTLVTVSS

413F3HUMANIZEDLIGHTCHAINFULL-LENGTHNUCLEOTIDESEQUENCE

SEQ ID NO: 145

GACATCCAGATGACCCAGTCTCCATCCTCCCTGTCTGCATCTGTAGGAGACAGAGTCACCATCACTTGCCAGGCCA

GTCAGAGCATTTACAGCAATTTAGCCTGGTATCAGCAGAAACCAGGGAAAGTTCCTAAGCTCCTGATCTATTCTAC

ATCCACTCTGGCATCTGGGGTCCCATCTCGGTTCAGTGGCAGTGGATCTGGGACAGATTTCACTCTCACCATCAGC

AGCCTGCAGCCTGAAGATGTTGCAACTTATTACTGTCAAAACTATTATGGTAGTAGTACTGATAGTTATGGGAATC

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

413F3HUMANIZEDLIGHTCHAINVARIABLELIGHTCHAINNUCLEOTIDESEQUENCE

SEQ ID NO: 146

GACATCCAGATGACCCAGTCTCCATCCTCCCTGTCTGCATCTGTAGGAGACAGAGTCACCATCACTTGCCAGGCCA

GTCAGAGCATTTACAGCAATTTAGCCTGGTATCAGCAGAAACCAGGGAAAGTTCCTAAGCTCCTGATCTATTCTAC

ATCCACTCTGGCATCTGGGGTCCCATCTCGGTTCAGTGGCAGTGGATCTGGGACAGATTTCACTCTCACCATCAGC

AGCCTGCAGCCTGAAGATGTTGCAACTTATTACTGTCAAAACTATTATGGTAGTAGTACTGATAGTTATGGGAATC

CTTTCGGCGGAGGGACCAAGGTGGAGATCAAA

413F3HUMANIZEDLIGHTCHAINFULL-LENGTHAMINOACIDSEQUENCE. HUMANKAPPACONSTANT DOMAINISUNDERLINED

SEQ ID NO: 147

DIQMTQSPSSLSASVGDRVTITCQASQSIYSNLAWYQQKPGKVPKLLIYSTSTLASGVPSRFSGSGSGTDFTLTISSLOPED

VATYYCQNYYGSSTDSYGNPFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

413F3HUMANIZEDLIGHTCHAINVARIABLELIGHTCHAINAMINOACIDSEQUENCE. COMPIMENTARITY DETERMININGREGIONSAREUNDERLINED

SEQ ID NO: 148

DIQMTQSPSSLSASVGDRVTITCQASQSIYSNLAWYQQKPGKVPKLLIYSTSTLASGVPSRFSGSGSGTDFTLTISSLOPED

VATYYCQNYYGSSTDSYGNPFGGGTKVEIK

413F3HUMANIZEDHEAVYCHAINFULL-LENGTHNUCLEOTIDESEQUENCE

SEQ ID NO: 149

GAGGTGCAGCTGGTGGAGTCTGGGGGAGGCTTGGTCCAGCCTGGGGGGTCCCTGAGACTCTCCTGTGCAGCCTC

TGGAATCGACTTCAGTAGCAACTACATGTGCTGGGTCCGCCAGGCTCCAGGGAAGGGGCTGGAGTGGATCGCAT

GCATTTATGGTGATAGTAGTGATAATAGTTACTCCGCGAGCTCCGCTAAAGGCAGATTCACCATCTCCAGAGACAA

TTCCAAGAACACGCTGTATCTTCAAATGAACAGCCTGAGAGCCGAGGACACGGCTGTGTATTACTGTGCGAGATCT

GGTTATAGCTATTTAGGCTACTTTAACTTGTGGGGCCAGGGAACCCTGGTCACCGTCTCGAGCGCTAGCACCAAGG

GCCCATCGGTCTTCCCCCTGGCACCCTCCTCCAAGAGCACCTCTGGGGGCACAGCGGCCCTGGGCTGCCTGGTCAA

GGACTACTTCCCCGAACCGGTGACGGTGTCGTGGAACTCAGGCGCCCTGACCAGCGGCGTGCACACCTTCCCGGC

TGTCCTACAGTCCTCAGGACTCTACTCCCTCAGCAGCGTGGTGACCGTGCCCTCCAGCAGCTTGGGCACCCAGACC

TACATCTGCAACGTGAATCACAAGCCCAGCAACACCAAGGTGGACAAGAGAGTTGAGCCCAAATCTTGTGACAAA

ACTCACACATGCCCACCGTGCCCAGCACCTGAAGCCGCGGGGGCACCGTCAGTCTTCCTCTTCCCCCCAAAACCCA

AGGACACCCTCATGATCTCCCGGACCCCTGAGGTCACATGCGTGGTGGTGGACGTGAGCCACGAAGACCCTGAGG

-continued

TCAAGTTCAACTGGTACGTGGACGGCGTGGAGGTGCATAATGCCAAGACAAAGCCGCGGGAGGAGCAGTACAAC

AGCACGTACCGTGTGGTCAGCGTCCTCACCGTCCTGCACCAGGACTGGCTGAATGGCAAGGAGTACAAGTGCGCG

GTCTCCAACAAAGCCCTCCCAGCCCCCATCGAGAAAACCATCTCCAAAGCCAAAGGGCAGCCCCGAGAACCACAG

GTGTACACCCTGCCCCCATCCCGGGATGAGCTGACCAAGAACCAGGTCAGCCTGACCTGCCTGGTCAAAGGCTTCT

ATCCCAGCGACATCGCCGTGGAGTGGGAGAGCAATGGGCAGCCGGAGAACAACTACAAGACCACGCCTCCCGTG

CTGGACTCCGACGGCTCCTTCTTCCTCTATAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCCCTGTCTCCGGGT

413F3HUMANIZEDHEAVYCHAINVARIABLEHEAVYCHAINNUCLEOTIDESEQUENCE

SEQ ID NO: 150

GAGGTGCAGCTGGTGGAGTCTGGGGGAGGCTTGGTCCAGCCTGGGGGGTCCCTGAGACTCTCCTGTGCAGCCTC

TGGAATCGACTTCAGTAGCAACTACATGTGCTGGGTCCGCCAGGCTCCAGGGAAGGGGCTGGAGTGGATCGCAT

GCATTTATGGTGATAGTAGTGATAATAGTTACTCCGCGAGCTCCGCTAAAGGCAGATTCACCATCTCCAGAGACAA

TTCCAAGAACACGCTGTATCTTCAAATGAACAGCCTGAGAGCCGAGGACACGGCTGTGTATTACTGTGCGAGATCT

GGTTATAGCTATTTAGGCTACTTTAACTTGTGGGGCCAGGGAACCCTGGTCACCGTCTCGAGC

413F3HUMANIZEDHEAVYCHAINFULL-LENGTHAMINOACIDSEQUENCE. HUMANGAMMA-1
CONSTANTDOMAINISUNDERLINED

SEQ ID NO: 151

EVQLVESGGGLVQPGGSLRLSCAASGIDFSSNYMCWVRQAPGKGLEWIACIYGDSSDNSYSASSAKGRFTISRDNSKNT

LYLQMNSLRAEDTAVYYCARSGYSYLGYFNLWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GAPSVFLFPPKPKDTLMISRTPEVTCVVVDVSHEDPEVKFNWYVDGVEVHNAKTKPREEQYNSTYRVVSVLTVLHQDW

LNGKEYKCAVSNKALPAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG

413F3HUMANIZEDHEAVYCHAINVARIABLEHEAVYCHAINAMINOACIDSEQUENCE.
COMPLIMENTARITYDETERMININGREGIONSAREUNDERLINED

SEQ ID NO: 152

EVQLVESGGGLVQPGGSLRLSCAASGIDFSSNYMCWVRQAPGKGLEWIACIYGDSSDNSYSASSAKGRFTISRDNSKNT

LYLQMNSLRAEDTAVYYCARSGYSYLGYFNLWGQGTLVTVSS

416F8HUMANIZEDLIGHTCHAINFULL-LENGTHNUCLEOTIDESEQUENCE

SEQ ID NO: 153

GACATCCAGATGACCCAGTCTCCATCCTCCCTGTCTGCATCTGTAGGAGACAGAGTCACCATCACTTGCCAGTCCA

GTCAGACTGTTTATAATAACAACTTGTTATCCTGGTATCAGCAGAAACCAGGGAAAGTTCCTAAGCTCCTGATCTAT

TATGCATCCACTCTGGCATTTGGGGTCCCATCTCGGTTCAGTGGCAGTGGATCTGGGACAGATTTCACTCTCACCAT

CAGCAGCCTGCAGCCTGAAGATGTTGCAACTTATTACTGTCAAGGCGGTTATAGTGGTTGGATTTATGTTTTCGGC

GGAGGGACCAAGGTGGAGATCAAACGTACGGTGGCTGCACCATCTGTCTTCATCTTCCCGCCATCTGATGAGCAG

TTGAAATCTGGAACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAGCACCTACAGC

CTCAGCAGCACCCTGACGCTGAGCAAAGCAGACTACGAGAAACACAAAGTCTACGCCTGCGAAGTCACCCATCAG

GGCCTGAGCTCGCCCGTCACAAAGAGCTTCAACAGGGGAGAGTGT

416F8HUMANIZEDLIGHTCHAINVARIABLELIGHTCHAINNUCLEOTIDESEQUENCE

SEQ ID NO: 154

GACATCCAGATGACCCAGTCTCCATCCTCCCTGTCTGCATCTGTAGGAGACAGAGTCACCATCACTTGCCAGTCCA

GTCAGACTGTTTATAATAACAACTTGTTATCCTGGTATCAGCAGAAACCAGGGAAAGTTCCTAAGCTCCTGATCTAT

TATGCATCCACTCTGGCATTTGGGGTCCCATCTCGGTTCAGTGGCAGTGGATCTGGGACAGATTTCACTCTCACCAT

CAGCAGCCTGCAGCCTGAAGATGTTGCAACTTATTACTGTCAAGGCGGTTATAGTGGTTGGATTTATGTTTTCGGC

GGAGGGACCAAGGTGGAGATCAAA

-continued

416F8HUMANIZEDLIGHTCHAINFULL-LENGTHAMINOACIDSEQUENCE. HUMANKAPPACONSTANT DOMAINISUNDERLINED

SEQ ID NO: 155

DIQMTQSPSSLSASVGDRVTITCQSSQTVYNNNLLSWYQQKPGKVPKLLIYYASTLAFGVPSRFSGSGSGTDFTLTISSLQ

PEDVATYYCQGGYSGWIYVFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

416F8HUMANIZEDLIGHTCHAINVARIABLELIGHTCHAINAMINOACIDSEQUENCE. COMPIMENTARITY DETERMININGREGIONSAREUNDERLINED

SEQ ID NO: 156

DIQMTQSPSSLSASVGDRVTITCQSSQTVYNNNLLSWYQQKPGKVPKLLIYYASTLAFGVPSRFSGSGSGTDFTLTISSLQ

PEDVATYYCQGGYSGWIYVFGGGTKVEIK

416F8HUMANIZEDHEAVYCHAINFULL-LENGTHNUCLEOTIDESEQUENCE

SEQ ID NO: 157

CAGTCGCTGGTGGAGTCTGGGGGAGGCTTGGTCCAGCCTGGGGGGTCCCTGAGACTCTCCTGTGCAGCCTCTGGA

TTCTCCCTCAGTAACTACTACATGAACTGGGTCCGCCAGGCTCCAGGGAAGGGGCTGGAGTACATCGGAATCATT

AGTAGTAGTGGTAGCGCATACTACGCGAGCTCCGCTAAAGGCAGATTCACCATCTCCAGAGACAATTCCAAGAAC

ACGCTGTATCTTCAAATGAACAGCCTGAGAGCCGAGGACACGGCTGTGTATTACTGTGCGAGAGGGGACTACGGC

ATGGACCTCTGGGGCCAGGGAACCCTGGTCACCGTCTCGAGCGCTAGCACCAAGGGCCCATCGGTCTTCCCCCTG

GCACCCTCCTCCAAGAGCACCTCTGGGGGCACAGCGGCCCTGGGCTGCCTGGTCAAGGACTACTTCCCCGAACCG

GTGACGGTGTCGTGGAACTCAGGCGCCCTGACCAGCGGCGTGCACACCTTCCCGGCTGTCCTACAGTCCTCAGGA

CTCTACTCCCTCAGCAGCGTGGTGACCGTGCCCTCCAGCAGCTTGGGCACCCAGACCTACATCTGCAACGTGAATC

ACAAGCCCAGCAACACCAAGGTGGACAAGAGAGTTGAGCCCAAATCTTGTGACAAAACTCACACATGCCCACCGT

GCCCAGCACCTGAAGCCGCGGGGGCACCGTCAGTCTTCCTCTTCCCCCCAAAACCCAAGGACACCCTCATGATCTC

CCGGACCCCTGAGGTCACATGCGTGGTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGTACAACAGCACGTACCGTGTGGTC

AGCGTCCTCACCGTCCTGCACCAGGACTGGCTGAATGGCAAGGAGTACAAGTGCGCGGTCTCCAACAAAGCCCTC

CCAGCCCCCATCGAGAAAACCATCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAAGGCTTCTATCCCAGCGACATCGCC

GTGGAGTGGGAGAGCAATGGGCAGCCGGAGAACAACTACAAGACCACGCCTCCCGTGCTGGACTCCGACGGCTC

CTTCTTCCTCTATAGCAAGCTCACCGTGGACAAGAGCAGGTGGCAGCAGGGGAACGTCTTCTCATGCTCCGTGATG

CATGAGGCTCTGCACAACCACTACACGCAGAAGAGCCTCTCCCTGTCTCCGGGT

416F8HUMANIZEDHEAVYCHAINVARIABLEHEAVYCHAINNUCLEOTIDESEQUENCE

SEQ ID NO: 158

CAGTCGCTGGTGGAGTCTGGGGGAGGCTTGGTCCAGCCTGGGGGGTCCCTGAGACTCTCCTGTGCAGCCTCTGGA

TTCTCCCTCAGTAACTACTACATGAACTGGGTCCGCCAGGCTCCAGGGAAGGGGCTGGAGTACATCGGAATCATT

AGTAGTAGTGGTAGCGCATACTACGCGAGCTCCGCTAAAGGCAGATTCACCATCTCCAGAGACAATTCCAAGAAC

ACGCTGTATCTTCAAATGAACAGCCTGAGAGCCGAGGACACGGCTGTGTATTACTGTGCGAGAGGGGACTACGGC

ATGGACCTCTGGGGCCAGGGAACCCTGGTCACCGTCTCGAGC

416F8HUMANIZEDHEAVYCHAINFULL-LENGTHAMINOACIDSEQUENCE. HUMANGAMMA-1 CONSTANTDOMAINISUNDERLINED

SEQ ID NO: 159

QSLVESGGGLVQPGGSLRLSCAASGFSLSNYYMNWVRQAPGKGLEYIGIISSSGSAYYASSAKGRFTISRDNSKNTLYLQ

MNSLRAEDTAVYYCARGDYGMDLWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

-continued

416F8HUMANIZEDHEAVYCHAINVARIABLEHEAVYCHAINAMINOACIDSEQUENCE. COMPLIMENTARITYDETERMININGREGIONSAREUNDERLINED

SEQ ID NO: 160

QSLVESGGGLVQPGGSLRLSCAASGFSLSNYYMNWVRQAPGKGLEYIGIISSSGSAYYASSAKGRFTISRDNSKNTLYLQ

MNSLRAEDTAVYYCARGDYGMDLWGQGTLVTVSS

416G1HUMANIZEDLIGHTCHAINFULL-LENGTHNUCLEOTIDESEQUENCE

SEQ ID NO: 161

GACGTTGTGATGACCCAGTCTCCATCTTCCGTGTCTGCATCTGTAGGAGACAGAGTCACCATCACCTGTCAGGCCA

GTCAGAGCATTGGTAGTGATTTAGCCTGGTATCAGCAGAAACCAGGGAAAGCCCCTAAGCTCCTGATCTATAGGG

CATCCACTCTGGCATCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAATCCATTTATTATGGTAGTGATGATGTCATATACCATA

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

416G1HUMANIZEDLIGHTCHAINVARIABLELIGHTCHAINNUCLEOTIDESEQUENCE

SEQ ID NO: 162

GACGTTGTGATGACCCAGTCTCCATCTTCCGTGTCTGCATCTGTAGGAGACAGAGTCACCATCACCTGTCAGGCCA

GTCAGAGCATTGGTAGTGATTTAGCCTGGTATCAGCAGAAACCAGGGAAAGCCCCTAAGCTCCTGATCTATAGGG

CATCCACTCTGGCATCTGGGGTCCCATCAAGGTTCAGCGGCAGTGGATCTGGGACAGATTTCACTCTCACCATCAG

CAGCCTGCAGCCTGAAGATTTTGCAACTTACTATTGTCAATCCATTTATTATGGTAGTGATGATGTCATATACCATA

CTTTCGGCGGAGGGACCAAGGTGGAGATCAAA

416G1HUMANIZEDLIGHTCHAINFULL-LENGTHAMINOACIDSEQUENCE. HUMANKAPPACONSTANT DOMAINISUNDERLINED

SEQ ID NO: 163

DVVMTQSPSSVSASVGDRVTITCQASQSIGSDLAWYQQKPGKAPKLLIYRASTLASGVPSRFSGSGSGTDFTLTISSLQPE

DFATYYCQSIYYGSDDVIYHTFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

416G1HUMANIZEDLIGHTCHAINVARIABLELIGHTCHAINAMINOACIDSEQUENCE. COMPIMENTARITY DETERMININGREGIONSAREUNDERLINED

SEQ ID NO: 164

DVVMTQSPSSVSASVGDRVTITCQASQSIGSDLAWYQQKPGKAPKLLIYRASTLASGVPSRFSGSGSGTDFTLTISSLQPE

DFATYYCQSIYYGSDDVIYHTFGGGTKVEIK

416G1HUMANIZEDHEAVYCHAINFULL-LENGTHNUCLEOTIDESEQUENCE

SEQ ID NO: 165

GAGGTGCAGCTGGTGGAGTCTGGGGGAGGCTTGGTCCAGCCTGGGGGGTCCCTGAGACTCTCCTGTGCAGCCTC

TGGATTCACTATCAATAGCTACCACATGATCTGGGTCCGCCAGGCTCCAGGGAAGGGGCTGGAGTACATCGGATT

CATTAATGATGGTGGTTTCACATACTACGCGAGCTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

GGTACTAGTTATCCTGACTTATGGGGCCAGGGAACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

-continued

ACCGTGTGGTCAGCGTCCTCACCGTCCTGCACCAGGACTGGCTGAATGGCAAGGAGTACAAGTGCGCGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGATGAGCTGACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACAAGACCACGCCTCCCGTGCTGGACT

CCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

416G1HUMANIZEDHEAVYCHAINVARIABLEHEAVYCHAINNUCLEOTIDESEQUENCE

SEQ ID NO: 166

GAGGTGCAGCTGGTGGAGTCTGGGGGAGGCTTGGTCCAGCCTGGGGGGTCCCTGAGACTCTCCTGTGCAGCCTC

TGGATTCACTATCAATAGCTACCACATGATCTGGGTCCGCCAGGCTCCAGGGAAGGGGCTGGAGTACATCGGATT

CATTAATGATGGTGGTTTCACATACTACGCGAGCTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGGTTGAT

GGTACTAGTTATCCTGACTTATGGGGCCAGGGAACCCTGGTCACCGTCTCGAGC

416G1HUMANIZEDHEAVYCHAINFULL-LENGTHAMINOACIDSEQUENCE. HUMANGAMMA-1 CONSTANTDOMAINISUNDERLINED

SEQ ID NO: 167

EVQLVESGGGLVQPGGSLRLSCAASGFTINSYHMIWVRQAPGKGLEYIGFINDGGFTYYASSAKGRFTISRDNSKNTLYL

QMNSLRAEDTAVYYCARGVDGTSYPDLWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPG

416G1HUMANIZEDHEAVYCHAINVARIABLEHEAVYCHAINAMINOACIDSEQUENCE. COMPLIMENTARITYDETERMININGREGIONSAREUNDERLINED

SEQ ID NO: 168

EVQLVESGGGLVQPGGSLRLSCAASGFTINSYHMIWVRQAPGKGLEYIGFINDGGFTYYASSAKGRFTISRDNSKNTLYL

QMNSLRAEDTAVYYCARGVDGTSYPDLWGQGTLVTVSS

418E10HUMANIZEDLIGHTCHAINFULL-LENGTHNUCLEOTIDESEQUENCE

SEQ ID NO: 169

GACATCCAGATGACCCAGTCTCCTTCCACCCTGTCTGCATCTGTAGGAGACAGAGTCACCATCACTTGCCAGGCCA

GTCAGAGCATTGGTAGTAACTTGAACTGGTATCAGCAGAAACCAGGGAAAGCCCCTAAGCTCCTGATCTATTATGT

ATCCACTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGACGGTACTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

418E10HUMANIZEDLIGHTCHAINVARIABLELIGHTCHAINNUCLEOTIDESEQUENCE

SEQ ID NO: 170

GACATCCAGATGACCCAGTCTCCTTCCACCCTGTCTGCATCTGTAGGAGACAGAGTCACCATCACTTGCCAGGCCA

GTCAGAGCATTGGTAGTAACTTGAACTGGTATCAGCAGAAACCAGGGAAAGCCCCTAAGCTCCTGATCTATTATGT

ATCCACTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGACGGTACTGCTTT

CGGCGGAGGGACCAAGGTGGAGATCAAA

418E10HUMANIZEDLIGHTCHAINFULL-LENGTHAMINOACIDSEQUENCE. HUMANKAPPACONSTANT DOMAINISUNDERLINED

-continued

SEQ ID NO: 171

DIQMTQSPSTLSASVGDRVTITCQASQSIGSNLNWYQQKPGKAPKLLIYYVSTLASGVPSRFSGSGSGTEFTLTISSLQPD

DFATYYCLGVWNYWGDDGTAFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

418E10HUMANIZEDLIGHTCHAINVARIABLELIGHTCHAINAMINOACIDSEQUENCE.
COMPIMENTARITYDETERMININGREGIONSAREUNDERLINED

SEQ ID NO: 172

DIQMTQSPSTLSASVGDRVTITCQASQSIGSNLNWYQQKPGKAPKLLIYYVSTLASGVPSRFSGSGSGTEFTLTISSLQPD

DFATYYCLGVWNYWGDDGTAFGGGTKVEIK

418E10HUMANIZEDHEAVYCHAINFULL-LENGTHNUCLEOTIDESEQUENCE

SEQ ID NO: 173

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTACCTATTATATGAGCTGGGTCCGCCAGGCTCCAGGGAAGGGGCTGGAGTGGATCGGAAG

TATTTATGATAGTGGTGCCGCATACTACGCGACCTCCGCGAAGGGCAGATTCACCATCTCCAGAGACAATTCCAAG

AACACGCTGTATCTTCAAATGAACAGCCTGAGAGCCGAGGACACGGCTGTGTATTACTGTGCGAGAGATCCTATT

AATAATGCCATCTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

418E10HUMANIZEDHEAVYCHAINVARIABLEHEAVYCHAINNUCLEOTIDESEQUENCE

SEQ ID NO: 174

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTACCTATTATATGAGCTGGGTCCGCCAGGCTCCAGGGAAGGGGCTGGAGTGGATCGGAAG

TATTTATGATAGTGGTGCCGCATACTACGCGACCTCCGCGAAGGGCAGATTCACCATCTCCAGAGACAATTCCAAG

AACACGCTGTATCTTCAAATGAACAGCCTGAGAGCCGAGGACACGGCTGTGTATTACTGTGCGAGAGATCCTATT

AATAATGCCATCTGGGGCCAGGGAACCCTGGTCACCGTCTCGAGC

418E10HUMANIZEDHEAVYCHAINFULL-LENGTHAMINOACIDSEQUENCE. HUMANGAMMA-1
CONSTANTDOMAINISUNDERLINED

SEQ ID NO: 175

EVQLVESGGGLVQPGGSLRLSCAASGFSLSTYYMSWVRQAPGKGLEWIGSIYDSGAAYYATSAKGRFTISRDNSKNTLY

LQMNSLRAEDTAVYYCARDPINNAIWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

418E10HUMANIZEDHEAVYCHAINVARIABLEHEAVYCHAINAMINOACIDSEQUENCE.
COMPLIMENTARITYDETERMININGREGIONSAREUNDERLINED

-continued

SEQ ID NO: 176

EVQLVESGGGLVQPGGSLRLSCAASGFSLSTYYMSWVRQAPGKGLEWIGSIYDSGAAYYATSAKGRFTISRDNSKNTLY

LQMNSLRAEDTAVYYCARDPINNAIWGQGTLVTVSS

418E4HUMANIZEDLIGHTCHAINFULL-LENGTHNUCLEOTIDESEQUENCE

SEQ ID NO: 177

GACATCCAGATGACCCAGTCTCCTTCCACCCTGTCTGCATCTGTAGGAGACAGAGTCACCATCACTTGCCAGGCCA

GTCAGAGTATTGCTACTAACTTGAACTGGTATCAGCAGAAACCAGGGAAAGCCCCTAAGCTCCTGATCTATTATAC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

418E4HUMANIZEDLIGHTCHAINVARIABLELIGHTCHAINNUCLEOTIDESEQUENCE

SEQ ID NO: 178

GACATCCAGATGACCCAGTCTCCTTCCACCCTGTCTGCATCTGTAGGAGACAGAGTCACCATCACTTGCCAGGCCA

GTCAGAGTATTGCTACTAACTTGAACTGGTATCAGCAGAAACCAGGGAAAGCCCCTAAGCTCCTGATCTATTATAC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGCTTT

CGGCGGAGGGACCAAGGTGGAGATCAAA

418E4HUMANIZEDLIGHTCHAINFULL-LENGTHAMINOACIDSEQUENCE. HUMANKAPPACONSTANT DOMAINISUNDERLINED

SEQ ID NO: 179

DIQMTQSPSTLSASVGDRVTITCQASQSIATNLNWYQQKPGKAPKLLIYYTSSLASGVPSRFSGSGSGTEFTLTISSLQPD

DFATYYCLGVWNYWGDDGTAFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

418E4HUMANIZEDLIGHTCHAINVARIABLELIGHTCHAINAMINOACIDSEQUENCE. COMPIMENTARITY DETERMININGREGIONSAREUNDERLINED

SEQ ID NO: 180

DIQMTQSPSTLSASVGDRVTITCQASQSIATNLNWYQQKPGKAPKLLIYYTSSLASGVPSRFSGSGSGTEFTLTISSLQPD

DFATYYCLGVWNYWGDDGTAFGGGTKVEIK

418E4HUMANIZEDHEAVYCHAINFULL-LENGTHNUCLEOTIDESEQUENCE

SEQ ID NO: 181

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGCTAGTGGTAGCGCATACTACGCGAGTTCCGCGAAGGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

TAACAATGACATCTGGGGCCAGGGAACCCTGGTCACCGTCTCGAGCGCTAGCACCAAGGGCCCATCGGTCTTCCC

CCTGGCACCCTCCTCCAAGAGCACCTCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGTGCGCGGTCTCCAACAAAGC

-continued

CCTCCCAGCCCCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

418E4HUMANIZEDHEAVYCHAINVARIABLEHEAVYCHAINNUCLEOTIDESEQUENCE

SEQ ID NO: 182

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGCTAGTGGTAGCGCATACTACGCGAGTTCCGCGAAGGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

TAACAATGACATCTGGGGCCAGGGAACCCTGGTCACCGTCTCGAGC

418E4HUMANIZEDHEAVYCHAINFULL-LENGTHAMINOACIDSEQUENCE. HUMANGAMMA-1 CONSTANTDOMAINISUNDERLINED

SEQ ID NO: 183

EVQLVESGGGLVQPGGSLRLSCAASGFSLSSYYMSWVRQAPGKGLEWIGSIYASGSAYYASSAKGRFTISRDNSKNTLYL

QMNSLRAEDTAVYYCARDPINNDIWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

418E4HUMANIZEDHEAVYCHAINVARIABLEHEAVYCHAINAMINOACIDSEQUENCE. COMPLIMENTARITYDETERMININGREGIONSAREUNDERLINED

SEQ ID NO: 184

EVQLVESGGGLVQPGGSLRLSCAASGFSLSSYYMSWVRQAPGKGLEWIGSIYASGSAYYASSAKGRFTISRDNSKNTLYL

QMNSLRAEDTAVYYCARDPINNDIWGQGTLVTVSS

418H5HUMANIZEDLIGHTCHAINFULL-LENGTHNUCLEOTIDESEQUENCE

SEQ ID NO: 185

GACATCCAGATGACCCAGTCTCCATCTTCCGTGTCTGCATCTGTAGGAGACAGAGTCACCATCACTTGTCAGTCCA

GTCCGAGTGTTTATAAGAACAACCAATTAGCCTGGTATCAGCAGAAACCAGGGAAAGCCCCTAAGCTCCTGATCTA

TCTGGCATCTACTCTGGCATCTGGGGTCCCATCAAGGTTCAGCGGCAGTGGATCTGGGACAGATTTCACTCTCACC

ATCAGCAGCCTGCAGCCTGAAGATTTTGCAACTTACTATTGTGCAGGCGGTTATAGTAGTAGTAGTGATACTGCTT

TCGGCGGAGGGACCAAGGTGGAGATCAAACGTACGGTGGCTGCACCATCTGTCTTCATCTTCCCGCCATCTGATG

AGCAGTTGAAATCTGGAACTGCCTCTGTTGTGTGCCTGCTGAATAACTTCTATCCCAGAGAGGCCAAAGTACAGTG

GAAGGTGGATAACGCCCTCCAATCGGGTAACTCCCAGGAGAGTGTCACAGAGCAGGACAGCAAGGACAGCACCT

ACAGCCTCAGCAGCACCCTGACGCTGAGCAAAGCAGACTACGAGAAACACAAAGTCTACGCCTGCGAAGTCACCC

ATCAGGGCCTGAGCTCGCCCGTCACAAAGAGCTTCAACAGGGGAGAGTGT

418H5HUMANIZEDLIGHTCHAINVARIABLELIGHTCHAINNUCLEOTIDESEQUENCE

SEQ ID NO: 186

GACATCCAGATGACCCAGTCTCCATCTTCCGTGTCTGCATCTGTAGGAGACAGAGTCACCATCACTTGTCAGTCCA

GTCCGAGTGTTTATAAGAACAACCAATTAGCCTGGTATCAGCAGAAACCAGGGAAAGCCCCTAAGCTCCTGATCTA

TCTGGCATCTACTCTGGCATCTGGGGTCCCATCAAGGTTCAGCGGCAGTGGATCTGGGACAGATTTCACTCTCACC

ATCAGCAGCCTGCAGCCTGAAGATTTTGCAACTTACTATTGTGCAGGCGGTTATAGTAGTAGTAGTGATACTGCTT

TCGGCGGAGGGACCAAGGTGGAGATCAAA

418H5HUMANIZEDLIGHTCHAINFULL-LENGTHAMINOACIDSEQUENCE. HUMANKAPPACONSTANT DOMAINISUNDERLINED

SEQ ID NO: 187

DIQMTQSPSSVSASVGDRVTITCQSSPSVYKNNQLAWYQQKPGKAPKLLIYLASTLASGVPSRFSGSGSGTDFTLTISSLQ

-continued

PEDFATYYCAGGYSSSSDTAFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

418H5HUMANIZEDLIGHTCHAINVARIABLELIGHTCHAINAMINOACIDSEQUENCE. COMPIMENTARITY DETERMININGREGIONSAREUNDERLINED

SEQ ID NO: 188

DIQMTQSPSSVSASVGDRVTITCQSSPSVYKNNQLAWYQQKPGKAPKLLIYLASTLASGVPSRFSGSGSGTDFTLTISSLQ

PEDFATYYCAGGYSSSSDTAFGGGTKVEIK

418H5HUMANIZEDHEAVYCHAINFULL-LENGTHNUCLEOTIDESEQUENCE

SEQ ID NO: 189

GAGGTGCAGCTGGTGGAGTCTGGGGGAGGCTTGGTCCAGCCTGGGGGGTCCCTGAGACTCTCCTGTACAGCCTC

TGGAATCGACCTCAGTGCCTACCACATGAGCTGGGTCCGCCAGGCTCCAGGGAAGGGGCTGGAGTACATCGGGA

TGATTGGTAGTAGTGGTACCATACACTACGCGAACTCCGCGAAAGGCAGATTCACCATCTCCAAAGACAATACCAA

GAACACGGTGGATCTTCAAATGAACAGCCTGAGAGCCGAGGACACGGCTGTGTATTACTGTGCGAGAGACAGTT

ATAATAGTGATTATGCCTTTAACTTATGGGGCCAGGGAACCCTGGTCACCGTCTCGAGCGCTAGCACCAAGGGCCC

ATCGGTCTTCCCCCTGGCACCCTCCTCCAAGAGCACCTCTGGGGGCACAGCGGCCCTGGGCTGCCTGGTCAAGGA

CTACTTCCCCGAACCGGTGACGGTGTCGTGGAACTCAGGCGCCCTGACCAGCGGCGTGCACACCTTCCCGGCTGTC

CTACAGTCCTCAGGACTCTACTCCCTCAGCAGCGTGGTGACCGTGCCCTCCAGCAGCTTGGGCACCCAGACCTACA

TCTGCAACGTGAATCACAAGCCCAGCAACACCAAGGTGGACAAGAGAGTTGAGCCCAAATCTTGTGACAAAACTC

ACACATGCCCACCGTGCCCAGCACCTGAAGCCGCGGGGGCACCGTCAGTCTTCCTCTTCCCCCCAAAACCCAAGGA

CACCCTCATGATCTCCCGGACCCCTGAGGTCACATGCGTGGTGGTGGACGTGAGCCACGAAGACCCTGAGGTCAA

GTTCAACTGGTACGTGGACGGCGTGGAGGTGCATAATGCCAAGACAAAGCCGCGGGAGGAGCAGTACAACAGCA

CGTACCGTGTGGTCAGCGTCCTCACCGTCCTGCACCAGGACTGGCTGAATGGCAAGGAGTACAAGTGCGCGGTCT

CCAACAAAGCCCTCCCAGCCCCCATCGAGAAAACCATCTCCAAAGCCAAAGGGCAGCCCCGAGAACCACAGGTGT

ACACCCTGCCCCCATCCCGGGATGAGCTGACCAAGAACCAGGTCAGCCTGACCTGCCTGGTCAAAGGCTTCTATCC

CAGCGACATCGCCGTGGAGTGGGAGAGCAATGGGCAGCCGGAGAACAACTACAAGACCACGCCTCCCGTGCTGG

ACTCCGACGGCTCCTTCTTCCTCTATAGCAAGCTCACCGTGGACAAGAGCAGGTGGCAGCAGGGGAACGTCTTCTC

ATGCTCCGTGATGCATGAGGCTCTGCACAACCACTACACGCAGAAGAGCCTCTCCCTGTCTCCGGGT

418H5HUMANIZEDHEAVYCHAINVARIABLEHEAVYCHAINNUCLEOTIDESEQUENCE

SEQ ID NO: 190

GAGGTGCAGCTGGTGGAGTCTGGGGGAGGCTTGGTCCAGCCTGGGGGGTCCCTGAGACTCTCCTGTACAGCCTC

TGGAATCGACCTCAGTGCCTACCACATGAGCTGGGTCCGCCAGGCTCCAGGGAAGGGGCTGGAGTACATCGGGA

TGATTGGTAGTAGTGGTACCATACACTACGCGAACTCCGCGAAAGGCAGATTCACCATCTCCAAAGACAATACCAA

GAACACGGTGGATCTTCAAATGAACAGCCTGAGAGCCGAGGACACGGCTGTGTATTACTGTGCGAGAGACAGTT

ATAATAGTGATTATGCCTTTAACTTATGGGGCCAGGGAACCCTGGTCACCGTCTCGAGC

418H5HUMANIZEDHEAVYCHAINFULL-LENGTHAMINOACIDSEQUENCE. HUMANGAMMA-1 CONSTANTDOMAINISUNDERLINED

SEQ ID NO: 191

EVQLVESGGGLVQPGGSLRLSCTASGIDLSAYHMSWVRQAPGKGLEYIGMIGSSGTIHYANSAKGRFTISKDNTKNTVD

LQMNSLRAEDTAVYYCARDSYNSDYAFNLWGQGTLVTVSSASTKGPSVFPLAPSSKSTSGGTAALGCLVKDYFPEPVTV

SWNSGALTSGVHTFPAVLQSSGLYSLSSVVTVPSSSLGTQTYICNVNHKPSNTKVDKRVEPKSCDKTHTCPPCPAPEAA

GAPSVFLFPPKPKDTLMISRTPEVTCVVVDVSHEDPEVKFNWYVDGVEVHNAKTKPREEQYNSTYRVVSVLTVLHQDW

LNGKEYKCAVSNKALPAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG

418H5HUMANIZEDHEAVYCHAINVARIABLEHEAVYCHAINAMINOACIDSEQUENCE. COMPLIMENTARITYDETERMININGREGIONSAREUNDERLINED

SEQ ID NO: 192

EVQLVESGGGLVQPGGSLRLSCTASGIDLSAYHMSWVRQAPGKGLEYIGMIGSSGTIHYANSAKGRFTISKDNTKNTVD

-continued

LQMNSLRAEDTAVYYCARDSYNSDYAFNLWGQGTLVTVSS

419D9HUMANIZEDLIGHTCHAINFULL-LENGTHNUCLEOTIDESEQUENCE

SEQ ID NO: 193

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTATCCTGGTATCAGCAGAAACCAGGGAAAGCCCCTAAGAGACTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTATAATACTGTTACTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

419D9HUMANIZEDLIGHTCHAINVARIABLELIGHTCHAINNUCLEOTIDESEQUENCE

SEQ ID NO: 194

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTATCCTGGTATCAGCAGAAACCAGGGAAAGCCCCTAAGAGACTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTATAATACTGTTACTGATACTTTTGCTTT

CGGCGGAGGGACCAAGGTGGAGATCAAA

419D9HUMANIZEDLIGHTCHAINFULL-LENGTHAMINOACIDSEQUENCE. HUMANKAPPACONSTANT DOMAINISUNDERLINED

SEQ ID NO: 195

DIQMTQSPSTLSASVGDRVTITCQSSQSVYSNWLSWYQQKPGKAPKRLIYSASTLASGVPSRFSGSGSGTEFTLTISSLQP

DDFATYYCAGGYNTVTDTFAFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

419D9HUMANIZEDLIGHTCHAINVARIABLELIGHTCHAINAMINOACIDSEQUENCE. COMPIMENTARITY DETERMININGREGIONSAREUNDERLINED

SEQ ID NO: 196

DIQMTQSPSTLSASVGDRVTITCQSSQSVYSNWLSWYQQKPGKAPKRLIYSASTLASGVPSRFSGSGSGTEFTLTISSLQP

DDFATYYCAGGYNTVTDTFAFGGGTKVEIK

419D9HUMANIZEDHEAVYCHAINFULL-LENGTHNUCLEOTIDESEQUENCE

SEQ ID NO: 197

GAGGTGCAGCTGTTGGAGTCTGGGGGAGGCTTGGTACAGCCTGGGGGGTCCCTGAGACTCTCCTGTACAGCCTCT

GGATTCTCCTTCAGTAGCAGGCACTACATGTGTTGGGTCCGCCAGGCTCCAGGGAAGGGGCTGGAGTGGATCGCA

TGCATTTATACTGGTAGTAGTGGTACTCCTCACTACGCGAGCTCCGCGAAAGGCCGGTTCACCATCTCCCAAGACA

ATTCCAAGAACACGGTGACTCTGCAAATGAACAGCCTGAGAGCCGAGGACACGGCCGTATATTACTGTGCGAGAG

AAGGTAACCTGTGGGGCCAGGGAACCCTGGTCACCGTCTCGAGCGCTAGCACCAAGGGCCCATCGGTCTTCCCCC

TGGCACCCTCCTCCAAGAGCACCTCTGGGGGCACAGCGGCCCTGGGCTGCCTGGTCAAGGACTACTTCCCCGAAC

CGGTGACGGTGTCGTGGAACTCAGGCGCCCTGACCAGCGGCGTGCACACCTTCCCGGCTGTCCTACAGTCCTCAG

GACTCTACTCCCTCAGCAGCGTGGTGACCGTGCCCTCCAGCAGCTTGGGCACCCAGACCTACATCTGCAACGTGAA

TCACAAGCCCAGCAACACCAAGGTGGACAAGAGAGTTGAGCCCAAATCTTGTGACAAAACTCACACATGCCCACC

GTGCCCAGCACCTGAAGCCGCGGGGGCACCGTCAGTCTTCCTCTTCCCCCCAAAACCCAAGGACACCCTCATGATC

TCCCGGACCCCTGAGGTCACATGCGTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAGTACAACAGCACGTACCGTGTGG

TCAGCGTCCTCACCGTCCTGCACCAGGACTGGCTGAATGGCAAGGAGTACAAGTGCGCGGTCTCCAACAAAGCCC

TCCCAGCCCCCATCGAGAAAACCATCTCCAAAGCCAAAGGGCAGCCCCGAGAACCACAGGTGTACACCCTGCCCC

CATCCCGGGATGAGCTGACCAAGAACCAGGTCAGCCTGACCTGCCTGGTCAAAGGCTTCTATCCCAGCGACATCG

-continued

CCGTGGAGTGGGAGAGCAATGGGCAGCCGGAGAACAACTACAAGACCACGCCTCCCGTGCTGGACTCCGACGGC

TCCTTCTTCCTCTATAGCAAGCTCACCGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCTCCGGGT

419D9HUMANIZEDHEAVYCHAINVARIABLEHEAVYCHAINNUCLEOTIDESEQUENCE

SEQ ID NO: 198

GAGGTGCAGCTGTTGGAGTCTGGGGGAGGCTTGGTACAGCCTGGGGGGTCCCTGAGACTCTCCTGTACAGCCTCT

GGATTCTCCTTCAGTAGCAGGCACTACATGTGTTGGGTCCGCCAGGCTCCAGGGAAGGGGCTGGAGTGGATCGCA

TGCATTTATACTGGTAGTAGTGGTACTCCTCACTACGCGAGCTCCGCGAAAGGCCGGTTCACCATCTCCCAAGACA

ATTCCAAGAACACGGTGACTCTGCAAATGAACAGCCTGAGAGCCGAGGACACGGCCGTATATTACTGTGCGAGAG

AAGGTAACCTGTGGGGCCAGGGAACCCTGGTCACCGTCTCGAGC

419D9HUMANIZEDHEAVYCHAINFULL-LENGTHAMINOACIDSEQUENCE. HUMANGAMMA-1 CONSTANTDOMAINISUNDERLINED

SEQ ID NO: 199

EVQLLESGGGLVQPGGSLRLSCTASGFSFSSRHYMCWVRQAPGKGLEWIACIYTGSSGTPHYASSAKGRFTISQDNSKN

TVTLQMNSLRAEDTAVYYCAREGNLWGQGTLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSNTKVDKRVEPKSCDKTHTCPPCPAPEAAGAPS

VFLFPPKPKDTLMISRTPEVTCVVVDVSHEDPEVKFNWYVDGVEVHNAKTKPREEQYNSTYRVVSVLTVLHQDWLNG

KEYKCAVSNKALPAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

419D9HUMANIZEDHEAVYCHAINVARIABLEHEAVYCHAINAMINOACIDSEQUENCE. COMPLIMENTARITYDETERMININGREGIONSAREUNDERLINED

SEQ ID NO: 200

EVQLLESGGGLVQPGGSLRLSCTASGFSFSSRHYMCWVRQAPGKGLEWIACIYTGSSGTPHYASSAKGRFTISQDNSKN

TVTLQMNSLRAEDTAVYYCAREGNLWGQGTLVTVSS

420H5HUMANIZEDLIGHTCHAINFULL-LENGTHNUCLEOTIDESEQUENCE

SEQ ID NO: 201

GCCCTTGTGATGACCCAGTCTCCTTCCACCCTGTCTGCATCTGTAGGAGACAGAGTCACCATCAATTGCCAGGCCA

GTGAGGACATTGATACCTATTTAGCCTGGTATCAGCAGAAACCAGGGAAAGCCCCTAAGCTCCTGATCTTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTGCTGATACGAGGGGTG

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

420H5HUMANIZEDLIGHTCHAINVARIABLELIGHTCHAINNUCLEOTIDESEQUENCE

SEQ ID NO: 202

GCCCTTGTGATGACCCAGTCTCCTTCCACCCTGTCTGCATCTGTAGGAGACAGAGTCACCATCAATTGCCAGGCCA

GTGAGGACATTGATACCTATTTAGCCTGGTATCAGCAGAAACCAGGGAAAGCCCCTAAGCTCCTGATCTTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTGCTGATACGAGGGGTG

CTTTCGGCGGAGGGACCAAGGTGGAGATCAAA

420H5HUMANIZEDLIGHTCHAINFULL-LENGTHAMINOACIDSEQUENCE. HUMANKAPPACONSTANT DOMAINISUNDERLINED

SEQ ID NO: 203

ALVMTQSPSTLSASVGDRVTINCQASEDIDTYLAWYQQKPGKAPKLLIFYASDLASGVPSRFSGSGSGTEFTLTISSLQPD

DFATYYCQGGYYTSSADTRGAFGGGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

-continued

420H5HUMANIZEDLIGHTCHAINVARIABLELIGHTCHAINAMINOACIDSEQUENCE. COMPIMENTARITY DETERMININGREGIONSAREUNDERLINED

SEQ ID NO: 204

ALVMTQSPSTLSASVGDRVTINCQASEDIDTYLAWYQQKPGKAPKLLIFYASDLASGVPSRFSGSGSGTEFTLTISSLQPD

DFATYYCQGGYYTSSADTRGAFGGGTKVEIK

420H5HUMANIZEDHEAVYCHAINFULL-LENGTHNUCLEOTIDESEQUENCE

SEQ ID NO: 205

CAGTCGCTGGTGGAGTCTGGGGGAGGCTTGGTACAGCCTGGGGGGTCCCTGAGACTCTCCTGTGCAGCCTCTGG

ATTCTCCTTCAGTAGCAACTACTGGATATGCTGGGTCCGCCAGGCTCCAGGGAAGGGGCTGGAGTGGATCGCATG

CATTTATGTTGGTAGTAGTGGTGACACTTACTACGCGAGCTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

AGTAGTAGTTATTATATGTTTAACTTGTGGGGCCAGGGAACCCTGGTCACCGTCTCGAGCGCTAGCACCAAGGGC

CCATCGGTCTTCCCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACACCTTCCCGGCTG

TCCTACAGTCCTCAGGACTCTACTCCCTCAGCAGCGTGGTGACCGTGCCCTCCAGCAGCTTGGGCACCCAGACCTA

CATCTGCAACGTGAATCACAAGCCCAGCAACACCAAGGTGGACAAGAGAGTTGAGCCCAAATCTTGTGACAAAAC

TCACACATGCCCACCGTGCCCAGCACCTGAAGCCGCGGGGGCACCGTCAGTCTTCCTCTTCCCCCCAAAACCCAAG

GACACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAACA

GCACGTACCGTGTGGTCAGCGTCCTCACCGTCCTGCACCAGGACTGGCTGAATGGCAAGGAGTACAAGTGCGCGG

TCTCCAACAAAGCCCTCCCAGCCCCCATCGAGAAAACCATCTCCAAAGCCAAAGGGCAGCCCCGAGAACCACAGG

TGTACACCCTGCCCCCATCCCGGGATGAGCTGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAGGTGGCAGCAGGGGAACGTCT

TCTCATGCTCCGTGATGCATGAGGCTCTGCACAACCACTACACGCAGAAGAGCCTCTCCCTGTCTCCGGGT

420H5HUMANIZEDHEAVYCHAINVARIABLEHEAVYCHAINNUCLEOTIDESEQUENCE

SEQ ID NO: 206

CAGTCGCTGGTGGAGTCTGGGGGAGGCTTGGTACAGCCTGGGGGGTCCCTGAGACTCTCCTGTGCAGCCTCTGG

ATTCTCCTTCAGTAGCAACTACTGGATATGCTGGGTCCGCCAGGCTCCAGGGAAGGGGCTGGAGTGGATCGCATG

CATTTATGTTGGTAGTAGTGGTGACACTTACTACGCGAGCTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

AGTAGTAGTTATTATATGTTTAACTTGTGGGGCCAGGGAACCCTGGTCACCGTCTCGAGC

420H5HUMANIZEDHEAVYCHAINFULL-LENGTHAMINOACIDSEQUENCE. HUMANGAMMA-1 CONSTANTDOMAINISUNDERLINED

SEQ ID NO: 207

QSLVESGGGLVQPGGSLRLSCAASGFSFSSNYWICWVRQAPGKGLEWIACIYVGSSGDTYYASSAKGRFTISRDNSKNT

LYLQMNSLRAEDTAVYYCARDSSSYYMFNLWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GAPSVFLFPPKPKDTLMISRTPEVTCVVVDVSHEDPEVKFNWYVDGVEVHNAKTKPREEQYNSTYRVVSVLTVLHQDW

LNGKEYKCAVSNKALPAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG

420H5HUMANIZEDHEAVYCHAINVARIABLEHEAVYCHAINAMINOACIDSEQUENCE. COMPLIMENTARITYDETERMININGREGIONSAREUNDERLINED

SEQ ID NO: 208

QSLVESGGGLVQPGGSLRLSCAASGFSFSSNYWICWVRQAPGKGLEWIACIYVGSSGDTYYASSAKGRFTISRDNSKNT

LYLQMNSLRAEDTAVYYCARDSSSYYMFNLWGQGTLVTVSS

420H6HUMANIZEDLIGHTCHAINFULL-LENGTHNUCLEOTIDESEQUENCE

-continued

SEQ ID NO: 209
GACATCCAGATGACCCAGTCTCCTTCCACCCTGTCTGCATCTGTAGGAGACAGAGTCACCATCACTTGCCAGGCCA

GTCAGAGTGTTTATAGTAACTGGTTATCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAATTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

420H6HUMANIZEDLIGHTCHAINVARIABLELIGHTCHAINNUCLEOTIDESEQUENCE

SEQ ID NO: 210
GACATCCAGATGACCCAGTCTCCTTCCACCCTGTCTGCATCTGTAGGAGACAGAGTCACCATCACTTGCCAGGCCA

GTCAGAGTGTTTATAGTAACTGGTTATCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAATTGATACTTTTGCTTT

CGGCGGAGGGACCAAGGTGGAGATCAAA

420H6HUMANIZEDLIGHTCHAINFULL-LENGTHAMINOACIDSEQUENCE. HUMANKAPPACONSTANT DOMAINISUNDERLINED

SEQ ID NO: 211
DIQMTQSPSTLSASVGDRVTITCQASQSVYSNWLSWYQQKPGKAPKLLIYSASTLASGVPSRFSGSGSGTEFTLTISSLQP

DDFATYYCAGGYNTVIDTFAFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

420H6HUMANIZEDLIGHTCHAINVARIABLELIGHTCHAINAMINOACIDSEQUENCE. COMPIMENTARITY DETERMININGREGIONSAREUNDERLINED

SEQ ID NO: 212
DIQMTQSPSTLSASVGDRVTITCQASQSVYSNWLSWYQQKPGKAPKLLIYSASTLASGVPSRFSGSGSGTEFTLTISSLQP

DDFATYYCAGGYNTVIDTFAFGGGTKVEIK

420H6HUMANIZEDHEAVYCHAINFULL-LENGTHNUCLEOTIDESEQUENCE

SEQ ID NO: 213
GAGGTGCAGCTGTTGGAGTCTGGGGGAGGCTTGGTACAGCCTGGGGGGTCCCTGAGACTCTCCTGTGCAGCCTCT

GGAATCGACTTCAGTAGTAGTTACTACATGTGCTGGGTCCGCCAGGCTCCAGGGAAGGGGCTGGAGTGGATCGC

ATGCATTTATACTGGTGGTAGTGGTACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAGCCTGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

-continued

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

420H6HUMANIZEDHEAVYCHAINVARIABLEHEAVYCHAINNUCLEOTIDESEQUENCE

SEQ ID NO: 214

GAGGTGCAGCTGTTGGAGTCTGGGGGAGGCTTGGTACAGCCTGGGGGGTCCCTGAGACTCTCCTGTGCAGCCTCT

GGAATCGACTTCAGTAGTAGTTACTACATGTGCTGGGTCCGCCAGGCTCCAGGGAAGGGGCTGGAGTGGATCGC

ATGCATTTATACTGGTGGTAGTGGTACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAGCCTGTGGGGCCAGGGAACCCTGGTCACCGTCTCGAGC

420H6HUMANIZEDHEAVYCHAINFULL-LENGTHAMINOACIDSEQUENCE. HUMANGAMMA-1 CONSTANTDOMAINISUNDERLINED

SEQ ID NO: 215

EVQLLESGGGLVQPGGSLRLSCAASGIDFSSSYYMCWVRQAPGKGLEWIACIYTGGSGTPHYASSAKGRFTISRDNSKN

TLYLQMNSLRAEDTAVYYCAREGSLWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

420H6HUMANIZEDHEAVYCHAINVARIABLEHEAVYCHAINAMINOACIDSEQUENCE. COMPLIMENTARITYDETERMININGREGIONSAREUNDERLINED

SEQ ID NO: 216

EVQLLESGGGLVQPGGSLRLSCAASGIDFSSSYYMCWVRQAPGKGLEWIACIYTGGSGTPHYASSAKGRFTISRDNSKN

TLYLQMNSLRAEDTAVYYCAREGSLWGQGTLVTVSS

459F1HUMANIZEDLIGHTCHAINFULL-LENGTHNUCLEOTIDESEQUENCE

SEQ ID NO: 217

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAACTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

459F1HUMANIZEDLIGHTCHAINVARIABLELIGHTCHAINNUCLEOTIDESEQUENCE

SEQ ID NO: 218

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTAACTGATACTTTTGCTTT

CGGCGGAGGGACCAAGGTGGAGATCAAA

459F1HUMANIZEDLIGHTCHAINFULL-LENGTHAMINOACIDSEQUENCE. HUMANKAPPACONSTANT DOMAINISUNDERLINED

SEQ ID NO: 219

DIQMTQSPSTLSASVGDRVTITCQSSQSVYSNWFSWYQQKPGKAPKLLIYSASTLASGVPSRFSGSGSGTEFTLTISSLQP

DDFATYYCAGGYNTVTDTFAFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

459F1HUMANIZEDLIGHTCHAINVARIABLELIGHTCHAINAMINOACIDSEQUENCE. COMPIMENTARITY DETERMININGREGIONSAREUNDERLINED

-continued

SEQ ID NO: 220
DIQMTQSPSTLSASVGDRVTITCQSSQSVYSNWFSWYQQKPGKAPKLLIYSASTLASGVPSRFSGSGSGTEFTLTISSLQP

DDFATYYCAGGYNTVTDTFAFGGGTKVEIK

459F1HUMANIZEDHEAVYCHAINFULL-LENGTHNUCLEOTIDESEQUENCE

SEQ ID NO: 221
GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATGTATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAACCTGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

459F1HUMANIZEDHEAVYCHAINVARIABLEHEAVYCHAINNUCLEOTIDESEQUENCE

SEQ ID NO: 222
GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATGTATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAACCTGTGGGGCCAGGGAACCCTGGTCACCGTCTCGAGC

459F1HUMANIZEDHEAVYCHAINFULL-LENGTHAMINOACIDSEQUENCE. HUMANGAMMA-1
CONSTANTDOMAINISUNDERLINED

SEQ ID NO: 223
EVQLLESGGGLVQPGGSLRLSCAASGIDFSRRYYMCWVRQAPGKGLEWIACMYTGSRDTPHYASSAKGRFTISRDNSK

NTLYLQMNSLRAEDTAVYYCAREGNLWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKRVEPKSCDKTHTCPPCPAPEAAGAP

SVFLFPPKPKDTLMISRTPEVTCVVVDVSHEDPEVKFNWYVDGVEVHNAKTKPREEQYNSTYRVVSVLTVLHQDWLNG

KEYKCAVSNKALPAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

459F1HUMANIZEDHEAVYCHAINVARIABLEHEAVYCHAINAMINOACIDSEQUENCE.
COMPLIMENTARITYDETERMININGREGIONSAREUNDERLINED

SEQ ID NO: 224
EVQLLESGGGLVQPGGSLRLSCAASGIDFSRRYYMCWVRQAPGKGLEWIACMYTGSRDTPHYASSAKGRFTISRDNSK

NTLYLQMNSLRAEDTAVYYCAREGNLWGQGTLVTVSS

460C3HUMANIZEDLIGHTCHAINFULL-LENGTHNUCLEOTIDESEQUENCE

SEQ ID NO: 225
GACATCCAGATGACCCAGTCTCCTTCCACCCTGTCTGCATCTGTAGGAGACAGAGTCACCATCACTTGCCAGTCCA

-continued

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTTATTGATACTTTTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

460C3HUMANIZEDLIGHTCHAINVARIABLELIGHTCHAINNUCLEOTIDESEQUENCE

SEQ ID NO: 226

GACATCCAGATGACCCAGTCTCCTTCCACCCTGTCTGCATCTGTAGGAGACAGAGTCACCATCACTTGCCAGTCCA

GTCAGAGTGTTTATAGTAACTGGTTCTCCTGGTATCAGCAGAAACCAGGGAAAGCCCCTAAGCTCCTGATCTATTC

TGCATCCACTCTGGCATCTGGGGTCCCATCAAGGTTCAGCGGCAGTGGATCTGGGACAGAATTCACTCTCACCATC

AGCAGCCTGCAGCCTGATGATTTTGCAACTTATTACTGCGCAGGCGGTTACAATACTGTTATTGATACTTTTGCTTT

CGGCGGAGGGACCAAGGTGGAGATCAAA

460C3HUMANIZEDLIGHTCHAINFULL-LENGTHAMINOACIDSEQUENCE. HUMANKAPPACONSTANT DOMAINISUNDERLINED

SEQ ID NO: 227

DIQMTQSPSTLSASVGDRVTITCQSSQSVYSNWFSWYQQKPGKAPKLLIYSASTLASGVPSRFSGSGSGTEFTLTISSLQP

DDFATYYCAGGYNTVIDTFAFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

460C3HUMANIZEDLIGHTCHAINVARIABLELIGHTCHAINAMINOACIDSEQUENCE. COMPIMENTARITY DETERMININGREGIONSAREUNDERLINED

SEQ ID NO: 228

DIQMTQSPSTLSASVGDRVTITCQSSQSVYSNWFSWYQQKPGKAPKLLIYSASTLASGVPSRFSGSGSGTEFTLTISSLQP

DDFATYYCAGGYNTVIDTFAFGGGTKVEIK

460C3HUMANIZEDHEAVYCHAINFULL-LENGTHNUCLEOTIDESEQUENCE

SEQ ID NO: 229

GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATATATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAGCCTGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

-continued

460C3HUMANIZEDHEAVYCHAINVARIABLEHEAVYCHAINNUCLEOTIDESEQUENCE

SEQ ID NO: 230

GAGGTGCAGCTGTTGGAGTCTGGGGGAGGCTTGGTACAGCCTGGGGGGTCCCTGAGACTCTCCTGTGCAGCCTCT

GGAATCGACTTCAGTAGGAGATACTACATGTGCTGGGTCCGCCAGGCTCCAGGGAAGGGGCTGGAGTGGATCGC

ATGCATATATACTGGTAGCCGCGATACTCCTCACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAGA

GAAGGTAGCCTGTGGGGCCAGGGAACCCTGGTCACCGTCTCGAGC

460C3HUMANIZEDHEAVYCHAINFULL-LENGTHAMINOACIDSEQUENCE. HUMANGAMMA-1 CONSTANTDOMAINISUNDERLINED

SEQ ID NO: 231

EVQLLESGGGLVQPGGSLRLSCAASGIDFSRRYYMCWVRQAPGKGLEWIACIYTGSRDTPHYASSAKGRFTISRDNSKN

TLYLQMNSLRAEDTAVYYCAREGSLWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

460C3HUMANIZEDHEAVYCHAINVARIABLEHEAVYCHAINAMINOACIDSEQUENCE. COMPLIMENTARITYDETERMININGREGIONSAREUNDERLINED

SEQ ID NO: 232

EVQLLESGGGLVQPGGSLRLSCAASGIDFSRRYYMCWVRQAPGKGLEWIACIYTGSRDTPHYASSAKGRFTISRDNSKN

TLYLQMNSLRAEDTAVYYCAREGSLWGQGTLVTVSS

464C11HUMANIZEDLIGHTCHAINFULL-LENGTHNUCLEOTIDESEQUENCE

SEQ ID NO: 233

GACATCCAGATGACCCAGTCTCCTTCCACCCTGTCTGCATCTGTAGGAGACAGAGTCACCATCACTTGCCAGTCCA

GTCAGAGTGTTTATAGTAACAGCTTCTTATCCTGGTATCAGCAGAAACCAGGGAAAGCCCCTAAGCTCCTGATCTA

TTCTGCATCCGATCTGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCGCAGGCGTTTATAGTGATAATACTTATGTTTTCGG

CGGAGGGACCAAGGTGGAGATCAAACGTACGGTGGCTGCACCATCTGTCTTCATCTTCCCGCCATCTGATGAGCA

GTTGAAATCTGGAACTGCCTCTGTTGTGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCAGGACAGCAAGGACAGCACCTACAG

CCTCAGCAGCACCCTGACGCTGAGCAAAGCAGACTACGAGAAACACAAAGTCTACGCCTGCGAAGTCACCCATCA

GGGCCTGAGCTCGCCCGTCACAAAGAGCTTCAACAGGGGAGAGTGT

464C11HUMANIZEDLIGHTCHAINVARIABLELIGHTCHAINNUCLEOTIDESEQUENCE

SEQ ID NO: 234

GACATCCAGATGACCCAGTCTCCTTCCACCCTGTCTGCATCTGTAGGAGACAGAGTCACCATCACTTGCCAGTCCA

GTCAGAGTGTTTATAGTAACAGCTTCTTATCCTGGTATCAGCAGAAACCAGGGAAAGCCCCTAAGCTCCTGATCTA

TTCTGCATCCGATCTGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCGCAGGCGTTTATAGTGATAATACTTATGTTTTCGG

CGGAGGGACCAAGGTGGAGATCAAA

464C11 HUMANIZED LIGHT CHAIN FULL-LENGTH AMINO ACID SEQUENCE. HUMAN KAPPA CONSTANT DOMAINISUNDERLINED

SEQ ID NO: 235

DIQMTQSPSTLSASVGDRVTITCQSSQSVYSNSFLSWYQQKPGKAPKLLIYSASDLASGVPSRFSGSGSGTEFTLTISSLQP

DDFATYYCAGVYSDNTYVFGGGTKVEIKRTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTKSFNRGEC

464C11HUMANIZEDLIGHTCHAINVARIABLELIGHTCHAINAMINOACIDSEQUENCE. COMPIMENTARITYDETERMININGREGIONSAREUNDERLINED

SEQ ID NO: 236

DIQMTQSPSTLSASVGDRVTITCQSSQSVYSNSFLSWYQQKPGKAPKLLIYSASDLASGVPSRFSGSGSGTEFTLTISSLQP

-continued

DDFATYYCAGVYSDNTYVFGGGTKVEIK

464C11HUMANIZEDHEAVYCHAINFULL-LENGTHNUCLEOTIDESEQUENCE

SEQ ID NO: 237

GAGGTGCAGCTGGTGGAGTCTGGGGGAGGCTTGGTACAGCCAGGGCCGTCCCTGAGACTCTCCTGTACAGCTTCT

GGATTCTCCCTCAGTCACTACTGGATGACTTGGGTCCGCCAGGCTCCAGGGAAGGGGCTGGAGTACATCGGATTC

ATTAATGTTGGTGGTGACACATCTTACGCGAGCTCTGTGAAAGGCAGATTCACCATCTCAAGAGATGATTCCAAAA

GCATCGCCTATCTGCAAATGAACAGCCTGAAAACCGAGGACACAGCCGTGTATTACTGTGGCAGAGGTGGTCTGA

CTTTTGGTTGGGACTTGTGGGGCCAGGGAACCCTGGTCACCGTCTCGAGCGCTAGCACCAAGGGCCCATCGGTCT

TCCCCCTGGCACCCTCCTCCAAGAGCACCTCTGGGGGCACAGCGGCCCTGGGCTGCCTGGTCAAGGACTACTTCCC

CGAACCGGTGACGGTGTCGTGGAACTCAGGCGCCCTGACCAGCGGCGTGCACACCTTCCCGGCTGTCCTACAGTC

CTCAGGACTCTACTCCCTCAGCAGCGTGGTGACCGTGCCCTCCAGCAGCTTGGGCACCCAGACCTACATCTGCAAC

GTGAATCACAAGCCCAGCAACACCAAGGTGGACAAGAGAGTTGAGCCCAAATCTTGTGACAAAACTCACACATGC

CCACCGTGCCCAGCACCTGAAGCCGCGGGGGCACCGTCAGTCTTCCTCTTCCCCCCAAAACCCAAGGACACCCTCA

TGATCTCCCGGACCCCTGAGGTCACATGCGTGGTGGTGGACGTGAGCCACGAAGACCCTGAGGTCAAGTTCAACT

GGTACGTGGACGGCGTGGAGGTGCATAATGCCAAGACAAAGCCGCGGGAGGAGCAGTACAACAGCACGTACCG

TGTGGTCAGCGTCCTCACCGTCCTGCACCAGGACTGGCTGAATGGCAAGGAGTACAAGTGCGCGGTCTCCAACAA

AGCCCTCCCAGCCCCCATCGAGAAAACCATCTCCAAAGCCAAAGGGCAGCCCCGAGAACCACAGGTGTACACCCT

GCCCCCATCCCGGGATGAGCTGACCAAGAACCAGGTCAGCCTGACCTGCCTGGTCAAAGGCTTCTATCCCAGCGA

CATCGCCGTGGAGTGGGAGAGCAATGGGCAGCCGGAGAACAACTACAAGACCACGCCTCCCGTGCTGGACTCCG

ACGGCTCCTTCTTCCTCTATAGCAAGCTCACCGTGGACAAGAGCAGGTGGCAGCAGGGGAACGTCTTCTCATGCTC

CGTGATGCATGAGGCTCTGCACAACCACTACACGCAGAAGAGCCTCTCCCTGTCTCCGGGT

464C11HUMANIZEDHEAVYCHAINVARIABLEHEAVYCHAINNUCLEOTIDESEQUENCE

SEQ ID NO: 238

GAGGTGCAGCTGGTGGAGTCTGGGGGAGGCTTGGTACAGCCAGGGCCGTCCCTGAGACTCTCCTGTACAGCTTCT

GGATTCTCCCTCAGTCACTACTGGATGACTTGGGTCCGCCAGGCTCCAGGGAAGGGGCTGGAGTACATCGGATTC

ATTAATGTTGGTGGTGACACATCTTACGCGAGCTCTGTGAAAGGCAGATTCACCATCTCAAGAGATGATTCCAAAA

GCATCGCCTATCTGCAAATGAACAGCCTGAAAACCGAGGACACAGCCGTGTATTACTGTGGCAGAGGTGGTCTGA

CTTTTGGTTGGGACTTGTGGGGCCAGGGAACCCTGGTCACCGTCTCGAGC

464C11HUMANIZEDHEAVYCHAINFULL-LENGTHAMINOACIDSEQUENCE. HUMANGAMMA-1 CONSTANTDOMAINISUNDERLINED

SEQ ID NO: 239

EVQLVESGGGLVQPGPSLRLSCTASGFSLSHYWMTWVRQAPGKGLEYIGFINVGGDTSYASSVKGRFTISRDDSKSIAYL

QMNSLKTEDTAVYYCGRGGLTFGWDLWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKRVEPKSCDKTHTCPPCPAPEAAGAP

SVFLFPPKPKDTLMISRTPEVTCVVVDVSHEDPEVKFNWYVDGVEVHNAKTKPREEQYNSTYRVVSVLTVLHQDWLNG

KEYKCAVSNKALPAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

464C11HUMANIZEDHEAVYCHAINVARIABLEHEAVYCHAINAMINOACIDSEQUENCE. COMPLIMENTARITYDETERMININGREGIONSAREUNDERLINED

SEQ ID NO: 240

EVQLVESGGGLVQPGPSLRLSCTASGFSLSHYWMTWVRQAPGKGLEYIGFINVGGDTSYASSVKGRFTISRDDSKSIAYL

QMNSLKTEDTAVYYCGRGGLTFGWDLWGQGTLVTVSS

466F6HUMANIZEDLIGHTCHAINFULL-LENGTHNUCLEOTIDESEQUENCE

SEQ ID NO: 241

GACGTTGTGATGACCCAGTCTCCATCTTCCGTGTCTGCATCTGTAGGAGACAGAGTCACCATCACCTGTCAGGCCA

GTCAGAACATTAGGACTTACTTATCCTGGTATCAGCAGAAACCAGGGAAAGCCCCTAAGCTCCTGATCTATGCTGC

AGCCAATCTGGCATCTGGGGTCCCATCAAGGTTCAGCGGCAGTGGATCTGGGACAGATTTCACTCTCACCATCAGC

-continued

GACCTGGAGCCTGGCGATGCTGCAACTTACTATTGTCAGTCTACCTATCTTGGTACTGATTATGTTGGCGGTGCTTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

466F6HUMANIZEDLIGHTCHAINVARIABLELIGHTCHAINNUCLEOTIDESEQUENCE

SEQ ID NO: 242

GACGTTGTGATGACCCAGTCTCCATCTTCCGTGTCTGCATCTGTAGGAGACAGAGTCACCATCACCTGTCAGGCCA

GTCAGAACATTAGGACTTACTTATCCTGGTATCAGCAGAAACCAGGGAAAGCCCCTAAGCTCCTGATCTATGCTGC

AGCCAATCTGGCATCTGGGGTCCCATCAAGGTTCAGCGGCAGTGGATCTGGGACAGATTTCACTCTCACCATCAGC

GACCTGGAGCCTGGCGATGCTGCAACTTACTATTGTCAGTCTACCTATCTTGGTACTGATTATGTTGGCGGTGCTTT

CGGCGGAGGGACCAAGGTGGAGATCAAA

466F6HUMANIZEDLIGHTCHAINFULL-LENGTHAMINOACIDSEQUENCE. HUMANKAPPACONSTANT DOMAINISUNDERLINED

SEQ ID NO: 243

DVVMTQSPSSVSASVGDRVTITCQASQNIRTYLSWYQQKPGKAPKLLIYAAANLASGVPSRFSGSGSGTDFTLTISDLEP

GDAATYYCQSTYLGTDYVGGAFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

466F6HUMANIZEDLIGHTCHAINVARIABLELIGHTCHAINAMINOACIDSEQUENCE. COMPIMENTARITY DETERMININGREGIONSAREUNDERLINED

SEQ ID NO: 244

DVVMTQSPSSVSASVGDRVTITCQASQNIRTYLSWYQQKPGKAPKLLIYAAANLASGVPSRFSGSGSGTDFTLTISDLEP

GDAATYYCQSTYLGTDYVGGAFGGGTKVEIK

466F6HUMANIZEDHEAVYCHAINFULL-LENGTHNUCLEOTIDESEQUENCE

SEQ ID NO: 245

CGGTCGCTGGTGGAGTCTGGGGGAGGCTTGGTCCAGCCTGGGGGGTCCCTGAGACTCTCCTGTACAGCCTCTGGA

TTCACCATCAGTAGCTACCACATGCAGTGGGTCCGCCAGGCTCCAGGGAAGGGGCTGGAGTACATCGGAACCATT

AGTAGTGGTGGTAATGTATACTACGCGAGCTCCGCGAGAGGCAGATTCACCATCTCCAGACCCTCGTCCAAGAAC

ACGGTGGATCTTCAAATGAACAGCCTGAGAGCCGAGGACACGGCTGTGTATTACTGTGCGAGAGACTCTGGTTAT

AGTGATCCTATGTGGGGCCAGGGAACCCTGGTCACCGTCTCGAGCGCTAGCACCAAGGGCCCATCGGTCTTCCCC

CTGGCACCCTCCTCCAAGAGCACCTCTGGGGGCACAGCGGCCCTGGGCTGCCTGGTCAAGGACTACTTCCCCGAA

CCGGTGACGGTGTCGTGGAACTCAGGCGCCCTGACCAGCGGCGTGCACACCTTCCCGGCTGTCCTACAGTCCTCA

GGACTCTACTCCCTCAGCAGCGTGGTGACCGTGCCCTCCAGCAGCTTGGGCACCCAGACCTACATCTGCAACGTGA

ATCACAAGCCCAGCAACACCAAGGTGGACAAGAGAGTTGAGCCCAAATCTTGTGACAAAACTCACACATGCCCAC

CGTGCCCAGCACCTGAAGCCGCGGGGGCACCGTCAGTCTTCCTCTTCCCCCCAAAACCCAAGGACACCCTCATGAT

CTCCCGGACCCCTGAGGTCACATGCGTGGTGGTGGACGTGAGCCACGAAGACCCTGAGGTCAAGTTCAACTGGTA

CGTGGACGGCGTGGAGGTGCATAATGCCAAGACAAAGCCGCGGGAGGAGCAGTACAACAGCACGTACCGTGTG

GTCAGCGTCCTCACCGTCCTGCACCAGGACTGGCTGAATGGCAAGGAGTACAAGTGCGCGGTCTCCAACAAAGCC

CTCCCAGCCCCCATCGAGAAAACCATCTCCAAAGCCAAAGGGCAGCCCCGAGAACCACAGGTGTACACCCTGCCC

CCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

466F6HUMANIZEDHEAVYCHAINVARIABLEHEAVYCHAINNUCLEOTIDESEQUENCE

-continued

SEQ ID NO: 246

CGGTCGCTGGTGGAGTCTGGGGGAGGCTTGGTCCAGCCTGGGGGGTCCCTGAGACTCTCCTGTACAGCCTCTGGA

TTCACCATCAGTAGCTACCACATGCAGTGGGTCCGCCAGGCTCCAGGGAAGGGGCTGGAGTACATCGGAACCATT

AGTAGTGGTGGTAATGTATACTACGCGAGCTCCGCGAGAGGCAGATTCACCATCTCCAGACCCTCGTCCAAGAAC

ACGGTGGATCTTCAAATGAACAGCCTGAGAGCCGAGGACACGGCTGTGTATTACTGTGCGAGAGACTCTGGTTAT

AGTGATCCTATGTGGGGCCAGGGAACCCTGGTCACCGTCTCGAGC

466F6HUMANIZEDHEAVYCHAINFULL-LENGTHAMINOACIDSEQUENCE. HUMANGAMMA-1 CONSTANTDOMAINISUNDERLINED

SEQ ID NO: 247

RSLVESGGGLVQPGGSLRLSCTASGFTISSYHMQWVRQAPGKGLEYIGTISSGGNVYYASSARGRFTISRPSSKNTVDLQ

MNSLRAEDTAVYYCARDSGYSDPMWGQGTLVTVSSASTKGPSVFPLAPSSKSTSGGTAALGCLVKDYFPEPVTVSWNS

GALTSGVHTFPAVLQSSGLYSLSSVVTVPSSSLGTQTYICNVNHKPSNTKVDKRVEPKSCDKTHTCPPCPAPEAAGAPSV

FLFPPKPKDTLMISRTPEVTCVVVDVSHEDPEVKFNWYVDGVEVHNAKTKPREEQYNSTYRVVSVLTVLHQDWLNGKE

YKCAVSNKALPAPIEKTISKAKGQPREPQVYTLPPSRDELTKNQVSLTCLVKGFYPSDIAVEWESNGQPENNYKTTPPVL

DSDGSFFLYSKLTVDKSRWQQGNVFSCSVMHEALHNHYTQKSLSLSPG

466F6HUMANIZEDHEAVYCHAINVARIABLEHEAVYCHAINAMINOACIDSEQUENCE. COMPLIMENTARITYDETERMININGREGIONSAREUNDERLINED

SEQ ID NO: 248

RSLVESGGGLVQPGGSLRLSCTASGFTISSYHMQWVRQAPGKGLEYIGTISSGGNVYYASSARGRFTISRPSSKNTVDLQ

MNSLRAEDTAVYYCARDSGYSDPMWGQGTLVTVSS

470B6HUMANIZEDLIGHTCHAINFULL-LENGTHNUCLEOTIDESEQUENCE

SEQ ID NO: 249

GACATCCAGATGACCCAGTCTCCTTCCACCCTGTCTGCATCTGTAGGAGACAGAGTCACCATCACTTGCCAGGCCA

GTCAGAGCATTAGTACTAACTTGAACTGGTATCAGCAGAAACCAGGGAAAGCCCCTAAGCTCCTGATCTATTATGC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGATTT

CGGCGGAGGGACCAAGGTGGAGATCAAACGTACGGTGGCTGCACCATCTGTCTTCATCTTCCCGCCATCTGATGA

GCAGTTGAAATCTGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGGACAGCACCTA

CAGCCTCAGCAGCACCCTGACGCTGAGCAAAGCAGACTACGAGAAACACAAAGTCTACGCCTGCGAAGTCACCCA

TCAGGGCCTGAGCTCGCCCGTCACAAAGAGCTTCAACAGGGGAGAGTGT

470B6HUMANIZEDLIGHTCHAINVARIABLELIGHTCHAINNUCLEOTIDESEQUENCE

SEQ ID NO: 250

GACATCCAGATGACCCAGTCTCCTTCCACCCTGTCTGCATCTGTAGGAGACAGAGTCACCATCACTTGCCAGGCCA

GTCAGAGCATTAGTACTAACTTGAACTGGTATCAGCAGAAACCAGGGAAAGCCCCTAAGCTCCTGATCTATTATGC

ATCCAGTCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCTAGGTGTTTGGAATTATTGGGGTGATGATGGTACTGATTT

CGGCGGAGGGACCAAGGTGGAGATCAAA

470B6HUMANIZEDLIGHTCHAINFULL-LENGTHAMINOACIDSEQUENCE. HUMANKAPPACONSTANT DOMAINISUNDERLINED

SEQ ID NO: 251

DIQMTQSPSTLSASVGDRVTITCQASQSISTNLNWYQQKPGKAPKLLIYYASSLASGVPSRFSGSGSGTEFTLTISSLQPD

DFATYYCLGVWNYWGDDGTDFGGGTKVEIKRTVAAPSVFIFPPSDEQLKSGTASVVCLLNNFYPREAKVQWKVDNAL

QSGNSQESVTEQDSKDSTYSLSSTLTLSKADYEKHKVYACEVTHQGLSSPVTKSFNRGEC

470B6HUMANIZEDLIGHTCHAINVARIABLELIGHTCHAINAMINOACIDSEQUENCE. COMPIMENTARITY DETERMININGREGIONSAREUNDERLINED

SEQ ID NO: 252

DIQMTQSPSTLSASVGDRVTITCQASQSISTNLNWYQQKPGKAPKLLIYYASSLASGVPSRFSGSGSGTEFTLTISSLQPD

DFATYYCLGVWNYWGDDGTDFGGGTKVEIK

-continued

470B6HUMANIZEDHEAVYCHAINFULL-LENGTHNUCLEOTIDESEQUENCE

SEQ ID NO: 253

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGGTAGTGGTGCCGCATACTACGCGAGCTCCGCTAAAGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

TAACAATGCCATGTGGGGCCAGGGAACCCTGGTCACCGTCTCGAGCGCTAGCACCAAGGGCCCATCGGTCTTCCC

CCTGGCACCCTCCTCCAAGAGCACCTCTGGGGGCACAGCGGCCCTGGGCTGCCTGGTCAAGGACTACTTCCCCGA

ACCGGTGACGGTGTCGTGGAACTCAGGCGCCCTGACCAGCGGCGTGCACACCTTCCCGGCTGTCCTACAGTCCTC

AGGACTCTACTCCCTCAGCAGCGTGGTGACCGTGCCCTCCAGCAGCTTGGGCACCCAGACCTACATCTGCAACGTG

AATCACAAGCCCAGCAACACCAAGGTGGACAAGAGAGTTGAGCCCAAATCTTGTGACAAAACTCACACATGCCCA

CCGTGCCCAGCACCTGAAGCCGCGGGGGCACCGTCAGTCTTCCTCTTCCCCCCAAAACCCAAGGACACCCTCATGA

TCTCCCGGACCCCTGAGGTCACATGCGTGGTGGTGGACGTGAGCCACGAAGACCCTGAGGTCAAGTTCAACTGGT

ACGTGGACGGCGTGGAGGTGCATAATGCCAAGACAAAGCCGCGGGAGGAGCAGTACAACAGCACGTACCGTGT

GGTCAGCGTCCTCACCGTCCTGCACCAGGACTGGCTGAATGGCAAGGAGTACAAGTGCGCGGTCTCCAACAAAGC

CCTCCCAGCCCCCATCGAGAAAACCATCTCCAAAGCCAAAGGGCAGCCCCGAGAACCACAGGTGTACACCCTGCC

CCCATCCCGGGATGAGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCTGGACTCCGACGG

CTCCTTCTTCCTCTATAGCAAGCTCACCGTGGACAAGAGCAGGTGGCAGCAGGGGAACGTCTTCTCATGCTCCGTG

ATGCATGAGGCTCTGCACAACCACTACACGCAGAAGAGCCTCTCCCTGTCTCCGGGT

470B6HUMANIZEDHEAVYCHAINVARIABLEHEAVYCHAINNUCLEOTIDESEQUENCE

SEQ ID NO: 254

GAGGTGCAGCTGGTGGAGTCTGGGGGAGGCTTGGTCCAGCCTGGGGGGTCCCTGAGACTCTCCTGTGCAGCCTC

TGGATTCTCCCTCAGTAGCTACTACATGAGCTGGGTCCGCCAGGCTCCAGGGAAGGGGCTGGAGTGGATCGGAA

GTATTTATGGTAGTGGTGCCGCATACTACGCGAGCTCCGCTAAAGGCAGATTCACCATCTCCAGAGACAATTCCAA

GAACACGCTGTATCTTCAAATGAACAGCCTGAGAGCCGAGGACACGGCTGTGTATTACTGTGCGAGAGATCCTAT

TAACAATGCCATGTGGGGCCAGGGAACCCTGGTCACCGTCTCGAGC

470B6HUMANIZEDHEAVYCHAINFULL-LENGTHAMINOACIDSEQUENCE. HUMANGAMMA-1 CONSTANTDOMAINISUNDERLINED

SEQ ID NO: 255

EVQLVESGGGLVQPGGSLRLSCAASGFSLSSYYMSWVRQAPGKGLEWIGSIYGSGAAYYASSAKGRFTISRDNSKNTLY

LQMNSLRAEDTAVYYCARDPINNAMWGQGTLVTVSSASTKGPSVFPLAPSSKSTSGGTAALGCLVKDYFPEPVTVSW

NSGALTSGVHTFPAVLQSSGLYSLSSVVTVPSSSLGTQTYICNVNHKPSNTKVDKRVEPKSCDKTHTCPPCPAPEAAGAP

SVFLFPPKPKDTLMISRTPEVTCVVVDVSHEDPEVKFNWYVDGVEVHNAKTKPREEQYNSTYRVVSVLTVLHQDWLNG

KEYKCAVSNKALPAPIEKTISKAKGQPREPQVYTLPPSRDELTKNQVSLTCLVKGFYPSDIAVEWESNGQPENNYKTTPP

VLDSDGSFFLYSKLTVDKSRWQQGNVFSCSVMHEALHNHYTQKSLSLSPG

470B6HUMANIZEDHEAVYCHAINVARIABLEHEAVYCHAINAMINOACIDSEQUENCE. COMPLIMENTARITYDETERMININGREGIONSAREUNDERLINED

SEQ ID NO: 256

EVQLVESGGGLVQPGGSLRLSCAASGFSLSSYYMSWVRQAPGKGLEWIGSIYGSGAAYYASSAKGRFTISRDNSKNTLY

LQMNSLRAEDTAVYYCARDPINNAMWGQGTLVTVSS

470C6HUMANIZEDLIGHTCHAINFULL-LENGTHNUCLEOTIDESEQUENCE

SEQ ID NO: 257

GCCCTTGTGATGACCCAGTCTCCTTCCACCCTGTCTGCATCTGTAGGAGACAGAGTCACCATCAATTGCCAGGCCA

GTGAGGACATTGATAACTATTTAGCCTGGTATCAGCAGAAACCAGGGAAAGCCCCTAAGCTCCTGATCTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTACTGATACGAGGGGTG

CTTTCGGCGGAGGGACCAAGGTGGAGATCAAACGTACGGTGGCTGCACCATCTGTCTTCATCTTCCCGCCATCTGA

TGAGCAGTTGAAATCTGGAACTGCCTCTGTTGTGTGCCTGCTGAATAACTTCTATCCCAGAGAGGCCAAAGTACAG

TGGAAGGTGGATAACGCCCTCCAATCGGGTAACTCCCAGGAGAGTGTCACAGAGCAGGACAGCAAGGACAGCAC

CTACAGCCTCAGCAGCACCCTGACGCTGAGCAAAGCAGACTACGAGAAACACAAAGTCTACGCCTGCGAAGTCAC

CCATCAGGGCCTGAGCTCGCCCGTCACAAAGAGCTTCAACAGGGGAGAGTGT

470C6HUMANIZEDLIGHTCHAINVARIABLELIGHTCHAINNUCLEOTIDESEQUENCE

SEQ ID NO: 258

GCCCTTGTGATGACCCAGTCTCCTTCCACCCTGTCTGCATCTGTAGGAGACAGAGTCACCATCAATTGCCAGGCCA

GTGAGGACATTGATAACTATTTAGCCTGGTATCAGCAGAAACCAGGGAAAGCCCCTAAGCTCCTGATCTTTTATGC

ATCCGATCTGGCATCTGGGGTCCCATCAAGGTTCAGCGGCAGTGGATCTGGGACAGAATTCACTCTCACCATCAGC

AGCCTGCAGCCTGATGATTTTGCAACTTATTACTGCCAAGGCGGTTACTATACTAGTAGTACTGATACGAGGGGTG

CTTTCGGCGGAGGGACCAAGGTGGAGATCAAA

470C6HUMANIZEDLIGHTCHAINFULL-LENGTHAMINOACIDSEQUENCE. HUMANKAPPACONSTANT DOMAINISUNDERLINED

SEQ ID NO: 259

ALVMTQSPSTLSASVGDRVTINCQASEDIDNYLAWYQQKPGKAPKLLIFYASDLASGVPSRFSGSGSGTEFTLTISSLQPD

DFATYYCQGGYYTSSTDTRGAFGGGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

470C6HUMANIZEDLIGHTCHAINVARIABLELIGHTCHAINAMINOACIDSEQUENCE. COMPIMENTARITY DETERMININGREGIONSAREUNDERLINED

SEQ ID NO: 260

ALVMTQSPSTLSASVGDRVTINCQASEDIDNYLAWYQQKPGKAPKLLIFYASDLASGVPSRFSGSGSGTEFTLTISSLQPD

DFATYYCQGGYYTSSTDTRGAFGGGTKVEIK

470C6HUMANIZEDHEAVYCHAINFULL-LENGTHNUCLEOTIDESEQUENCE

SEQ ID NO: 261

CAGTCGCTGGTGGAGTCTGGGGGAGGCTTGGTACAGCCTGGGGGGTCCCTGAGACTCTCCTGTGCAGCCTCTGG

ATTCTCCTTCACTAGCAGCTACTACATGTGCTGGGTCCGCCAGGCTCCAGGGAAGGGGCTGGAGTGGATCGCATG

CATTTATACTGGTAGTAGTGGTAGCACTTACTACGCGAACTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

AGTAGTAGTTATTATATGTTTAACTTGTGGGGCCAGGGAACCCTGGTCACCGTCTCGAGCGCTAGCACCAAGGGC

CCATCGGTCTTCCCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACACCTTCCCGGCTG

TCCTACAGTCCTCAGGACTCTACTCCCTCAGCAGCGTGGTGACCGTGCCCTCCAGCAGCTTGGGCACCCAGACCTA

CATCTGCAACGTGAATCACAAGCCCAGCAACACCAAGGTGGACAAGAGAGTTGAGCCCAAATCTTGTGACAAAAC

TCACACATGCCCACCGTGCCCAGCACCTGAAGCCGCGGGGGCACCGTCAGTCTTCCTCTTCCCCCCAAAACCCAAG

GACACCCTCATGATCTCCCGGACCCCTGAGGTCACATGCGTGGTGGTGGACGTGAGCCACGAAGACCCTGAGGTC

AAGTTCAACTGGTACGTGGACGGCGTGGAGGTGCATAATGCCAAGACAAAGCCGCGGGAGGAGCAGTACAACA

GCACGTACCGTGTGGTCAGCGTCCTCACCGTCCTGCACCAGGACTGGCTGAATGGCAAGGAGTACAAGTGCGCGG

TCTCCAACAAAGCCCTCCCAGCCCCCATCGAGAAAACCATCTCCAAAGCCAAAGGGCAGCCCCGAGAACCACAGG

TGTACACCCTGCCCCCATCCCGGGATGAGCTGACCAAGAACCAGGTCAGCCTGACCTGCCTGGTCAAAGGCTTCTA

TCCCAGCGACATCGCCGTGGAGTGGGAGAGCAATGGGCAGCCGGAGAACAACTACAAGACCACGCCTCCCGTGC

TGGACTCCGACGGCTCCTTCTTCCTCTATAGCAAGCTCACCGTGGACAAGAGCAGGTGGCAGCAGGGGAACGTCT

TCTCATGCTCCGTGATGCATGAGGCTCTGCACAACCACTACACGCAGAAGAGCCTCTCCCTGTCTCCGGGT

470C6HUMANIZEDHEAVYCHAINVARIABLEHEAVYCHAINNUCLEOTIDESEQUENCE

SEQ ID NO: 262

CAGTCGCTGGTGGAGTCTGGGGGAGGCTTGGTACAGCCTGGGGGGTCCCTGAGACTCTCCTGTGCAGCCTCTGG

-continued

ATTCTCCTTCACTAGCAGCTACTACATGTGCTGGGTCCGCCAGGCTCCAGGGAAGGGGCTGGAGTGGATCGCATG

CATTTATACTGGTAGTAGTGGTAGCACTTACTACGCGAACTCCGCGAAAGGCCGGTTCACCATCTCCAGAGACAAT

TCCAAGAACACGCTGTATCTGCAAATGAACAGCCTGAGAGCCGAGGACACGGCCGTATATTACTGTGCGAGAGAT

AGTAGTAGTTATTATATGTTTAACTTGTGGGGCCAGGGAACCCTGGTCACCGTCTCGAGC

470C6HUMANIZEDHEAVYCHAINFULL-LENGTHAMINOACIDSEQUENCE. HUMANGAMMA-1 CONSTANTDOMAINISUNDERLINED

SEQ ID NO: 263

QSLVESGGGLVQPGGSLRLSCAASGFSFTSSYYMCWVRQAPGKGLEWIACIYTGSSGSTYYANSAKGRFTISRDNSKNT

LYLQMNSLRAEDTAVYYCARDSSSYYMFNLWGQGTLVTVSSASTKGPSVFPLAPSSKSTSGGTAALGCLVKDYFPEPVT

VSWNSGALTSGVHTFPAVLQSSGLYSLSSVVTVPSSSLGTQTYICNVNHKPSNTKVDKRVEPKSCDKTHTCPPCPAPEAA

GAPSVFLFPPKPKDTLMISRTPEVTCVVVDVSHEDPEVKFNWYVDGVEVHNAKTKPREEQYNSTYRVVSVLTVLHQDW

LNGKEYKCAVSNKALPAPIEKTISKAKGQPREPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSLSPG

470C6HUMANIZEDHEAVYCHAINVARIABLEHEAVYCHAINAMINOACIDSEQUENCE. COMPLIMENTARITYDETERMININGREGIONSAREUNDERLINED

SEQ ID NO: 264

QSLVESGGGLVQPGGSLRLSCAASGFSFTSSYYMCWVRQAPGKGLEWIACIYTGSSGSTYYANSAKGRFTISRDNSKNT

LYLQMNSLRAEDTAVYYCARDSSSYYMFNLWGQGTLVTVSS

472E4HUMANIZEDLIGHTCHAINFULL-LENGTHNUCLEOTIDESEQUENCE

SEQ ID NO: 265

GACATCCAGATGACCCAGTCTCCATCCTCCCTGTCTGCATCTGTAGGAGACAGAGTCACCATCACTTGCCAGTCCA

GTCAGAGTGTTTATAATAACAATGCTTTAGCCTGGTATCAGCAGAAACCAGGGAAAGTTCCTAAGCTCCTGATCTA

TTTGGCTTCCACTCTGGCATCTGGGGTCCCATCTCGGTTCAGTGGCAGTGGATCTGGGACAGATTTCACTCTCACCA

TCAGCAGCCTGCAGCCTGAAGATGTTGCAACTTATTACTGTCTAGGTGTTTATAATGATGATGTTGATAATGGTTTC

GGCGGAGGGACCAAGGTGGAGATCAAACGTACGGTGGCTGCACCATCTGTCTTCATCTTCCCGCCATCTGATGAG

CAGTTGAAATCTGGAACTGCCTCTGTTGTGTGCCTGCTGAATAACTTCTATCCCAGAGAGGCCAAAGTACAGTGGA

AGGTGGATAACGCCCTCCAATCGGGTAACTCCCAGGAGAGTGTCACAGAGCAGGACAGCAAGGACAGCACCTAC

AGCCTCAGCAGCACCCTGACGCTGAGCAAAGCAGACTACGAGAAACACAAAGTCTACGCCTGCGAAGTCACCCAT

CAGGGCCTGAGCTCGCCCGTCACAAAGAGCTTCAACAGGGGAGAGTGT

472E4HUMANIZEDLIGHTCHAINVARIABLELIGHTCHAINNUCLEOTIDESEQUENCE

SEQ ID NO: 266

GACATCCAGATGACCCAGTCTCCATCCTCCCTGTCTGCATCTGTAGGAGACAGAGTCACCATCACTTGCCAGTCCA

GTCAGAGTGTTTATAATAACAATGCTTTAGCCTGGTATCAGCAGAAACCAGGGAAAGTTCCTAAGCTCCTGATCTA

TTTGGCTTCCACTCTGGCATCTGGGGTCCCATCTCGGTTCAGTGGCAGTGGATCTGGGACAGATTTCACTCTCACCA

TCAGCAGCCTGCAGCCTGAAGATGTTGCAACTTATTACTGTCTAGGTGTTTATAATGATGATGTTGATAATGGTTTC

GGCGGAGGGACCAAGGTGGAGATCAAA

472E4HUMANIZEDLIGHTCHAINFULL-LENGTHAMINOACIDSEQUENCE. HUMANKAPPACONSTANT DOMAINISUNDERLINED

SEQ ID NO: 267

DIQMTQSPSSLSASVGDRVTITCQSSQSVYNNNALAWYQQKPGKVPKLLIYLASTLASGVPSRFSGSGSGTDFTLTISSLQ

PEDVATYYCLGVYNDDVDNGFGGGTKVEIKRTVAAPSVFIFPPSDEQLKSGTASVVCLLNNFYPREAKVQWKVDNALQ

SGNSQESVTEQDSKDSTYSLSSTLTLSKADYEKHKVYACEVTHQGLSSPVTKSFNRGEC

472E4HUMANIZEDLIGHTCHAINVARIABLELIGHTCHAINAMINOACIDSEQUENCE. COMPIMENTARITY DETERMININGREGIONSAREUNDERLINED

SEQ ID NO: 268

DIQMTQSPSSLSASVGDRVTITCQSSQSVYNNNALAWYQQKPGKVPKLLIYLASTLASGVPSRFSGSGSGTDFTLTISSLQ

PEDVATYYCLGVYNDDVDNGFGGGTKVEIK

472E4HUMANIZEDHEAVYCHAINFULL-LENGTHNUCLEOTIDESEQUENCE

SEQ ID NO: 269

GAGGTGCAGCTGGTGGAGTCTGGGGGAGGCTTGGTCCAGCCTGGGGGGTCCCTGAGACTCTCCTGTGCAGCCTC

-continued

TGGATTCTCCCTCAATAACAATGCAATAAGCTGGGTCCGCCAGGCTCCAGGGAAGGGGCTGGAGTGGGTTGCAAT

CATACAAAATACTGGTACCACAGACTACGCGAGGTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGTATGGT

TTTGAGTCGGAGCTTGTCATCTGGGGCCAGGGAACCCTGGTCACCGTCTCGAGCGCTAGCACCAAGGGCCCATCG

GTCTTCCCCCTGGCACCCTCCTCCAAGAGCACCTCTGGGGGCACAGCGGCCCTGGGCTGCCTGGTCAAGGACTACT

TCCCCGAACCGGTGACGGTGTCGTGGAACTCAGGCGCCCTGACCAGCGGCGTGCACACCTTCCCGGCTGTCCTAC

AGTCCTCAGGACTCTACTCCCTCAGCAGCGTGGTGACCGTGCCCTCCAGCAGCTTGGGCACCCAGACCTACATCTG

CAACGTGAATCACAAGCCCAGCAACACCAAGGTGGACAAGAGAGTTGAGCCCAAATCTTGTGACAAAACTCACAC

ATGCCCACCGTGCCCAGCACCTGAAGCCGCGGGGGCACCGTCAGTCTTCCTCTTCCCCCCAAAACCCAAGGACACC

CTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGT

ACCGTGTGGTCAGCGTCCTCACCGTCCTGCACCAGGACTGGCTGAATGGCAAGGAGTACAAGTGCGCGGTCTCCA

ACAAAGCCCTCCCAGCCCCCATCGAGAAAACCATCTCCAAAGCCAAAGGGCAGCCCCGAGAACCACAGGTGTACA

CCCTGCCCCCATCCCGGGATGAGCTGACCAAGAACCAGGTCAGCCTGACCTGCCTGGTCAAAGGCTTCTATCCCAG

CGACATCGCCGTGGAGTGGGAGAGCAATGGGCAGCCGGAGAACAACTACAAGACCACGCCTCCCGTGCTGGACT

CCGACGGCTCCTTCTTCCTCTATAGCAAGCTCACCGTGGACAAGAGCAGGTGGCAGCAGGGGAACGTCTTCTCAT

GCTCCGTGATGCATGAGGCTCTGCACAACCACTACACGCAGAAGAGCCTCTCCCTGTCTCCGGGT

472E4HUMANIZEDHEAVYCHAINVARIABLEHEAVYCHAINNUCLEOTIDESEQUENCE

SEQ ID NO: 270

GAGGTGCAGCTGGTGGAGTCTGGGGGAGGCTTGGTCCAGCCTGGGGGGTCCCTGAGACTCTCCTGTGCAGCCTC

TGGATTCTCCCTCAATAACAATGCAATAAGCTGGGTCCGCCAGGCTCCAGGGAAGGGGCTGGAGTGGGTTGCAAT

CATACAAAATACTGGTACCACAGACTACGCGAGGTCCGCTAAAGGCAGATTCACCATCTCCAGAGACAATTCCAAG

AACACGCTGTATCTTCAAATGAACAGCCTGAGAGCCGAGGACACGGCTGTGTATTACTGTGCGAGAGGGTATGGT

TTTGAGTCGGAGCTTGTCATCTGGGGCCAGGGAACCCTGGTCACCGTCTCGAGC

472E4HUMANIZEDHEAVYCHAINFULL-LENGTHAMINOACIDSEQUENCE. HUMANGAMMA-1 CONSTANTDOMAINISUNDERLINED

SEQ ID NO: 271

EVQLVESGGGLVQPGGSLRLSCAASGFSLNNNAISWVRQAPGKGLEWVAIIQNTGTTDYARSAKGRFTISRDNSKNTLY

LQMNSLRAEDTAVYYCARGYGFESELVIWGQGTLVTVSSASTKGPSVFPLAPSSKSTSGGTAALGCLVKDYFPEPVTVS

WNSGALTSGVHTFPAVLQSSGLYSLSSVVTVPSSSLGTQTYICNVNHKPSNTKVDKRVEPKSCDKTHTCPPCPAPEAAG

APSVFLFPPKPKDTLMISRTPEVTCVVVDVSHEDPEVKFNWYVDGVEVHNAKTKPREEQYNSTYRVVSVLTVLHQDWL

NGKEYKCAVSNKALPAPIEKTISKAKGQPREPQVYTLPPSRDELTKNQVSLTCLVKGFYPSDIAVEWESNGQPENNYKTT

PPVLDSDGSFFLYSKLTVDKSRWQQGNVFSCSVMHEALHNHYTQKSLSLSPG

472E4HUMANIZEDHEAVYCHAINVARIABLEHEAVYCHAINAMINOACIDSEQUENCE. COMPLIMENTARITYDETERMININGREGIONSAREUNDERLINED

SEQ ID NO: 272

EVQLVESGGGLVQPGGSLRLSCAASGFSLNNNAISWVRQAPGKGLEWVAIIQNTGTTDYARSAKGRFTISRDNSKNTLY

LQMNSLRAEDTAVYYCARGYGFESELVIWGQGTLVTVSS

CDR1 OF THE VL OF SEQ ID NO: 228

SEQ ID NO: 273

QSSQSVYSNWFS

CDR2 OF THE VL OF SEQ ID NO: 228

SEQ ID NO: 274

SASTLAS

CDR3 OF THE VL OF SEQ ID NO: 228

SEQ ID NO: 275

AGGYNTVIDTFA

CDR1 OF THE VH OF SEQ IS NO: 232

SEQ ID NO: 276

RRYYMC

CDR2 OF THE VH OF SEQ ID NO: 232

SEQ ID NO: 277

CIYTGSRDTPHYASSAKG

CDR3 OF THE VH OF SEQ ID NO: 232

SEQ ID NO: 278

EGSL

SEQUENCE LISTING

```
Sequence total quantity: 278
SEQ ID NO: 1           moltype = DNA  length = 657
FEATURE                Location/Qualifiers
source                 1..657
                       mol_type = other DNA
                       organism = synthetic construct
SEQUENCE: 1
gatgttgtga tgacccagac tccagcctcc gtgtctgaac ctgtgagagc cacagtcacc  60
atcaagtgcc aggccagtca gagcattggt gctgatttag cctggtatca gcagaaacca  120
gggcagcctc ccaagctcct gatctacagg gcatccactc tggcctctgg ggtcccatcg  180
cggttcagcg gcagtggatc tgggacagag ttcactctca ccatcagcga cctggagtgt  240
gccgatgctg ccacttacta ctgtcaatgt atttattatg gtactgatga tgtcatatac  300
catactttcg gcggagggac cgaggtggtg ttcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 2           moltype = DNA  length = 336
FEATURE                Location/Qualifiers
source                 1..336
                       mol_type = other DNA
                       organism = synthetic construct
SEQUENCE: 2
gatgttgtga tgacccagac tccagcctcc gtgtctgaac ctgtgagagc cacagtcacc  60
atcaagtgcc aggccagtca gagcattggt gctgatttag cctggtatca gcagaaacca  120
gggcagcctc ccaagctcct gatctacagg gcatccactc tggcctctgg ggtcccatcg  180
cggttcagcg gcagtggatc tgggacagag ttcactctca ccatcagcga cctggagtgt  240
gccgatgctg ccacttacta ctgtcaatgt atttattatg gtactgatga tgtcatatac  300
catactttcg gcggagggac cgaggtggtg ttcaaa                           336

SEQ ID NO: 3           moltype = AA  length = 219
FEATURE                Location/Qualifiers
source                 1..219
                       mol_type = protein
                       organism = synthetic construct
SEQUENCE: 3
DVVMTQTPAS VSEPVRATVT IKCQASQSIG ADLAWYQQKP GQPPKLLIYR ASTLASGVPS  60
RFSGSGSGTE FTLTISDLEC ADAATYYCQC IYYGTDDVIY HTFGGGTEVV FKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 4           moltype = AA  length = 112
FEATURE                Location/Qualifiers
source                 1..112
                       mol_type = protein
                       organism = synthetic construct
SEQUENCE: 4
DVVMTQTPAS VSEPVRATVT IKCQASQSIG ADLAWYQQKP GQPPKLLIYR ASTLASGVPS  60
RFSGSGSGTE FTLTISDLEC ADAATYYCQC IYYGTDDVIY HTFGGGTEVV FK          112

SEQ ID NO: 5           moltype = DNA  length = 1332
FEATURE                Location/Qualifiers
source                 1..1332
                       mol_type = other DNA
                       organism = synthetic construct
SEQUENCE: 5
cagtcggtgg aggagtccgg gggtcgcctg gtcacgcctg ggacacccct aacactcacc  60
tgcacagtat ctggattcac catcagtagc caccacatga tctgggtccg ccaggctcca  120
ggagaggggc tgcaatacat cggattcatt aatgatggtg actatacata ctacacgaac  180
tgggcaaaag gccgattcac catctccaga acctcgacta cggtggacct gaaaatgacc  240
agtctgacag ccgcggacac ggccacctat ttctgtgcca gaggggttga tggtactagt  300
```

```
tatcctggct tgtggggccc aggcaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg gggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                       1332

SEQ ID NO: 6            moltype = DNA  length = 345
FEATURE                 Location/Qualifiers
source                  1..345
                        mol_type = other DNA
                        organism = synthetic construct
SEQUENCE: 6
cagtcggtgg aggagtccgg gggtcgcctg gtcacgcctg ggacacccct aacactcacc  60
tgcacagtat ctggattcac catcagtagc caccacatga tctgggtccg ccaggctcca  120
ggagaggggc tgcaatacat cggattcatt aatgatggtg actatacata ctacacgaac  180
tgggcaaaag gccgattcac catctccaga acctcgacta cggtggacct gaaaatgacc  240
agtctgacag ccgcggacac ggccacctat ttctgtgcca gaggggttga tggtactagt  300
tatcctggct tgtggggccc aggcaccctg gtcaccgtct cgagc                   345

SEQ ID NO: 7            moltype = AA  length = 444
FEATURE                 Location/Qualifiers
source                  1..444
                        mol_type = protein
                        organism = synthetic construct
SEQUENCE: 7
QSVEESGGRL VTPGTPLTLT CTVSGFTISS HHMIWVRQAP GEGLQYIGFI NDGDYTYYTN  60
WAKGRFTISR TSTTVDLKMT SLTAADTATY FCARGVDGTS YPGLWGPGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                          444

SEQ ID NO: 8            moltype = AA  length = 115
FEATURE                 Location/Qualifiers
source                  1..115
                        mol_type = protein
                        organism = synthetic construct
SEQUENCE: 8
QSVEESGGRL VTPGTPLTLT CTVSGFTISS HHMIWVRQAP GEGLQYIGFI NDGDYTYYTN  60
WAKGRFTISR TSTTVDLKMT SLTAADTATY FCARGVDGTS YPGLWGPGTL VTVSS        115

SEQ ID NO: 9            moltype = DNA  length = 657
FEATURE                 Location/Qualifiers
source                  1..657
                        mol_type = other DNA
                        organism = synthetic construct
SEQUENCE: 9
gacgtcgtga tgacccagac tccagcctcc gtggaggcag ctgtgggagg cacagtcacc  60
atcaagtgcc aggccagtca gagcatttac agcaatttag cctggtatca gcagaaacca  120
gggcagcctc ccaaactcct aatctattct acatccactc tggcatctgg ggtcccatcg  180
cggttcagcg gcagtggatc cgggacagag ttcactctca ccatcagcga cctggagtgt  240
gccgatgctg ccacttacta ctgtcaaaac tattatggta gtagtactga tagttatggg  300
aatcctttcg gcggaggcac cgaggtggtg ttcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 10           moltype = DNA  length = 336
FEATURE                 Location/Qualifiers
source                  1..336
                        mol_type = other DNA
                        organism = synthetic construct
```

```
SEQUENCE: 10
gacgtcgtga tgacccagac tccagcctcc gtggaggcag ctgtgggagg cacagtcacc  60
atcaagtgcc aggccagtca gagcatttac agcaatttag cctggtatca gcagaaacca  120
gggcagcctc ccaaactcct aatctattct acatccactc tggcatctgg ggtcccatcg  180
cggttcagcg gcagtggatc cgggacagag ttcactctca ccatcagcga cctggagtgt  240
gccgatgctg ccacttacta ctgtcaaaac tattatggta gtagtactga tagttatggg  300
aatcctttcg gcggaggcac cgaggtggtg ttcaaa                             336

SEQ ID NO: 11          moltype = AA  length = 219
FEATURE                Location/Qualifiers
source                 1..219
                       mol_type = protein
                       organism = synthetic construct
SEQUENCE: 11
DVVMTQTPAS VEAAVGGTVT IKCQASQSIY SNLAWYQQKP GQPPKLLIYS TSTLASGVPS  60
RFSGSGSGTE FTLTISDLEC ADAATYYCQN YYGSSTDSYG NPFGGGTEVV FKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 12          moltype = AA  length = 112
FEATURE                Location/Qualifiers
source                 1..112
                       mol_type = protein
                       organism = synthetic construct
SEQUENCE: 12
DVVMTQTPAS VEAAVGGTVT IKCQASQSIY SNLAWYQQKP GQPPKLLIYS TSTLASGVPS  60
RFSGSGSGTE FTLTISDLEC ADAATYYCQN YYGSSTDSYG NPFGGGTEVV FK           112

SEQ ID NO: 13          moltype = DNA  length = 1344
FEATURE                Location/Qualifiers
source                 1..1344
                       mol_type = other DNA
                       organism = synthetic construct
SEQUENCE: 13
cagtcgctgg aggagtccgg gggagacctg gtcaagcctg agggatccct gacactcacc  60
tgcacaggct ctggaatcga cttcagtagc aactacatgt gctgggtccg ccaggctcca  120
gggaaggggc tggagtggat cgcatgcatt tatggtgata gtagtgataa tagttactcc  180
gcgagctggg cgaaagggcg attcaccatc tccaaaacct cgtcgaccac ggtgactctg  240
caaatgacca gtctgacagc cgcggacacg gccacctatt tctgtgcgag atctggttat  300
agctatttag gctactttaa cttgtggggc ccagggaccc tggtcaccgt ctcgagcgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaagccgc gggggcaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgcg cggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggt                                          1344

SEQ ID NO: 14          moltype = DNA  length = 357
FEATURE                Location/Qualifiers
source                 1..357
                       mol_type = other DNA
                       organism = synthetic construct
SEQUENCE: 14
cagtcgctgg aggagtccgg gggagacctg gtcaagcctg agggatccct gacactcacc  60
tgcacaggct ctggaatcga cttcagtagc aactacatgt gctgggtccg ccaggctcca  120
gggaaggggc tggagtggat cgcatgcatt tatggtgata gtagtgataa tagttactcc  180
gcgagctggg cgaaagggcg attcaccatc tccaaaacct cgtcgaccac ggtgactctg  240
caaatgacca gtctgacagc cgcggacacg gccacctatt tctgtgcgag atctggttat  300
agctatttag gctactttaa cttgtggggc ccagggaccc tggtcaccgt ctcgagc     357

SEQ ID NO: 15          moltype = AA  length = 448
FEATURE                Location/Qualifiers
source                 1..448
                       mol_type = protein
                       organism = synthetic construct
SEQUENCE: 15
QSLEESGGDL VKPEGSLTLT CTGSGIDFSS NYMCWVRQAP GKGLEWIACI YGDSSDNSYS  60
ASWAKGRFTI SKTSSTTVTL QMTSLTAADT ATYFCARSGY SYLGYFNLWG PGTLVTVSSA  120
```

```
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCAVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                   448

SEQ ID NO: 16          moltype = AA  length = 119
FEATURE                Location/Qualifiers
source                 1..119
                       mol_type = protein
                       organism = synthetic construct
SEQUENCE: 16
QSLEESGGDL VKPEGSLTLT CTGSGIDFSS NYMCWVRQAP GKGLEWIACI YGDSSDNSYS  60
ASWAKGRFTI SKTSSTTVTL QMTSLTAADT ATYFCARSGY SYLGYFNLWG PGTLVTVSS   119

SEQ ID NO: 17          moltype = DNA  length = 651
FEATURE                Location/Qualifiers
source                 1..651
                       mol_type = other DNA
                       organism = synthetic construct
SEQUENCE: 17
gcgcaagtgc tgacccagac tgcatcgtcc gtgtctgcac ctgtgggcgg cacagtcacc  60
atcagttgcc agtccagtca gactgtttat aataacaact tgttatcctg gtatcagcag  120
aaaccagggc agcgtcccaa gctcctgatc tattatgcat ccactctggc atttggggtc  180
ccatcgcggt tcaaaggcag tggatctggg acagagttca ctctcaccat cagcgacctg  240
gagtgtgacg atgctgccac ttacttctgt caaggcggtt atagtggttg gatttatgtt  300
ttcggcggag gcaccgaggt ggaggtcaaa cgtacggtgg ctgcaccatc tgtcttcatc  360
ttcccgccat ctgatgagca gttgaaatct ggaactgcct ctgttgtgtg cctgctgaat  420
aacttctatc ccagagaggc caaagtacag tggaaggtgg ataacgccct ccaatcgggt  480
aactcccagg agagtgtcac agagcaggac agcaaggaca gcacctacag cctcagcagc  540
accctgacgc tgagcaaagc agactacgag aaacacaaag tctacgcctg cgaagtcacc  600
catcagggcc tgagctcgcc cgtcacaaag agcttcaaca ggggagagtg t           651

SEQ ID NO: 18          moltype = DNA  length = 330
FEATURE                Location/Qualifiers
source                 1..330
                       mol_type = other DNA
                       organism = synthetic construct
SEQUENCE: 18
gcgcaagtgc tgacccagac tgcatcgtcc gtgtctgcac ctgtgggcgg cacagtcacc  60
atcagttgcc agtccagtca gactgtttat aataacaact tgttatcctg gtatcagcag  120
aaaccagggc agcgtcccaa gctcctgatc tattatgcat ccactctggc atttggggtc  180
ccatcgcggt tcaaaggcag tggatctggg acagagttca ctctcaccat cagcgacctg  240
gagtgtgacg atgctgccac ttacttctgt caaggcggtt atagtggttg gatttatgtt  300
ttcggcggag gcaccgaggt ggaggtcaaa                                   330

SEQ ID NO: 19          moltype = AA  length = 217
FEATURE                Location/Qualifiers
source                 1..217
                       mol_type = protein
                       organism = synthetic construct
SEQUENCE: 19
AQVLTQTASS VSAPVGGTVT ISCQSSQTVY NNNLLSWYQQ KPGQRPKLLI YYASTLAFGV  60
PSRFKGSGSG TEFTLTISDL ECDDAATYFC QGGYSGWIYV FGGGTEVEVK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                          217

SEQ ID NO: 20          moltype = AA  length = 110
FEATURE                Location/Qualifiers
source                 1..110
                       mol_type = protein
                       organism = synthetic construct
SEQUENCE: 20
AQVLTQTASS VSAPVGGTVT ISCQSSQTVY NNNLLSWYQQ KPGQRPKLLI YYASTLAFGV  60
PSRFKGSGSG TEFTLTISDL ECDDAATYFC QGGYSGWIYV FGGGTEVEVK            110

SEQ ID NO: 21          moltype = DNA  length = 1323
FEATURE                Location/Qualifiers
source                 1..1323
                       mol_type = other DNA
                       organism = synthetic construct
SEQUENCE: 21
cagtcgctgg aggagtccgg gggtcgcctg gtcacgcctg ggacacccct gacactcacc  60
tgcacagcct ctggattctc cctcagtaac tactacatga actgggtccg ccaggctcca  120
gggaaggggc tggaatacat cggaatcatt agtagtagtg gtagcgcata ctacgcgagc  180
tgggctaaag gccgattcac catctccaga acctcgacca cggtggacct gagaatcacc  240
agtccgacaa ccgaggacac ggccacctat ttctgtgcca gaggggacta cggcatggac  300
ctctggggcc aagggaccct ggtcaccgtc tcgagcgcta gcaccaaggg cccatcggtc  360
```

```
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagagagtt gagcccaaat cttgtgacaa aactcacaca  660
tgcccaccgt gcccagcacc tgaagccgcg ggggcaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacaacagca cgtaccgtgt ggtcagcgtc  900
ctcaccgtcc tgcaccagga ctggctgaat ggcaaggagt acaagtgcgc ggtctccaac  960
aaagccctcc cagcccccat cgagaaaacc atctccaaag ccaaagggca gccccgagaa  1020
ccacaggtgt acaccctgcc cccatcccgg gatgagctga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctatagca agctcaccgt ggacaagagc aggtggcagc aggggaacgt cttctcatgc  1260
tccgtgatgc atgaggctct gcacaaccac tacacgcaga agagcctctc cctgtctccg  1320
ggt                                                                1323

SEQ ID NO: 22          moltype = DNA  length = 336
FEATURE                Location/Qualifiers
source                 1..336
                       mol_type = other DNA
                       organism = synthetic construct
SEQUENCE: 22
cagtcgctgg aggagtccgg gggtcgcctg gtcacgcctg ggacacccct gacactcacc  60
tgcacagcct ctggattctc cctcagtaac tactacatga actgggtccg ccaggctcca  120
gggaaggggc tggaatacat cggaatcatt agtagtagtg gtagcgcata ctacgcgagc  180
tgggctaaag gccgattcac catctccaga acctcgacca cggtggacct gagaatcacc  240
agtccgacaa ccgaggacac ggccacctat ttctgtgcca gaggggacta cggcatggac  300
ctctggggcc aagggaccct ggtcaccgtc tcgagc                            336

SEQ ID NO: 23          moltype = AA  length = 441
FEATURE                Location/Qualifiers
source                 1..441
                       mol_type = protein
                       organism = synthetic construct
SEQUENCE: 23
QSLEESGGRL VTPGTPLTLT CTASGFSLSN YYMNWVRQAP GKGLEYIGII SSSGSAYYAS  60
WAKGRFTISR TSTTVDLRIT SPTTEDTATY FCARGDYGMD LWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKRV EPKSCDKTHT CPPCPAPEAA GAPSVFLFPP  240
KPKDTLMISR TPEVTCVVVD VSHEDPEVKF NWYVDGVEVH NAKTKPREEQ YNSTYRVVSV  300
LTVLHQDWLN GKEYKCAVSN KALPAPIEKT ISKAKGQPRE PQVYTLPPSR DELTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP G                                            441

SEQ ID NO: 24          moltype = AA  length = 112
FEATURE                Location/Qualifiers
source                 1..112
                       mol_type = protein
                       organism = synthetic construct
SEQUENCE: 24
QSLEESGGRL VTPGTPLTLT CTASGFSLSN YYMNWVRQAP GKGLEYIGII SSSGSAYYAS  60
WAKGRFTISR TSTTVDLRIT SPTTEDTATY FCARGDYGMD LWGQGTLVTV SS          112

SEQ ID NO: 25          moltype = DNA  length = 657
FEATURE                Location/Qualifiers
source                 1..657
                       mol_type = other DNA
                       organism = synthetic construct
SEQUENCE: 25
gacgtcgtga tgacccagac tccagcctcc gtgtctgaac ctgtgggagg cgcagtcacc  60
atcaagtgcc aggccagtca gagcattggt agtgatttag cctggtatca gcagaaacca  120
gggcagcctc ccaagctcct gatctacagg gcatccactc tggcatctgg ggtctcatcg  180
cggttcaaag gcagtggatc tgggacagag ttcactctca ccatcagcga cctggagtgt  240
gccgatgctg ccacttacta ctgtcaatgt atttattatg gtagtgatga tgtcatatac  300
catactttcg gcggagggac cgaggtggtg gtcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 26          moltype = DNA  length = 336
FEATURE                Location/Qualifiers
source                 1..336
                       mol_type = other DNA
                       organism = synthetic construct
SEQUENCE: 26
```

```
gacgtcgtga tgacccagac tccagcctcc gtgtctgaac ctgtgggagg cgcagtcacc  60
atcaagtgcc aggccagtca gagcattggt agtgatttag cctggtatca gcagaaacca  120
gggcagcctc ccaagctcct gatctacagg gcatccactc tggcatctgg ggtctcatcg  180
cggttcaaag gcagtggatc tgggacagag ttcactctca ccatcagcga cctggagtgt  240
gccgatgctg ccacttacta ctgtcaatgt atttattatg gtagtgatga tgtcatatac  300
catactttcg gcggagggac cgaggtggtg gtcaaa                            336

SEQ ID NO: 27          moltype = AA  length = 219
FEATURE                Location/Qualifiers
source                 1..219
                       mol_type = protein
                       organism = synthetic construct
SEQUENCE: 27
DVVMTQTPAS VSEPVGGAVT IKCQASQSIG SDLAWYQQKP GQPPKLLIYR ASTLASGVSS  60
RFKGSGSGTE FTLTISDLEC ADAATYYCQC IYYGSDDVIY HTFGGGTEVV VKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 28          moltype = AA  length = 112
FEATURE                Location/Qualifiers
source                 1..112
                       mol_type = protein
                       organism = synthetic construct
SEQUENCE: 28
DVVMTQTPAS VSEPVGGAVT IKCQASQSIG SDLAWYQQKP GQPPKLLIYR ASTLASGVSS  60
RFKGSGSGTE FTLTISDLEC ADAATYYCQC IYYGSDDVIY HTFGGGTEVV VK          112

SEQ ID NO: 29          moltype = DNA  length = 1332
FEATURE                Location/Qualifiers
source                 1..1332
                       mol_type = other DNA
                       organism = synthetic construct
SEQUENCE: 29
cagtcggtgg aggagtccgg gggtcgcctg gtcacgcctg ggacacccct gacactcacc  60
tgcacagtct ctggattcac tatcaatagc taccacatga tctgggtccg ccaggctcca  120
ggggaggggc tggaatacat cggattcatt aatgatggtg gtttcacata ctacgcgagc  180
tgggcaaaag gccgatttat catctccaga acctcgacca cggtggatct gaaaatgacc  240
agtctgacag tcgcggacac ggccacctat ttctgtgcca gaggggttga tggtactagt  300
tatcctgact tatggggccc gggcaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg ggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 30          moltype = DNA  length = 345
FEATURE                Location/Qualifiers
source                 1..345
                       mol_type = other DNA
                       organism = synthetic construct
SEQUENCE: 30
cagtcggtgg aggagtccgg gggtcgcctg gtcacgcctg ggacacccct gacactcacc  60
tgcacagtct ctggattcac tatcaatagc taccacatga tctgggtccg ccaggctcca  120
ggggaggggc tggaatacat cggattcatt aatgatggtg gtttcacata ctacgcgagc  180
tgggcaaaag gccgatttat catctccaga acctcgacca cggtggatct gaaaatgacc  240
agtctgacag tcgcggacac ggccacctat ttctgtgcca gaggggttga tggtactagt  300
tatcctgact tatggggccc gggcaccctg gtcaccgtct cgagc                  345

SEQ ID NO: 31          moltype = AA  length = 444
FEATURE                Location/Qualifiers
source                 1..444
                       mol_type = protein
                       organism = synthetic construct
SEQUENCE: 31
QSVEESGGRL VTPGTPLTLT CTVSGFTINS YHMIWVRQAP GEGLEYIGFI NDGGFTYYAS  60
WAKGRFIISR TSTTVDLKMT SLTVADTATY FCARGVDGTS YPDLWGPGTL VTVSSASTKG  120
PSVFPLAPSS KSTSGGTAAL GCLVKDYFPE PVTVSWNSGA LTSGVHTFPA VLQSSGLYSL  180
```

```
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 32          moltype = AA  length = 115
FEATURE                Location/Qualifiers
source                 1..115
                       mol_type = protein
                       organism = synthetic construct
SEQUENCE: 32
QSVEESGGRL VTPGTPLTLT CTVSGFTINS YHMIWVRQAP GEGLEYIGFI NDGGFTYYAS  60
WAKGRFIISR TSTTVDLKMT SLTVADTATY FCARGVDGTS YPDLWGPGTL VTVSS       115

SEQ ID NO: 33          moltype = DNA  length = 654
FEATURE                Location/Qualifiers
source                 1..654
                       mol_type = other DNA
                       organism = synthetic construct
SEQUENCE: 33
gccctggtga tgacccagac tccatcccct gtgtctgcgg ctgtgggagg cacagtcacc  60
atcaactgcc aggccagtca gagcattggt agtaacttga actggtatca gcagaaacca  120
gggcagcctc ccaagctcct gatttattat gtatccactc tggcatctgg ggtcccatcg  180
cggttcaaag gcagtggatc tgggacagag tacactctca ccatcagcgg cgtgcagtgt  240
gacgatgctg ccacttacta ctgcctaggt gtttggaatt attggggtga tgacggtact  300
gctttcggcg gaggcaccga ggtggaggtc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 34          moltype = DNA  length = 333
FEATURE                Location/Qualifiers
source                 1..333
                       mol_type = other DNA
                       organism = synthetic construct
SEQUENCE: 34
gccctggtga tgacccagac tccatcccct gtgtctgcgg ctgtgggagg cacagtcacc  60
atcaactgcc aggccagtca gagcattggt agtaacttga actggtatca gcagaaacca  120
gggcagcctc ccaagctcct gatttattat gtatccactc tggcatctgg ggtcccatcg  180
cggttcaaag gcagtggatc tgggacagag tacactctca ccatcagcgg cgtgcagtgt  240
gacgatgctg ccacttacta ctgcctaggt gtttggaatt attggggtga tgacggtact  300
gctttcggcg gaggcaccga ggtggaggtc aaa                               333

SEQ ID NO: 35          moltype = AA  length = 218
FEATURE                Location/Qualifiers
source                 1..218
                       mol_type = protein
                       organism = synthetic construct
SEQUENCE: 35
ALVMTQTPSP VSAAVGGTVT INCQASQSIG SNLNWYQQKP GQPPKLLIYY VSTLASGVPS  60
RFKGSGSGTE YTLTISGVQC DDAATYYCLG VWNYWGDDGT AFGGGTEVEV KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                           218

SEQ ID NO: 36          moltype = AA  length = 111
FEATURE                Location/Qualifiers
source                 1..111
                       mol_type = protein
                       organism = synthetic construct
SEQUENCE: 36
ALVMTQTPSP VSAAVGGTVT INCQASQSIG SNLNWYQQKP GQPPKLLIYY VSTLASGVPS  60
RFKGSGSGTE YTLTISGVQC DDAATYYCLG VWNYWGDDGT AFGGGTEVEV K            111

SEQ ID NO: 37          moltype = DNA  length = 1323
FEATURE                Location/Qualifiers
source                 1..1323
                       mol_type = other DNA
                       organism = synthetic construct
SEQUENCE: 37
cagtcgctgg aggagtccgg gggtcgcctg gtcacgcctg ggacacccct gacactcacc  60
tgcacagcct ctgatttctc cctcagtacc tattatatga gctgggtccg ccaggctcca  120
gggaaggggc tggagtggat cggaagtatt tatgatagtg gtgccgcata ctacgcgacc  180
tgggcgaagg gccgattcac catctccaga acgtcgacca cggtggatct gagaatgacc  240
agtctgacag ccgcggacac ggccacctat ttctgtgcca gagatcctat taataatgcc  300
atctggggcc aagggaccct cgtcaccgtc tcgagcgcta gcaccaaggg cccatcggtc  360
ttccccctgg caccctcctc caagagcacc tctgggggca cagcggccct gggctgcctg  420
```

```
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagagagtt gagcccaaat cttgtgacaa aactcacaca  660
tgcccaccgt gcccagcacc tgaagccgcg ggggcaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacaacagca cgtaccgtgt ggtcagcgtc  900
ctcaccgtcc tgcaccagga ctggctgaat ggcaaggagt acaagtgcgc ggtctccaac  960
aaagccctcc cagcccccat cgagaaaacc atctccaaag ccaaagggca gccccgagaa  1020
ccacaggtgt acaccctgcc cccatcccgg gatgagctga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctatagca agctcaccgt ggacaagagc aggtggcagc aggggaacgt cttctcatgc  1260
tccgtgatgc atgaggctct gcacaaccac tacacgcaga agagcctctc cctgtctccg  1320
ggt                                                                1323

SEQ ID NO: 38          moltype = DNA  length = 336
FEATURE                Location/Qualifiers
source                 1..336
                       mol_type = other DNA
                       organism = synthetic construct
SEQUENCE: 38
cagtcgctgg aggagtccgg gggtcgcctg gtcacgcctg ggacacccct gacactcacc  60
tgcacagcct ctgatttctc cctcagtacc tattatatga gctgggtccg ccaggctcca  120
gggaaggggc tggagtggat cggaagtatt tatgatagtg gtgccgcata ctacgcgacc  180
tgggcgaagg gccgattcac catctccaga acgtcgacca cggtggatct gagaatgacc  240
agtctgacag ccgcggacac ggccacctat ttctgtgcca gagatcctat taataatgcc  300
atctggggcc aagggaccct cgtcaccgtc tcgagc                            336

SEQ ID NO: 39          moltype = AA  length = 441
FEATURE                Location/Qualifiers
source                 1..441
                       mol_type = protein
                       organism = synthetic construct
SEQUENCE: 39
QSLEESGGRL VTPGTPLTLT CTASDFSLST YYMSWVRQAP GKGLEWIGSI YDSGAAYYAT  60
WAKGRFTISR TSTTVDLRMT SLTAADTATY FCARDPINNA IWGQGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKRV EPKSCDKTHT CPPCPAPEAA GAPSVFLFPP  240
KPKDTLMISR TPEVTCVVVD VSHEDPEVKF NWYVDGVEVH NAKTKPREEQ YNSTYRVVSV  300
LTVLHQDWLN GKEYKCAVSN KALPAPIEKT ISKAKGQPRE PQVYTLPPSR DELTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP G                                            441

SEQ ID NO: 40          moltype = AA  length = 112
FEATURE                Location/Qualifiers
source                 1..112
                       mol_type = protein
                       organism = synthetic construct
SEQUENCE: 40
QSLEESGGRL VTPGTPLTLT CTASDFSLST YYMSWVRQAP GKGLEWIGSI YDSGAAYYAT  60
WAKGRFTISR TSTTVDLRMT SLTAADTATY FCARDPINNA IWGQGTLVTV SS          112

SEQ ID NO: 41          moltype = DNA  length = 654
FEATURE                Location/Qualifiers
source                 1..654
                       mol_type = other DNA
                       organism = synthetic construct
SEQUENCE: 41
gccctggtga tgacccagac tccatcccct gtgtctgcgg ctgtgggagg cacagtcacc  60
atcaactgcc aggccagtca gagtattgct actaacttga actggtatca gcagaaacca  120
gggcagcctc ccaagctcct gatctattat acatccagtc tggcatctgg ggtcccatcg  180
cggttcagcg gcagtggatc tggcacagag ttcactctca ccatcagcgg tgtgcagtgt  240
gacgatgctg ccacttacta ctgcctaggt gtttggaatt attggggtga tgatggtact  300
gctttcggcg gagggaccga ggtggagttc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 42          moltype = DNA  length = 333
FEATURE                Location/Qualifiers
source                 1..333
                       mol_type = other DNA
                       organism = synthetic construct
SEQUENCE: 42
gccctggtga tgacccagac tccatcccct gtgtctgcgg ctgtgggagg cacagtcacc  60
```

```
atcaactgcc aggccagtca gagtattgct actaacttga actggtatca gcagaaacca  120
gggcagcctc ccaagctcct gatctattat acatccagtc tggcatctgg ggtcccatcg  180
cggttcagcg gcagtggatc tggcacagag ttcactctca ccatcagcgg tgtgcagtgt  240
gacgatgctg ccacttacta ctgcctaggt gtttggaatt attggggtga tgatggtact  300
gctttcggcg gagggaccga ggtggagttc aaa                                333

SEQ ID NO: 43          moltype = AA  length = 218
FEATURE                Location/Qualifiers
source                 1..218
                       mol_type = protein
                       organism = synthetic construct
SEQUENCE: 43
ALVMTQTPSP VSAAVGGTVT INCQASQSIA TNLNWYQQKP GQPPKLLIYY TSSLASGVPS  60
RFSGSGSGTE FTLTISGVQC DDAATYYCLG VWNYWGDDGT AFGGGTEVEF KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                           218

SEQ ID NO: 44          moltype = AA  length = 111
FEATURE                Location/Qualifiers
source                 1..111
                       mol_type = protein
                       organism = synthetic construct
SEQUENCE: 44
ALVMTQTPSP VSAAVGGTVT INCQASQSIA TNLNWYQQKP GQPPKLLIYY TSSLASGVPS  60
RFSGSGSGTE FTLTISGVQC DDAATYYCLG VWNYWGDDGT AFGGGTEVEF K            111

SEQ ID NO: 45          moltype = DNA  length = 1323
FEATURE                Location/Qualifiers
source                 1..1323
                       mol_type = other DNA
                       organism = synthetic construct
SEQUENCE: 45
cagtcgctgg aggagtccgg gggtcgcctg gtcacgcctg ggacacccct gacactcacc  60
tgcacagcct ctgaattctc cctcagtagc tactacatga gctgggtccg ccaggctcca  120
gggaaggggc tggaatggat cggaagtatt tatgctagtg gtagcgcata ctacgcgagt  180
tgggcgaagg gccgattcac catctccaga acgtcgacca cggtggatct gaaaatgacc  240
agtctgacag ccgcggacac ggccacctat ttctgtgtca gagatcctat taacaatgac  300
atctggggcc caggcaccct ggtcaccgtc tcgagcgcta gcaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagagagtt gagcccaaat cttgtgacaa aactcacaca  660
tgcccaccgt gcccagcacc tgaagccgcg gggggaccgt cagtcttcct cttcccccca  720
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacaacagca cgtaccgtgt ggtcagcgtc  900
ctcaccgtcc tgcaccagga ctggctgaat ggcaaggagt acaagtgcgc ggtctccaac  960
aaagccctcc cagcccccat cgagaaaacc atctccaaag ccaaagggca gccccgagaa  1020
ccacaggtgt acaccctgcc cccatcccgg gatgagctga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctatagca agctcaccgt ggacaagagc aggtggcagc aggggaacgt cttctcatgc  1260
tccgtgatgc atgaggctct gcacaaccac tacacgcaga agagcctctc cctgtctccg  1320
ggt                                                                 1323

SEQ ID NO: 46          moltype = DNA  length = 336
FEATURE                Location/Qualifiers
source                 1..336
                       mol_type = other DNA
                       organism = synthetic construct
SEQUENCE: 46
cagtcgctgg aggagtccgg gggtcgcctg gtcacgcctg ggacacccct gacactcacc  60
tgcacagcct ctgaattctc cctcagtagc tactacatga gctgggtccg ccaggctcca  120
gggaaggggc tggaatggat cggaagtatt tatgctagtg gtagcgcata ctacgcgagt  180
tgggcgaagg gccgattcac catctccaga acgtcgacca cggtggatct gaaaatgacc  240
agtctgacag ccgcggacac ggccacctat ttctgtgtca gagatcctat taacaatgac  300
atctggggcc caggcaccct ggtcaccgtc tcgagc                             336

SEQ ID NO: 47          moltype = AA  length = 441
FEATURE                Location/Qualifiers
source                 1..441
                       mol_type = protein
                       organism = synthetic construct
SEQUENCE: 47
QSLEESGGRL VTPGTPLTLT CTASEFSLSS YYMSWVRQAP GKGLEWIGSI YASGSAYYAS  60
WAKGRFTISR TSTTVDLKMT SLTAADTATY FCVRDPINND IWGPGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKRV EPKSCDKTHT CPPCPAPEAA GAPSVFLFPP  240
```

```
KPKDTLMISR TPEVTCVVVD VSHEDPEVKF NWYVDGVEVH NAKTKPREEQ YNSTYRVVSV  300
LTVLHQDWLN GKEYKCAVSN KALPAPIEKT ISKAKGQPRE PQVYTLPPSR DELTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP G                                            441

SEQ ID NO: 48          moltype = AA  length = 112
FEATURE                Location/Qualifiers
source                 1..112
                       mol_type = protein
                       organism = synthetic construct
SEQUENCE: 48
QSLEESGGRL VTPGTPLTLT CTASEFSLSS YYMSWVRQAP GKGLEWIGSI YASGSAYYAS  60
WAKGRFTISR TSTTVDLKMT SLTAADTATY FCVRDPINND IWGPGTLVTV SS          112

SEQ ID NO: 49          moltype = DNA  length = 654
FEATURE                Location/Qualifiers
source                 1..654
                       mol_type = other DNA
                       organism = synthetic construct
SEQUENCE: 49
gcccaagtgc tgacccagac tccagcctcc gtgtctgcaa ctgtgggaag cacagtcacc  60
atcagttgcc agtccagtcc gagtgtttat aagaacaacc aattagcctg gtatcagcag  120
aaaccagggc agcctcccaa actcctgatc tatctggcat ctactctggc atctggggtc  180
ccatcgcggt tcaaaggcag tggatctggg acagagttca ctctcaccat cagcgacctg  240
gagtgtgccg atgctgccac ttactactgt gcaggcggtt atagtagtag tagtgatact  300
gctttcggcg gagggaccga ggtggaggtc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 50          moltype = DNA  length = 333
FEATURE                Location/Qualifiers
source                 1..333
                       mol_type = other DNA
                       organism = synthetic construct
SEQUENCE: 50
gcccaagtgc tgacccagac tccagcctcc gtgtctgcaa ctgtgggaag cacagtcacc  60
atcagttgcc agtccagtcc gagtgtttat aagaacaacc aattagcctg gtatcagcag  120
aaaccagggc agcctcccaa actcctgatc tatctggcat ctactctggc atctggggtc  180
ccatcgcggt tcaaaggcag tggatctggg acagagttca ctctcaccat cagcgacctg  240
gagtgtgccg atgctgccac ttactactgt gcaggcggtt atagtagtag tagtgatact  300
gctttcggcg gagggaccga ggtggaggtc aaa                               333

SEQ ID NO: 51          moltype = AA  length = 218
FEATURE                Location/Qualifiers
source                 1..218
                       mol_type = protein
                       organism = synthetic construct
SEQUENCE: 51
AQVLTQTPAS VSATVGSTVT ISCQSSPSVY KNNQLAWYQQ KPGQPPKLLI YLASTLASGV  60
PSRFKGSGSG TEFTLTISDL ECADAATYYC AGGYSSSSDT AFGGGTEVEV KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 52          moltype = AA  length = 111
FEATURE                Location/Qualifiers
source                 1..111
                       mol_type = protein
                       organism = synthetic construct
SEQUENCE: 52
AQVLTQTPAS VSATVGSTVT ISCQSSPSVY KNNQLAWYQQ KPGQPPKLLI YLASTLASGV  60
PSRFKGSGSG TEFTLTISDL ECADAATYYC AGGYSSSSDT AFGGGTEVEV K           111

SEQ ID NO: 53          moltype = DNA  length = 1335
FEATURE                Location/Qualifiers
source                 1..1335
                       mol_type = other DNA
                       organism = synthetic construct
SEQUENCE: 53
cagtcgctgg aggagtccgg gggtcgcctg gtcacgcctg ggacacccct gacactcacc  60
tgcacagtct ctggaatcga cctcagtgcc taccacatga gctgggtccg ccaggctcca  120
gggaaggggc tggaatacat cggaatgatt ggtagtagtg gtaccataca ctacgcgaac  180
tgggcgaaag gccgattcac catctccaaa acctcgacca cggtggatct gaaaatcacc  240
agtccgacaa ccgaggacac ggccacctat ttctgtgcca gggacagtta taatagtgat  300
tatgccttta acttatgggg cccagggacc ctggtcaccg tctcgagcgc tagcaccaag  360
ggcccatcgg tcttccccct ggcaccctcc tccaagagca cctctggggg cacagcggcc  420
ctgggctgcc tggtcaagga ctacttcccc gaaccggtga cggtgtcgtg gaactcaggc  480
```

```
gccctgacca gcggcgtgca caccttcccg gctgtcctac agtcctcagg actctactcc  540
ctcagcagcg tggtgaccgt gccctccagc agcttgggca cccagaccta catctgcaac  600
gtgaatcaca agcccagcaa caccaaggtg gacaagagag ttgagcccaa atcttgtgac  660
aaaactcaca catgcccacc gtgcccagca cctgaagccg cgggggcacc gtcagtcttc  720
ctcttccccc caaaacccaa ggacaccctc atgatctccc ggacccctga ggtcacatgc  780
gtggtggtgg acgtgagcca cgaagaccct gaggtcaagt tcaactggta cgtggacggc  840
gtggaggtgc ataatgccaa gacaaagccg cgggaggagc agtacaacag cacgtaccgt  900
gtggtcagcg tcctcaccgt cctgcaccag gactggctga atggcaagga gtacaagtgc  960
gcggtctcca acaaagccct cccagccccc atcgagaaaa ccatctccaa agccaaaggg  1020
cagccccgag aaccacaggt gtacaccctg cccccatccc gggatgagct gaccaagaac  1080
caggtcagcc tgacctgcct ggtcaaaggc ttctatccca gcgacatcgc cgtggagtgg  1140
gagagcaatg ggcagccgga gaacaactac aagaccacgc ctcccgtgct ggactccgac  1200
ggctccttct tcctctatag caagctcacc gtggacaaga gcaggtggca gcaggggaac  1260
gtcttctcat gctccgtgat gcatgaggct ctgcacaacc actacacgca gaagagcctc  1320
tccctgtctc cgggt                                                  1335

SEQ ID NO: 54          moltype = DNA  length = 348
FEATURE                Location/Qualifiers
source                 1..348
                       mol_type = other DNA
                       organism = synthetic construct
SEQUENCE: 54
cagtcgctgg aggagtccgg gggtcgcctg gtcacgcctg ggacacccct gacactcacc  60
tgcacagtct ctggaatcga cctcagtgcc taccacatga gctgggtccg ccaggctcca  120
gggaaggggc tggaatacat cggaatgatt ggtagtagtg gtaccataca ctacgcgaac  180
tgggcgaaag gccgattcac catctccaaa acctcgacca cggtggatct gaaaatcacc  240
agtccgacaa ccgaggacac ggccacctat ttctgtgcca gggacagtta taatagtgat  300
tatgccttta acttatgggg cccagggacc ctggtcaccg tctcgagc              348

SEQ ID NO: 55          moltype = AA  length = 445
FEATURE                Location/Qualifiers
source                 1..445
                       mol_type = protein
                       organism = synthetic construct
SEQUENCE: 55
QSLEESGGRL VTPGTPLTLT CTVSGIDLSA YHMSWVRQAP GKGLEYIGMI GSSGTIHYAN  60
WAKGRFTISK TSTTVDLKIT SPTTEDTATY FCARDSYNSD YAFNLWGPGT LVTVSSASTK  120
GPSVFPLAPS SKSTSGGTAA LGCLVKDYFP EPVTVSWNSG ALTSGVHTFP AVLQSSGLYS  180
LSSVVTVPSS SLGTQTYICN VNHKPSNTKV DKRVEPKSCD KTHTCPPCPA PEAAGAPSVF  240
LFPPKPKDTL MISRTPEVTC VVVDVSHEDP EVKFNWYVDG VEVHNAKTKP REEQYNSTYR  300
VVSVLTVLHQ DWLNGKEYKC AVSNKALPAP IEKTISKAKG QPREPQVYTL PPSRDELTKN  360
QVSLTCLVKG FYPSDIAVEW ESNGQPENNY KTTPPVLDSD GSFFLYSKLT VDKSRWQQGN  420
VFSCSVMHEA LHNHYTQKSL SLSPG                                       445

SEQ ID NO: 56          moltype = AA  length = 116
FEATURE                Location/Qualifiers
source                 1..116
                       mol_type = protein
                       organism = synthetic construct
SEQUENCE: 56
QSLEESGGRL VTPGTPLTLT CTVSGIDLSA YHMSWVRQAP GKGLEYIGMI GSSGTIHYAN  60
WAKGRFTISK TSTTVDLKIT SPTTEDTATY FCARDSYNSD YAFNLWGPGT LVTVSS     116

SEQ ID NO: 57          moltype = DNA  length = 654
FEATURE                Location/Qualifiers
source                 1..654
                       mol_type = other DNA
                       organism = synthetic construct
SEQUENCE: 57
gctcaagtgc tgacccagac tgcatcgccc gtgtctgccg ctgtgggagg cacagtcacc  60
atcaactgcc agtccagtca gagtgtttat agtaactggt tatcctggta tcagcagaaa  120
ccagggcagc ctcccaagcg cctgatctat tctgcatcca ctctggcatc tggggtccca  180
tcgcggttca aaggcagtgg atctgggaca cagttcactc tcaccatcag cgacctggag  240
tgtgacgatg ctgccactta ctactgtgca ggcggttata atactgttac tgatactttt  300
gctttcggca gaggcaccga ggtggaggtc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt       654

SEQ ID NO: 58          moltype = DNA  length = 333
FEATURE                Location/Qualifiers
source                 1..333
                       mol_type = other DNA
                       organism = synthetic construct
SEQUENCE: 58
gctcaagtgc tgacccagac tgcatcgccc gtgtctgccg ctgtgggagg cacagtcacc  60
atcaactgcc agtccagtca gagtgtttat agtaactggt tatcctggta tcagcagaaa  120
```

```
ccagggcagc ctcccaagcg cctgatctat tctgcatcca ctctggcatc tggggtccca  180
tcgcggttca aaggcagtgg atctgggaca cagttcactc tcaccatcag cgacctggag  240
tgtgacgatg ctgccactta ctactgtgca ggcggttata atactgttac tgatactttt  300
gctttcggca gaggcaccga ggtggaggtc aaa                               333

SEQ ID NO: 59          moltype = AA  length = 218
FEATURE                Location/Qualifiers
source                 1..218
                       mol_type = protein
                       organism = synthetic construct
SEQUENCE: 59
AQVLTQTASP VSAAVGGTVT INCQSSQSVY SNWLSWYQQK PGQPPKRLIY SASTLASGVP  60
SRFKGSGSGT QFTLTISDLE CDDAATYYCA GGYNTVTDTF AFGRGTEVEV KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 60          moltype = AA  length = 111
FEATURE                Location/Qualifiers
source                 1..111
                       mol_type = protein
                       organism = synthetic construct
SEQUENCE: 60
AQVLTQTASP VSAAVGGTVT INCQSSQSVY SNWLSWYQQK PGQPPKRLIY SASTLASGVP  60
SRFKGSGSGT QFTLTISDLE CDDAATYYCA GGYNTVTDTF AFGRGTEVEV K           111

SEQ ID NO: 61          moltype = DNA  length = 1326
FEATURE                Location/Qualifiers
source                 1..1326
                       mol_type = other DNA
                       organism = synthetic construct
SEQUENCE: 61
cagtcgttgg aggagtccgg gggagacctg gtcaagcctg ggcatccct gacactcacc  60
tgcacagcct ctggattctc cttcagtagc aggcactaca tgtgttgggt ccgccaggct  120
ccaggggagg ggctggagtg gatcgcatgc atttatactg gtagtagtgg tactcctcac  180
tacgcgagct gggcgaaagg ccgattcacc atctcccaaa cctcgtcgac cacggtgact  240
ctgcaaatga ccagtctgac agccgcggac acggccacct atttctgttc gagcgaaggt  300
aacctgtggg gcccaggcac cctggtcacc gtctcgagcg ctagcaccaa gggcccatcg  360
gtcttccccc tggcaccctc ctccaagagc acctctgggg gcacagcggc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acccagacct acatctgcaa cgtgaatcac  600
aagcccagca acaccaaggt ggacaagaga gttgagccca aatcttgtga caaaactcac  660
acatgcccac cgtgcccagc acctgaagcc gcggggggcac cgtcagtctt cctcttcccc  720
ccaaaaccca aggacaccct catgatctcc cggacccctg aggtcacatg cgtggtggtg  780
gacgtgagcc acgaagaccc tgaggtcaag ttcaactggt acgtggacgg cgtggaggtg  840
cataatgcca agacaaagcc gcgggaggag cagtacaaca gcacgtaccg tgtggtcagc  900
gtcctcaccg tcctgcacca ggactggctg aatggcaagg agtacaagtg cgcggtctcc  960
aacaaagccc tcccagcccc catcgagaaa accatctcca aagccaaagg gcagccccga  1020
gaaccacagg tgtacaccct gcccccatcc cgggatgagc tgaccaagaa ccaggtcagc  1080
ctgacctgcc tggtcaaagg cttctatccc agcgacatcg ccgtggagtg ggagagcaat  1140
gggcagccgg agaacaacta caagaccacg cctcccgtgc tggactccga cggctccttc  1200
ttcctctata gcaagctcac cgtggacaag agcaggtggc agcaggggaa cgtcttctca  1260
tgctccgtga tgcatgaggc tctgcacaac cactacacgc agaagagcct ctccctgtct  1320
ccgggt                                                             1326

SEQ ID NO: 62          moltype = DNA  length = 339
FEATURE                Location/Qualifiers
source                 1..339
                       mol_type = other DNA
                       organism = synthetic construct
SEQUENCE: 62
cagtcgttgg aggagtccgg gggagacctg gtcaagcctg ggcatccct gacactcacc  60
tgcacagcct ctggattctc cttcagtagc aggcactaca tgtgttgggt ccgccaggct  120
ccaggggagg ggctggagtg gatcgcatgc atttatactg gtagtagtgg tactcctcac  180
tacgcgagct gggcgaaagg ccgattcacc atctcccaaa cctcgtcgac cacggtgact  240
ctgcaaatga ccagtctgac agccgcggac acggccacct atttctgttc gagcgaaggt  300
aacctgtggg gcccaggcac cctggtcacc gtctcgagc                         339

SEQ ID NO: 63          moltype = AA  length = 442
FEATURE                Location/Qualifiers
source                 1..442
                       mol_type = protein
                       organism = synthetic construct
SEQUENCE: 63
QSLEESGGDL VKPGASLTLT CTASGFSFSS RHYMCWVRQA PGEGLEWIAC IYTGSSGTPH  60
YASWAKGRFT ISQTSSTTVT LQMTSLTAAD TATYFCSSEG NLWGPGTLVT VSSASTKGPS  120
VFPLAPSSKS TSGGTAALGC LVKDYFPEPV TVSWNSGALT SGVHTFPAVL QSSGLYSLSS  180
VVTVPSSSLG TQTYICNVNH KPSNTKVDKR VEPKSCDKTH TCPPCPAPEA AGAPSVFLFP  240
PKPKDTLMIS RTPEVTCVVV DVSHEDPEVK FNWYVDGVEV HNAKTKPREE QYNSTYRVVS  300
```

-continued

```
VLTVLHQDWL NGKEYKCAVS NKALPAPIEK TISKAKGQPR EPQVYTLPPS RDELTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PG                                          442

SEQ ID NO: 64          moltype = AA  length = 113
FEATURE                Location/Qualifiers
source                 1..113
                       mol_type = protein
                       organism = synthetic construct
SEQUENCE: 64
QSLEESGGDL VKPGASLTLT CTASGFSFSS RHYMCWVRQA PGEGLEWIAC IYTGSSGTPH  60
YASWAKGRFT ISQTSSTTVT LQMTSLTAAD TATYFCSSEG NLWGPGTLVT VSS         113

SEQ ID NO: 65          moltype = DNA  length = 657
FEATURE                Location/Qualifiers
source                 1..657
                       mol_type = other DNA
                       organism = synthetic construct
SEQUENCE: 65
gcccttgtga tgacccagac tccagcctcc gtgtctgcag ctgtgggagg cacagtcacc  60
atcaattgcc aggccagtga ggacattgat acctatttag cctggtatca gcagaaacca  120
gggcagcctc ccaagctcct gatcttttat gcatccgatc tggcatctgg ggtcccatcg  180
cggttcaaag gcagtggatc tgggacagag ttcactctca ccatcagcgg tgtgcagtgt  240
gacgatgctg ccacttacta ctgtcaaggc ggttactata ctagtagtgc tgatacgagg  300
ggtgctttcg gcggaggcac cgaggtggtg gtcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 66          moltype = DNA  length = 336
FEATURE                Location/Qualifiers
source                 1..336
                       mol_type = other DNA
                       organism = synthetic construct
SEQUENCE: 66
gcccttgtga tgacccagac tccagcctcc gtgtctgcag ctgtgggagg cacagtcacc  60
atcaattgcc aggccagtga ggacattgat acctatttag cctggtatca gcagaaacca  120
gggcagcctc ccaagctcct gatcttttat gcatccgatc tggcatctgg ggtcccatcg  180
cggttcaaag gcagtggatc tgggacagag ttcactctca ccatcagcgg tgtgcagtgt  240
gacgatgctg ccacttacta ctgtcaaggc ggttactata ctagtagtgc tgatacgagg  300
ggtgctttcg gcggaggcac cgaggtggtg gtcaaa                            336

SEQ ID NO: 67          moltype = AA  length = 219
FEATURE                Location/Qualifiers
source                 1..219
                       mol_type = protein
                       organism = synthetic construct
SEQUENCE: 67
ALVMTQTPAS VSAAVGGTVT INCQASEDID TYLAWYQQKP GQPPKLLIFY ASDLASGVPS  60
RFKGSGSGTE FTLTISGVQC DDAATYYCQG GYYTSSADTR GAFGGGTEVV VKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 68          moltype = AA  length = 112
FEATURE                Location/Qualifiers
source                 1..112
                       mol_type = protein
                       organism = synthetic construct
SEQUENCE: 68
ALVMTQTPAS VSAAVGGTVT INCQASEDID TYLAWYQQKP GQPPKLLIFY ASDLASGVPS  60
RFKGSGSGTE FTLTISGVQC DDAATYYCQG GYYTSSADTR GAFGGGTEVV VK          112

SEQ ID NO: 69          moltype = DNA  length = 1344
FEATURE                Location/Qualifiers
source                 1..1344
                       mol_type = other DNA
                       organism = synthetic construct
SEQUENCE: 69
cagtcgttgg aggagtccgg gggagacctg gtcaagcctg ggcatccct gacactcacc   60
tgcacagcct ctggattctc cttcagtagc aactactgga tatgctgggt ccgccaggct  120
ccagggaagg ggctggagtg gatcgcatgc atttatgttg gtagtagtgg tgacacttac  180
tacgcgagct gggcgaaagg ccgattcacc atctccaaaa cctcgtcgac cacggtgact  240
ctgcaaatga ccagtctgac agccgcggac acggccacct atttctgtgc gagagatagt  300
agtagttatt atatgtttaa cttgtggggc caggggaccc tggtcaccgt ctcgagcgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
```

```
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaagccgc gggggcaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgcg cggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggt                                         1344

SEQ ID NO: 70          moltype = DNA  length = 357
FEATURE                Location/Qualifiers
source                 1..357
                       mol_type = other DNA
                       organism = synthetic construct
SEQUENCE: 70
cagtcgttgg aggagtccgg gggagacctg gtcaagcctg ggcatccct gacactcacc  60
tgcacagcct ctggattctc cttcagtagc aactactgga tatgctgggt ccgccaggct  120
ccagggaagg ggctggagtg gatcgcatgc atttatgttg gtagtagtgg tgacacttac  180
tacgcgagct gggcgaaagg ccgattcacc atctccaaaa cctcgtcgac cacggtgact  240
ctgcaaatga ccagtctgac agccgcggac acggccacct atttctgtgc gagagatagt  300
agtagttatt atatgtttaa cttgtggggc caggggaccc tggtcaccgt ctcgagc     357

SEQ ID NO: 71          moltype = AA  length = 448
FEATURE                Location/Qualifiers
source                 1..448
                       mol_type = protein
                       organism = synthetic construct
SEQUENCE: 71
QSLEESGGDL VKPGASLTLT CTASGFSFSS NYWICWVRQA PGKGLEWIAC IYVGSSGDTY  60
YASWAKGRFT ISKTSSTTVT LQMTSLTAAD TATYFCARDS SSYYMFNLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCAVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 72          moltype = AA  length = 119
FEATURE                Location/Qualifiers
source                 1..119
                       mol_type = protein
                       organism = synthetic construct
SEQUENCE: 72
QSLEESGGDL VKPGASLTLT CTASGFSFSS NYWICWVRQA PGKGLEWIAC IYVGSSGDTY  60
YASWAKGRFT ISKTSSTTVT LQMTSLTAAD TATYFCARDS SSYYMFNLWG QGTLVTVSS   119

SEQ ID NO: 73          moltype = DNA  length = 654
FEATURE                Location/Qualifiers
source                 1..654
                       mol_type = other DNA
                       organism = synthetic construct
SEQUENCE: 73
gctcaagtgc tgacccagac tgcatcgccc gtgtctgccg ctgtgggagg cacagtcacc  60
atcaactgcc aggccagtca gagtgtttat agtaactggt tatcctggta tcagcagaaa  120
ccagggcagc ctcccaagcg cctgatctat tctgcatcca ctctggcatc tggggtccca  180
tcgcggttca aaggcagtgg atctgggaca cagttcactc tcaccattag cgacctggag  240
tgtgacgatg ctgccactta ctactgtgca ggcggttaca atactgttat tgatactttt  300
gctttcggcg gaggcaccga ggtggagttc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 74          moltype = DNA  length = 333
FEATURE                Location/Qualifiers
source                 1..333
                       mol_type = other DNA
                       organism = synthetic construct
SEQUENCE: 74
gctcaagtgc tgacccagac tgcatcgccc gtgtctgccg ctgtgggagg cacagtcacc  60
atcaactgcc aggccagtca gagtgtttat agtaactggt tatcctggta tcagcagaaa  120
ccagggcagc ctcccaagcg cctgatctat tctgcatcca ctctggcatc tggggtccca  180
```

```
tcgcggttca aaggcagtgg atctgggaca cagttcactc tcaccattag cgacctggag  240
tgtgacgatg ctgccactta ctactgtgca ggcggttaca atactgttat tgatactttt  300
gctttcggcg gaggcaccga ggtggagttc aaa                               333

SEQ ID NO: 75          moltype = AA  length = 218
FEATURE                Location/Qualifiers
source                 1..218
                       mol_type = protein
                       organism = synthetic construct
SEQUENCE: 75
AQVLTQTASP VSAAVGGTVT INCQASQSVY SNWLSWYQQK PGQPPKRLIY SASTLASGVP  60
SRFKGSGSGT QFTLTISDLE CDDAATYYCA GGYNTVIDTF AFGGGTEVEF KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 76          moltype = AA  length = 111
FEATURE                Location/Qualifiers
source                 1..111
                       mol_type = protein
                       organism = synthetic construct
SEQUENCE: 76
AQVLTQTASP VSAAVGGTVT INCQASQSVY SNWLSWYQQK PGQPPKRLIY SASTLASGVP  60
SRFKGSGSGT QFTLTISDLE CDDAATYYCA GGYNTVIDTF AFGGGTEVEF K           111

SEQ ID NO: 77          moltype = DNA  length = 1329
FEATURE                Location/Qualifiers
source                 1..1329
                       mol_type = other DNA
                       organism = synthetic construct
SEQUENCE: 77
cagcagcagc tggaggagtc cgggggaggc ctggtcaagc ctggaggaac cctgacactc  60
acctgcaaag cctctggaat tgacttcagt agtagttact acatgtgctg ggtccgccag  120
gctccagggg aggggctgga gtggatcgca tgcatttata ctggtggtag tggtactcct  180
cactacgcga gctgggcgaa aggccgattc accatctccc aaacctcgtc gaccacggtg  240
actctgcaaa tgaccagtct gacagccgcg gacacggcca cctatttctg tgcgagagaa  300
ggtagcctgt ggggccaggg caccctggtc accgtctcga gcgctagcac caagggccca  360
tcggtcttcc ccctggcacc ctcctccaag agcacctctg ggggcacagc ggccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacccaga cctacatctg caacgtgaat  600
cacaagccca gcaacaccaa ggtggacaag agagttgagc ccaaatcttg tgacaaaact  660
cacacatgcc caccgtgccc agcacctgaa gccgcggggg caccgtcagt cttcctcttc  720
cccccaaaac ccaaggacac cctcatgatc tcccggaccc ctgaggtcac atgcgtggtg  780
gtggacgtga gccacgaaga ccctgaggtc aagttcaact ggtacgtgga cggcgtggag  840
gtgcataatg ccaagacaaa gccgcgggag gagcagtaca acagcacgta ccgtgtggtc  900
agcgtcctca ccgtcctgca ccaggactgg ctgaatggca aggagtacaa gtgcgcggtc  960
tccaacaaag ccctcccagc ccccatcgag aaaaccatct ccaaagccaa agggcagccc  1020
cgagaaccac aggtgtacac cctgccccca tcccgggatg agctgaccaa gaaccaggtc  1080
agcctgacct gcctggtcaa aggcttctat cccagcgaca tcgccgtgga gtgggagagc  1140
aatgggcagc cggagaacaa ctacaagacc acgcctcccg tgctggactc cgacggctcc  1200
ttcttcctct atagcaagct caccgtggac aagagcaggt ggcagcaggg gaacgtcttc  1260
tcatgctccg tgatgcatga ggctctgcac aaccactaca cgcagaagag cctctccctg  1320
tctccgggt                                                          1329

SEQ ID NO: 78          moltype = DNA  length = 342
FEATURE                Location/Qualifiers
source                 1..342
                       mol_type = other DNA
                       organism = synthetic construct
SEQUENCE: 78
cagcagcagc tggaggagtc cgggggaggc ctggtcaagc ctggaggaac cctgacactc  60
acctgcaaag cctctggaat tgacttcagt agtagttact acatgtgctg ggtccgccag  120
gctccagggg aggggctgga gtggatcgca tgcatttata ctggtggtag tggtactcct  180
cactacgcga gctgggcgaa aggccgattc accatctccc aaacctcgtc gaccacggtg  240
actctgcaaa tgaccagtct gacagccgcg gacacggcca cctatttctg tgcgagagaa  300
ggtagcctgt ggggccaggg caccctggtc accgtctcga gc                     342

SEQ ID NO: 79          moltype = AA  length = 443
FEATURE                Location/Qualifiers
source                 1..443
                       mol_type = protein
                       organism = synthetic construct
SEQUENCE: 79
QQQLEESGGG LVKPGGTLTL TCKASGIDFS SSYYMCWVRQ APGEGLEWIA CIYTGGSGTP  60
HYASWAKGRF TISQTSSTTV TLQMTSLTAA DTATYFCARE GSLWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK RVEPKSCDKT HTCPPCPAPE AAGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCAV SNKALPAPIE KTISKAKGQP REPQVYTLPP SRDELTKNQV  360
```

```
SLTCLVKGFY PSDIAVEWES NGQPENNYKT TPPVLDSDGS FFLYSKLTVD KSRWQQGNVF  420
SCSVMHEALH NHYTQKSLSL SPG                                         443

SEQ ID NO: 80          moltype = AA  length = 114
FEATURE                Location/Qualifiers
source                 1..114
                       mol_type = protein
                       organism = synthetic construct
SEQUENCE: 80
QQQLEESGGG LVKPGGTLTL TCKASGIDFS SSYYMCWVRQ APGEGLEWIA CIYTGGSGTP  60
HYASWAKGRF TISQTSSTTV TLQMTSLTAA DTATYFCARE GSLWGQGTLV TVSS        114

SEQ ID NO: 81          moltype = DNA  length = 654
FEATURE                Location/Qualifiers
source                 1..654
                       mol_type = other DNA
                       organism = synthetic construct
SEQUENCE: 81
gctcaagtgc tgacccagac tgcatcgccc gtgtctgccg ctgtgggagg cacagtcacc  60
atcaactgcc agtccagtca gagtgtttat agtaactggt tctcctggta tcagcagaaa  120
ccagggcagc ctcccaagct cctgatctat tctgcatcca ctctggcatc tggggtcccc  180
tcgcggttta aaggcagtgg atctgggaca cagttcactc tcaccatcag cgacctggag  240
tgtgacgatg ctgccactta ctactgtgca ggcggttaca atactgtaac tgatactttt  300
gctttcggcg gaggcaccga ggtggagttc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 82          moltype = DNA  length = 333
FEATURE                Location/Qualifiers
source                 1..333
                       mol_type = other DNA
                       organism = synthetic construct
SEQUENCE: 82
gctcaagtgc tgacccagac tgcatcgccc gtgtctgccg ctgtgggagg cacagtcacc  60
atcaactgcc agtccagtca gagtgtttat agtaactggt tctcctggta tcagcagaaa  120
ccagggcagc ctcccaagct cctgatctat tctgcatcca ctctggcatc tggggtcccc  180
tcgcggttta aaggcagtgg atctgggaca cagttcactc tcaccatcag cgacctggag  240
tgtgacgatg ctgccactta ctactgtgca ggcggttaca atactgtaac tgatactttt  300
gctttcggcg gaggcaccga ggtggagttc aaa                               333

SEQ ID NO: 83          moltype = AA  length = 218
FEATURE                Location/Qualifiers
source                 1..218
                       mol_type = protein
                       organism = synthetic construct
SEQUENCE: 83
AQVLTQTASP VSAAVGGTVT INCQSSQSVY SNWFSWYQQK PGQPPKLLIY SASTLASGVP  60
SRFKGSGSGT QFTLTISDLE CDDAATYYCA GGYNTVTDTF AFGGGTEVEF KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 84          moltype = AA  length = 111
FEATURE                Location/Qualifiers
source                 1..111
                       mol_type = protein
                       organism = synthetic construct
SEQUENCE: 84
AQVLTQTASP VSAAVGGTVT INCQSSQSVY SNWFSWYQQK PGQPPKLLIY SASTLASGVP  60
SRFKGSGSGT QFTLTISDLE CDDAATYYCA GGYNTVTDTF AFGGGTEVEF K           111

SEQ ID NO: 85          moltype = DNA  length = 1326
FEATURE                Location/Qualifiers
source                 1..1326
                       mol_type = other DNA
                       organism = synthetic construct
SEQUENCE: 85
gagtcgttgg aggagtccgg gggagacctg gtcaagcctg ggcatccct gacactcacc  60
tgcacagcct ctggaatcga cttcagtagg agatactaca tgtgctgggt ccgccaggct  120
ccagggaagg ggctggagtg gatcgcatgc atgtatactg gtagccgcga tactcctcac  180
tacgcgagct gggcgaaagg ccggttcacc atctcccaaa cctcgtcgac cacggtgact  240
ctgcaaatga ccagtctgac agccgcggac acggccacct atttctgtgc gagagaaggt  300
aacctgtggg gcccggggac cctggtcacc gtctcgagcg ctagcaccaa gggcccatcg  360
gtcttccccc tggcaccctc ctccaagagc acctctgggg gcacagcggc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acccagacct acatctgcaa cgtgaatcac  600
```

```
aagcccagca acaccaaggt ggacaagaga gttgagccca aatcttgtga caaaactcac  660
acatgcccac cgtgcccagc acctgaagcc gcggggggcac cgtcagtctt cctcttcccc  720
ccaaaaccca aggacaccct catgatctcc cggacccctg aggtcacatg cgtggtggtg  780
gacgtgagcc acgaagaccc tgaggtcaag ttcaactggt acgtggacgg cgtggaggtg  840
cataatgcca agacaaagcc gcgggaggag cagtacaaca gcacgtaccg tgtggtcagc  900
gtcctcaccg tcctgcacca ggactggctg aatggcaagg agtacaagtg cgcggtctcc  960
aacaaagccc tcccagcccc catcgagaaa accatctcca aagccaaagg gcagccccga  1020
gaaccacagg tgtacaccct gcccccatcc cgggatgagc tgaccaagaa ccaggtcagc  1080
ctgacctgcc tggtcaaagg cttctatccc agcgacatcg ccgtggagtg ggagagcaat  1140
gggcagccgg agaacaacta caagaccacg cctcccgtgc tggactccga cggctccttc  1200
ttcctctata gcaagctcac cgtggacaag agcaggtggc agcaggggaa cgtcttctca  1260
tgctccgtga tgcatgaggc tctgcacaac cactacacgc agaagagcct ctccctgtct  1320
ccgggt                                                             1326

SEQ ID NO: 86          moltype = DNA  length = 339
FEATURE                Location/Qualifiers
source                 1..339
                       mol_type = other DNA
                       organism = synthetic construct
SEQUENCE: 86
gagtcgttgg aggagtccgg gggagacctg gtcaagcctg gggcatccct gacactcacc  60
tgcacagcct ctggaatcga cttcagtagg agatactaca tgtgctgggt ccgccaggct  120
ccagggaagg ggctggagtg gatcgcatgc atgtatactg gtagccgcga tactcctcac  180
tacgcgagct gggcgaaagg ccggttcacc atctcccaaa cctcgtcgac cacggtgact  240
ctgcaaatga ccagtctgac agccgcggac acggccacct atttctgtgc gagagaaggt  300
aacctgtggg gcccggggac cctggtcacc gtctcgagc                        339

SEQ ID NO: 87          moltype = AA  length = 442
FEATURE                Location/Qualifiers
source                 1..442
                       mol_type = protein
                       organism = synthetic construct
SEQUENCE: 87
ESLEESGGDL VKPGASLTLT CTASGIDFSR RYYMCWVRQA PGKGLEWIAC MYTGSRDTPH  60
YASWAKGRFT ISQTSSTTVT LQMTSLTAAD TATYFCAREG NLWGPGTLVT VSSASTKGPS  120
VFPLAPSSKS TSGGTAALGC LVKDYFPEPV TVSWNSGALT SGVHTFPAVL QSSGLYSLSS  180
VVTVPSSSLG TQTYICNVNH KPSNTKVDKR VEPKSCDKTH TCPPCPAPEA AGAPSVFLFP  240
PKPKDTLMIS RTPEVTCVVV DVSHEDPEVK FNWYVDGVEV HNAKTKPREE QYNSTYRVVS  300
VLTVLHQDWL NGKEYKCAVS NKALPAPIEK TISKAKGQPR EPQVYTLPPS RDELTKNQVS  360
LTCLVKGFYP SDIAVEWESN GQPENNYKTT PPVLDSDGSF FLYSKLTVDK SRWQQGNVFS  420
CSVMHEALHN HYTQKSLSLS PG                                           442

SEQ ID NO: 88          moltype = AA  length = 113
FEATURE                Location/Qualifiers
source                 1..113
                       mol_type = protein
                       organism = synthetic construct
SEQUENCE: 88
ESLEESGGDL VKPGASLTLT CTASGIDFSR RYYMCWVRQA PGKGLEWIAC MYTGSRDTPH  60
YASWAKGRFT ISQTSSTTVT LQMTSLTAAD TATYFCAREG NLWGPGTLVT VSS         113

SEQ ID NO: 89          moltype = DNA  length = 654
FEATURE                Location/Qualifiers
source                 1..654
                       mol_type = other DNA
                       organism = synthetic construct
SEQUENCE: 89
gcccaagtgc tgacccagac tccatcgtcc gtgtctgcag ctgtgggagg cacagtcagc  60
atcagttgcc agtccagtca gagtgtttat agtaactggt tctcctggta tcagcagaaa  120
ccagggcagc ctcccaagct cctgatctat tctgcatcca ctctggcatc tggggtcccc  180
tcgcggttta aaggcagtgg atctgggaca cagttcactc tcaccatcag cgacctggag  240
tgtgacgatg ctgccactta ctactgtgca ggcggttaca atactgttat tgatactttt  300
gctttcggcg gaggcaccga ggtggagttc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 90          moltype = DNA  length = 333
FEATURE                Location/Qualifiers
source                 1..333
                       mol_type = other DNA
                       organism = synthetic construct
SEQUENCE: 90
gcccaagtgc tgacccagac tccatcgtcc gtgtctgcag ctgtgggagg cacagtcagc  60
atcagttgcc agtccagtca gagtgtttat agtaactggt tctcctggta tcagcagaaa  120
ccagggcagc ctcccaagct cctgatctat tctgcatcca ctctggcatc tggggtcccc  180
tcgcggttta aaggcagtgg atctgggaca cagttcactc tcaccatcag cgacctggag  240
```

```
tgtgacgatg ctgccactta ctactgtgca ggcggttaca atactgttat tgatactttt  300
gctttcggcg gaggcaccga ggtggagttc aaa                               333

SEQ ID NO: 91          moltype = AA  length = 218
FEATURE                Location/Qualifiers
source                 1..218
                       mol_type = protein
                       organism = synthetic construct
SEQUENCE: 91
AQVLTQTPSS VSAAVGGTVS ISCQSSQSVY SNWFSWYQQK PGQPPKLLIY SASTLASGVP  60
SRFKGSGSGT QFTLTISDLE CDDAATYYCA GGYNTVIDTF AFGGGTEVEF KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 92          moltype = AA  length = 111
FEATURE                Location/Qualifiers
source                 1..111
                       mol_type = protein
                       organism = synthetic construct
SEQUENCE: 92
AQVLTQTPSS VSAAVGGTVS ISCQSSQSVY SNWFSWYQQK PGQPPKLLIY SASTLASGVP  60
SRFKGSGSGT QFTLTISDLE CDDAATYYCA GGYNTVIDTF AFGGGTEVEF K           111

SEQ ID NO: 93          moltype = DNA  length = 1326
FEATURE                Location/Qualifiers
source                 1..1326
                       mol_type = other DNA
                       organism = synthetic construct
SEQUENCE: 93
cagtcgttgg aggagtccgg gggagacctg gtcaagcctg ggcatccct gacactcacc  60
tgcacagcct ctggaatcga cttcagtagg agatactaca tgtgctgggt ccgccaggct  120
ccagggaagg ggctggagtg gatcgcatgc atatatactg gtagccgcga tactcctcac  180
tacgcgagct gggcgaaagg ccgattcacc atctcccaaa cctcgtcgac cacggtgact  240
ctgcaaatga ccagtctgac agccgcggac acggccacct atttctgtgc gagagaaggt  300
agcctgtggg gccagggcac cctggtcacc gtctcgagcg ctagcaccaa gggcccatcg  360
gtcttccccc tggcaccctc ctccaagagc acctctgggg gcacagcggc cctgggctgc  420
ctggtcaagg actacttccc cgaaccggtg acggtgtcgt ggaactcagg cgccctgacc  480
agcggcgtgc acaccttccc ggctgtccta cagtcctcag gactctactc cctcagcagc  540
gtggtgaccg tgccctccag cagcttgggc acccagacct acatctgcaa cgtgaatcac  600
aagcccagca acaccaaggt ggacaagaga gttgagccca aatcttgtga caaaactcac  660
acatgcccac cgtgcccagc acctgaagcc gcgggggcac cgtcagtctt cctcttcccc  720
ccaaaaccca aggacaccct catgatctcc cggacccctg aggtcacatg cgtggtggtg  780
gacgtgagcc acgaagaccc tgaggtcaag ttcaactggt acgtggacgg cgtggaggtg  840
cataatgcca agacaaagcc gcgggaggag cagtacaaca gcacgtaccg tgtggtcagc  900
gtcctcaccg tcctgcacca ggactggctg aatggcaagg agtacaagtg cgcggtctcc  960
aacaaagccc tcccagcccc catcgagaaa accatctcca aagccaaagg gcagccccga  1020
gaaccacagg tgtacaccct gcccccatcc cgggatgagc tgaccaagaa ccaggtcagc  1080
ctgacctgcc tggtcaaagg cttctatccc agcgacatcg ccgtggagtg ggagagcaat  1140
gggcagccgg agaacaacta caagaccacg cctcccgtgc tggactccga cggctccttc  1200
ttcctctata gcaagctcac cgtggacaag agcaggtggc agcaggggaa cgtcttctca  1260
tgctccgtga tgcatgaggc tctgcacaac cactacacgc agaagagcct ctccctgtct  1320
ccgggt                                                             1326

SEQ ID NO: 94          moltype = DNA  length = 339
FEATURE                Location/Qualifiers
source                 1..339
                       mol_type = other DNA
                       organism = synthetic construct
SEQUENCE: 94
cagtcgttgg aggagtccgg gggagacctg gtcaagcctg ggcatccct gacactcacc  60
tgcacagcct ctggaatcga cttcagtagg agatactaca tgtgctgggt ccgccaggct  120
ccagggaagg ggctggagtg gatcgcatgc atatatactg gtagccgcga tactcctcac  180
tacgcgagct gggcgaaagg ccgattcacc atctcccaaa cctcgtcgac cacggtgact  240
ctgcaaatga ccagtctgac agccgcggac acggccacct atttctgtgc gagagaaggt  300
agcctgtggg gccagggcac cctggtcacc gtctcgagc                         339

SEQ ID NO: 95          moltype = AA  length = 442
FEATURE                Location/Qualifiers
source                 1..442
                       mol_type = protein
                       organism = synthetic construct
SEQUENCE: 95
QSLEESGGDL VKPGASLTLT CTASGIDFSR RYYMCWVRQA PGKGLEWIAC IYTGSRDTPH  60
YASWAKGRFT ISQTSSTTVT LQMTSLTAAD TATYFCAREG SLWGQGTLVT VSSASTKGPS  120
VFPLAPSSKS TSGGTAALGC LVKDYFPEPV TVSWNSGALT SGVHTFPAVL QSSGLYSLSS  180
VVTVPSSSLG TQTYICNVNH KPSNTKVDKR VEPKSCDKTH TCPPCPAPEA AGAPSVFLFP  240
PKPKDTLMIS RTPEVTCVVV DVSHEDPEVK FNWYVDGVEV HNAKTKPREE QYNSTYRVVS  300
VLTVLHQDWL NGKEYKCAVS NKALPAPIEK TISKAKGQPR EPQVYTLPPS RDELTKNQVS  360
LTCLVKGFYP SDIAVEWESN GQPENNYKTT PPVLDSDGSF FLYSKLTVDK SRWQQGNVFS  420
```

```
CSVMHEALHN HYTQKSLSLS PG                                          442

SEQ ID NO: 96           moltype = AA  length = 113
FEATURE                 Location/Qualifiers
source                  1..113
                        mol_type = protein
                        organism = synthetic construct
SEQUENCE: 96
QSLEESGGDL VKPGASLTLT CTASGIDFSR RYYMCWVRQA PGKGLEWIAC IYTGSRDTPH  60
YASWAKGRFT ISQTSSTTVT LQMTSLTAAD TATYFCAREG SLWGQGTLVT VSS         113

SEQ ID NO: 97           moltype = DNA  length = 651
FEATURE                 Location/Qualifiers
source                  1..651
                        mol_type = other DNA
                        organism = synthetic construct
SEQUENCE: 97
gcgcaagtgc tgacccagac tccatcgcct gtgtctgcag ctgtgggagg cacagtcacc  60
atcaattgcc agtccagtca gagtgtttat agtaacagct tcttatcctg gtatcagcag  120
aaaccagggc agcctcccaa gcgcctgatc tattctgcat ccgatctggc atctggggtc  180
ccatcgcggt tcaaaggcag tggatctggg acacagttca ctctcaccat cagcgacctg  240
gagtgtgacg atgctgccac ttactactgt gcaggcgttt atagtgataa tacttatgtt  300
ttcggcggag gcaccgaggt ggagttcaaa cgtacggtgg ctgcaccatc tgtcttcatc  360
ttcccgccat ctgatgagca gttgaaatct ggaactgcct ctgttgtgtg cctgctgaat  420
aacttctatc ccagagaggc caaagtacag tggaaggtgg ataacgccct ccaatcgggt  480
aactcccagg agagtgtcac agagcaggac agcaaggaca gcacctacag cctcagcagc  540
accctgacgc tgagcaaagc agactacgag aaacacaaag tctacgcctg cgaagtcacc  600
catcagggcc tgagctcgcc cgtcacaaag agcttcaaca ggggagagtg t           651

SEQ ID NO: 98           moltype = DNA  length = 330
FEATURE                 Location/Qualifiers
source                  1..330
                        mol_type = other DNA
                        organism = synthetic construct
SEQUENCE: 98
gcgcaagtgc tgacccagac tccatcgcct gtgtctgcag ctgtgggagg cacagtcacc  60
atcaattgcc agtccagtca gagtgtttat agtaacagct tcttatcctg gtatcagcag  120
aaaccagggc agcctcccaa gcgcctgatc tattctgcat ccgatctggc atctggggtc  180
ccatcgcggt tcaaaggcag tggatctggg acacagttca ctctcaccat cagcgacctg  240
gagtgtgacg atgctgccac ttactactgt gcaggcgttt atagtgataa tacttatgtt  300
ttcggcggag gcaccgaggt ggagttcaaa                                   330

SEQ ID NO: 99           moltype = AA  length = 217
FEATURE                 Location/Qualifiers
source                  1..217
                        mol_type = protein
                        organism = synthetic construct
SEQUENCE: 99
AQVLTQTPSP VSAAVGGTVT INCQSSQSVY SNSFLSWYQQ KPGQPPKRLI YSASDLASGV  60
PSRFKGSGSG TQFTLTISDL ECDDAATYYC AGVYSDNTYV FGGGTEVEFK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 100          moltype = AA  length = 110
FEATURE                 Location/Qualifiers
source                  1..110
                        mol_type = protein
                        organism = synthetic construct
SEQUENCE: 100
AQVLTQTPSP VSAAVGGTVT INCQSSQSVY SNSFLSWYQQ KPGQPPKRLI YSASDLASGV  60
PSRFKGSGSG TQFTLTISDL ECDDAATYYC AGVYSDNTYV FGGGTEVEFK             110

SEQ ID NO: 101          moltype = DNA  length = 1329
FEATURE                 Location/Qualifiers
source                  1..1329
                        mol_type = other DNA
                        organism = synthetic construct
SEQUENCE: 101
cagtcggtgg aggagtccgg cggtcgcctg gtaaagcctg acgaatccct gacactcacc  60
tgcacagcct ctggattctc cctcagtcac tactggatga cttgggtccg acaggctcca  120
gggaagggac tggaatacat cggattcatt aatgttggtg gtgacacatc ttacgcgagc  180
tggtcgaaag gccgattcac catctccaag gcctcgacca cggtggatct gaagatcagt  240
agtctgacaa ccgaggacac ggccacctat ttctgtggca gaggtggtct gacttttggt  300
tgggacttgt ggggcccagg gaccctcgtc accgtctcga gcgctagcac caagggccca  360
tcggtcttcc ccctggcacc ctcctccaag agcacctctg ggggcacagc ggccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacccaga cctacatctg caacgtgaat  600
cacaagccca gcaacaccaa ggtggacaag agagttgagc ccaaatcttg tgacaaaact  660
```

```
cacacatgcc caccgtgccc agcacctgaa gccgcggggg caccgtcagt cttcctcttc  720
cccccaaaac ccaaggacac cctcatgatc tcccggaccc ctgaggtcac atgcgtggtg  780
gtggacgtga gccacgaaga ccctgaggtc aagttcaact ggtacgtgga cggcgtggag  840
gtgcataatg ccaagacaaa gccgcgggag gagcagtaca acagcacgta ccgtgtggtc  900
agcgtcctca ccgtcctgca ccaggactgg ctgaatggca aggagtacaa gtgcgcggtc  960
tccaacaaag ccctcccagc ccccatcgag aaaaccatct ccaaagccaa agggcagccc  1020
cgagaaccac aggtgtacac cctgccccca tcccgggatg agctgaccaa gaaccaggtc  1080
agcctgacct gcctggtcaa aggcttctat cccagcgaca tcgccgtgga gtgggagagc  1140
aatgggcagc cggagaacaa ctacaagacc acgcctcccg tgctggactc cgacggctcc  1200
ttcttcctct atagcaagct caccgtggac aagagcaggt ggcagcaggg gaacgtcttc  1260
tcatgctccg tgatgcatga ggctctgcac aaccactaca cgcagaagag cctctccctg  1320
tctccgggt                                                          1329

SEQ ID NO: 102         moltype = DNA  length = 342
FEATURE                Location/Qualifiers
source                 1..342
                       mol_type = other DNA
                       organism = synthetic construct
SEQUENCE: 102
cagtcggtgg aggagtccgg cggtcgcctg gtaaagcctg acgaatccct gacactcacc  60
tgcacagcct ctggattctc cctcagtcac tactggatga cttgggtccg acaggctcca  120
gggaagggac tggaatacat cggattcatt aatgttggtg gtgacacatc ttacgcgagc  180
tggtcgaaag gccgattcac catctccaag gcctcgacca cggtggatct gaagatcagt  240
agtctgacaa ccgaggacac ggccacctat ttctgtggca gaggtggtct gacttttggt  300
tgggacttgt ggggcccagg gaccctcgtc accgtctcga gc                     342

SEQ ID NO: 103         moltype = AA  length = 444
FEATURE                Location/Qualifiers
source                 1..444
                       mol_type = protein
                       organism = synthetic construct
SEQUENCE: 103
QSVEESGGRL VKPDESLTLT CTASGFSLSH YWMTWVRQAP GKGLEYIGFI NVGGDTSYAS  60
WSKGRFTISK ASTTVDLKIS SLTTEDTATY FCGRGGLTFG WDLWGPGTLV TVSSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 104         moltype = AA  length = 114
FEATURE                Location/Qualifiers
source                 1..114
                       mol_type = protein
                       organism = synthetic construct
SEQUENCE: 104
QSVEESGGRL VKPDESLTLT CTASGFSLSH YWMTWVRQAP GKGLEYIGFI NVGGDTSYAS  60
WSKGRFTISK ASTTVDLKIS SLTTEDTATY FCGRGGLTFG WDLWGPGTLV TVSS        114

SEQ ID NO: 105         moltype = DNA  length = 654
FEATURE                Location/Qualifiers
source                 1..654
                       mol_type = other DNA
                       organism = synthetic construct
SEQUENCE: 105
gatgttgtga tgacccagac tccagcctcc gtgtctgaac ctgtgggagg cacagtcacc  60
atcaagtgcc aggccagtca gaacattagg acttacttat cctggtatca gcagaaacca  120
gggcagcgtc ccaagctcct gatctatgct gcagccaatc tggcatctgg ggtcccatcg  180
cggttcagtg gcagtagatc tgggacagag ttcactctca ccatcagcga cctggagtgt  240
gccgatgctg ccacttacta ttgtcagtgt acctatcttg gtactgatta tgttggcggt  300
gctttcggcg gaggcaccga ggtggagttc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 106         moltype = DNA  length = 333
FEATURE                Location/Qualifiers
source                 1..333
                       mol_type = other DNA
                       organism = synthetic construct
SEQUENCE: 106
gatgttgtga tgacccagac tccagcctcc gtgtctgaac ctgtgggagg cacagtcacc  60
atcaagtgcc aggccagtca gaacattagg acttacttat cctggtatca gcagaaacca  120
gggcagcgtc ccaagctcct gatctatgct gcagccaatc tggcatctgg ggtcccatcg  180
cggttcagtg gcagtagatc tgggacagag ttcactctca ccatcagcga cctggagtgt  240
gccgatgctg ccacttacta ttgtcagtgt acctatcttg gtactgatta tgttggcggt  300
```

```
gctttcggcg gaggcaccga ggtggagttc aaa                            333

SEQ ID NO: 107          moltype = AA  length = 218
FEATURE                 Location/Qualifiers
source                  1..218
                        mol_type = protein
                        organism = synthetic construct
SEQUENCE: 107
DVVMTQTPAS VSEPVGGTVT IKCQASQNIR TYLSWYQQKP GQRPKLLIYA AANLASGVPS  60
RFSGSRSGTE FTLTISDLEC ADAATYYCQC TYLGTDYVGG AFGGGTEVEF KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                        218

SEQ ID NO: 108          moltype = AA  length = 111
FEATURE                 Location/Qualifiers
source                  1..111
                        mol_type = protein
                        organism = synthetic construct
SEQUENCE: 108
DVVMTQTPAS VSEPVGGTVT IKCQASQNIR TYLSWYQQKP GQRPKLLIYA AANLASGVPS  60
RFSGSRSGTE FTLTISDLEC ADAATYYCQC TYLGTDYVGG AFGGGTEVEF K          111

SEQ ID NO: 109          moltype = DNA  length = 1329
FEATURE                 Location/Qualifiers
source                  1..1329
                        mol_type = other DNA
                        organism = synthetic construct
SEQUENCE: 109
cggtcgctgg aggagtccgg gggtcgcctg gtcacgcctg ggacacccct gacactcacc  60
tgcacagcct ctggattcac catcagtagc taccacatgc agtgggtccg ccaggctcca  120
gggaaggggc tggaatacat cggaaccatt agtagtggtg gtaatgtata ctacgcgagc  180
tgggcgagag gccgattcac catctccaga ccctcgtcga ccacggtgga tctgaagatg  240
accagtctga caaccgagga cacggccacc tatttctgtg ccagagactc tggttatagt  300
gatcctatgt ggggcccggg caccctggtc accgtctcga gcgctagcac caagggccca  360
tcggtcttcc ccctggcacc ctcctccaag agcacctctg gggcacagc ggccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacccaga cctacatctg caacgtgaat  600
cacaagccca gcaacaccaa ggtggacaag agagttgagc ccaaatcttg tgacaaaact  660
cacacatgcc caccgtgccc agcacctgaa gccgcggggg caccgtcagt cttcctcttc  720
cccccaaaac ccaaggacac cctcatgatc tcccggaccc ctgaggtcac atgcgtggtg  780
gtggacgtga gccacgaaga ccctgaggtc aagttcaact ggtacgtgga cggcgtggag  840
gtgcataatg ccaagacaaa gccgcgggag gagcagtaca acagcacgta ccgtgtggtc  900
agcgtcctca ccgtcctgca ccaggactgg ctgaatggca aggagtacaa gtgcgcggtc  960
tccaacaaag ccctcccagc ccccatcgag aaaaccatct ccaaagccaa agggcagccc  1020
cgagaaccac aggtgtacac cctgccccca tcccgggatg agctgaccaa gaaccaggtc  1080
agcctgacct gcctggtcaa aggcttctat cccagcgaca tcgccgtgga gtgggagagc  1140
aatgggcagc cggagaacaa ctacaagacc acgcctcccg tgctggactc cgacggctcc  1200
ttcttcctct atagcaagct caccgtggac aagagcaggt ggcagcaggg gaacgtcttc  1260
tcatgctccg tgatgcatga ggctctgcac aaccactaca cgcagaagag cctctccctg  1320
tctccgggt                                                        1329

SEQ ID NO: 110          moltype = DNA  length = 342
FEATURE                 Location/Qualifiers
source                  1..342
                        mol_type = other DNA
                        organism = synthetic construct
SEQUENCE: 110
cggtcgctgg aggagtccgg gggtcgcctg gtcacgcctg ggacacccct gacactcacc  60
tgcacagcct ctggattcac catcagtagc taccacatgc agtgggtccg ccaggctcca  120
gggaaggggc tggaatacat cggaaccatt agtagtggtg gtaatgtata ctacgcgagc  180
tgggcgagag gccgattcac catctccaga ccctcgtcga ccacggtgga tctgaagatg  240
accagtctga caaccgagga cacggccacc tatttctgtg ccagagactc tggttatagt  300
gatcctatgt ggggcccggg caccctggtc accgtctcga gc                   342

SEQ ID NO: 111          moltype = AA  length = 443
FEATURE                 Location/Qualifiers
source                  1..443
                        mol_type = protein
                        organism = synthetic construct
SEQUENCE: 111
RSLEESGGRL VTPGTPLTLT CTASGFTISS YHMQWVRQAP GKGLEYIGTI SSGGNVYYAS  60
WARGRFTISR PSSTTVDLKM TSLTTEDTAT YFCARDSGYS DPMWGPGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK RVEPKSCDKT HTCPPCPAPE AAGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCAV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                        443
```

```
SEQ ID NO: 112          moltype = AA  length = 114
FEATURE                 Location/Qualifiers
source                  1..114
                        mol_type = protein
                        organism = synthetic construct
SEQUENCE: 112
RSLEESGGRL VTPGTPLTLT CTASGFTISS YHMQWVRQAP GKGLEYIGTI SSGGNVYYAS  60
WARGRFTISR PSSTTVDLKM TSLTTEDTAT YFCARDSGYS DPMWGPGTLV TVSS        114

SEQ ID NO: 113          moltype = DNA  length = 654
FEATURE                 Location/Qualifiers
source                  1..654
                        mol_type = other DNA
                        organism = synthetic construct
SEQUENCE: 113
gcagccgtgc tgacccagac accatcgccc gtgtctgcag ctgtgggagg cacagtcacc  60
atcagttgcc agtccagtca gagtgtttat agtaacaacc aattatcctg gtttcagcag  120
aaatcagggc agcctcccaa gctcctgatc tatgatgcat ccaatctggc atctggggtc  180
ccatcacggt tcagcggcag tggatctggg acacagttca ctctcaccat cagcagcgtg  240
cagtgtgacg atgctgccac ttaccactgt ctaggcggta gtgatgatga tggtgatatt  300
gctttcggcg gaggcaccga ggtggtgttc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 114          moltype = DNA  length = 333
FEATURE                 Location/Qualifiers
source                  1..333
                        mol_type = other DNA
                        organism = synthetic construct
SEQUENCE: 114
gcagccgtgc tgacccagac accatcgccc gtgtctgcag ctgtgggagg cacagtcacc  60
atcagttgcc agtccagtca gagtgtttat agtaacaacc aattatcctg gtttcagcag  120
aaatcagggc agcctcccaa gctcctgatc tatgatgcat ccaatctggc atctggggtc  180
ccatcacggt tcagcggcag tggatctggg acacagttca ctctcaccat cagcagcgtg  240
cagtgtgacg atgctgccac ttaccactgt ctaggcggta gtgatgatga tggtgatatt  300
gctttcggcg gaggcaccga ggtggtgttc aaa                               333

SEQ ID NO: 115          moltype = AA  length = 218
FEATURE                 Location/Qualifiers
source                  1..218
                        mol_type = protein
                        organism = synthetic construct
SEQUENCE: 115
AAVLTQTPSP VSAAVGGTVT ISCQSSQSVY SNNQLSWFQQ KSGQPPKLLI YDASNLASGV  60
PSRFSGSGSG TQFTLTISSV QCDDAATYHC LGGSDDDGDI AFGGGTEVVF KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 116          moltype = AA  length = 111
FEATURE                 Location/Qualifiers
source                  1..111
                        mol_type = protein
                        organism = synthetic construct
SEQUENCE: 116
AAVLTQTPSP VSAAVGGTVT ISCQSSQSVY SNNQLSWFQQ KSGQPPKLLI YDASNLASGV  60
PSRFSGSGSG TQFTLTISSV QCDDAATYHC LGGSDDDGDI AFGGGTEVVF K           111

SEQ ID NO: 117          moltype = DNA  length = 1323
FEATURE                 Location/Qualifiers
source                  1..1323
                        mol_type = other DNA
                        organism = synthetic construct
SEQUENCE: 117
cagtcactgg aggagtccgg gggtcgcctg gtcacgcctg ggacacccct gacactcacc  60
tgcacagcct ctggattctc cctcagtagc tactacatga gctgggtccg ccaggctcca  120
gggaagggac tggaatggat cggaagtatt tatggtagtg gtgccgcata ctacgcgagc  180
tgggcgaaag gccgattcac catctccaga acgtcgacca cggtggatct gaaaatgacc  240
agtctgacag ccgcggacac ggccacctat ttctgtgcca gagatcctat taacaatgcc  300
atgtggggcc caggcaccct ggtcaccgtc tcgagcgcta gcaccaaggg cccatcggtc  360
ttccccctgg caccctcctc caagagcacc tctgggggca cagcggccct gggctgcctg  420
gtcaaggact acttccccga accggtgacg gtgtcgtgga actcaggcgc cctgaccagc  480
ggcgtgcaca ccttcccggc tgtcctacag tcctcaggac tctactccct cagcagcgtg  540
gtgaccgtgc cctccagcag cttgggcacc cagacctaca tctgcaacgt gaatcacaag  600
cccagcaaca ccaaggtgga caagagagtt gagcccaaat cttgtgacaa aactcacaca  660
tgcccaccgt gcccagcacc tgaagccgcg ggggcaccgt cagtcttcct cttcccccca  720
```

```
aaacccaagg acaccctcat gatctcccgg acccctgagg tcacatgcgt ggtggtggac  780
gtgagccacg aagaccctga ggtcaagttc aactggtacg tggacggcgt ggaggtgcat  840
aatgccaaga caaagccgcg ggaggagcag tacaacagca cgtaccgtgt ggtcagcgtc  900
ctcaccgtcc tgcaccagga ctggctgaat ggcaaggagt acaagtgcgc ggtctccaac  960
aaagccctcc cagcccccat cgagaaaacc atctccaaag ccaaagggca gccccgagaa  1020
ccacaggtgt acaccctgcc cccatcccgg gatgagctga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctatagca agctcaccgt ggacaagagc aggtggcagc aggggaacgt cttctcatgc  1260
tccgtgatgc atgaggctct gcacaaccac tacacgcaga agagcctctc cctgtctccg  1320
ggt                                                                1323

SEQ ID NO: 118          moltype = DNA  length = 336
FEATURE                 Location/Qualifiers
source                  1..336
                        mol_type = other DNA
                        organism = synthetic construct
SEQUENCE: 118
cagtcactgg aggagtccgg gggtcgcctg gtcacgcctg ggacacccct gacactcacc  60
tgcacagcct ctggattctc cctcagtagc tactacatga gctgggtccg ccaggctcca  120
gggaagggac tggaatggat cggaagtatt tatggtagtg gtgccgcata ctacgcgagc  180
tgggcgaaag gccgattcac catctccaga acgtcgacca cggtggatct gaaaatgacc  240
agtctgacag ccgcggacac ggccacctat ttctgtgcca gagatcctat taacaatgcc  300
atgtggggcc caggcaccct ggtcaccgtc tcgagc                             336

SEQ ID NO: 119          moltype = AA  length = 441
FEATURE                 Location/Qualifiers
source                  1..441
                        mol_type = protein
                        organism = synthetic construct
SEQUENCE: 119
QSLEESGGRL VTPGTPLTLT CTASGFSLSS YYMSWVRQAP GKGLEWIGSI YGSGAAYYAS  60
WAKGRFTISR TSTTVDLKMT SLTAADTATY FCARDPINNA MWGPGTLVTV SSASTKGPSV  120
FPLAPSSKST SGGTAALGCL VKDYFPEPVT VSWNSGALTS GVHTFPAVLQ SSGLYSLSSV  180
VTVPSSSLGT QTYICNVNHK PSNTKVDKRV EPKSCDKTHT CPPCPAPEAA GAPSVFLFPP  240
KPKDTLMISR TPEVTCVVVD VSHEDPEVKF NWYVDGVEVH NAKTKPREEQ YNSTYRVVSV  300
LTVLHQDWLN GKEYKCAVSN KALPAPIEKT ISKAKGQPRE PQVYTLPPSR DELTKNQVSL  360
TCLVKGFYPS DIAVEWESNG QPENNYKTTP PVLDSDGSFF LYSKLTVDKS RWQQGNVFSC  420
SVMHEALHNH YTQKSLSLSP G                                            441

SEQ ID NO: 120          moltype = AA  length = 112
FEATURE                 Location/Qualifiers
source                  1..112
                        mol_type = protein
                        organism = synthetic construct
SEQUENCE: 120
QSLEESGGRL VTPGTPLTLT CTASGFSLSS YYMSWVRQAP GKGLEWIGSI YGSGAAYYAS  60
WAKGRFTISR TSTTVDLKMT SLTAADTATY FCARDPINNA MWGPGTLVTV SS          112

SEQ ID NO: 121          moltype = DNA  length = 657
FEATURE                 Location/Qualifiers
source                  1..657
                        mol_type = other DNA
                        organism = synthetic construct
SEQUENCE: 121
gcccttgtga tgacccagac tccagcctcc gtgtctgcag ctgtgggagg cacagtcacc  60
atcaattgcc aggccagtga ggacattgat aactatttag cctggtatca gcagaaacca  120
gggcagcctc ccaagctcct gatcttttat gcatccgatc tggcatctgg ggtcccatcg  180
cggttctcag gcagtggatc tgggacacag ttcactctca ccatcagcgg tgtgcagtgt  240
gacgatgctg ccacttacta ctgtcaaggc ggttactata ctagtagtac tgatacgagg  300
ggtgctttcg gcggaggcac cgaggtggtg gtcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt      657

SEQ ID NO: 122          moltype = DNA  length = 336
FEATURE                 Location/Qualifiers
source                  1..336
                        mol_type = other DNA
                        organism = synthetic construct
SEQUENCE: 122
gcccttgtga tgacccagac tccagcctcc gtgtctgcag ctgtgggagg cacagtcacc  60
atcaattgcc aggccagtga ggacattgat aactatttag cctggtatca gcagaaacca  120
gggcagcctc ccaagctcct gatcttttat gcatccgatc tggcatctgg ggtcccatcg  180
cggttctcag gcagtggatc tgggacacag ttcactctca ccatcagcgg tgtgcagtgt  240
gacgatgctg ccacttacta ctgtcaaggc ggttactata ctagtagtac tgatacgagg  300
ggtgctttcg gcggaggcac cgaggtggtg gtcaaa                             336
```

```
SEQ ID NO: 123          moltype = AA  length = 219
FEATURE                 Location/Qualifiers
source                  1..219
                        mol_type = protein
                        organism = synthetic construct
SEQUENCE: 123
ALVMTQTPAS VSAAVGGTVT INCQASEDID NYLAWYQQKP GQPPKLLIFY ASDLASGVPS  60
RFSGSGSGTQ FTLTISGVQC DDAATYYCQG GYYTSSTDTR GAFGGGTEVV VKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 124          moltype = AA  length = 112
FEATURE                 Location/Qualifiers
source                  1..112
                        mol_type = protein
                        organism = synthetic construct
SEQUENCE: 124
ALVMTQTPAS VSAAVGGTVT INCQASEDID NYLAWYQQKP GQPPKLLIFY ASDLASGVPS  60
RFSGSGSGTQ FTLTISGVQC DDAATYYCQG GYYTSSTDTR GAFGGGTEVV VK          112

SEQ ID NO: 125          moltype = DNA  length = 1344
FEATURE                 Location/Qualifiers
source                  1..1344
                        mol_type = other DNA
                        organism = synthetic construct
SEQUENCE: 125
cagtcattgg aggaggccgg gggagacctg gtcaagcctg gggcatccct gacactcacc  60
tgcacagcct ctggcttctc cttcactagc agctactaca tgtgctgggt ccgccaggct  120
ccagggaagg ggctggagtg gatcgcatgc atttatactg gtagtagtgg tagcacttac  180
tacgcgaact gggcgaaagg ccgattcacc atctccaaaa cctcgtcgac cacggtgact  240
ctgcaaatga ccagtctgac agccgcggac acggccacct atttctgtgc gagagatagt  300
agtagttatt atatgtttaa cttgtggggc cagggcaccc tcgtcaccgt ctcgagcgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaagccgc gggggcaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgcg cggtctccaa caaagccctc ccagccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggt                                         1344

SEQ ID NO: 126          moltype = DNA  length = 357
FEATURE                 Location/Qualifiers
source                  1..357
                        mol_type = other DNA
                        organism = synthetic construct
SEQUENCE: 126
cagtcattgg aggaggccgg gggagacctg gtcaagcctg gggcatccct gacactcacc  60
tgcacagcct ctggcttctc cttcactagc agctactaca tgtgctgggt ccgccaggct  120
ccagggaagg ggctggagtg gatcgcatgc atttatactg gtagtagtgg tagcacttac  180
tacgcgaact gggcgaaagg ccgattcacc atctccaaaa cctcgtcgac cacggtgact  240
ctgcaaatga ccagtctgac agccgcggac acggccacct atttctgtgc gagagatagt  300
agtagttatt atatgtttaa cttgtggggc cagggcaccc tcgtcaccgt ctcgagc     357

SEQ ID NO: 127          moltype = AA  length = 448
FEATURE                 Location/Qualifiers
source                  1..448
                        mol_type = protein
                        organism = synthetic construct
SEQUENCE: 127
QSLEEAGGDL VKPGASLTLT CTASGFSFTS SYYMCWVRQA PGKGLEWIAC IYTGSSGSTY  60
YANWAKGRFT ISKTSSTTVT LQMTSLTAAD TATYFCARDS SSYYMFNLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCAVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                     448
```

```
SEQ ID NO: 128          moltype = AA  length = 119
FEATURE                 Location/Qualifiers
source                  1..119
                        mol_type = protein
                        organism = synthetic construct
SEQUENCE: 128
QSLEEAGGDL VKPGASLTLT CTASGFSFTS SYYMCWVRQA PGKGLEWIAC IYTGSSGSTY  60
YANWAKGRFT ISKTSSTTVT LQMTSLTAAD TATYFCARDS SSYYMFNLWG QGTLVTVSS   119

SEQ ID NO: 129          moltype = DNA  length = 654
FEATURE                 Location/Qualifiers
source                  1..654
                        mol_type = other DNA
                        organism = synthetic construct
SEQUENCE: 129
gcagccgtgc tgacccagac tccatcttcc acgtctgcag ctgtgggagg cacagtcacc  60
atcagttgcc agtccagtca gagtgtttat aataacaatg ctttagcctg gtatcagaaa  120
aaaccaggac agcctcccaa gctcctgatc tatttggctt ccactctggc atctggggtc  180
ccatcgcggt tcagcggcag tggatctggg acacagttca ctctcaccat cagcgacctg  240
gagtgtgacg atgctgccac ttattattgt ctaggtgttt ataatgatga tgttgataat  300
ggtttcggcg gaggcaccga ggtggtgttc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 130          moltype = DNA  length = 333
FEATURE                 Location/Qualifiers
source                  1..333
                        mol_type = other DNA
                        organism = synthetic construct
SEQUENCE: 130
gcagccgtgc tgacccagac tccatcttcc acgtctgcag ctgtgggagg cacagtcacc  60
atcagttgcc agtccagtca gagtgtttat aataacaatg ctttagcctg gtatcagaaa  120
aaaccaggac agcctcccaa gctcctgatc tatttggctt ccactctggc atctggggtc  180
ccatcgcggt tcagcggcag tggatctggg acacagttca ctctcaccat cagcgacctg  240
gagtgtgacg atgctgccac ttattattgt ctaggtgttt ataatgatga tgttgataat  300
ggtttcggcg gaggcaccga ggtggtgttc aaa                               333

SEQ ID NO: 131          moltype = AA  length = 218
FEATURE                 Location/Qualifiers
source                  1..218
                        mol_type = protein
                        organism = synthetic construct
SEQUENCE: 131
AAVLTQTPSS TSAAVGGTVT ISCQSSQSVY NNNALAWYQK KPGQPPKLLI YLASTLASGV  60
PSRFSGSGSG TQFTLTISDL ECDDAATYYC LGVYNDDVDN GFGGGTEVVF KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 132          moltype = AA  length = 111
FEATURE                 Location/Qualifiers
source                  1..111
                        mol_type = protein
                        organism = synthetic construct
SEQUENCE: 132
AAVLTQTPSS TSAAVGGTVT ISCQSSQSVY NNNALAWYQK KPGQPPKLLI YLASTLASGV  60
PSRFSGSGSG TQFTLTISDL ECDDAATYYC LGVYNDDVDN GFGGGTEVVF K           111

SEQ ID NO: 133          moltype = DNA  length = 1332
FEATURE                 Location/Qualifiers
source                  1..1332
                        mol_type = other DNA
                        organism = synthetic construct
SEQUENCE: 133
cagtcgctgg aggagtccgg gggtcgcctg gtcacgcctg gaggatccct gacactcacc  60
tgcaccgtct ctggattctc cctcaataac aatgcaataa gctgggtccg ccaggctcca  120
gggaaggggc tggaatgggt tgcaatcata caaaatactg gtaccacaga ctacgcgagg  180
tgggcgaaag gccgattcac catctccaaa acctcgacca cggtggattt gaaaatcaac  240
agtccgacaa ccgaggacac ggccacctat ttctgtggca gagggtatgg ttttgagtcg  300
gagcttgtca tctggggccc gggcaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg ggcaccgtc agtcttcctc  720
ttccccccaa aacccaagga caccctcatg atctcccgga cccctgaggt cacatgcgtg  780
```

```
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 134          moltype = DNA  length = 345
FEATURE                 Location/Qualifiers
source                  1..345
                        mol_type = other DNA
                        organism = synthetic construct
SEQUENCE: 134
cagtcgctgg aggagtccgg gggtcgcctg gtcacgcctg gaggatccct gacactcacc  60
tgcaccgtct ctggattctc cctcaataac aatgcaataa gctgggtccg ccaggctcca  120
gggaaggggc tggaatgggt tgcaatcata caaaatactg gtaccacaga ctacgcgagg  180
tgggcgaaag gccgattcac catctccaaa acctcgacca cggtggattt gaaaatcaac  240
agtccgacaa ccgaggacac ggccacctat ttctgtggca gagggtatgg ttttgagtcg  300
gagcttgtca tctggggccc gggcaccctg gtcaccgtct cgagc                 345

SEQ ID NO: 135          moltype = AA  length = 444
FEATURE                 Location/Qualifiers
source                  1..444
                        mol_type = protein
                        organism = synthetic construct
SEQUENCE: 135
QSLEESGGRL VTPGGSLTLT CTVSGFSLNN NAISWVRQAP GKGLEWVAII QNTGTTDYAR  60
WAKGRFTISK TSTTVDLKIN SPTTEDTATY FCGRGYGFES ELVIWGPGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 136          moltype = AA  length = 115
FEATURE                 Location/Qualifiers
source                  1..115
                        mol_type = protein
                        organism = synthetic construct
SEQUENCE: 136
QSLEESGGRL VTPGGSLTLT CTVSGFSLNN NAISWVRQAP GKGLEWVAII QNTGTTDYAR  60
WAKGRFTISK TSTTVDLKIN SPTTEDTATY FCGRGYGFES ELVIWGPGTL VTVSS       115

SEQ ID NO: 137          moltype = DNA  length = 657
FEATURE                 Location/Qualifiers
source                  1..657
                        mol_type = other DNA
                        organism = synthetic construct
SEQUENCE: 137
gacgttgtga tgacccagtc tccatcttcc gtgtctgcat ctgtaggaga cagagtcacc  60
atcacctgtc aggccagtca gagcattggt gctgatttag cctggtatca gcagaaacca  120
gggaaagccc ctaagctcct gatctatagg gcatccactc tggcctctgg ggtcccatca  180
aggttcagcg gcagtggatc tgggacagat ttcactctca ccatcagcag cctgcagcct  240
gaagattttg caacttacta ttgtcaagct atttattatg gtactgatga tgtcatatac  300
catactttcg gcggagggac caaggtggag atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 138          moltype = DNA  length = 336
FEATURE                 Location/Qualifiers
source                  1..336
                        mol_type = other DNA
                        organism = synthetic construct
SEQUENCE: 138
gacgttgtga tgacccagtc tccatcttcc gtgtctgcat ctgtaggaga cagagtcacc  60
atcacctgtc aggccagtca gagcattggt gctgatttag cctggtatca gcagaaacca  120
gggaaagccc ctaagctcct gatctatagg gcatccactc tggcctctgg ggtcccatca  180
aggttcagcg gcagtggatc tgggacagat ttcactctca ccatcagcag cctgcagcct  240
gaagattttg caacttacta ttgtcaagct atttattatg gtactgatga tgtcatatac  300
catactttcg gcggagggac caaggtggag atcaaa                           336
```

```
SEQ ID NO: 139          moltype = AA  length = 219
FEATURE                 Location/Qualifiers
source                  1..219
                        mol_type = protein
                        organism = synthetic construct
SEQUENCE: 139
DVVMTQSPSS VSASVGDRVT ITCQASQSIG ADLAWYQQKP GKAPKLLIYR ASTLASGVPS  60
RFSGSGSGTD FTLTISSLQP EDFATYYCQA IYYGTDDVIY HTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                        219

SEQ ID NO: 140          moltype = AA  length = 112
FEATURE                 Location/Qualifiers
source                  1..112
                        mol_type = protein
                        organism = synthetic construct
SEQUENCE: 140
DVVMTQSPSS VSASVGDRVT ITCQASQSIG ADLAWYQQKP GKAPKLLIYR ASTLASGVPS  60
RFSGSGSGTD FTLTISSLQP EDFATYYCQA IYYGTDDVIY HTFGGGTKVE IK         112

SEQ ID NO: 141          moltype = DNA  length = 1341
FEATURE                 Location/Qualifiers
source                  1..1341
                        mol_type = other DNA
                        organism = synthetic construct
SEQUENCE: 141
gaggtgcagc tggtggagtc tgggggaggc ttggtccagc ctggggggtc cctgagactc  60
tcctgtgcag cctctggatt caccatcagt agccaccaca tgatctgggt ccgccaggct  120
ccagggaagg ggctgcaata catcggattc attaatgatg gtgactatac atactacacg  180
aactccgcaa aaggcagatt caccatctcc agagacaatt ccaagaacac gctgtatctt  240
caaatgaaca gcctgagagc cgaggacacg gctgtgtatt actgtgcgag aggggttgat  300
ggtactagtt atcctggctt gtggggccag ggaaccctgg tcaccgtctc gagcgctagc  360
accaagggcc catcggtctt ccccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga atcacaagcc cagcaacacc aaggtggaca agagagttga gcccaaatct  660
tgtgacaaaa ctcacacatg cccaccgtgc ccagcacctg aagccgcggg ggcaccgtca  720
gtcttcctct tccccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcgcgg tctccaacaa agccctccca gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctatagcaag ctcaccgtgg acaagagcag gtggcagcag  1260
gggaacgtct tctcatgctc cgtgatgcat gaggctctgc acaaccacta cacgcagaag  1320
agcctctccc tgtctccggg t                                           1341

SEQ ID NO: 142          moltype = DNA  length = 354
FEATURE                 Location/Qualifiers
source                  1..354
                        mol_type = other DNA
                        organism = synthetic construct
SEQUENCE: 142
gaggtgcagc tggtggagtc tgggggaggc ttggtccagc ctggggggtc cctgagactc  60
tcctgtgcag cctctggatt caccatcagt agccaccaca tgatctgggt ccgccaggct  120
ccagggaagg ggctgcaata catcggattc attaatgatg gtgactatac atactacacg  180
aactccgcaa aaggcagatt caccatctcc agagacaatt ccaagaacac gctgtatctt  240
caaatgaaca gcctgagagc cgaggacacg gctgtgtatt actgtgcgag aggggttgat  300
ggtactagtt atcctggctt gtggggccag ggaaccctgg tcaccgtctc gagc       354

SEQ ID NO: 143          moltype = AA  length = 447
FEATURE                 Location/Qualifiers
source                  1..447
                        mol_type = protein
                        organism = synthetic construct
SEQUENCE: 143
EVQLVESGGG LVQPGGSLRL SCAASGFTIS SHHMIWVRQA PGKGLQYIGF INDGDYTYYT  60
NSAKGRFTIS RDNSKNTLYL QMNSLRAEDT AVYYCARGVD GTSYPGLWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGAPS  240
VFLFPPKPKD TLMISRTPEV TCVVVDVSHE DPEVKFNWYV DGVEVHNAKT KPREEQYNST  300
YRVVSVLTVL HQDWLNGKEY KCAVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                     447

SEQ ID NO: 144          moltype = AA  length = 118
```

```
FEATURE                Location/Qualifiers
source                 1..118
                       mol_type = protein
                       organism = synthetic construct
SEQUENCE: 144
EVQLVESGGG LVQPGGSLRL SCAASGFTIS SHHMIWVRQA PGKGLQYIGF INDGDYTYYT  60
NSAKGRFTIS RDNSKNTLYL QMNSLRAEDT AVYYCARGVD GTSYPGLWGQ GTLVTVSS    118

SEQ ID NO: 145         moltype = DNA  length = 657
FEATURE                Location/Qualifiers
source                 1..657
                       mol_type = other DNA
                       organism = synthetic construct
SEQUENCE: 145
gacatccaga tgacccagtc tccatcctcc ctgtctgcat ctgtaggaga cagagtcacc  60
atcacttgcc aggccagtca gagcatttac agcaatttag cctggtatca gcagaaacca  120
gggaaagttc ctaagctcct gatctattct acatccactc tggcatctgg ggtcccatct  180
cggttcagtg gcagtggatc tgggacagat ttcactctca ccatcagcag cctgcagcct  240
gaagatgttg caacttatta ctgtcaaaac tattatggta gtagtactga tagttatggg  300
aatcctttcg gcggagggac caaggtggag atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 146         moltype = DNA  length = 336
FEATURE                Location/Qualifiers
source                 1..336
                       mol_type = other DNA
                       organism = synthetic construct
SEQUENCE: 146
gacatccaga tgacccagtc tccatcctcc ctgtctgcat ctgtaggaga cagagtcacc  60
atcacttgcc aggccagtca gagcatttac agcaatttag cctggtatca gcagaaacca  120
gggaaagttc ctaagctcct gatctattct acatccactc tggcatctgg ggtcccatct  180
cggttcagtg gcagtggatc tgggacagat ttcactctca ccatcagcag cctgcagcct  240
gaagatgttg caacttatta ctgtcaaaac tattatggta gtagtactga tagttatggg  300
aatcctttcg gcggagggac caaggtggag atcaaa                            336

SEQ ID NO: 147         moltype = AA  length = 219
FEATURE                Location/Qualifiers
source                 1..219
                       mol_type = protein
                       organism = synthetic construct
SEQUENCE: 147
DIQMTQSPSS LSASVGDRVT ITCQASQSIY SNLAWYQQKP GKVPKLLIYS TSTLASGVPS  60
RFSGSGSGTD FTLTISSLQP EDVATYYCQN YYGSSTDSYG NPFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 148         moltype = AA  length = 112
FEATURE                Location/Qualifiers
source                 1..112
                       mol_type = protein
                       organism = synthetic construct
SEQUENCE: 148
DIQMTQSPSS LSASVGDRVT ITCQASQSIY SNLAWYQQKP GKVPKLLIYS TSTLASGVPS  60
RFSGSGSGTD FTLTISSLQP EDVATYYCQN YYGSSTDSYG NPFGGGTKVE IK          112

SEQ ID NO: 149         moltype = DNA  length = 1350
FEATURE                Location/Qualifiers
source                 1..1350
                       mol_type = other DNA
                       organism = synthetic construct
SEQUENCE: 149
gaggtgcagc tggtggagtc tgggggaggc ttggtccagc ctgggggtc cctgagactc  60
tcctgtgcag cctctggaat cgacttcagt agcaactaca tgtgctgggt ccgccaggct  120
ccagggaagg ggctggagtg gatcgcatgc atttatggtg atagtagtga taatagttac  180
tccgcgagct ccgctaaagg cagattcacc atctccagag acaattccaa gaacacgctg  240
tatcttcaaa tgaacagcct gagagccgag gacacggctg tgtattactg tgcgagatct  300
ggttatagct atttaggcta ctttaacttg tggggccagg gaaccctggt caccgtctcg  360
agcgctagca ccaagggccc atcggtcttc cccctggcac cctcctccaa gagcacctct  420
gggggcacag cggccctggg ctgcctggtc aaggactact tccccgaacc ggtgacggtg  480
tcgtggaact caggcgccct gaccagcggc gtgcacacct tcccggctgt cctacagtcc  540
tcaggactct actccctcag cagcgtggtg accgtgccct ccagcagctt gggcacccag  600
acctacatct gcaacgtgaa tcacaagccc agcaacacca aggtggacaa gagagttgag  660
cccaaatctt gtgacaaaac tcacacatgc ccaccgtgcc cagcacctga agccgcgggg  720
gcaccgtcag tcttcctctt ccccccaaaa cccaaggaca ccctcatgat ctcccggacc  780
cctgaggtca catgcgtggt ggtggacgtg agccacgaag accctgaggt caagttcaac  840
```

```
tggtacgtgg acggcgtgga ggtgcataat gccaagacaa agccgcggga ggagcagtac  900
aacagcacgt accgtgtggt cagcgtcctc accgtcctgc accaggactg gctgaatggc  960
aaggagtaca agtgcgcggt ctccaacaaa gccctcccag cccccatcga gaaaaccatc  1020
tccaaagcca aagggcagcc ccgagaacca caggtgtaca ccctgccccc atcccgggat  1080
gagctgacca agaaccaggt cagcctgacc tgcctggtca aaggcttcta tcccagcgac  1140
atcgccgtgg agtgggagag caatgggcag ccggagaaca actacaagac cacgcctccc  1200
gtgctggact ccgacggctc cttcttcctc tatagcaagc tcaccgtgga caagagcagg  1260
tggcagcagg ggaacgtctt ctcatgctcc gtgatgcatg aggctctgca caaccactac  1320
acgcagaaga gcctctccct gtctccgggt                                  1350

SEQ ID NO: 150          moltype = DNA  length = 363
FEATURE                 Location/Qualifiers
source                  1..363
                        mol_type = other DNA
                        organism = synthetic construct
SEQUENCE: 150
gaggtgcagc tggtggagtc tgggggaggc ttggtccagc ctggggggtc cctgagactc  60
tcctgtgcag cctctggaat cgacttcagt agcaactaca tgtgctgggt ccgccaggct  120
ccagggaagg ggctggagtg gatcgcatgc atttatggtg atagtagtga taatagttac  180
tccgcgagct ccgctaaagg cagattcacc atctccagag acaattccaa gaacacgctg  240
tatcttcaaa tgaacagcct gagagccgag gacacggctg tgtattactg tgcgagatct  300
ggttatagct atttaggcta ctttaacttg tggggccagg gaaccctggt caccgtctcg  360
agc                                                               363

SEQ ID NO: 151          moltype = AA  length = 450
FEATURE                 Location/Qualifiers
source                  1..450
                        mol_type = protein
                        organism = synthetic construct
SEQUENCE: 151
EVQLVESGGG LVQPGGSLRL SCAASGIDFS SNYMCWVRQA PGKGLEWIAC IYGDSSDNSY  60
SASSAKGRFT ISRDNSKNTL YLQMNSLRAE DTAVYYCARS GYSYLGYFNL WGQGTLVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSCDKTHTC PPCPAPEAAG  240
APSVFLFPPK PKDTLMISRT PEVTCVVVDV SHEDPEVKFN WYVDGVEVHN AKTKPREEQY  300
NSTYRVVSVL TVLHQDWLNG KEYKCAVSNK ALPAPIEKTI SKAKGQPREP QVYTLPPSRD  360
ELTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 152          moltype = AA  length = 121
FEATURE                 Location/Qualifiers
source                  1..121
                        mol_type = protein
                        organism = synthetic construct
SEQUENCE: 152
EVQLVESGGG LVQPGGSLRL SCAASGIDFS SNYMCWVRQA PGKGLEWIAC IYGDSSDNSY  60
SASSAKGRFT ISRDNSKNTL YLQMNSLRAE DTAVYYCARS GYSYLGYFNL WGQGTLVTVS  120
S                                                                 121

SEQ ID NO: 153          moltype = DNA  length = 651
FEATURE                 Location/Qualifiers
source                  1..651
                        mol_type = other DNA
                        organism = synthetic construct
SEQUENCE: 153
gacatccaga tgacccagtc tccatcctcc ctgtctgcat ctgtaggaga cagagtcacc  60
atcacttgcc agtccagtca gactgtttat aataacaact tgttatcctg gtatcagcag  120
aaaccaggga aagttcctaa gctcctgatc tattatgcat ccactctggc atttggggtc  180
ccatctcggt tcagtggcag tggatctggg acagatttca ctctcaccat cagcagcctg  240
cagcctgaag atgttgcaac ttattactgt caaggcggtt atagtggttg gatttatgtt  300
ttcggcggag ggaccaaggt ggagatcaaa cgtacggtgg ctgcaccatc tgtcttcatc  360
ttcccgccat ctgatgagca gttgaaatct ggaactgcct ctgttgtgtg cctgctgaat  420
aacttctatc ccagagaggc caaagtacag tggaaggtgg ataacgccct ccaatcgggt  480
aactcccagg agagtgtcac agagcaggac agcaaggaca gcacctacag cctcagcagc  540
accctgacgc tgagcaaagc agactacgag aaacacaaag tctacgcctg cgaagtcacc  600
catcagggcc tgagctcgcc cgtcacaaag agcttcaaca ggggagagtg t          651

SEQ ID NO: 154          moltype = DNA  length = 330
FEATURE                 Location/Qualifiers
source                  1..330
                        mol_type = other DNA
                        organism = synthetic construct
SEQUENCE: 154
gacatccaga tgacccagtc tccatcctcc ctgtctgcat ctgtaggaga cagagtcacc  60
atcacttgcc agtccagtca gactgtttat aataacaact tgttatcctg gtatcagcag  120
aaaccaggga aagttcctaa gctcctgatc tattatgcat ccactctggc atttggggtc  180
ccatctcggt tcagtggcag tggatctggg acagatttca ctctcaccat cagcagcctg  240
cagcctgaag atgttgcaac ttattactgt caaggcggtt atagtggttg gatttatgtt  300
ttcggcggag ggaccaaggt ggagatcaaa                                  330
```

```
SEQ ID NO: 155          moltype = AA  length = 217
FEATURE                 Location/Qualifiers
source                  1..217
                        mol_type = protein
                        organism = synthetic construct
SEQUENCE: 155
DIQMTQSPSS LSASVGDRVT ITCQSSQTVY NNNLLSWYQQ KPGKVPKLLI YYASTLAFGV  60
PSRFSGSGSG TDFTLTISSL QPEDVATYYC QGGYSGWIYV FGGGTKVEIK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                          217

SEQ ID NO: 156          moltype = AA  length = 110
FEATURE                 Location/Qualifiers
source                  1..110
                        mol_type = protein
                        organism = synthetic construct
SEQUENCE: 156
DIQMTQSPSS LSASVGDRVT ITCQSSQTVY NNNLLSWYQQ KPGKVPKLLI YYASTLAFGV  60
PSRFSGSGSG TDFTLTISSL QPEDVATYYC QGGYSGWIYV FGGGTKVEIK            110

SEQ ID NO: 157          moltype = DNA  length = 1329
FEATURE                 Location/Qualifiers
source                  1..1329
                        mol_type = other DNA
                        organism = synthetic construct
SEQUENCE: 157
cagtcgctgg tggagtctgg gggaggcttg gtccagcctg gggggtccct gagactctcc  60
tgtgcagcct ctggattctc cctcagtaac tactacatga actgggtccg ccaggctcca  120
gggaaggggc tggagtacat cggaatcatt agtagtagtg gtagcgcata ctacgcgagc  180
tccgctaaag gcagattcac catctccaga gacaattcca agaacacgct gtatcttcaa  240
atgaacagcc tgagagccga ggacacggct gtgtattact gtgcgagagg ggactacggc  300
atggacctct ggggccaggg aaccctggtc accgtctcga gcgctagcac caagggccca  360
tcggtcttcc ccctggcacc ctcctccaag agcacctctg ggggcacagc ggccctgggc  420
tgcctggtca aggactactt ccccgaaccg gtgacggtgt cgtggaactc aggcgccctg  480
accagcggcg tgcacacctt cccggctgtc ctacagtcct caggactcta ctccctcagc  540
agcgtggtga ccgtgccctc cagcagcttg ggcacccaga cctacatctg caacgtgaat  600
cacaagccca gcaacaccaa ggtggacaag agagttgagc ccaaatcttg tgacaaaact  660
cacacatgcc caccgtgccc agcacctgaa gccgcggggg caccgtcagt cttcctcttc  720
cccccaaaac ccaaggacac cctcatgatc tcccggaccc ctgaggtcac atgcgtggtg  780
gtggacgtga gccacgaaga ccctgaggtc aagttcaact ggtacgtgga cggcgtggag  840
gtgcataatg ccaagacaaa gccgcgggag gagcagtaca acagcacgta ccgtgtggtc  900
agcgtcctca ccgtcctgca ccaggactgg ctgaatggca aggagtacaa gtgcgcggtc  960
tccaacaaag ccctcccagc ccccatcgag aaaaccatct ccaaagccaa agggcagccc  1020
cgagaaccac aggtgtacac cctgccccca tcccgggatg agctgaccaa gaaccaggtc  1080
agcctgacct gcctggtcaa aggcttctat cccagcgaca tcgccgtgga gtgggagagc  1140
aatgggcagc cggagaacaa ctacaagacc acgcctcccg tgctggactc cgacggctcc  1200
ttcttcctct atagcaagct caccgtggac aagagcaggt ggcagcaggg gaacgtcttc  1260
tcatgctccg tgatgcatga ggctctgcac aaccactaca cgcagaagag cctctccctg  1320
tctccgggt                                                         1329

SEQ ID NO: 158          moltype = DNA  length = 342
FEATURE                 Location/Qualifiers
source                  1..342
                        mol_type = other DNA
                        organism = synthetic construct
SEQUENCE: 158
cagtcgctgg tggagtctgg gggaggcttg gtccagcctg gggggtccct gagactctcc  60
tgtgcagcct ctggattctc cctcagtaac tactacatga actgggtccg ccaggctcca  120
gggaaggggc tggagtacat cggaatcatt agtagtagtg gtagcgcata ctacgcgagc  180
tccgctaaag gcagattcac catctccaga gacaattcca agaacacgct gtatcttcaa  240
atgaacagcc tgagagccga ggacacggct gtgtattact gtgcgagagg ggactacggc  300
atggacctct ggggccaggg aaccctggtc accgtctcga gc                    342

SEQ ID NO: 159          moltype = AA  length = 443
FEATURE                 Location/Qualifiers
source                  1..443
                        mol_type = protein
                        organism = synthetic construct
SEQUENCE: 159
QSLVESGGGL VQPGGSLRLS CAASGFSLSN YYMNWVRQAP GKGLEYIGII SSSGSAYYAS  60
SAKGRFTISR DNSKNTLYLQ MNSLRAEDTA VYYCARGDYG MDLWGQGTLV TVSSASTKGP  120
SVFPLAPSSK STSGGTAALG CLVKDYFPEP VTVSWNSGAL TSGVHTFPAV LQSSGLYSLS  180
SVVTVPSSSL GTQTYICNVN HKPSNTKVDK RVEPKSCDKT HTCPPCPAPE AAGAPSVFLF  240
PPKPKDTLMI SRTPEVTCVV VDVSHEDPEV KFNWYVDGVE VHNAKTKPRE EQYNSTYRVV  300
SVLTVLHQDW LNGKEYKCAV SNKALPAPIE KTISKAKGQP REPQVYTLPP SRDELTKNQV  360
SLTCLVKGFY PSDIAVEWES NGQPENNYKT TPPVLDSDGS FFLYSKLTVD KSRWQQGNVF  420
SCSVMHEALH NHYTQKSLSL SPG                                         443
```

```
SEQ ID NO: 160         moltype = AA  length = 114
FEATURE                Location/Qualifiers
source                 1..114
                       mol_type = protein
                       organism = synthetic construct
SEQUENCE: 160
QSLVESGGGL VQPGGSLRLS CAASGFSLSN YYMNWVRQAP GKGLEYIGII SSSGSAYYAS  60
SAKGRFTISR DNSKNTLYLQ MNSLRAEDTA VYYCARGDYG MDLWGQGTLV TVSS        114

SEQ ID NO: 161         moltype = DNA  length = 657
FEATURE                Location/Qualifiers
source                 1..657
                       mol_type = other DNA
                       organism = synthetic construct
SEQUENCE: 161
gacgttgtga tgacccagtc tccatcttcc gtgtctgcat ctgtaggaga cagagtcacc  60
atcacctgtc aggccagtca gagcattggt agtgatttag cctggtatca gcagaaacca  120
gggaaagccc ctaagctcct gatctatagg gcatccactc tggcatctgg ggtcccatca  180
aggttcagcg gcagtggatc tgggacagat ttcactctca ccatcagcag cctgcagcct  240
gaagattttg caacttacta ttgtcaatcc atttattatg gtagtgatga tgtcatatac  300
catactttcg gcggagggac caaggtggag atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 162         moltype = DNA  length = 336
FEATURE                Location/Qualifiers
source                 1..336
                       mol_type = other DNA
                       organism = synthetic construct
SEQUENCE: 162
gacgttgtga tgacccagtc tccatcttcc gtgtctgcat ctgtaggaga cagagtcacc  60
atcacctgtc aggccagtca gagcattggt agtgatttag cctggtatca gcagaaacca  120
gggaaagccc ctaagctcct gatctatagg gcatccactc tggcatctgg ggtcccatca  180
aggttcagcg gcagtggatc tgggacagat ttcactctca ccatcagcag cctgcagcct  240
gaagattttg caacttacta ttgtcaatcc atttattatg gtagtgatga tgtcatatac  300
catactttcg gcggagggac caaggtggag atcaaa                            336

SEQ ID NO: 163         moltype = AA  length = 219
FEATURE                Location/Qualifiers
source                 1..219
                       mol_type = protein
                       organism = synthetic construct
SEQUENCE: 163
DVVMTQSPSS VSASVGDRVT ITCQASQSIG SDLAWYQQKP GKAPKLLIYR ASTLASGVPS  60
RFSGSGSGTD FTLTISSLQP EDFATYYCQS IYYGSDDVIY HTFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                          219

SEQ ID NO: 164         moltype = AA  length = 112
FEATURE                Location/Qualifiers
source                 1..112
                       mol_type = protein
                       organism = synthetic construct
SEQUENCE: 164
DVVMTQSPSS VSASVGDRVT ITCQASQSIG SDLAWYQQKP GKAPKLLIYR ASTLASGVPS  60
RFSGSGSGTD FTLTISSLQP EDFATYYCQS IYYGSDDVIY HTFGGGTKVE IK          112

SEQ ID NO: 165         moltype = DNA  length = 1341
FEATURE                Location/Qualifiers
source                 1..1341
                       mol_type = other DNA
                       organism = synthetic construct
SEQUENCE: 165
gaggtgcagc tggtggagtc tgggggaggc ttggtccagc ctggggggtc cctgagactc  60
tcctgtgcag cctctggatt cactatcaat agctaccaca tgatctgggt ccgccaggct  120
ccagggaagg ggctggagta catcggattc attaatgatg gtggtttcac atactacgcg  180
agctccgcta aaggcagatt caccatctcc agagacaatt ccaagaacac gctgtatctt  240
caaatgaaca gcctgagagc cgaggacacg gctgtgtatt actgtgcgag aggggttgat  300
ggtactagtt atcctgactt atggggccag ggaaccctgg tcaccgtctc gagcgctagc  360
accaagggcc catcggtctt ccccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga atcacaagcc cagcaacacc aaggtggaca agagagttga gcccaaatct  660
tgtgacaaaa ctcacacatg cccaccgtgc ccagcacctg aagccgcggg ggcaccgtca  720
gtcttcctct tccccccaaa acccaaggac accctcatga tctcccggac ccctgaggtc  780
```

```
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcgcgg tctccaacaa agccctccca gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctatagcaag ctcaccgtgg acaagagcag gtggcagcag  1260
gggaacgtct tctcatgctc cgtgatgcat gaggctctgc acaaccacta cacgcagaag  1320
agcctctccc tgtctccggg t                                            1341

SEQ ID NO: 166         moltype = DNA  length = 354
FEATURE                Location/Qualifiers
source                 1..354
                       mol_type = other DNA
                       organism = synthetic construct
SEQUENCE: 166
gaggtgcagc tggtggagtc tgggggaggc ttggtccagc ctggggggtc cctgagactc  60
tcctgtgcag cctctggatt cactatcaat agctaccaca tgatctgggt ccgccaggct  120
ccagggaagg ggctggagta catcggattc attaatgatg gtggtttcac atactacgcg  180
agctccgcta aaggcagatt caccatctcc agagacaatt ccaagaacac gctgtatctt  240
caaatgaaca gcctgagagc cgaggacacg gctgtgtatt actgtgcgag aggggttgat  300
ggtactagtt atcctgactt atggggccag ggaaccctgg tcaccgtctc gagc        354

SEQ ID NO: 167         moltype = AA  length = 447
FEATURE                Location/Qualifiers
source                 1..447
                       mol_type = protein
                       organism = synthetic construct
SEQUENCE: 167
EVQLVESGGG LVQPGGSLRL SCAASGFTIN SYHMIWVRQA PGKGLEYIGF INDGGFTYYA  60
SSAKGRFTIS RDNSKNTLYL QMNSLRAEDT AVYYCARGVD GTSYPDLWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGAPS  240
VFLFPPKPKD TLMISRTPEV TCVVVDVSHE DPEVKFNWYV DGVEVHNAKT KPREEQYNST  300
YRVVSVLTVL HQDWLNGKEY KCAVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 168         moltype = AA  length = 118
FEATURE                Location/Qualifiers
source                 1..118
                       mol_type = protein
                       organism = synthetic construct
SEQUENCE: 168
EVQLVESGGG LVQPGGSLRL SCAASGFTIN SYHMIWVRQA PGKGLEYIGF INDGGFTYYA  60
SSAKGRFTIS RDNSKNTLYL QMNSLRAEDT AVYYCARGVD GTSYPDLWGQ GTLVTVSS    118

SEQ ID NO: 169         moltype = DNA  length = 654
FEATURE                Location/Qualifiers
source                 1..654
                       mol_type = other DNA
                       organism = synthetic construct
SEQUENCE: 169
gacatccaga tgacccagtc tccttccacc ctgtctgcat ctgtaggaga cagagtcacc  60
atcacttgcc aggccagtca gagcattggt agtaacttga actggtatca gcagaaacca  120
gggaaagccc ctaagctcct gatctattat gtatccactc tggcatctgg ggtcccatca  180
aggttcagcg gcagtggatc tgggacagaa ttcactctca ccatcagcag cctgcagcct  240
gatgattttg caacttatta ctgcctaggt gtttggaatt attggggtga tgacggtact  300
gctttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 170         moltype = DNA  length = 333
FEATURE                Location/Qualifiers
source                 1..333
                       mol_type = other DNA
                       organism = synthetic construct
SEQUENCE: 170
gacatccaga tgacccagtc tccttccacc ctgtctgcat ctgtaggaga cagagtcacc  60
atcacttgcc aggccagtca gagcattggt agtaacttga actggtatca gcagaaacca  120
gggaaagccc ctaagctcct gatctattat gtatccactc tggcatctgg ggtcccatca  180
aggttcagcg gcagtggatc tgggacagaa ttcactctca ccatcagcag cctgcagcct  240
gatgattttg caacttatta ctgcctaggt gtttggaatt attggggtga tgacggtact  300
gctttcggcg gagggaccaa ggtggagatc aaa                               333
```

```
SEQ ID NO: 171          moltype = AA  length = 218
FEATURE                 Location/Qualifiers
source                  1..218
                        mol_type = protein
                        organism = synthetic construct
SEQUENCE: 171
DIQMTQSPST LSASVGDRVT ITCQASQSIG SNLNWYQQKP GKAPKLLIYY VSTLASGVPS  60
RFSGSGSGTE FTLTISSLQP DDFATYYCLG VWNYWGDDGT AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 172          moltype = AA  length = 111
FEATURE                 Location/Qualifiers
source                  1..111
                        mol_type = protein
                        organism = synthetic construct
SEQUENCE: 172
DIQMTQSPST LSASVGDRVT ITCQASQSIG SNLNWYQQKP GKAPKLLIYY VSTLASGVPS  60
RFSGSGSGTE FTLTISSLQP DDFATYYCLG VWNYWGDDGT AFGGGTKVEI K           111

SEQ ID NO: 173          moltype = DNA  length = 1332
FEATURE                 Location/Qualifiers
source                  1..1332
                        mol_type = other DNA
                        organism = synthetic construct
SEQUENCE: 173
gaggtgcagc tggtggagtc tgggggaggc ttggtccagc ctggggggtc cctgagactc  60
tcctgtgcag cctctggatt ctccctcagt acctattata tgagctgggt ccgccaggct  120
ccagggaagg ggctggagtg gatcggaagt atttatgata gtggtgccgc atactacgcg  180
acctccgcga agggcagatt caccatctcc agagacaatt ccaagaacac gctgtatctt  240
caaatgaaca gcctgagagc cgaggacacg gctgtgtatt actgtgcgag agatcctatt  300
aataatgcca tctggggcca gggaaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg gggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 174          moltype = DNA  length = 345
FEATURE                 Location/Qualifiers
source                  1..345
                        mol_type = other DNA
                        organism = synthetic construct
SEQUENCE: 174
gaggtgcagc tggtggagtc tgggggaggc ttggtccagc ctggggggtc cctgagactc  60
tcctgtgcag cctctggatt ctccctcagt acctattata tgagctgggt ccgccaggct  120
ccagggaagg ggctggagtg gatcggaagt atttatgata gtggtgccgc atactacgcg  180
acctccgcga agggcagatt caccatctcc agagacaatt ccaagaacac gctgtatctt  240
caaatgaaca gcctgagagc cgaggacacg gctgtgtatt actgtgcgag agatcctatt  300
aataatgcca tctggggcca gggaaccctg gtcaccgtct cgagc                  345

SEQ ID NO: 175          moltype = AA  length = 444
FEATURE                 Location/Qualifiers
source                  1..444
                        mol_type = protein
                        organism = synthetic construct
SEQUENCE: 175
EVQLVESGGG LVQPGGSLRL SCAASGFSLS TYYMSWVRQA PGKGLEWIGS IYDSGAAYYA  60
TSAKGRFTIS RDNSKNTLYL QMNSLRAEDT AVYYCARDPI NNAIWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 176          moltype = AA  length = 115
```

```
FEATURE                 Location/Qualifiers
source                  1..115
                        mol_type = protein
                        organism = synthetic construct
SEQUENCE: 176
EVQLVESGGG LVQPGGSLRL SCAASGFSLS TYYMSWVRQA PGKGLEWIGS IYDSGAAYYA  60
TSAKGRFTIS RDNSKNTLYL QMNSLRAEDT AVYYCARDPI NNAIWGQGTL VTVSS       115

SEQ ID NO: 177          moltype = DNA  length = 654
FEATURE                 Location/Qualifiers
source                  1..654
                        mol_type = other DNA
                        organism = synthetic construct
SEQUENCE: 177
gacatccaga tgacccagtc tccttccacc ctgtctgcat ctgtaggaga cagagtcacc  60
atcacttgcc aggccagtca gagtattgct actaacttga actggtatca gcagaaacca  120
gggaaagccc ctaagctcct gatctattat acatccagtc tggcatctgg ggtcccatca  180
aggttcagcg gcagtggatc tgggacagaa ttcactctca ccatcagcag cctgcagcct  240
gatgattttg caacttatta ctgcctaggt gtttggaatt attggggtga tgatggtact  300
gctttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 178          moltype = DNA  length = 333
FEATURE                 Location/Qualifiers
source                  1..333
                        mol_type = other DNA
                        organism = synthetic construct
SEQUENCE: 178
gacatccaga tgacccagtc tccttccacc ctgtctgcat ctgtaggaga cagagtcacc  60
atcacttgcc aggccagtca gagtattgct actaacttga actggtatca gcagaaacca  120
gggaaagccc ctaagctcct gatctattat acatccagtc tggcatctgg ggtcccatca  180
aggttcagcg gcagtggatc tgggacagaa ttcactctca ccatcagcag cctgcagcct  240
gatgattttg caacttatta ctgcctaggt gtttggaatt attggggtga tgatggtact  300
gctttcggcg gagggaccaa ggtggagatc aaa                               333

SEQ ID NO: 179          moltype = AA  length = 218
FEATURE                 Location/Qualifiers
source                  1..218
                        mol_type = protein
                        organism = synthetic construct
SEQUENCE: 179
DIQMTQSPST LSASVGDRVT ITCQASQSIA TNLNWYQQKP GKAPKLLIYY TSSLASGVPS  60
RFSGSGSGTE FTLTISSLQP DDFATYYCLG VWNYWGDDGT AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 180          moltype = AA  length = 111
FEATURE                 Location/Qualifiers
source                  1..111
                        mol_type = protein
                        organism = synthetic construct
SEQUENCE: 180
DIQMTQSPST LSASVGDRVT ITCQASQSIA TNLNWYQQKP GKAPKLLIYY TSSLASGVPS  60
RFSGSGSGTE FTLTISSLQP DDFATYYCLG VWNYWGDDGT AFGGGTKVEI K           111

SEQ ID NO: 181          moltype = DNA  length = 1332
FEATURE                 Location/Qualifiers
source                  1..1332
                        mol_type = other DNA
                        organism = synthetic construct
SEQUENCE: 181
gaggtgcagc tggtggagtc tgggggaggc ttggtccagc ctgggggtc cctgagactc  60
tcctgtgcag cctctggatt ctccctcagt agctactaca tgagctgggt ccgccaggct  120
ccagggaagg ggctggagtg gatcggaagt atttatgcta gtggtagcgc atactacgcg  180
agttccgcga agggcagatt caccatctcc agagacaatt ccaagaacac gctgtatctt  240
caaatgaaca gcctgagagc cgaggacacg gctgtgtatt actgtgcgag agatcctatt  300
aacaatgaca tctggggcca gggaaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg ggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
```

```
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                     1332

SEQ ID NO: 182          moltype = DNA  length = 345
FEATURE                 Location/Qualifiers
source                  1..345
                        mol_type = other DNA
                        organism = synthetic construct
SEQUENCE: 182
gaggtgcagc tggtggagtc tgggggaggc ttggtccagc ctggggggtc cctgagactc  60
tcctgtgcag cctctggatt ctccctcagt agctactaca tgagctgggt ccgccaggct  120
ccagggaagg ggctggagtg gatcggaagt atttatgcta gtggtagcgc atactacgcg  180
agttccgcga agggcagatt caccatctcc agagacaatt ccaagaacac gctgtatctt  240
caaatgaaca gcctgagagc cgaggacacg gctgtgtatt actgtgcgag agatcctatt  300
aacaatgaca tctggggcca gggaaccctg gtcaccgtct cgagc                 345

SEQ ID NO: 183          moltype = AA  length = 444
FEATURE                 Location/Qualifiers
source                  1..444
                        mol_type = protein
                        organism = synthetic construct
SEQUENCE: 183
EVQLVESGGG LVQPGGSLRL SCAASGFSLS SYYMSWVRQA PGKGLEWIGS IYASGSAYYA  60
SSAKGRFTIS RDNSKNTLYL QMNSLRAEDT AVYYCARDPI NNDIWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                        444

SEQ ID NO: 184          moltype = AA  length = 115
FEATURE                 Location/Qualifiers
source                  1..115
                        mol_type = protein
                        organism = synthetic construct
SEQUENCE: 184
EVQLVESGGG LVQPGGSLRL SCAASGFSLS SYYMSWVRQA PGKGLEWIGS IYASGSAYYA  60
SSAKGRFTIS RDNSKNTLYL QMNSLRAEDT AVYYCARDPI NNDIWGQGTL VTVSS       115

SEQ ID NO: 185          moltype = DNA  length = 654
FEATURE                 Location/Qualifiers
source                  1..654
                        mol_type = other DNA
                        organism = synthetic construct
SEQUENCE: 185
gacatccaga tgacccagtc tccatcttcc gtgtctgcat ctgtaggaga cagagtcacc  60
atcacttgtc agtccagtcc gagtgtttat aagaacaacc aattagcctg gtatcagcag  120
aaaccaggga aagcccctaa gctcctgatc tatctggcat ctactctggc atctggggtc  180
ccatcaaggt tcagcggcag tggatctggg acagatttca ctctcaccat cagcagcctg  240
cagcctgaag attttgcaac ttactattgt gcaggcggtt atagtagtag tagtgatact  300
gctttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt       654

SEQ ID NO: 186          moltype = DNA  length = 333
FEATURE                 Location/Qualifiers
source                  1..333
                        mol_type = other DNA
                        organism = synthetic construct
SEQUENCE: 186
gacatccaga tgacccagtc tccatcttcc gtgtctgcat ctgtaggaga cagagtcacc  60
atcacttgtc agtccagtcc gagtgtttat aagaacaacc aattagcctg gtatcagcag  120
aaaccaggga aagcccctaa gctcctgatc tatctggcat ctactctggc atctggggtc  180
ccatcaaggt tcagcggcag tggatctggg acagatttca ctctcaccat cagcagcctg  240
cagcctgaag attttgcaac ttactattgt gcaggcggtt atagtagtag tagtgatact  300
gctttcggcg gagggaccaa ggtggagatc aaa                              333

SEQ ID NO: 187          moltype = AA  length = 218
```

```
FEATURE               Location/Qualifiers
source                1..218
                      mol_type = protein
                      organism = synthetic construct
SEQUENCE: 187
DIQMTQSPSS VSASVGDRVT ITCQSSPSVY KNNQLAWYQQ KPGKAPKLLI YLASTLASGV  60
PSRFSGSGSG TDFTLTISSL QPEDFATYYC AGGYSSSSDT AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 188        moltype = AA  length = 111
FEATURE               Location/Qualifiers
source                1..111
                      mol_type = protein
                      organism = synthetic construct
SEQUENCE: 188
DIQMTQSPSS VSASVGDRVT ITCQSSPSVY KNNQLAWYQQ KPGKAPKLLI YLASTLASGV  60
PSRFSGSGSG TDFTLTISSL QPEDFATYYC AGGYSSSSDT AFGGGTKVEI K           111

SEQ ID NO: 189        moltype = DNA  length = 1344
FEATURE               Location/Qualifiers
source                1..1344
                      mol_type = other DNA
                      organism = synthetic construct
SEQUENCE: 189
gaggtgcagc tggtggagtc tgggggaggc ttggtccagc ctgggggggtc cctgagactc  60
tcctgtacag cctctggaat cgacctcagt gcctaccaca tgagctgggt ccgccaggct  120
ccagggaagg ggctggagta catcgggatg attggtagta gtggtaccat acactacgcg  180
aactccgcga aaggcagatt caccatctcc aaagacaata ccaagaacac ggtggatctt  240
caaatgaaca gcctgagagc cgaggacacg gctgtgtatt actgtgcgag agacagttat  300
aatagtgatt atgcctttaa cttatggggc cagggaaccc tggtcaccgt ctcgagcgct  360
agcaccaagg gcccatcggt cttccccctg gcaccctcct ccaagagcac ctctgggggc  420
acagcggccc tgggctgcct ggtcaaggac tacttccccg aaccggtgac ggtgtcgtgg  480
aactcaggcg ccctgaccag cggcgtgcac accttcccgg ctgtcctaca gtcctcagga  540
ctctactccc tcagcagcgt ggtgaccgtg ccctccagca gcttgggcac ccagacctac  600
atctgcaacg tgaatcacaa gcccagcaac accaaggtgg acaagagagt tgagcccaaa  660
tcttgtgaca aaactcacac atgcccaccg tgcccagcac ctgaagccgc gggggcaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgcg cggtctccaa caaagccctc ccagcccccca tcgagaaaac catctccaaa  1020
gccaaagggc agccccgaga accacaggtg tacaccctgc ccccatcccg ggatgagctg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctatagc aagctcaccg tggacaagag caggtggcag  1260
caggggaacg tcttctcatg ctccgtgatg catgaggctc tgcacaacca ctacacgcag  1320
aagagcctct ccctgtctcc gggt                                        1344

SEQ ID NO: 190        moltype = DNA  length = 357
FEATURE               Location/Qualifiers
source                1..357
                      mol_type = other DNA
                      organism = synthetic construct
SEQUENCE: 190
gaggtgcagc tggtggagtc tgggggaggc ttggtccagc ctgggggggtc cctgagactc  60
tcctgtacag cctctggaat cgacctcagt gcctaccaca tgagctgggt ccgccaggct  120
ccagggaagg ggctggagta catcgggatg attggtagta gtggtaccat acactacgcg  180
aactccgcga aaggcagatt caccatctcc aaagacaata ccaagaacac ggtggatctt  240
caaatgaaca gcctgagagc cgaggacacg gctgtgtatt actgtgcgag agacagttat  300
aatagtgatt atgcctttaa cttatggggc cagggaaccc tggtcaccgt ctcgagc     357

SEQ ID NO: 191        moltype = AA  length = 448
FEATURE               Location/Qualifiers
source                1..448
                      mol_type = protein
                      organism = synthetic construct
SEQUENCE: 191
EVQLVESGGG LVQPGGSLRL SCTASGIDLS AYHMSWVRQA PGKGLEYIGM IGSSGTIHYA  60
NSAKGRFTIS KDNTKNTVDL QMNSLRAEDT AVYYCARDSY NSDYAFNLWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKRVEPK SCDKTHTCPP CPAPEAAGAP  240
SVFLFPPKPK DTLMISRTPE VTCVVVDVSH EDPEVKFNWY VDGVEVHNAK TKPREEQYNS  300
TYRVVSVLTV LHQDWLNGKE YKCAVSNKAL PAPIEKTISK AKGQPREPQV YTLPPSRDEL  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPG                                    448

SEQ ID NO: 192        moltype = AA  length = 119
FEATURE               Location/Qualifiers
```

```
source                  1..119
                        mol_type = protein
                        organism = synthetic construct
SEQUENCE: 192
EVQLVESGGG LVQPGGSLRL SCTASGIDLS AYHMSWVRQA PGKGLEYIGM IGSSGTIHYA  60
NSAKGRFTIS KDNTKNTVDL QMNSLRAEDT AVYYCARDSY NSDYAFNLWG QGTLVTVSS   119

SEQ ID NO: 193          moltype = DNA  length = 654
FEATURE                 Location/Qualifiers
source                  1..654
                        mol_type = other DNA
                        organism = synthetic construct
SEQUENCE: 193
gacatccaga tgacccagtc tccttccacc ctgtctgcat ctgtaggaga cagagtcacc  60
atcacttgcc agtccagtca gagtgtttat agtaactggt tatcctggta tcagcagaaa  120
ccagggaaag cccctaagag actgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttata atactgttac tgatactttt  300
gctttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 194          moltype = DNA  length = 333
FEATURE                 Location/Qualifiers
source                  1..333
                        mol_type = other DNA
                        organism = synthetic construct
SEQUENCE: 194
gacatccaga tgacccagtc tccttccacc ctgtctgcat ctgtaggaga cagagtcacc  60
atcacttgcc agtccagtca gagtgtttat agtaactggt tatcctggta tcagcagaaa  120
ccagggaaag cccctaagag actgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttata atactgttac tgatactttt  300
gctttcggcg gagggaccaa ggtggagatc aaa                               333

SEQ ID NO: 195          moltype = AA  length = 218
FEATURE                 Location/Qualifiers
source                  1..218
                        mol_type = protein
                        organism = synthetic construct
SEQUENCE: 195
DIQMTQSPST LSASVGDRVT ITCQSSQSVY SNWLSWYQQK PGKAPKRLIY SASTLASGVP  60
SRFSGSGSGT EFTLTISSLQ PDDFATYYCA GGYNTVTDTF AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 196          moltype = AA  length = 111
FEATURE                 Location/Qualifiers
source                  1..111
                        mol_type = protein
                        organism = synthetic construct
SEQUENCE: 196
DIQMTQSPST LSASVGDRVT ITCQSSQSVY SNWLSWYQQK PGKAPKRLIY SASTLASGVP  60
SRFSGSGSGT EFTLTISSLQ PDDFATYYCA GGYNTVTDTF AFGGGTKVEI K           111

SEQ ID NO: 197          moltype = DNA  length = 1332
FEATURE                 Location/Qualifiers
source                  1..1332
                        mol_type = other DNA
                        organism = synthetic construct
SEQUENCE: 197
gaggtgcagc tgttggagtc tggggggaggc ttggtacagc ctgggggggtc cctgagactc  60
tcctgtacag cctctggatt ctccttcagt agcaggcact acatgtgttg ggtccgccag  120
gctccaggga aggggctgga gtggatcgca tgcatttata ctggtagtag tggtactcct  180
cactacgcga gctccgcgaa aggccggttc accatctccc aagacaattc caagaacacg  240
gtgactctgc aaatgaacag cctgagagcc gaggacacgg ccgtatatta ctgtgcgaga  300
gaaggtaacc tgtggggcca gggaaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg gggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
```

```
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 198         moltype = DNA  length = 345
FEATURE                Location/Qualifiers
source                 1..345
                       mol_type = other DNA
                       organism = synthetic construct
SEQUENCE: 198
gaggtgcagc tgttggagtc tggggggaggc ttggtacagc ctgggggggtc cctgagactc  60
tcctgtacag cctctggatt ctccttcagt agcaggcact acatgtgttg ggtccgccag  120
gctccaggga aggggctgga gtggatcgca tgcatttata ctggtagtag tggtactcct  180
cactacgcga gctccgcgaa aggccggttc accatctccc aagacaattc caagaacacg  240
gtgactctgc aaatgaacag cctgagagcc gaggacacgg ccgtatatta ctgtgcgaga  300
gaaggtaacc tgtggggcca gggaaccctg gtcaccgtct cgagc                  345

SEQ ID NO: 199         moltype = AA  length = 444
FEATURE                Location/Qualifiers
source                 1..444
                       mol_type = protein
                       organism = synthetic construct
SEQUENCE: 199
EVQLLESGGG LVQPGGSLRL SCTASGFSFS SRHYMCWVRQ APGKGLEWIA CIYTGSSGTP  60
HYASSAKGRF TISQDNSKNT VTLQMNSLRA EDTAVYYCAR EGNLWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 200         moltype = AA  length = 115
FEATURE                Location/Qualifiers
source                 1..115
                       mol_type = protein
                       organism = synthetic construct
SEQUENCE: 200
EVQLLESGGG LVQPGGSLRL SCTASGFSFS SRHYMCWVRQ APGKGLEWIA CIYTGSSGTP  60
HYASSAKGRF TISQDNSKNT VTLQMNSLRA EDTAVYYCAR EGNLWGQGTL VTVSS       115

SEQ ID NO: 201         moltype = DNA  length = 657
FEATURE                Location/Qualifiers
source                 1..657
                       mol_type = other DNA
                       organism = synthetic construct
SEQUENCE: 201
gcccttgtga tgacccagtc tccttccacc ctgtctgcat ctgtaggaga cagagtcacc  60
atcaattgcc aggccagtga ggacattgat acctatttag cctggtatca gcagaaacca  120
gggaaagccc ctaagctcct gatcttttat gcatccgatc tggcatctgg ggtcccatca  180
aggttcagcg gcagtggatc tgggacagaa ttcactctca ccatcagcag cctgcagcct  240
gatgattttg caacttatta ctgccaaggc ggttactata ctagtagtgc tgatacgagg  300
ggtgctttcg gcggagggac caaggtggag atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 202         moltype = DNA  length = 336
FEATURE                Location/Qualifiers
source                 1..336
                       mol_type = other DNA
                       organism = synthetic construct
SEQUENCE: 202
gcccttgtga tgacccagtc tccttccacc ctgtctgcat ctgtaggaga cagagtcacc  60
atcaattgcc aggccagtga ggacattgat acctatttag cctggtatca gcagaaacca  120
gggaaagccc ctaagctcct gatcttttat gcatccgatc tggcatctgg ggtcccatca  180
aggttcagcg gcagtggatc tgggacagaa ttcactctca ccatcagcag cctgcagcct  240
gatgattttg caacttatta ctgccaaggc ggttactata ctagtagtgc tgatacgagg  300
ggtgctttcg gcggagggac caaggtggag atcaaa                            336

SEQ ID NO: 203         moltype = AA  length = 219
FEATURE                Location/Qualifiers
```

```
source                  1..219
                        mol_type = protein
                        organism = synthetic construct
SEQUENCE: 203
ALVMTQSPST LSASVGDRVT INCQASEDID TYLAWYQQKP GKAPKLLIFY ASDLASGVPS  60
RFSGSGSGTE FTLTISSLQP DDFATYYCQG GYYTSSADTR GAFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 204          moltype = AA  length = 112
FEATURE                 Location/Qualifiers
source                  1..112
                        mol_type = protein
                        organism = synthetic construct
SEQUENCE: 204
ALVMTQSPST LSASVGDRVT INCQASEDID TYLAWYQQKP GKAPKLLIFY ASDLASGVPS  60
RFSGSGSGTE FTLTISSLQP DDFATYYCQG GYYTSSADTR GAFGGGTKVE IK          112

SEQ ID NO: 205          moltype = DNA  length = 1347
FEATURE                 Location/Qualifiers
source                  1..1347
                        mol_type = other DNA
                        organism = synthetic construct
SEQUENCE: 205
cagtcgctgg tggagtctgg gggaggcttg gtacagcctg gggggtccct gagactctcc  60
tgtgcagcct ctggattctc cttcagtagc aactactgga tatgctgggt ccgccaggct  120
ccagggaagg ggctggagtg gatcgcatgc atttatgttg gtagtagtgg tgacacttac  180
tacgcgagct ccgcgaaagg ccggttcacc atctccagag acaattccaa gaacacgctg  240
tatctgcaaa tgaacagcct gagagccgag gacacggccg tatattactg tgcgagagat  300
agtagtagtt attatatgtt taacttgtgg ggccagggaa ccctggtcac cgtctcgagc  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagag agttgagccc  660
aaatcttgtg acaaaactca cacatgccca ccgtgcccag cacctgaagc cgcgggggca  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcgcggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggt                                      1347

SEQ ID NO: 206          moltype = DNA  length = 360
FEATURE                 Location/Qualifiers
source                  1..360
                        mol_type = other DNA
                        organism = synthetic construct
SEQUENCE: 206
cagtcgctgg tggagtctgg gggaggcttg gtacagcctg gggggtccct gagactctcc  60
tgtgcagcct ctggattctc cttcagtagc aactactgga tatgctgggt ccgccaggct  120
ccagggaagg ggctggagtg gatcgcatgc atttatgttg gtagtagtgg tgacacttac  180
tacgcgagct ccgcgaaagg ccggttcacc atctccagag acaattccaa gaacacgctg  240
tatctgcaaa tgaacagcct gagagccgag gacacggccg tatattactg tgcgagagat  300
agtagtagtt attatatgtt taacttgtgg ggccagggaa ccctggtcac cgtctcgagc  360

SEQ ID NO: 207          moltype = AA  length = 449
FEATURE                 Location/Qualifiers
source                  1..449
                        mol_type = protein
                        organism = synthetic construct
SEQUENCE: 207
QSLVESGGGL VQPGGSLRLS CAASGFSFSS NYWICWVRQA PGKGLEWIAC IYVGSSGDTY  60
YASSAKGRFT ISRDNSKNTL YLQMNSLRAE DTAVYYCARD SSSYYMFNLW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCAVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 208          moltype = AA  length = 120
FEATURE                 Location/Qualifiers
source                  1..120
```

```
                        mol_type = protein
                        organism = synthetic construct
SEQUENCE: 208
QSLVESGGGL VQPGGSLRLS CAASGFSFSS NYWICWVRQA PGKGLEWIAC IYVGSSGDTY  60
YASSAKGRFT ISRDNSKNTL YLQMNSLRAE DTAVYYCARD SSSYYMFNLW GQGTLVTVSS  120

SEQ ID NO: 209          moltype = DNA  length = 654
FEATURE                 Location/Qualifiers
source                  1..654
                        mol_type = other DNA
                        organism = synthetic construct
SEQUENCE: 209
gacatccaga tgacccagtc tccttccacc ctgtctgcat ctgtaggaga cagagtcacc  60
atcacttgcc aggccagtca gagtgtttat agtaactggt tatcctggta tcagcagaaa  120
ccagggaaag cccctaagct cctgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttaca atactgtaat tgatactttt  300
gctttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 210          moltype = DNA  length = 333
FEATURE                 Location/Qualifiers
source                  1..333
                        mol_type = other DNA
                        organism = synthetic construct
SEQUENCE: 210
gacatccaga tgacccagtc tccttccacc ctgtctgcat ctgtaggaga cagagtcacc  60
atcacttgcc aggccagtca gagtgtttat agtaactggt tatcctggta tcagcagaaa  120
ccagggaaag cccctaagct cctgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttaca atactgtaat tgatactttt  300
gctttcggcg gagggaccaa ggtggagatc aaa                                333

SEQ ID NO: 211          moltype = AA  length = 218
FEATURE                 Location/Qualifiers
source                  1..218
                        mol_type = protein
                        organism = synthetic construct
SEQUENCE: 211
DIQMTQSPST LSASVGDRVT ITCQASQSVY SNWLSWYQQK PGKAPKLLIY SASTLASGVP  60
SRFSGSGSGT EFTLTISSLQ PDDFATYYCA GGYNTVIDTF AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 212          moltype = AA  length = 111
FEATURE                 Location/Qualifiers
source                  1..111
                        mol_type = protein
                        organism = synthetic construct
SEQUENCE: 212
DIQMTQSPST LSASVGDRVT ITCQASQSVY SNWLSWYQQK PGKAPKLLIY SASTLASGVP  60
SRFSGSGSGT EFTLTISSLQ PDDFATYYCA GGYNTVIDTF AFGGGTKVEI K           111

SEQ ID NO: 213          moltype = DNA  length = 1332
FEATURE                 Location/Qualifiers
source                  1..1332
                        mol_type = other DNA
                        organism = synthetic construct
SEQUENCE: 213
gaggtgcagc tgttggagtc tggggggaggc ttggtacagc ctggggggtc cctgagactc  60
tcctgtgcag cctctggaat cgacttcagt agtagttact acatgtgctg ggtccgccag  120
gctccaggga aggggctgga gtggatcgca tgcatttata ctggtggtag tggtactcct  180
cactacgcga gctccgcgaa aggccggttc accatctcca gagacaattc caagaacacg  240
ctgtatctgc aaatgaacag cctgagagcc gaggacacgg ccgtatatta ctgtgcgaga  300
gaaggtagcc tgtggggcca gggaaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg ggcaccgtc agtcttcctc   720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
```

```
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 214         moltype = DNA  length = 345
FEATURE                Location/Qualifiers
source                 1..345
                       mol_type = other DNA
                       organism = synthetic construct
SEQUENCE: 214
gaggtgcagc tgttggagtc tgggggaggc ttggtacagc ctggggggtc cctgagactc  60
tcctgtgcag cctctggaat cgacttcagt agtagttact acatgtgctg ggtccgccag  120
gctccaggga aggggctgga gtggatcgca tgcatttata ctggtggtag tggtactcct  180
cactacgcga gctccgcgaa aggccggttc accatctcca gagacaattc caagaacacg  240
ctgtatctgc aaatgaacag cctgagagcc gaggacacgg ccgtatatta ctgtgcgaga  300
gaaggtagcc tgtggggcca gggaaccctg gtcaccgtct cgagc                  345

SEQ ID NO: 215         moltype = AA  length = 444
FEATURE                Location/Qualifiers
source                 1..444
                       mol_type = protein
                       organism = synthetic construct
SEQUENCE: 215
EVQLLESGGG LVQPGGSLRL SCAASGIDFS SSYYMCWVRQ APGKGLEWIA CIYTGGSGTP  60
HYASSAKGRF TISRDNSKNT LYLQMNSLRA EDTAVYYCAR EGSLWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 216         moltype = AA  length = 115
FEATURE                Location/Qualifiers
source                 1..115
                       mol_type = protein
                       organism = synthetic construct
SEQUENCE: 216
EVQLLESGGG LVQPGGSLRL SCAASGIDFS SSYYMCWVRQ APGKGLEWIA CIYTGGSGTP  60
HYASSAKGRF TISRDNSKNT LYLQMNSLRA EDTAVYYCAR EGSLWGQGTL VTVSS       115

SEQ ID NO: 217         moltype = DNA  length = 654
FEATURE                Location/Qualifiers
source                 1..654
                       mol_type = other DNA
                       organism = synthetic construct
SEQUENCE: 217
gacatccaga tgacccagtc tccttccacc ctgtctgcat ctgtaggaga cagagtcacc  60
atcacttgcc agtccagtca gagtgtttat agtaactggt tctcctggta tcagcagaaa  120
ccagggaaag cccctaagct cctgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttaca atactgtaac tgatactttt  300
gctttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 218         moltype = DNA  length = 333
FEATURE                Location/Qualifiers
source                 1..333
                       mol_type = other DNA
                       organism = synthetic construct
SEQUENCE: 218
gacatccaga tgacccagtc tccttccacc ctgtctgcat ctgtaggaga cagagtcacc  60
atcacttgcc agtccagtca gagtgtttat agtaactggt tctcctggta tcagcagaaa  120
ccagggaaag cccctaagct cctgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttaca atactgtaac tgatactttt  300
gctttcggcg gagggaccaa ggtggagatc aaa                               333

SEQ ID NO: 219         moltype = AA  length = 218
FEATURE                Location/Qualifiers
source                 1..218
```

```
                         mol_type = protein
                         organism = synthetic construct
SEQUENCE: 219
DIQMTQSPST LSASVGDRVT ITCQSSQSVY SNWFSWYQQK PGKAPKLLIY SASTLASGVP  60
SRFSGSGSGT EFTLTISSLQ PDDFATYYCA GGYNTVTDTF AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 220           moltype = AA  length = 111
FEATURE                  Location/Qualifiers
source                   1..111
                         mol_type = protein
                         organism = synthetic construct
SEQUENCE: 220
DIQMTQSPST LSASVGDRVT ITCQSSQSVY SNWFSWYQQK PGKAPKLLIY SASTLASGVP  60
SRFSGSGSGT EFTLTISSLQ PDDFATYYCA GGYNTVTDTF AFGGGTKVEI K           111

SEQ ID NO: 221           moltype = DNA  length = 1332
FEATURE                  Location/Qualifiers
source                   1..1332
                         mol_type = other DNA
                         organism = synthetic construct
SEQUENCE: 221
gaggtgcagc tgttggagtc tggggggaggc ttggtacagc ctgggggggtc cctgagactc  60
tcctgtgcag cctctggaat cgacttcagt aggagatact acatgtgctg ggtccgccag  120
gctccaggga aggggctgga gtggatcgca tgcatgtata ctggtagccg cgatactcct  180
cactacgcga gctccgcgaa aggccggttc accatctcca gagacaattc caagaacacg  240
ctgtatctgc aaatgaacag cctgagagcc gaggacacgg ccgtatatta ctgtgcgaga  300
gaaggtaacc tgtggggcca gggaaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg gggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 222           moltype = DNA  length = 345
FEATURE                  Location/Qualifiers
source                   1..345
                         mol_type = other DNA
                         organism = synthetic construct
SEQUENCE: 222
gaggtgcagc tgttggagtc tggggggaggc ttggtacagc ctgggggggtc cctgagactc  60
tcctgtgcag cctctggaat cgacttcagt aggagatact acatgtgctg ggtccgccag  120
gctccaggga aggggctgga gtggatcgca tgcatgtata ctggtagccg cgatactcct  180
cactacgcga gctccgcgaa aggccggttc accatctcca gagacaattc caagaacacg  240
ctgtatctgc aaatgaacag cctgagagcc gaggacacgg ccgtatatta ctgtgcgaga  300
gaaggtaacc tgtggggcca gggaaccctg gtcaccgtct cgagc                  345

SEQ ID NO: 223           moltype = AA  length = 444
FEATURE                  Location/Qualifiers
source                   1..444
                         mol_type = protein
                         organism = synthetic construct
SEQUENCE: 223
EVQLLESGGG LVQPGGSLRL SCAASGIDFS RRYYMCWVRQ APGKGLEWIA CMYTGSRDTP  60
HYASSAKGRF TISRDNSKNT LYLQMNSLRA EDTAVYYCAR EGNLWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 224           moltype = AA  length = 115
FEATURE                  Location/Qualifiers
source                   1..115
                         mol_type = protein
```

```
                          organism = synthetic construct
SEQUENCE: 224
EVQLLESGGG LVQPGGSLRL SCAASGIDFS RRYYMCWVRQ APGKGLEWIA CMYTGSRDTP  60
HYASSAKGRF TISRDNSKNT LYLQMNSLRA EDTAVYYCAR EGNLWGQGTL VTVSS       115

SEQ ID NO: 225            moltype = DNA  length = 654
FEATURE                   Location/Qualifiers
source                    1..654
                          mol_type = other DNA
                          organism = synthetic construct
SEQUENCE: 225
gacatccaga tgacccagtc tccttccacc ctgtctgcat ctgtaggaga cagagtcacc  60
atcacttgcc agtccagtca gagtgtttat agtaactggt tctcctggta tcagcagaaa  120
ccagggaaag cccctaagct cctgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttaca atactgttat tgatactttt  300
gctttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 226            moltype = DNA  length = 333
FEATURE                   Location/Qualifiers
source                    1..333
                          mol_type = other DNA
                          organism = synthetic construct
SEQUENCE: 226
gacatccaga tgacccagtc tccttccacc ctgtctgcat ctgtaggaga cagagtcacc  60
atcacttgcc agtccagtca gagtgtttat agtaactggt tctcctggta tcagcagaaa  120
ccagggaaag cccctaagct cctgatctat tctgcatcca ctctggcatc tggggtccca  180
tcaaggttca gcggcagtgg atctgggaca gaattcactc tcaccatcag cagcctgcag  240
cctgatgatt ttgcaactta ttactgcgca ggcggttaca atactgttat tgatactttt  300
gctttcggcg gagggaccaa ggtggagatc aaa                               333

SEQ ID NO: 227            moltype = AA  length = 218
FEATURE                   Location/Qualifiers
source                    1..218
                          mol_type = protein
                          organism = synthetic construct
SEQUENCE: 227
DIQMTQSPST LSASVGDRVT ITCQSSQSVY SNWFSWYQQK PGKAPKLLIY SASTLASGVP  60
SRFSGSGSGT EFTLTISSLQ PDDFATYYCA GGYNTVIDTF AFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 228            moltype = AA  length = 111
FEATURE                   Location/Qualifiers
source                    1..111
                          mol_type = protein
                          organism = synthetic construct
SEQUENCE: 228
DIQMTQSPST LSASVGDRVT ITCQSSQSVY SNWFSWYQQK PGKAPKLLIY SASTLASGVP  60
SRFSGSGSGT EFTLTISSLQ PDDFATYYCA GGYNTVIDTF AFGGGTKVEI K           111

SEQ ID NO: 229            moltype = DNA  length = 1332
FEATURE                   Location/Qualifiers
source                    1..1332
                          mol_type = other DNA
                          organism = synthetic construct
SEQUENCE: 229
gaggtgcagc tgttggagtc tgggggaggc ttggtacagc ctggggggtc cctgagactc  60
tcctgtgcag cctctggaat cgacttcagt aggagatact acatgtgctg ggtccgccag  120
gctccaggga aggggctgga gtggatcgca tgcatatata ctggtagccg cgatactcct  180
cactacgcga gctccgcgaa aggccggttc accatctcca gagacaattc caagaacacg  240
ctgtatctgc aaatgaacag cctgagagcc gaggacacgg ccgtatatta ctgtgcgaga  300
gaaggtagcc tgtggggcca gggaaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg ggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
```

```
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 230          moltype = DNA  length = 345
FEATURE                 Location/Qualifiers
source                  1..345
                        mol_type = other DNA
                        organism = synthetic construct
SEQUENCE: 230
gaggtgcagc tgttggagtc tgggggaggc ttggtacagc ctggggggtc cctgagactc  60
tcctgtgcag cctctggaat cgacttcagt aggagatact acatgtgctg ggtccgccag  120
gctccaggga aggggctgga gtggatcgca tgcatatata ctggtagccg cgatactcct  180
cactacgcga gctccgcgaa aggccggttc accatctcca gagacaattc caagaacacg  240
ctgtatctgc aaatgaacag cctgagagcc gaggacacgg ccgtatatta ctgtgcgaga  300
gaaggtagcc tgtggggcca gggaaccctg gtcaccgtct cgagc                  345

SEQ ID NO: 231          moltype = AA  length = 444
FEATURE                 Location/Qualifiers
source                  1..444
                        mol_type = protein
                        organism = synthetic construct
SEQUENCE: 231
EVQLLESGGG LVQPGGSLRL SCAASGIDFS RRYYMCWVRQ APGKGLEWIA CIYTGSRDTP  60
HYASSAKGRF TISRDNSKNT LYLQMNSLRA EDTAVYYCAR EGSLWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 232          moltype = AA  length = 115
FEATURE                 Location/Qualifiers
source                  1..115
                        mol_type = protein
                        organism = synthetic construct
SEQUENCE: 232
EVQLLESGGG LVQPGGSLRL SCAASGIDFS RRYYMCWVRQ APGKGLEWIA CIYTGSRDTP  60
HYASSAKGRF TISRDNSKNT LYLQMNSLRA EDTAVYYCAR EGSLWGQGTL VTVSS        115

SEQ ID NO: 233          moltype = DNA  length = 651
FEATURE                 Location/Qualifiers
source                  1..651
                        mol_type = other DNA
                        organism = synthetic construct
SEQUENCE: 233
gacatccaga tgacccagtc tccttccacc ctgtctgcat ctgtaggaga cagagtcacc  60
atcacttgcc agtccagtca gagtgtttat agtaacagct tcttatcctg gtatcagcag  120
aaaccaggga aagcccctaa gctcctgatc tattctgcat ccgatctggc atctggggtc  180
ccatcaaggt tcagcggcag tggatctggg acagaattca ctctcaccat cagcagcctg  240
cagcctgatg attttgcaac ttattactgc gcaggcgttt atagtgataa tacttatgtt  300
ttcggcggag ggaccaaggt ggagatcaaa cgtacggtgg ctgcaccatc tgtcttcatc  360
ttcccgccat ctgatgagca gttgaaatct ggaactgcct ctgttgtgtg cctgctgaat  420
aacttctatc ccagagaggc caaagtacag tggaaggtgg ataacgccct ccaatcgggt  480
aactcccagg agagtgtcac agagcaggac agcaaggaca gcacctacag cctcagcagc  540
accctgacgc tgagcaaagc agactacgag aaacacaaag tctacgcctg cgaagtcacc  600
catcagggcc tgagctcgcc cgtcacaaag agcttcaaca ggggagagtg t            651

SEQ ID NO: 234          moltype = DNA  length = 330
FEATURE                 Location/Qualifiers
source                  1..330
                        mol_type = other DNA
                        organism = synthetic construct
SEQUENCE: 234
gacatccaga tgacccagtc tccttccacc ctgtctgcat ctgtaggaga cagagtcacc  60
atcacttgcc agtccagtca gagtgtttat agtaacagct tcttatcctg gtatcagcag  120
aaaccaggga aagcccctaa gctcctgatc tattctgcat ccgatctggc atctggggtc  180
ccatcaaggt tcagcggcag tggatctggg acagaattca ctctcaccat cagcagcctg  240
cagcctgatg attttgcaac ttattactgc gcaggcgttt atagtgataa tacttatgtt  300
ttcggcggag ggaccaaggt ggagatcaaa                                    330

SEQ ID NO: 235          moltype = AA  length = 217
FEATURE                 Location/Qualifiers
source                  1..217
                        mol_type = protein
```

```
                        organism = synthetic construct
SEQUENCE: 235
DIQMTQSPST LSASVGDRVT ITCQSSQSVY SNSFLSWYQQ KPGKAPKLLI YSASDLASGV  60
PSRFSGSGSG TEFTLTISSL QPDDFATYYC AGVYSDNTYV FGGGTKVEIK RTVAAPSVFI  120
FPPSDEQLKS GTASVVCLLN NFYPREAKVQ WKVDNALQSG NSQESVTEQD SKDSTYSLSS  180
TLTLSKADYE KHKVYACEVT HQGLSSPVTK SFNRGEC                           217

SEQ ID NO: 236          moltype = AA  length = 110
FEATURE                 Location/Qualifiers
source                  1..110
                        mol_type = protein
                        organism = synthetic construct
SEQUENCE: 236
DIQMTQSPST LSASVGDRVT ITCQSSQSVY SNSFLSWYQQ KPGKAPKLLI YSASDLASGV  60
PSRFSGSGSG TEFTLTISSL QPDDFATYYC AGVYSDNTYV FGGGTKVEIK             110

SEQ ID NO: 237          moltype = DNA  length = 1338
FEATURE                 Location/Qualifiers
source                  1..1338
                        mol_type = other DNA
                        organism = synthetic construct
SEQUENCE: 237
gaggtgcagc tggtggagtc tgggggaggc ttggtacagc cagggccgtc cctgagactc  60
tcctgtacag cttctggatt ctccctcagt cactactgga tgacttgggt ccgccaggct  120
ccagggaagg ggctggagta catcggattc attaatgttg gtggtgacac atcttacgcg  180
agctctgtga aaggcagatt caccatctca agagatgatt ccaaaagcat cgcctatctg  240
caaatgaaca gcctgaaaac cgaggacaca gccgtgtatt actgtggcag aggtggtctg  300
acttttggtt gggacttgtg gggccaggga accctggtca ccgtctcgag cgctagcacc  360
aagggcccat cggtcttccc cctggcaccc tcctccaaga gcacctctgg gggcacagcg  420
gccctgggct gcctggtcaa ggactacttc cccgaaccgg tgacggtgtc gtggaactca  480
ggcgccctga ccagcggcgt gcacaccttc ccggctgtcc tacagtcctc aggactctac  540
tccctcagca gcgtggtgac cgtgccctcc agcagcttgg gcacccagac ctacatctgc  600
aacgtgaatc acaagcccag caacaccaag gtggacaaga gagttgagcc caaatcttgt  660
gacaaaactc acacatgccc accgtgccca gcacctgaag ccgcgggggc accgtcagtc  720
ttcctcttcc ccccaaaacc caaggacacc ctcatgatct cccggacccc tgaggtcaca  780
tgcgtggtgg tggacgtgag ccacgaagac cctgaggtca agttcaactg gtacgtggac  840
ggcgtggagg tgcataatgc caagacaaag ccgcgggagg agcagtacaa cagcacgtac  900
cgtgtggtca gcgtcctcac cgtcctgcac caggactggc tgaatggcaa ggagtacaag  960
tgcgcggtct ccaacaaagc cctcccagcc cccatcgaga aaaccatctc caaagccaaa  1020
gggcagcccc gagaaccaca ggtgtacacc ctgcccccat cccgggatga gctgaccaag  1080
aaccaggtca gcctgacctg cctggtcaaa ggcttctatc ccagcgacat cgccgtggag  1140
tgggagagca atgggcagcc ggagaacaac tacaagacca cgcctcccgt gctggactcc  1200
gacggctcct tcttcctcta tagcaagctc accgtggaca agagcaggtg gcagcagggg  1260
aacgtcttct catgctccgt gatgcatgag gctctgcaca accactacac gcagaagagc  1320
ctctccctgt ctccgggt                                                1338

SEQ ID NO: 238          moltype = DNA  length = 351
FEATURE                 Location/Qualifiers
source                  1..351
                        mol_type = other DNA
                        organism = synthetic construct
SEQUENCE: 238
gaggtgcagc tggtggagtc tgggggaggc ttggtacagc cagggccgtc cctgagactc  60
tcctgtacag cttctggatt ctccctcagt cactactgga tgacttgggt ccgccaggct  120
ccagggaagg ggctggagta catcggattc attaatgttg gtggtgacac atcttacgcg  180
agctctgtga aaggcagatt caccatctca agagatgatt ccaaaagcat cgcctatctg  240
caaatgaaca gcctgaaaac cgaggacaca gccgtgtatt actgtggcag aggtggtctg  300
acttttggtt gggacttgtg gggccaggga accctggtca ccgtctcgag c           351

SEQ ID NO: 239          moltype = AA  length = 446
FEATURE                 Location/Qualifiers
source                  1..446
                        mol_type = protein
                        organism = synthetic construct
SEQUENCE: 239
EVQLVESGGG LVQPGPSLRL SCTASGFSLS HYWMTWVRQA PGKGLEYIGF INVGGDTSYA  60
SSVKGRFTIS RDDSKSIAYL QMNSLKTEDT AVYYCGRGGL TFGWDLWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APEAAGAPSV  240
FLFPPKPKDT LMISRTPEVT CVVVDVSHED PEVKFNWYVD GVEVHNAKTK PREEQYNSTY  300
RVVSVLTVLH QDWLNGKEYK CAVSNKALPA PIEKTISKAK GQPREPQVYT LPPSRDELTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                       446

SEQ ID NO: 240          moltype = AA  length = 117
FEATURE                 Location/Qualifiers
source                  1..117
                        mol_type = protein
                        organism = synthetic construct
```

SEQUENCE: 240
EVQLVESGGG LVQPGPSLRL SCTASGFSLS HYWMTWVRQA PGKGLEYIGF INVGGDTSYA 60
SSVKGRFTIS RDDSKSIAYL QMNSLKTEDT AVYYCGRGGL TFGWDLWGQG TLVTVSS 117

SEQ ID NO: 241 moltype = DNA length = 654
FEATURE Location/Qualifiers
source 1..654
mol_type = other DNA
organism = synthetic construct
SEQUENCE: 241
gacgttgtga tgacccagtc tccatcttcc gtgtctgcat ctgtaggaga cagagtcacc 60
atcacctgtc aggccagtca gaacattagg acttacttat cctggtatca gcagaaacca 120
gggaaagccc ctaagctcct gatctatgct gcagccaatc tggcatctgg ggtcccatca 180
aggttcagcg gcagtggatc tgggacagat ttcactctca ccatcagcga cctggagcct 240
ggcgatgctg caacttacta ttgtcagtct acctatcttg gtactgatta tgttggcggt 300
gctttcggcg gagggaccaa ggtggagatc aaacgtacgg tggctgcacc atctgtcttc 360
atcttcccgc catctgatga gcagttgaaa tctggaactg cctctgttgt gtgcctgctg 420
aataacttct atcccagaga ggccaaagta cagtggaagg tggataacgc cctccaatcg 480
ggtaactccc aggagagtgt cacagagcag gacagcaagg acagcaccta cagcctcagc 540
agcaccctga cgctgagcaa agcagactac gagaaacaca aagtctacgc ctgcgaagtc 600
acccatcagg gcctgagctc gcccgtcaca aagagcttca acaggggaga gtgt 654

SEQ ID NO: 242 moltype = DNA length = 333
FEATURE Location/Qualifiers
source 1..333
mol_type = other DNA
organism = synthetic construct
SEQUENCE: 242
gacgttgtga tgacccagtc tccatcttcc gtgtctgcat ctgtaggaga cagagtcacc 60
atcacctgtc aggccagtca gaacattagg acttacttat cctggtatca gcagaaacca 120
gggaaagccc ctaagctcct gatctatgct gcagccaatc tggcatctgg ggtcccatca 180
aggttcagcg gcagtggatc tgggacagat ttcactctca ccatcagcga cctggagcct 240
ggcgatgctg caacttacta ttgtcagtct acctatcttg gtactgatta tgttggcggt 300
gctttcggcg gagggaccaa ggtggagatc aaa 333

SEQ ID NO: 243 moltype = AA length = 218
FEATURE Location/Qualifiers
source 1..218
mol_type = protein
organism = synthetic construct
SEQUENCE: 243
DVVMTQSPSS VSASVGDRVT ITCQASQNIR TYLSWYQQKP GKAPKLLIYA AANLASGVPS 60
RFSGSGSGTD FTLTISDLEP GDAATYYCQS TYLGTDYVGG AFGGGTKVEI KRTVAAPSVF 120
IFPPSDEQLK SGTASVVCLL NNFYPREAKV QWKVDNALQS GNSQESVTEQ DSKDSTYSLS 180
STLTLSKADY EKHKVYACEV THQGLSSPVT KSFNRGEC 218

SEQ ID NO: 244 moltype = AA length = 111
FEATURE Location/Qualifiers
source 1..111
mol_type = protein
organism = synthetic construct
SEQUENCE: 244
DVVMTQSPSS VSASVGDRVT ITCQASQNIR TYLSWYQQKP GKAPKLLIYA AANLASGVPS 60
RFSGSGSGTD FTLTISDLEP GDAATYYCQS TYLGTDYVGG AFGGGTKVEI K 111

SEQ ID NO: 245 moltype = DNA length = 1332
FEATURE Location/Qualifiers
source 1..1332
mol_type = other DNA
organism = synthetic construct
SEQUENCE: 245
cggtcgctgg tggagtctgg gggaggcttg gtccagcctg gggggtccct gagactctcc 60
tgtacagcct ctggattcac catcagtagc taccacatgc agtgggtccg ccaggctcca 120
gggaaggggc tggagtacat cggaaccatt agtagtggtg gtaatgtata ctacgcgagc 180
tccgcgagag gcagattcac catctccaga ccctcgtcca agaacacggt ggatcttcaa 240
atgaacagcc tgagagccga ggacacggct gtgtattact gtgcgagaga ctctggttat 300
agtgatccta tgtggggcca gggaaccctg gtcaccgtct cgagcgctag caccaagggc 360
ccatcggtct tccccctggc accctcctcc aagagcacct ctgggggcac agcggccctg 420
ggctgcctgg tcaaggacta cttccccgaa ccggtgacgg tgtcgtggaa ctcaggcgcc 480
ctgaccagcg gcgtgcacac cttcccggct gtcctacagt cctcaggact ctactccctc 540
agcagcgtgg tgaccgtgcc ctccagcagc ttgggcaccc agacctacat ctgcaacgtg 600
aatcacaagc ccagcaacac caaggtggac aagagagttg agcccaaatc ttgtgacaaa 660
actcacacat gcccaccgtg cccagcacct gaagccgcgg ggcaccgtc agtcttcctc 720
ttccccccaa aacccaagga caccctcatg atctcccgga cccctgaggt cacatgcgtg 780
gtggtggacg tgagccacga agaccctgag gtcaagttca actggtacgt ggacggcgtg 840
gaggtgcata atgccaagac aaagccgcgg gaggagcagt acaacagcac gtaccgtgtg 900
gtcagcgtcc tcaccgtcct gcaccaggac tggctgaatg gcaaggagta caagtgcgcg 960
gtctccaaca aagccctccc agcccccatc gagaaaacca tctccaaagc caaagggcag 1020
ccccgagaac cacaggtgta caccctgccc ccatcccggg atgagctgac caagaaccag 1080

```
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 246          moltype = DNA  length = 345
FEATURE                 Location/Qualifiers
source                  1..345
                        mol_type = other DNA
                        organism = synthetic construct
SEQUENCE: 246
cggtcgctgg tggagtctgg gggaggcttg gtccagcctg gggggtccct gagactctcc  60
tgtacagcct ctggattcac catcagtagc taccacatgc agtgggtccg ccaggctcca  120
gggaaggggc tggagtacat cggaaccatt agtagtggtg gtaatgtata ctacgcgagc  180
tccgcgagag gcagattcac catctccaga ccctcgtcca agaacacggt ggatcttcaa  240
atgaacagcc tgagagccga ggacacggct gtgtattact gtgcgagaga ctctggttat  300
agtgatccta tgtggggcca gggaaccctg gtcaccgtct cgagc                  345

SEQ ID NO: 247          moltype = AA  length = 444
FEATURE                 Location/Qualifiers
source                  1..444
                        mol_type = protein
                        organism = synthetic construct
SEQUENCE: 247
RSLVESGGGL VQPGGSLRLS CTASGFTISS YHMQWVRQAP GKGLEYIGTI SSGGNVYYAS  60
SARGRFTISR PSSKNTVDLQ MNSLRAEDTA VYYCARDSGY SDPMWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 248          moltype = AA  length = 115
FEATURE                 Location/Qualifiers
source                  1..115
                        mol_type = protein
                        organism = synthetic construct
SEQUENCE: 248
RSLVESGGGL VQPGGSLRLS CTASGFTISS YHMQWVRQAP GKGLEYIGTI SSGGNVYYAS  60
SARGRFTISR PSSKNTVDLQ MNSLRAEDTA VYYCARDSGY SDPMWGQGTL VTVSS       115

SEQ ID NO: 249          moltype = DNA  length = 654
FEATURE                 Location/Qualifiers
source                  1..654
                        mol_type = other DNA
                        organism = synthetic construct
SEQUENCE: 249
gacatccaga tgacccagtc tccttccacc ctgtctgcat ctgtaggaga cagagtcacc  60
atcacttgcc aggccagtca gagcattagt actaacttga actggtatca gcagaaacca  120
gggaaagccc ctaagctcct gatctattat gcatccagtc tggcatctgg ggtcccatca  180
aggttcagcg gcagtggatc tgggacagaa ttcactctca ccatcagcag cctgcagcct  240
gatgattttg caacttatta ctgcctaggt gtttggaatt attggggtga tgatggtact  300
gatttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 250          moltype = DNA  length = 333
FEATURE                 Location/Qualifiers
source                  1..333
                        mol_type = other DNA
                        organism = synthetic construct
SEQUENCE: 250
gacatccaga tgacccagtc tccttccacc ctgtctgcat ctgtaggaga cagagtcacc  60
atcacttgcc aggccagtca gagcattagt actaacttga actggtatca gcagaaacca  120
gggaaagccc ctaagctcct gatctattat gcatccagtc tggcatctgg ggtcccatca  180
aggttcagcg gcagtggatc tgggacagaa ttcactctca ccatcagcag cctgcagcct  240
gatgattttg caacttatta ctgcctaggt gtttggaatt attggggtga tgatggtact  300
gatttcggcg gagggaccaa ggtggagatc aaa                               333

SEQ ID NO: 251          moltype = AA  length = 218
FEATURE                 Location/Qualifiers
source                  1..218
                        mol_type = protein
                        organism = synthetic construct
```

```
SEQUENCE: 251
DIQMTQSPST LSASVGDRVT ITCQASQSIS TNLNWYQQKP GKAPKLLIYY ASSLASGVPS  60
RFSGSGSGTE FTLTISSLQP DDFATYYCLG VWNYWGDDGT DFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 252          moltype = AA  length = 111
FEATURE                 Location/Qualifiers
source                  1..111
                        mol_type = protein
                        organism = synthetic construct
SEQUENCE: 252
DIQMTQSPST LSASVGDRVT ITCQASQSIS TNLNWYQQKP GKAPKLLIYY ASSLASGVPS  60
RFSGSGSGTE FTLTISSLQP DDFATYYCLG VWNYWGDDGT DFGGGTKVEI K           111

SEQ ID NO: 253          moltype = DNA  length = 1332
FEATURE                 Location/Qualifiers
source                  1..1332
                        mol_type = other DNA
                        organism = synthetic construct
SEQUENCE: 253
gaggtgcagc tggtggagtc tgggggaggc ttggtccagc ctggggggtc cctgagactc  60
tcctgtgcag cctctggatt ctccctcagt agctactaca tgagctgggt ccgccaggct  120
ccagggaagg ggctggagtg gatcggaagt atttatggta gtggtgccgc atactacgcg  180
agctccgcta aaggcagatt caccatctcc agagacaatt ccaagaacac gctgtatctt  240
caaatgaaca gcctgagagc cgaggacacg gctgtgtatt actgtgcgag agatcctatt  300
aacaatgcca tgtggggcca gggaaccctg gtcaccgtct cgagcgctag caccaagggc  360
ccatcggtct tccccctggc accctcctcc aagagcacct ctgggggcac agcggccctg  420
ggctgcctgg tcaaggacta cttccccgaa ccggtgacgg tgtcgtggaa ctcaggcgcc  480
ctgaccagcg gcgtgcacac cttcccggct gtcctacagt cctcaggact ctactccctc  540
agcagcgtgg tgaccgtgcc ctccagcagc ttgggcaccc agacctacat ctgcaacgtg  600
aatcacaagc ccagcaacac caaggtggac aagagagttg agcccaaatc ttgtgacaaa  660
actcacacat gcccaccgtg cccagcacct gaagccgcgg ggcaccgtc agtcttcctc  720
ttccccccaa aacccaagga caccctcatg atctcccgga cccctgaggt cacatgcgtg  780
gtggtggacg tgagccacga agaccctgag gtcaagttca actggtacgt ggacggcgtg  840
gaggtgcata atgccaagac aaagccgcgg gaggagcagt acaacagcac gtaccgtgtg  900
gtcagcgtcc tcaccgtcct gcaccaggac tggctgaatg gcaaggagta caagtgcgcg  960
gtctccaaca aagccctccc agcccccatc gagaaaacca tctccaaagc caaagggcag  1020
ccccgagaac cacaggtgta caccctgccc ccatcccggg atgagctgac caagaaccag  1080
gtcagcctga cctgcctggt caaaggcttc tatcccagcg acatcgccgt ggagtgggag  1140
agcaatgggc agccggagaa caactacaag accacgcctc ccgtgctgga ctccgacggc  1200
tccttcttcc tctatagcaa gctcaccgtg gacaagagca ggtggcagca ggggaacgtc  1260
ttctcatgct ccgtgatgca tgaggctctg cacaaccact acacgcagaa gagcctctcc  1320
ctgtctccgg gt                                                      1332

SEQ ID NO: 254          moltype = DNA  length = 345
FEATURE                 Location/Qualifiers
source                  1..345
                        mol_type = other DNA
                        organism = synthetic construct
SEQUENCE: 254
gaggtgcagc tggtggagtc tgggggaggc ttggtccagc ctggggggtc cctgagactc  60
tcctgtgcag cctctggatt ctccctcagt agctactaca tgagctgggt ccgccaggct  120
ccagggaagg ggctggagtg gatcggaagt atttatggta gtggtgccgc atactacgcg  180
agctccgcta aaggcagatt caccatctcc agagacaatt ccaagaacac gctgtatctt  240
caaatgaaca gcctgagagc cgaggacacg gctgtgtatt actgtgcgag agatcctatt  300
aacaatgcca tgtggggcca gggaaccctg gtcaccgtct cgagc                  345

SEQ ID NO: 255          moltype = AA  length = 444
FEATURE                 Location/Qualifiers
source                  1..444
                        mol_type = protein
                        organism = synthetic construct
SEQUENCE: 255
EVQLVESGGG LVQPGGSLRL SCAASGFSLS SYYMSWVRQA PGKGLEWIGS IYGSGAAYYA  60
SSAKGRFTIS RDNSKNTLYL QMNSLRAEDT AVYYCARDPI NNAMWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGAPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCA VSNKALPAPI EKTISKAKGQ PREPQVYTLP PSRDELTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPG                                         444

SEQ ID NO: 256          moltype = AA  length = 115
FEATURE                 Location/Qualifiers
source                  1..115
                        mol_type = protein
                        organism = synthetic construct
SEQUENCE: 256
```

```
EVQLVESGGG LVQPGGSLRL SCAASGFSLS SYYMSWVRQA PGKGLEWIGS IYGSGAAYYA  60
SSAKGRFTIS RDNSKNTLYL QMNSLRAEDT AVYYCARDPI NNAMWGQGTL VTVSS       115

SEQ ID NO: 257          moltype = DNA  length = 657
FEATURE                 Location/Qualifiers
source                  1..657
                        mol_type = other DNA
                        organism = synthetic construct
SEQUENCE: 257
gcccttgtga tgacccagtc tccttccacc ctgtctgcat ctgtaggaga cagagtcacc  60
atcaattgcc aggccagtga ggacattgat aactatttag cctggtatca gcagaaacca  120
gggaaagccc ctaagctcct gatcttttat gcatccgatc tggcatctgg ggtcccatca  180
aggttcagcg gcagtggatc tgggacagaa ttcactctca ccatcagcag cctgcagcct  240
gatgattttg caacttatta ctgccaaggc ggttactata ctagtagtac tgatacgagg  300
ggtgctttcg gcggagggac caaggtggag atcaaacgta cggtggctgc accatctgtc  360
ttcatcttcc cgccatctga tgagcagttg aaatctggaa ctgcctctgt tgtgtgcctg  420
ctgaataact tctatcccag agaggccaaa gtacagtgga aggtggataa cgccctccaa  480
tcgggtaact cccaggagag tgtcacagag caggacagca aggacagcac ctacagcctc  540
agcagcaccc tgacgctgag caaagcagac tacgagaaac acaaagtcta cgcctgcgaa  600
gtcacccatc agggcctgag ctcgcccgtc acaaagagct tcaacagggg agagtgt     657

SEQ ID NO: 258          moltype = DNA  length = 336
FEATURE                 Location/Qualifiers
source                  1..336
                        mol_type = other DNA
                        organism = synthetic construct
SEQUENCE: 258
gcccttgtga tgacccagtc tccttccacc ctgtctgcat ctgtaggaga cagagtcacc  60
atcaattgcc aggccagtga ggacattgat aactatttag cctggtatca gcagaaacca  120
gggaaagccc ctaagctcct gatcttttat gcatccgatc tggcatctgg ggtcccatca  180
aggttcagcg gcagtggatc tgggacagaa ttcactctca ccatcagcag cctgcagcct  240
gatgattttg caacttatta ctgccaaggc ggttactata ctagtagtac tgatacgagg  300
ggtgctttcg gcggagggac caaggtggag atcaaa                            336

SEQ ID NO: 259          moltype = AA  length = 219
FEATURE                 Location/Qualifiers
source                  1..219
                        mol_type = protein
                        organism = synthetic construct
SEQUENCE: 259
ALVMTQSPST LSASVGDRVT INCQASEDID NYLAWYQQKP GKAPKLLIFY ASDLASGVPS  60
RFSGSGSGTE FTLTISSLQP DDFATYYCQG GYYTSSTDTR GAFGGGTKVE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 260          moltype = AA  length = 112
FEATURE                 Location/Qualifiers
source                  1..112
                        mol_type = protein
                        organism = synthetic construct
SEQUENCE: 260
ALVMTQSPST LSASVGDRVT INCQASEDID NYLAWYQQKP GKAPKLLIFY ASDLASGVPS  60
RFSGSGSGTE FTLTISSLQP DDFATYYCQG GYYTSSTDTR GAFGGGTKVE IK          112

SEQ ID NO: 261          moltype = DNA  length = 1347
FEATURE                 Location/Qualifiers
source                  1..1347
                        mol_type = other DNA
                        organism = synthetic construct
SEQUENCE: 261
cagtcgctgg tggagtctgg gggaggcttg gtacagcctg gggggtccct gagactctcc  60
tgtgcagcct ctggattctc cttcactagc agctactaca tgtgctgggt ccgccaggct  120
ccagggaagg ggctggagtg gatcgcatgc atttatactg gtagtagtgg tagcacttac  180
tacgcgaact ccgcgaaagg ccggttcacc atctccagag acaattccaa gaacacgctg  240
tatctgcaaa tgaacagcct gagagccgag gacacggccg tatattactg tgcgagagat  300
agtagtagtt attatatgtt taacttgtgg ggccagggaa ccctggtcac cgtctcgagc  360
gctagcacca agggcccatc ggtcttcccc ctggcaccct cctccaagag cacctctggg  420
ggcacagcgg ccctgggctg cctggtcaag gactacttcc ccgaaccggt gacggtgtcg  480
tggaactcag gcgccctgac cagcggcgtg cacaccttcc cggctgtcct acagtcctca  540
ggactctact ccctcagcag cgtggtgacc gtgccctcca gcagcttggg cacccagacc  600
tacatctgca acgtgaatca caagcccagc aacaccaagg tggacaagag agttgagccc  660
aaatcttgtg acaaaactca cacatgccca ccgtgcccag cacctgaagc cgcgggggca  720
ccgtcagtct tcctcttccc cccaaaaccc aaggacaccc tcatgatctc ccggacccct  780
gaggtcacat gcgtggtggt ggacgtgagc cacgaagacc ctgaggtcaa gttcaactgg  840
tacgtggacg gcgtggaggt gcataatgcc aagacaaagc cgcgggagga gcagtacaac  900
agcacgtacc gtgtggtcag cgtcctcacc gtcctgcacc aggactggct gaatggcaag  960
gagtacaagt gcgcggtctc caacaaagcc ctcccagccc ccatcgagaa aaccatctcc  1020
aaagccaaag ggcagccccg agaaccacag gtgtacaccc tgcccccatc ccgggatgag  1080
ctgaccaaga accaggtcag cctgacctgc ctggtcaaag gcttctatcc cagcgacatc  1140
```

```
gccgtggagt gggagagcaa tgggcagccg gagaacaact acaagaccac gcctcccgtg  1200
ctggactccg acggctcctt cttcctctat agcaagctca ccgtggacaa gagcaggtgg  1260
cagcagggga acgtcttctc atgctccgtg atgcatgagg ctctgcacaa ccactacacg  1320
cagaagagcc tctccctgtc tccgggt                                      1347

SEQ ID NO: 262          moltype = DNA  length = 360
FEATURE                 Location/Qualifiers
source                  1..360
                        mol_type = other DNA
                        organism = synthetic construct
SEQUENCE: 262
cagtcgctgg tggagtctgg gggaggcttg gtacagcctg gggggtccct gagactctcc  60
tgtgcagcct ctggattctc cttcactagc agctactaca tgtgctgggt ccgccaggct  120
ccagggaagg ggctggagtg gatcgcatgc atttatactg gtagtagtgg tagcacttac  180
tacgcgaact ccgcgaaagg ccggttcacc atctccagag acaattccaa gaacacgctg  240
tatctgcaaa tgaacagcct gagagccgag gacacggccg tatattactg tgcgagagat  300
agtagtagtt attatatgtt taacttgtgg ggccagggaa ccctggtcac cgtctcgagc  360

SEQ ID NO: 263          moltype = AA  length = 449
FEATURE                 Location/Qualifiers
source                  1..449
                        mol_type = protein
                        organism = synthetic construct
SEQUENCE: 263
QSLVESGGGL VQPGGSLRLS CAASGFSFTS SYYMCWVRQA PGKGLEWIAC IYTGSSGSTY  60
YANSAKGRFT ISRDNSKNTL YLQMNSLRAE DTAVYYCARD SSSYYMFNLW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGA  240
PSVFLFPPKP KDTLMISRTP EVTCVVVDVS HEDPEVKFNW YVDGVEVHNA KTKPREEQYN  300
STYRVVSVLT VLHQDWLNGK EYKCAVSNKA LPAPIEKTIS KAKGQPREPQ VYTLPPSRDE  360
LTKNQVSLTC LVKGFYPSDI AVEWESNGQP ENNYKTTPPV LDSDGSFFLY SKLTVDKSRW  420
QQGNVFSCSV MHEALHNHYT QKSLSLSPG                                    449

SEQ ID NO: 264          moltype = AA  length = 120
FEATURE                 Location/Qualifiers
source                  1..120
                        mol_type = protein
                        organism = synthetic construct
SEQUENCE: 264
QSLVESGGGL VQPGGSLRLS CAASGFSFTS SYYMCWVRQA PGKGLEWIAC IYTGSSGSTY  60
YANSAKGRFT ISRDNSKNTL YLQMNSLRAE DTAVYYCARD SSSYYMFNLW GQGTLVTVSS  120

SEQ ID NO: 265          moltype = DNA  length = 654
FEATURE                 Location/Qualifiers
source                  1..654
                        mol_type = other DNA
                        organism = synthetic construct
SEQUENCE: 265
gacatccaga tgacccagtc tccatcctcc ctgtctgcat ctgtaggaga cagagtcacc  60
atcacttgcc agtccagtca gagtgtttat aataacaatg ctttagcctg gtatcagcag  120
aaaccaggga aagttcctaa gctcctgatc tatttggctt ccactctggc atctggggtc  180
ccatctcggt tcagtggcag tggatctggg acagatttca ctctcaccat cagcagcctg  240
cagcctgaag atgttgcaac ttattactgt ctaggtgttt ataatgatga tgttgataat  300
ggtttcggcg gagggaccaa ggtggagatc aaacgtacgg tggctgcacc atctgtcttc  360
atcttcccgc catctgatga gcagttgaaa tctggaactg cctctgttgt gtgcctgctg  420
aataacttct atcccagaga ggccaaagta cagtggaagg tggataacgc cctccaatcg  480
ggtaactccc aggagagtgt cacagagcag gacagcaagg acagcaccta cagcctcagc  540
agcaccctga cgctgagcaa agcagactac gagaaacaca aagtctacgc ctgcgaagtc  600
acccatcagg gcctgagctc gcccgtcaca aagagcttca acaggggaga gtgt        654

SEQ ID NO: 266          moltype = DNA  length = 333
FEATURE                 Location/Qualifiers
source                  1..333
                        mol_type = other DNA
                        organism = synthetic construct
SEQUENCE: 266
gacatccaga tgacccagtc tccatcctcc ctgtctgcat ctgtaggaga cagagtcacc  60
atcacttgcc agtccagtca gagtgtttat aataacaatg ctttagcctg gtatcagcag  120
aaaccaggga aagttcctaa gctcctgatc tatttggctt ccactctggc atctggggtc  180
ccatctcggt tcagtggcag tggatctggg acagatttca ctctcaccat cagcagcctg  240
cagcctgaag atgttgcaac ttattactgt ctaggtgttt ataatgatga tgttgataat  300
ggtttcggcg gagggaccaa ggtggagatc aaa                               333

SEQ ID NO: 267          moltype = AA  length = 218
FEATURE                 Location/Qualifiers
source                  1..218
                        mol_type = protein
                        organism = synthetic construct
SEQUENCE: 267
```

```
DIQMTQSPSS LSASVGDRVT ITCQSSQSVY NNNALAWYQQ KPGKVPKLLI YLASTLASGV  60
PSRFSGSGSG TDFTLTISSL QPEDVATYYC LGVYNDDVDN GFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 268          moltype = AA  length = 111
FEATURE                 Location/Qualifiers
source                  1..111
                        mol_type = protein
                        organism = synthetic construct
SEQUENCE: 268
DIQMTQSPSS LSASVGDRVT ITCQSSQSVY NNNALAWYQQ KPGKVPKLLI YLASTLASGV  60
PSRFSGSGSG TDFTLTISSL QPEDVATYYC LGVYNDDVDN GFGGGTKVEI K           111

SEQ ID NO: 269          moltype = DNA  length = 1341
FEATURE                 Location/Qualifiers
source                  1..1341
                        mol_type = other DNA
                        organism = synthetic construct
SEQUENCE: 269
gaggtgcagc tggtggagtc tgggggaggc ttggtccagc ctggggggtc cctgagactc  60
tcctgtgcag cctctggatt ctccctcaat aacaatgcaa taagctgggt ccgccaggct  120
ccagggaagg ggctggagtg ggttgcaatc atacaaaata ctggtaccac agactacgcg  180
aggtccgcta aaggcagatt caccatctcc agagacaatt ccaagaacac gctgtatctt  240
caaatgaaca gcctgagagc cgaggacacg gctgtgtatt actgtgcgag agggtatggt  300
tttgagtcgg agcttgtcat ctggggccag ggaaccctgg tcaccgtctc gagcgctagc  360
accaagggcc catcggtctt ccccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct tgggcaccca gacctacatc  600
tgcaacgtga atcacaagcc cagcaacacc aaggtggaca agagagttga gcccaaatct  660
tgtgacaaaa ctcacacatg cccaccgtgc ccagcacctg aagccgcggg ggcaccgtca  720
gtcttcctct tccccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
aagtgcgcgg tctccaacaa agccctccca gcccccatcg agaaaaccat ctccaaagcc  1020
aaagggcagc cccgagaacc acaggtgtac accctgcccc catcccggga tgagctgacc  1080
aagaaccagg tcagcctgac ctgcctggtc aaaggcttct atcccagcga catcgccgtg  1140
gagtgggaga gcaatgggca gccggagaac aactacaaga ccacgcctcc cgtgctggac  1200
tccgacggct ccttcttcct ctatagcaag ctcaccgtgg acaagagcag gtggcagcag  1260
gggaacgtct tctcatgctc cgtgatgcat gaggctctgc acaaccacta cacgcagaag  1320
agcctctccc tgtctccggg t                                            1341

SEQ ID NO: 270          moltype = DNA  length = 354
FEATURE                 Location/Qualifiers
source                  1..354
                        mol_type = other DNA
                        organism = synthetic construct
SEQUENCE: 270
gaggtgcagc tggtggagtc tgggggaggc ttggtccagc ctggggggtc cctgagactc  60
tcctgtgcag cctctggatt ctccctcaat aacaatgcaa taagctgggt ccgccaggct  120
ccagggaagg ggctggagtg ggttgcaatc atacaaaata ctggtaccac agactacgcg  180
aggtccgcta aaggcagatt caccatctcc agagacaatt ccaagaacac gctgtatctt  240
caaatgaaca gcctgagagc cgaggacacg gctgtgtatt actgtgcgag agggtatggt  300
tttgagtcgg agcttgtcat ctggggccag ggaaccctgg tcaccgtctc gagc        354

SEQ ID NO: 271          moltype = AA  length = 447
FEATURE                 Location/Qualifiers
source                  1..447
                        mol_type = protein
                        organism = synthetic construct
SEQUENCE: 271
EVQLVESGGG LVQPGGSLRL SCAASGFSLN NNAISWVRQA PGKGLEWVAI IQNTGTTDYA  60
RSAKGRFTIS RDNSKNTLYL QMNSLRAEDT AVYYCARGYG FESELVIWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKRVEPKS CDKTHTCPPC PAPEAAGAPS  240
VFLFPPKPKD TLMISRTPEV TCVVVDVSHE DPEVKFNWYV DGVEVHNAKT KPREEQYNST  300
YRVVSVLTVL HQDWLNGKEY KCAVSNKALP APIEKTISKA KGQPREPQVY TLPPSRDELT  360
KNQVSLTCLV KGFYPSDIAV EWESNGQPEN NYKTTPPVLD SDGSFFLYSK LTVDKSRWQQ  420
GNVFSCSVMH EALHNHYTQK SLSLSPG                                      447

SEQ ID NO: 272          moltype = AA  length = 118
FEATURE                 Location/Qualifiers
source                  1..118
                        mol_type = protein
                        organism = synthetic construct
SEQUENCE: 272
EVQLVESGGG LVQPGGSLRL SCAASGFSLN NNAISWVRQA PGKGLEWVAI IQNTGTTDYA  60
```

-continued

```
RSAKGRFTIS RDNSKNTLYL QMNSLRAEDT AVYYCARGYG FESELVIWGQ GTLVTVSS    118

SEQ ID NO: 273          moltype = AA  length = 12
FEATURE                 Location/Qualifiers
source                  1..12
                        mol_type = protein
                        organism = synthetic construct
SEQUENCE: 273
QSSQSVYSNW FS                                                      12

SEQ ID NO: 274          moltype = AA  length = 7
FEATURE                 Location/Qualifiers
source                  1..7
                        mol_type = protein
                        organism = synthetic construct
SEQUENCE: 274
SASTLAS                                                            7

SEQ ID NO: 275          moltype = AA  length = 12
FEATURE                 Location/Qualifiers
source                  1..12
                        mol_type = protein
                        organism = synthetic construct
SEQUENCE: 275
AGGYNTVIDT FA                                                      12

SEQ ID NO: 276          moltype = AA  length = 6
FEATURE                 Location/Qualifiers
source                  1..6
                        mol_type = protein
                        organism = synthetic construct
SEQUENCE: 276
RRYYMC                                                             6

SEQ ID NO: 277          moltype = AA  length = 18
FEATURE                 Location/Qualifiers
source                  1..18
                        mol_type = protein
                        organism = synthetic construct
SEQUENCE: 277
CIYTGSRDTP HYASSAKG                                                18

SEQ ID NO: 278          moltype = AA  length = 4
FEATURE                 Location/Qualifiers
source                  1..4
                        mol_type = protein
                        organism = synthetic construct
SEQUENCE: 278
EGSL                                                               4
```

What is claimed is:

1. An isolated monoclonal antibody (mAb) or antigen-binding fragment thereof that binds specifically to human or cynomolgus 4-1BB, comprising a variable light chain comprising SEQ ID NO:228, and a variable heavy chain comprising SEQ ID NO: 232.

2. The isolated mAb or antigen-binding fragment thereof according to claim 1, wherein the isolated mAb is an IgG, a recombinant antibody, a bispecific antibody, tri-specific antibody, or multi-specific antibody.

3. The isolated mAb or antigen-binding fragment thereof according to claim 1, wherein the antigen-binding fragment is a Fv, a Fab, a F(ab')2, a scFV or a scFV2 fragment.

4. A pharmaceutical composition, comprising the isolated mAb or antigen-binding fragment thereof of claim 1 and a pharmaceutically acceptable carrier.

5. The pharmaceutical composition of claim 4, further comprising a radioisotope, a radionuclide, a toxin, a therapeutic agent, a chemotherapeutic agent or a combination thereof.

6. An isolated mAb or antigen-binding fragment thereof having a binding specificity to human or cynomolgus 4-1BB, comprising a light chain and a heavy chain, wherein the isolated mAb or antigen-binding fragment thereof comprises SEQ ID NO: 273 as complementarity determining region (CDR) 1, SEQ ID NO: 274 as CDR2, and SEQ ID NO: 275 as CDR3 of the light chain, and SEQ ID NO: 276 as CDR1, SEQ ID NO: 277 as CDR2, and SEQ ID NO: 278 as CDR3 of the heavy chain.

7. A pharmaceutical composition, comprising the isolated mAb or antigen-binding fragment thereof of claim 6 and a pharmaceutically acceptable carrier.

8. The pharmaceutical composition of claim 7, further comprising a radioisotope, a radionuclide, a toxin, a therapeutic agent, a chemotherapeutic agent or a combination thereof.

* * * * *